(12) United States Patent
Shair et al.

(10) Patent No.: US 6,797,819 B1
(45) Date of Patent: Sep. 28, 2004

(54) ALKALOIDS

(75) Inventors: Matthew Shair, Boston, MA (US); Nicholas Westwood, St. Andrews Fife (GB); Henry Efrem Pelish, Boston, MA (US)

(73) Assignees: President and Fellows of Harvard College, Cambridge, MA (US); CBR Institute for Biomedical Research, Inc., Boston, MA (US)

( * ) Notice: Subject to any disclaimer, the term of this patent is extended or adjusted under 35 U.S.C. 154(b) by 253 days.

(21) Appl. No.: 09/863,141

(22) Filed: May 22, 2001

Related U.S. Application Data

(63) Continuation-in-part of application No. 09/838,760, filed on Apr. 19, 2001, now abandoned, which is a continuation of application No. 09/329,970, filed on Jun. 10, 1999, now abandoned.
(60) Provisional application No. 60/089,124, filed on Jun. 11, 1998.

(51) Int. Cl.$^7$ ............................................. C07D 223/14
(52) U.S. Cl. ....................... 540/543; 540/546; 540/581
(58) Field of Search ................................ 540/543, 546, 540/581

(56) References Cited

FOREIGN PATENT DOCUMENTS

| EP | 0 774 464 A2 | 5/1997 |
|---|---|---|
| WO | WO 96/03424 | 2/1996 |
| WO | WO 97/22594 | 6/1997 |
| WO | WO 97 35199 | 9/1997 |
| WO | WO 97/40034 | 10/1997 |

OTHER PUBLICATIONS

U.S. patent application Ser. No. 09/838,760, Shair et al., filed Apr. 19, 2001.
U.S. patent application Ser. No. 09/329,970, Shair et al., filed Jun. 10, 1999.
Atuegbu et al., "Combinatorial Modification of Natural Products: Preparation of Unencoded and Encoded Libraries of Rauwolfia Alkaloids" *Bioorg. & Med. Chem.* 4(7):1097–1106, 1996.
Babine et al., Molecular Recognition of Protein–Ligand Complexes: Applications to Drug Design Chem. Rev. 97(5):1359–1472, 1997.
Hall, D. G.; Manku, S.; Wang, F., "Solution– and Solid–Phase Strategies for the Design, Synthesis, and Screening of Libraries Based on Natural Product Templates: A Comprehensive Survey", *J. Comb. Chem.*, 3(2):125–150, 2001.
Kita et al., "Oxidative Intramolecular Phenolic Coupling Reation Induced by a Hypervalent Iodine (III) Reagent: Leading to Galanthamine–Type Amaryllidaccae Alkaloids", *J. Org. Chem.*, 63:6625–6633, 1998.
Lee et al., "Soluble–Polymer Supported Synthesis of Prostanoid Library: Identification of Antiviral Activity", *Org. Lett.*, 1:1859–1862, 1999.
Mayer et al., "Small Molecule Inhibitor of Mitotic Spindle Bipolarity Identified in a Phenotype–Based Screen", *Science*, 286:971–974, 1999.
Nicolaou et al., "Designed Epothilones: Combinatorial Synthesis, Tubulin Assembly Properties, and Cytotoxic Action against Taxol–Resistant Tumor Cells", *Angew. Chem., Int. Ed. Engl.*, 36:2097–2103, 1997.
Nicolaou et al., "Solid and Solution Phase Synthesis and Biological Evaluation of Combinatorial Sarcodictyin Libraries", *J. Am. Chem. Soc.*, 120:10814–10826, 1998.
Nicolaou et al., "Natural Product–like Combinatorial Libraries Based on Privileged Structures. 3. The "Libraries from Libraries" Principle for Diversity Enhancement of Benzopyran Libraries", *J. Am. Chem. Soc.*, 122:9968–9976, 2000.
Ohlmeyer et al., "Complex synthetic chemical libraries indexed with molecular tags", *Proc. Natl. Acad. Sci.*, 90:10922–10926, 1993.
Pelish et al., "Use of Biomimetic Diversity–Oriented Synthesis to Discover Galanthamine–like molecules with Biological Properties beyond Those of the Natural Product" *J. Am. Chem. Soc.*, 123:6740–6741, 2001.
Schreiber, S. L., "Chemical Genetics Resulting from a Passion for Synthetic Organic Chemistry", *Bioorg. Med. Chem.*, 6:1127–1152, 1998.
Shimizu et al., "Stereochemical Studies. LIV. A Biogenetic–type Asymmetric Synthesis of Optically Active Galanthamine from L–Tyrosine", *Chem. Pharm. Bull.* 26:3765–3771, 1978.
Tallarico et al., "An Alkylsilyl–Tethered, High Capacity Solid Support Amenable to One Compound–One Encoded Bead Diversity–Oriented Synthesis", *J. Comb. Chem.*, 3(3):312–318, 2001.
Wipf et al., "Synthesis and Biological Evaluation of a Focused Mixture Library of Analogues of the Biomitotic Marine Natural Product Curacin A", *J. Am. Chem. Soc.*, 122:9391–9395, 2000.
Xu et al., "Combinatorial Library Approach for the Identification of Synthetic Receptors Targeting Vacomycin–Resistant Bacteria", *J. Am. Chem. Soc.*, 121:4898–4899, 1999.
Gallop et al., "Applications of Combinatorial Technologies to Drug Discovery. 1. Background and Peptide Combinatorial Libraries" *J. Med. Chem.* 37(9):1233–51, 1994.
Gante J., "Peptidomimetics–Taylored Enzyme Inhibitors" *Chem. Int. Ed. Engl.* 33:1699–1720, 1994.

(List continued on next page.)

*Primary Examiner*—Bennett Celsa
(74) *Attorney, Agent, or Firm*—Brenda Herschbach Jarrell; Nèdege M. Lagneau; Choate, Hall & Stewart

(57) ABSTRACT

The present invention provides novel alkaloid compounds and collections of these compounds, and provides methods for the synthesis of these compounds using biomimetic synthetic strategies. Additionally, the present invention provides pharmaceutical compositions and methods for treating disorders such as bacterial infections, proliferative diseases, and reproductive disorders, to name a few.

22 Claims, 74 Drawing Sheets

OTHER PUBLICATIONS

Hoveyda A., "Catalyst discovery through combinatorial chemistry" *Chem. & Biol.* 5(8):R188–191, 1998.

Huff et al., "The Nonadrides. Part VI. Dimerization of the $C_9$ Unit in vivo and in vitro" Chem. Dept., Imperial College, London SW7, 2584–2590.

Iyer, Meera R. et al: "Silver (I) Oxide Catalyzed Oxidation of o–allyl–and o– )1–Propenyl) Phenols" *Bull. Chemistry Society Jpn.* 65(6):1662–4, 1992.

Jakupovic J. et al., "Benzoxanthenone Derivations from Polemannia Montana", *Phytochemistry* 2427–2429, 1987.

Kamenati et al., "Studies on the Synthesis of Heterocyclic Compounds. CCCXCVI.[1] An Alternative Total Synthesis of (±)–Galanthamine" *J. Org. Chem.* 36(9):1295–7, 1971.

Kazmeirski, "recent advances in the design and synthesis od small–molecule mimetic drugs" *Tibtec* 12:216–8, 1994.

Kita et al., "An oxidative Intramolecular Phenolic Coupling Reaction for the Synthesis of Amaryllidaceae Alkaloids Using a Hypervalent Iodine (III) Reagent" *J. Org. Chem.* 61:5857–64, 1996.

Lewis J., "Amaryllidaceae and Sceletium alkaloids" 107–110, Dept. of Chem., Aberdeen Univ., Old Aberdeen, UK AB24 3 UE, 1996.

Lombardo L. and Mander L., "Phenolic Oxidative Coupling with Hypervalent Iodine. A synthesis of a 6a–Epipretazettine" *J. Org. Chem.* 48:2300–2, 1983.

Lowe G., "Combinatorial Chemistry" *Chem. Soc. Rev.* 309–17, 1995.

Matsumoto; Masakatsu, et al., "Transition Metal (II) Schiff's Base Complexes Catalyzed Oxidation of trans–2–(1–Propenyl)–4,5–Methylenedioxphenol to Carpanone by Molecular Oxygen" *Tet. Lett.* 22(44):4437–40, 1981.

Mitchinson T., "Towards a pharmacological genetics" *Curr. Biol. Ldt.* 1(1):3–6, 1994.

Nestler H., "A General Method for Molecular Tagging of Encoded Combinatorial Chemistry Libraries" *J. Am. Chem. Soc.* 59(17):4724–5, 1994.

Plunkett M. and Ellman J., "Combinatorial Chemistry and New Drugs" *Sci. Am.* 69–73, Apr. 1997.

Steffans J. and Chipman D., "The Total Synthesis of Carpanone" *J. Am. Chem. Soc.* 93:24–6, 1971.

Szewczyk et al., "An Improved Synthesis of Galanthamine" *J. Het. Chem.* 25:1809–11, 1988.

Thompson L. and Ellman J., "Synthesis and Application of Small Molecule Libraries" *Chem. Rev.* 96:555–600, 1996.

Wirth T. and Hirt U., "Chiral hypervalent iodine compounds" *Tetrahedron: Asymm.* 8(1):23–6, 1997.

You et al., "A miniaturized arrayed assay format for detecting small molecule–protein interactions in cells" *Chem. & Biol.* 4(12):969–75, 1997.

Barton, D.H.R.; Kirby, G.W., "Phenol Oxidation and Biosynthesis. Part V.* The Synthesis of Galanthamine", *J. Chem. Soc.*, 806–817, 1962.

Boger, D.L.; Fink, B.E.; Hedrick, M.P., "Total Synthesis of Distamycin A and 2640 Analogues: A Solution–phase Combinatorial Approach to the Discovery of New, Bioactive DNA Binding Agents and Development of a Rapid, High-Throughput Screen for Determining Relative DNA Binding Affinity or DNA Binding Sequence Selectivity", *J. Am. Chem. Soc*, 122:6382–6394, 2000.

Craig et al., "Solid–Phase Biomimetic Synthesis of Carpanone–like Molecules" *J. Am. Chem. Soc.* 122(2):422–423, 2000.

Baldwin et al., "Synthesis of a Small Molecule Combinatorial Library Encoded with Molecular Tags" *J. Am. Chem. Soc.* 117:5588–5589, 1995.

Balkenhohl et al., "Combinatorial Synthesis of Small Organic Molecules" *Angew. Chem. Int. Ed. Engl.* 35:2288–2337, 1996.

Barton et al., "Phenol Oxidation and Biosynthesis. Part V.* The Synthesis of Galanthamine" *Imper. College Sci. Technol.*, S. Kesington, London, S.W.7. 153:806–8017.

Barton et al., "The Synthesis of Galanthamine" *Proceedings*, Imperial College, London, 392–3, Nov. 1960.

Baxter, Anthony, "Synthesis utilizing insoluble polymers: new reactions and small molecules" *Chem. Biol.*, 1:79–85.

Beeley, "Peptidomimetics and small–molecule drug design: towards improved bioavailability and in vivo stability" *Tibtech*, 12:213–216, Jun., 1994.

Borchardt et al., "Synthetic Receptor Elucidated with a Encoded Combinatorial Library" *J. Am. Chem. Soc.* 116:373–4, 1994.

Borchardt et al., "Small molecule–dependent genetic selection in stochastic nanodroplets as a means of detecting protein–ligand interactions on a large scale" *Chem. & Biol.* 4(12):961–968, 1997.

Borman, Stu, "Combinatorial Chemistry: Researchers continue to refine techniques for identifying potential drugs in 'libraries' of small organic molecules" *C&EN*, Feb. 24, 1997.

Brown, Richard, "Recent developments in solid–phase organic synthesis" pp. 216–237, *Contemporary Organic Synthesis*, Dept. of Chemistry, The University, Highfield, Southampton, SO17 1BJ, UK.

Burman J. and Sigal N., "New technologies for high-throughput screening" *Chem. Biol.* 1:72–78, 1997.

Cargill J. and Lebl M., "New methods in combinatorial chemistry–robotics and parallel synthesis" *Chem. Biol.* 67–71, 1997.

Chabala et al., "Binary encoded small–molecule libraries in drug discovery and optimization" *Persp. Drug. Discov. Design* 2:305–318, 1994.

Chaplin et al., "A concise scaleable synthesis of Narwedine" *Tet. Lett.* 38(45):7931–7932, 1997.

Chen et al., "Stereospecific Synthesis of the CP–263,114 Core Structure" *J. Am. Chem. Soc.* 120:10784–5, 1998.

Combs et al., "Protein Structure–Based Combinatorial Chemistry: Discovery of Non–Peptide Binding Elements to Src Sh3 Domain" *J. Am. Chem. Soc.* 118:287–8, 1996

Cornia, Mara et al., "Oxygen Heterocycles by Oxidation of Ortho–Alkylphenols. Oxidation of Ortho–Propenylphenols" *Gazzetta Chimica Italiana*, 200–304, 1977.

Czarnik A., "Encoding methods for combinatorial chemistry" *Chem. Biol.* 1:60–6, 1997.

Dean P., "Recent Advances in Drug Design Methods: Where Will They Lead" *BioEssays* 16(9):683–7, 1994.

Denison C. and Kodadek T., "Small–molecule–based strategies for controlling gene expression" *Chem. & Biol.* 5:R129–R145, 1998.

Enger et al., "Tagging in combinatorial chemistry: the use of coloured and fluorescent beads" *Chem. Commun.*, 735–6, 1997.

Eichler et al., "Peptide, Peptidomimetic, and Organic Synthetic Combinatorial Libraries" *Medicinal Res. Rev.* 15:481–96, 1995.

Früchtel J. and Jung G., "Organic Chemistry on Solid Supports**" *Chem. Int. Ed. Engl.* 35:17, 1996.

Biomimetic Diversity-Oriented Synthesis Parallels the Biosynthesis of Galanthamine.

FIG. 7A

| R1 | R2 | R3 | R4 | Plate | Loc. |
|---|---|---|---|---|---|
| 1 | 3 | 7 | 1 | 3 | Z |
| 1 | 4 | 7 | 1 | 3 | C08 |
| 1 | 5 | 7 | 1 | 3 | B06 |
| 1 | 6 | 7 | 1 | 3 | E09 |
| 1 | 7 | 7 | 1 | 3 | B03 |
| 1 | 8 | 7 | 1 | 3 | B08 |
| 2 | 1 | 7 | 1 | 3 | E05 |
| 2 | 2 | 7 | 1 | 3 | E11 |
| 2 | 3 | 7 | 1 | 3 | C10 |
| 2 | 4 | 7 | 1 | 3 | B05 |
| 2 | 5 | 7 | 1 | 3 | Z |
| 2 | 6 | 7 | 1 | 3 | D06 |
| 2 | 7 | 7 | 1 | 3 | B09 |
| 2 | 8 | 7 | 1 | 3 | C04 |
| 3 | 1 | 7 | 1 | 3 | D02 |
| 3 | 2 | 7 | 1 | 3 | E06 |
| 3 | 3 | 7 | 1 | 3 | B10 |
| 3 | 4 | 7 | 1 | 3 | E03 |
| 3 | 5 | 7 | 1 | 3 | C07 |
| 3 | 6 | 7 | 1 | 3 | D03 |
| 3 | 7 | 7 | 1 | 3 | Z |
| 3 | 8 | 7 | 1 | 3 | F02* |
| 4 | 1 | 7 | 1 | 3 | E08 |
| 4 | 2 | 7 | 1 | 3 | Z |
| 4 | 3 | 7 | 1 | 3 | D09 |

| R1 | R2 | R3 | R4 | Plate | Loc. |
|---|---|---|---|---|---|
| 1 | 3 | 7 | 3 | 3 | N11 |
| 1 | 4 | 7 | 3 | 3 | K10 |
| 1 | 5 | 7 | 3 | 3 | L09 |
| 1 | 6 | 7 | 3 | 3 | L02 |
| 1 | 7 | 7 | 3 | 3 | N06 |
| 1 | 8 | 7 | 3 | 3 | M03 |
| 2 | 1 | 7 | 3 | 3 | K08 |
| 2 | 2 | 7 | 3 | 3 | N09 |
| 2 | 3 | 7 | 3 | 3 | L11 |
| 2 | 4 | 7 | 3 | 3 | O07 |
| 2 | 5 | 7 | 3 | 3 | K02 |
| 2 | 6 | 7 | 3 | 3 | N05* |
| 2 | 7 | 7 | 3 | 3 | K03 |
| 2 | 8 | 7 | 3 | 3 | L04 |
| 3 | 1 | 7 | 3 | 3 | K06 |
| 3 | 2 | 7 | 3 | 3 | O03 |
| 3 | 3 | 7 | 3 | 3 | L06 |
| 3 | 4 | 7 | 3 | 3 | K05 |
| 3 | 5 | 7 | 3 | 3 | O09 |
| 3 | 6 | 7 | 3 | 3 | N07 |
| 3 | 7 | 7 | 3 | 3 | M08 |
| 3 | 8 | 7 | 3 | 3 | K09 |
| 4 | 1 | 7 | 3 | 3 | K04 |
| 4 | 2 | 7 | 3 | 3 | Z |
| 4 | 3 | 7 | 3 | 3 | M11 |

| R1 | R2 | R3 | R4 | Plate | Loc. |
|---|---|---|---|---|---|
| 1 | 3 | 7 | 2 | 3 | C18 |
| 1 | 4 | 7 | 2 | 3 | F14 |
| 1 | 5 | 7 | 2 | 3 | B16 |
| 1 | 6 | 7 | 2 | 3 | D19 |
| 1 | 7 | 7 | 2 | 3 | Z |
| 1 | 8 | 7 | 2 | 3 | F17 |
| 2 | 1 | 7 | 2 | 3 | E18 |
| 2 | 2 | 7 | 2 | 3 | D17 |
| 2 | 3 | 7 | 2 | 3 | D15 |
| 2 | 4 | 7 | 2 | 3 | E23 |
| 2 | 5 | 7 | 2 | 3 | E17 |
| 2 | 6 | 7 | 2 | 3 | E22 |
| 2 | 7 | 7 | 2 | 3 | E21* |
| 2 | 8 | 7 | 2 | 3 | D22 |
| 3 | 1 | 7 | 2 | 3 | B18 |
| 3 | 2 | 7 | 2 | 3 | D23 |
| 3 | 3 | 7 | 2 | 3 | D16 |
| 3 | 4 | 7 | 2 | 3 | G14 |
| 3 | 5 | 7 | 2 | 3 | C20 |
| 3 | 6 | 7 | 2 | 3 | E16 |
| 3 | 7 | 7 | 2 | 3 | E14 |
| 3 | 8 | 7 | 2 | 3 | C14 |
| 4 | 1 | 7 | 2 | 3 | B20 |
| 4 | 2 | 7 | 2 | 3 | Z |
| 4 | 3 | 7 | 2 | 3 | B21 |

| R1 | R2 | R3 | R4 | Plate | Loc. |
|---|---|---|---|---|---|
| 1 | 3 | 7 | 4 | 3 | Z |
| 1 | 4 | 7 | 4 | 3 | L16 |
| 1 | 5 | 7 | 4 | 3 | K17 |
| 1 | 6 | 7 | 4 | 3 | Z |
| 1 | 7 | 7 | 4 | 3 | K20 |
| 1 | 8 | 7 | 4 | 3 | M18 |
| 2 | 1 | 7 | 4 | 3 | K18 |
| 2 | 2 | 7 | 4 | 3 | N17 |
| 2 | 3 | 7 | 4 | 3 | O17 |
| 2 | 4 | 7 | 4 | 3 | K23 |
| 2 | 5 | 7 | 4 | 3 | M23 |
| 2 | 6 | 7 | 4 | 3 | O15 |
| 2 | 7 | 7 | 4 | 3 | M15 |
| 2 | 8 | 7 | 4 | 3 | L14 |
| 3 | 1 | 7 | 4 | 3 | N15 |
| 3 | 2 | 7 | 4 | 3 | M20 |
| 3 | 3 | 7 | 4 | 3 | K14 |
| 3 | 4 | 7 | 4 | 3 | K22 |
| 3 | 5 | 7 | 4 | 3 | N23 |
| 3 | 6 | 7 | 4 | 3 | N18* |
| 3 | 7 | 7 | 4 | 3 | L18 |
| 3 | 8 | 7 | 4 | 3 | L17 |
| 4 | 1 | 7 | 4 | 3 | O18 |
| 4 | 2 | 7 | 4 | 3 | Z |
| 4 | 3 | 7 | 4 | 3 | K19 |

FIG. 7B

| | | | | | |
|---|---|---|---|---|---|
| 4 | 4 | 7 | 1 | 3 | Z |
| 4 | 5 | 7 | 1 | 3 | F05 |
| 4 | 6 | 7 | 1 | 3 | D10 |
| 4 | 7 | 7 | 1 | 3 | D07* |
| 4 | 8 | 7 | 1 | 3 | D08 |
| 5 | 1 | 7 | 1 | 3 | F07 |
| 5 | 2 | 7 | 1 | 3 | Z |
| 5 | 3 | 7 | 1 | 3 | B07 |
| 5 | 4 | 7 | 1 | 3 | Z |
| 5 | 5 | 7 | 1 | 3 | Z |
| 5 | 6 | 7 | 1 | 3 | Z |
| 5 | 7 | 7 | 1 | 3 | D04 |
| 5 | 8 | 7 | 1 | 3 | C02 |
| 6 | 1 | 7 | 1 | 3 | E04 |
| 6 | 2 | 7 | 1 | 3 | C03 |
| 6 | 3 | 7 | 1 | 3 | B04 |
| 6 | 4 | 7 | 1 | 3 | C06 |
| 6 | 5 | 7 | 1 | 3 | B02 |
| 6 | 6 | 7 | 1 | 3 | C09 |
| 6 | 7 | 7 | 1 | 3 | E02 |
| 6 | 8 | 7 | 1 | 3 | E07 |

| | | | | | |
|---|---|---|---|---|---|
| 4 | 4 | 7 | 3 | 3 | M06 |
| 4 | 5 | 7 | 3 | 3 | L08 |
| 4 | 6 | 7 | 3 | 3 | N04 |
| 4 | 7 | 7 | 3 | 3 | M07 |
| 4 | 8 | 7 | 3 | 3 | M09 |
| 5 | 1 | 7 | 3 | 3 | N10 |
| 5 | 2 | 7 | 3 | 3 | N03 |
| 5 | 3 | 7 | 3 | 3 | L07* |
| 5 | 4 | 7 | 3 | 3 | O05 |
| 5 | 5 | 7 | 3 | 3 | L03 |
| 5 | 6 | 7 | 3 | 3 | O04 |
| 5 | 7 | 7 | 3 | 3 | O08 |
| 5 | 8 | 7 | 3 | 3 | O06 |
| 6 | 1 | 7 | 3 | 3 | O02 |
| 6 | 2 | 7 | 3 | 3 | L05 |
| 6 | 3 | 7 | 3 | 3 | M04 |
| 6 | 4 | 7 | 3 | 3 | M02 |
| 6 | 5 | 7 | 3 | 3 | N08 |
| 6 | 6 | 7 | 3 | 3 | L10 |
| 6 | 7 | 7 | 3 | 3 | N02 |
| 6 | 8 | 7 | 3 | 3 | M10 |

| | | | | | |
|---|---|---|---|---|---|
| 4 | 4 | 7 | 2 | 3 | B23 |
| 4 | 5 | 7 | 2 | 3 | F19 |
| 4 | 6 | 7 | 2 | 3 | B17 |
| 4 | 7 | 7 | 2 | 3 | Z |
| 4 | 8 | 7 | 2 | 3 | B22 |
| 5 | 1 | 7 | 2 | 3 | D21 |
| 5 | 2 | 7 | 2 | 3 | B19 |
| 5 | 3 | 7 | 2 | 3 | C17 |
| 5 | 4 | 7 | 2 | 3 | D18 |
| 5 | 5 | 7 | 2 | 3 | E19 |
| 5 | 6 | 7 | 2 | 3 | B14 |
| 5 | 7 | 7 | 2 | 3 | E15 |
| 5 | 8 | 7 | 2 | 3 | D14* |
| 6 | 1 | 7 | 2 | 3 | B15 |
| 6 | 2 | 7 | 2 | 3 | F21 |
| 6 | 3 | 7 | 2 | 3 | C16 |
| 6 | 4 | 7 | 2 | 3 | F15 |
| 6 | 5 | 7 | 2 | 3 | C22 |
| 6 | 6 | 7 | 2 | 3 | E20 |
| 6 | 7 | 7 | 2 | 3 | F16 |
| 6 | 8 | 7 | 2 | 3 | F22 |

| | | | | | |
|---|---|---|---|---|---|
| 4 | 4 | 7 | 4 | 3 | N16 |
| 4 | 5 | 7 | 4 | 3 | K16 |
| 4 | 6 | 7 | 4 | 3 | L15 |
| 4 | 7 | 7 | 4 | 3 | N14 |
| 4 | 8 | 7 | 4 | 3 | N19 |
| 5 | 1 | 7 | 4 | 3 | L19 |
| 5 | 2 | 7 | 4 | 3 | M22 |
| 5 | 3 | 7 | 4 | 3 | M16 |
| 5 | 4 | 7 | 4 | 3 | O16 |
| 5 | 5 | 7 | 4 | 3 | L21 |
| 5 | 6 | 7 | 4 | 3 | K15 |
| 5 | 7 | 7 | 4 | 3 | M19 |
| 5 | 8 | 7 | 4 | 3 | M17* |
| 6 | 1 | 7 | 4 | 3 | M14 |
| 6 | 2 | 7 | 4 | 3 | M21 |
| 6 | 3 | 7 | 4 | 3 | N22 |
| 6 | 4 | 7 | 4 | 3 | L23 |
| 6 | 5 | 7 | 4 | 3 | K21 |
| 6 | 6 | 7 | 4 | 3 | L20 |
| 6 | 7 | 7 | 4 | 3 | N20 |
| 6 | 8 | 7 | 4 | 3 | Z |

| R1 | R2 | R3 | R4 | Plate | Loc. |
|---|---|---|---|---|---|
| 1 | 3 | 7 | 5 | 4 | E06 |
| 1 | 4 | 7 | 5 | 4 | E02* |
| 1 | 5 | 7 | 5 | 4 | D03 |
| 1 | 6 | 7 | 5 | 4 | E10 |
| 1 | 7 | 7 | 5 | 4 | B07 |
| 1 | 8 | 7 | 5 | 4 | Z |
| 2 | 1 | 7 | 5 | 4 | E05 |
| 2 | 2 | 7 | 5 | 4 | D11 |
| 2 | 3 | 7 | 5 | 4 | B04 |
| 2 | 4 | 7 | 5 | 4 | C10 |
| 2 | 5 | 7 | 5 | 4 | E07 |
| 2 | 6 | 7 | 5 | 4 | B02 |
| 2 | 7 | 7 | 5 | 4 | Z |
| 2 | 8 | 7 | 5 | 4 | B09 |
| 3 | 1 | 7 | 5 | 4 | E11 |
| 3 | 2 | 7 | 5 | 4 | Z |
| 3 | 3 | 7 | 5 | 4 | E04 |
| 3 | 4 | 7 | 5 | 4 | D05 |
| 3 | 5 | 7 | 5 | 4 | D08 |
| 3 | 6 | 7 | 5 | 4 | Z |
| 3 | 7 | 7 | 5 | 4 | C03 |
| 3 | 8 | 7 | 5 | 4 | Z |
| 4 | 1 | 7 | 5 | 4 | B10 |
| 4 | 2 | 7 | 5 | 4 | Z |
| 4 | 3 | 7 | 5 | 4 | D02 |

| R1 | R2 | R3 | R4 | Plate | Loc. |
|---|---|---|---|---|---|
| 1 | 3 | 7 | 7 | 4 | M09 |
| 1 | 4 | 7 | 7 | 4 | N02 |
| 1 | 5 | 7 | 7 | 4 | L02 |
| 1 | 6 | 7 | 7 | 4 | N06 |
| 1 | 7 | 7 | 7 | 4 | L09 |
| 1 | 8 | 7 | 7 | 4 | M02 |
| 2 | 1 | 7 | 7 | 4 | M11 |
| 2 | 2 | 7 | 7 | 4 | K06 |
| 2 | 3 | 7 | 7 | 4 | K04 |
| 2 | 4 | 7 | 7 | 4 | L08 |
| 2 | 5 | 7 | 7 | 4 | L03 |
| 2 | 6 | 7 | 7 | 4 | O06 |
| 2 | 7 | 7 | 7 | 4 | K02* |
| 2 | 8 | 7 | 7 | 4 | O09 |
| 3 | 1 | 7 | 7 | 4 | N04 |
| 3 | 2 | 7 | 7 | 4 | N11 |
| 3 | 3 | 7 | 7 | 4 | L06 |
| 3 | 4 | 7 | 7 | 4 | M07 |
| 3 | 5 | 7 | 7 | 4 | M04 |
| 3 | 6 | 7 | 7 | 4 | Z |
| 3 | 7 | 7 | 7 | 4 | K10 |
| 3 | 8 | 7 | 7 | 4 | O08 |
| 4 | 1 | 7 | 7 | 4 | M05 |
| 4 | 2 | 7 | 7 | 4 | Z |
| 4 | 3 | 7 | 7 | 4 | L05 |

| R1 | R2 | R3 | R4 | Plate | Loc. |
|---|---|---|---|---|---|
| 1 | 3 | 7 | 6 | 4 | D17 |
| 1 | 4 | 7 | 6 | 4 | B15 |
| 1 | 5 | 7 | 6 | 4 | E23 |
| 1 | 6 | 7 | 6 | 4 | F22 |
| 1 | 7 | 7 | 6 | 4 | B14 |
| 1 | 8 | 7 | 6 | 4 | E18 |
| 2 | 1 | 7 | 6 | 4 | Z |
| 2 | 2 | 7 | 6 | 4 | B22 |
| 2 | 3 | 7 | 6 | 4 | G14 |
| 2 | 4 | 7 | 6 | 4 | C22 |
| 2 | 5 | 7 | 6 | 4 | F21 |
| 2 | 6 | 7 | 6 | 4 | Z |
| 2 | 7 | 7 | 6 | 4 | E20 |
| 2 | 8 | 7 | 6 | 4 | F18 |
| 3 | 1 | 7 | 6 | 4 | E19 |
| 3 | 2 | 7 | 6 | 4 | C17 |
| 3 | 3 | 7 | 6 | 4 | D20 |
| 3 | 4 | 7 | 6 | 4 | F17 |
| 3 | 5 | 7 | 6 | 4 | B17* |
| 3 | 6 | 7 | 6 | 4 | C20 |
| 3 | 7 | 7 | 6 | 4 | D18 |
| 3 | 8 | 7 | 6 | 4 | G15 |
| 4 | 1 | 7 | 6 | 4 | C14 |
| 4 | 2 | 7 | 6 | 4 | Z |
| 4 | 3 | 7 | 6 | 4 | C21 |

| | | | | |
|---|---|---|---|---|
| 4 D16 | 6 | 7 | 4 | 4 |
| 4 D19 | 6 | 7 | 5 | 4 |
| 4 C16 | 6 | 7 | 6 | 4 |
| 4 B18 | 6 | 7 | 7 | 4 |
| 4 D15 | 6 | 7 | 8 | 4 |
| 4 C18 | 6 | 7 | 1 | 5 |
| 4 E14 | 6 | 7 | 2 | 5 |
| 4 B21 | 6 | 7 | 3 | 5 |
| 4 E21 | 6 | 7 | 4 | 5 |
| 4 E22 | 6 | 7 | 5 | 5 |
| 4 C15 | 6 | 7 | 6 | 5 |
| 4 D22 | 6 | 7 | 7 | 5 |
| 4 E15 | 6 | 7 | 8 | 5 |
| 4 B20 | 6 | 7 | 1 | 6 |
| 4 D14* | 6 | 7 | 2 | 6 |
| 4 Z | 6 | 7 | 3 | 6 |
| 4 B16 | 6 | 7 | 4 | 6 |
| 4 B23 | 6 | 7 | 5 | 6 |
| 4 D21 | 6 | 7 | 6 | 6 |
| 4 C19 | 6 | 7 | 7 | 6 |
| 4 E17 | 6 | 7 | 8 | 6 |

| | | | | |
|---|---|---|---|---|
| 4 N05 | 7 | 7 | 4 | 4 |
| 4 J03 | 7 | 7 | 5 | 4 |
| 4 N03 | 7 | 7 | 6 | 4 |
| 4 L04 | 7 | 7 | 7 | 4 |
| 4 N08 | 7 | 7 | 8 | 4 |
| 4 K09 | 7 | 7 | 1 | 5 |
| 4 L07 | 7 | 7 | 2 | 5 |
| 4 M10* | 7 | 7 | 3 | 5 |
| 4 L10 | 7 | 7 | 4 | 5 |
| 4 K05 | 7 | 7 | 5 | 5 |
| 4 O07 | 7 | 7 | 6 | 5 |
| 4 K03 | 7 | 7 | 7 | 5 |
| 4 O02 | 7 | 7 | 8 | 5 |
| 4 K11 | 7 | 7 | 1 | 6 |
| 4 L11 | 7 | 7 | 2 | 6 |
| 4 M06 | 7 | 7 | 3 | 6 |
| 4 K07 | 7 | 7 | 4 | 6 |
| 4 M08 | 7 | 7 | 5 | 6 |
| 4 K08 | 7 | 7 | 6 | 6 |
| 4 O03 | 7 | 7 | 7 | 6 |
| 4 Z | 7 | 7 | 8 | 6 |

| | | | | |
|---|---|---|---|---|
| 4 F02 | 5 | 7 | 4 | 4 |
| 4 C07 | 5 | 7 | 5 | 4 |
| 4 C08 | 5 | 7 | 6 | 4 |
| 4 B06* | 5 | 7 | 7 | 4 |
| 4 C02 | 5 | 7 | 8 | 4 |
| 4 Z | 5 | 7 | 1 | 5 |
| 4 C06 | 5 | 7 | 2 | 5 |
| 4 B03 | 5 | 7 | 3 | 5 |
| 4 D04 | 5 | 7 | 4 | 5 |
| 4 B08 | 5 | 7 | 5 | 5 |
| 4 D10 | 5 | 7 | 6 | 5 |
| 4 C05 | 5 | 7 | 7 | 5 |
| 4 C11 | 5 | 7 | 8 | 5 |
| 4 Z | 5 | 7 | 1 | 6 |
| 4 E03 | 5 | 7 | 2 | 6 |
| 4 D09 | 5 | 7 | 3 | 6 |
| 4 C04 | 5 | 7 | 4 | 6 |
| 4 B05 | 5 | 7 | 5 | 6 |
| 4 D06 | 5 | 7 | 6 | 6 |
| 4 C09 | 5 | 7 | 7 | 6 |
| 4 D07 | 5 | 7 | 8 | 6 |

FIG. 9A

| R1 | R2 | R3 | R4 | Plate | Loc. |
|---|---|---|---|---|---|
| 1 | 3 | 8 | 1 | 5 | E10 |
| 1 | 4 | 8 | 1 | 5 | B7 |
| 1 | 5 | 8 | 1 | 5 | B8 |
| 1 | 6 | 8 | 1 | 5 | C8 |
| 1 | 7 | 8 | 1 | 5 | E7 |
| 1 | 8 | 8 | 1 | 5 | C8 |
| 2 | 1 | 8 | 1 | 5 | B3 |
| 2 | 2 | 8 | 1 | 5 | E11 |
| 2 | 3 | 8 | 1 | 5 | D6 |
| 2 | 4 | 8 | 1 | 5 | D5* |
| 2 | 5 | 8 | 1 | 5 | C2 |
| 2 | 6 | 8 | 1 | 5 | C6 |
| 2 | 7 | 8 | 1 | 5 | C4 |
| 2 | 8 | 8 | 1 | 5 | C7 |
| 3 | 1 | 8 | 1 | 5 | Z |
| 3 | 2 | 8 | 1 | 5 | C11 |
| 3 | 3 | 8 | 1 | 5 | E4 |
| 3 | 4 | 8 | 1 | 5 | B10 |
| 3 | 5 | 8 | 1 | 5 | F4 |
| 3 | 6 | 8 | 1 | 5 | F9 |
| 3 | 7 | 8 | 1 | 5 | E8 |
| 3 | 8 | 8 | 1 | 5 | E5 |
| 4 | 1 | 8 | 1 | 5 | C3 |
| 4 | 2 | 8 | 1 | 5 | C10 |
| 4 | 3 | 8 | 1 | 5 | D3 |

| R1 | R2 | R3 | R4 | Plate | Loc. |
|---|---|---|---|---|---|
| 1 | 3 | 8 | 3 | 5 | L9 |
| 1 | 4 | 8 | 3 | 5 | N3 |
| 1 | 5 | 8 | 3 | 5 | K7 |
| 1 | 6 | 8 | 3 | 5 | Z |
| 1 | 7 | 8 | 3 | 5 | M11 |
| 1 | 8 | 8 | 3 | 5 | M7 |
| 2 | 1 | 8 | 3 | 5 | L7* |
| 2 | 2 | 8 | 3 | 5 | K8 |
| 2 | 3 | 8 | 3 | 5 | M5 |
| 2 | 4 | 8 | 3 | 5 | K2 |
| 2 | 5 | 8 | 3 | 5 | M2 |
| 2 | 6 | 8 | 3 | 5 | L6 |
| 2 | 7 | 8 | 3 | 5 | K5 |
| 2 | 8 | 8 | 3 | 5 | L10 |
| 3 | 1 | 8 | 3 | 5 | Z |
| 3 | 2 | 8 | 3 | 5 | K10 |
| 3 | 3 | 8 | 3 | 5 | N4 |
| 3 | 4 | 8 | 3 | 5 | N6 |
| 3 | 5 | 8 | 3 | 5 | K3 |
| 3 | 6 | 8 | 3 | 5 | K4 |
| 3 | 7 | 8 | 3 | 5 | Z |
| 3 | 8 | 8 | 3 | 5 | N22 |
| 4 | 1 | 8 | 3 | 5 | K6 |
| 4 | 2 | 8 | 3 | 5 | M9 |
| 4 | 3 | 8 | 3 | 5 | L5 |

| R1 | R2 | R3 | R4 | Plate | Loc. |
|---|---|---|---|---|---|
| 1 | 3 | 8 | 2 | 5 | B18 |
| 1 | 4 | 8 | 2 | 5 | B21 |
| 1 | 5 | 8 | 2 | 5 | E21 |
| 1 | 6 | 8 | 2 | 5 | E14 |
| 1 | 7 | 8 | 2 | 5 | E22 |
| 1 | 8 | 8 | 2 | 5 | D22 |
| 2 | 1 | 8 | 2 | 5 | E19 |
| 2 | 2 | 8 | 2 | 5 | Z |
| 2 | 3 | 8 | 2 | 5 | C19 |
| 2 | 4 | 8 | 2 | 5 | C23 |
| 2 | 5 | 8 | 2 | 5 | E16 |
| 2 | 6 | 8 | 2 | 5 | C14 |
| 2 | 7 | 8 | 2 | 5 | E20* |
| 2 | 8 | 8 | 2 | 5 | C15 |
| 3 | 1 | 8 | 2 | 5 | F15 |
| 3 | 2 | 8 | 2 | 5 | D19 |
| 3 | 3 | 8 | 2 | 5 | E17 |
| 3 | 4 | 8 | 2 | 5 | F17 |
| 3 | 5 | 8 | 2 | 5 | D17 |
| 3 | 6 | 8 | 2 | 5 | Z |
| 3 | 7 | 8 | 2 | 5 | Z |
| 3 | 8 | 8 | 2 | 5 | E23 |
| 4 | 1 | 8 | 2 | 5 | D23 |
| 4 | 2 | 8 | 2 | 5 | C22 |
| 4 | 3 | 8 | 2 | 5 | D15 |

| R1 | R2 | R3 | R4 | Plate | Loc. |
|---|---|---|---|---|---|
| 1 | 3 | 8 | 4 | 5 | O20 |
| 1 | 4 | 8 | 4 | 5 | M20 |
| 1 | 5 | 8 | 4 | 5 | M22 |
| 1 | 6 | 8 | 4 | 5 | N21 |
| 1 | 7 | 8 | 4 | 5 | Z |
| 1 | 8 | 8 | 4 | 5 | O21 |
| 2 | 1 | 8 | 4 | 5 | M19 |
| 2 | 2 | 8 | 4 | 5 | O17 |
| 2 | 3 | 8 | 4 | 5 | L15 |
| 2 | 4 | 8 | 4 | 5 | N22 |
| 2 | 5 | 8 | 4 | 5 | N19 |
| 2 | 6 | 8 | 4 | 5 | L17* |
| 2 | 7 | 8 | 4 | 5 | O15 |
| 2 | 8 | 8 | 4 | 5 | K17 |
| 3 | 1 | 8 | 4 | 5 | M21 |
| 3 | 2 | 8 | 4 | 5 | O23 |
| 3 | 3 | 8 | 4 | 5 | K16 |
| 3 | 4 | 8 | 4 | 5 | M15 |
| 3 | 5 | 8 | 4 | 5 | K20 |
| 3 | 6 | 8 | 4 | 5 | Z |
| 3 | 7 | 8 | 4 | 5 | N23 |
| 3 | 8 | 8 | 4 | 5 | K22 |
| 4 | 1 | 8 | 4 | 5 | K19 |
| 4 | 2 | 8 | 4 | 5 | O18 |
| 4 | 3 | 8 | 4 | 5 | K21* |

| R1 | R2 | R3 | R4 | Plate | Loc. |
|---|---|---|---|---|---|
| 1 | 3 | 8 | 5 | 6 | Z |
| 1 | 4 | 8 | 5 | 6 | Z |
| 1 | 5 | 8 | 5 | 6 | Z |
| 1 | 6 | 8 | 5 | 6 | E6 |
| 1 | 7 | 8 | 5 | 6 | F6 |
| 1 | 8 | 8 | 5 | 6 | C11 |
| 2 | 1 | 8 | 5 | 6 | E11 |
| 2 | 2 | 8 | 5 | 6 | C6* |
| 2 | 3 | 8 | 5 | 6 | D7 |
| 2 | 4 | 8 | 5 | 6 | B8 |
| 2 | 5 | 8 | 5 | 6 | E9 |
| 2 | 6 | 8 | 5 | 6 | D4 |
| 2 | 7 | 8 | 5 | 6 | C5 |
| 2 | 8 | 8 | 5 | 6 | C8 |
| 3 | 1 | 8 | 5 | 6 | C9 |
| 3 | 2 | 8 | 5 | 6 | E7 |
| 3 | 3 | 8 | 5 | 6 | F2 |
| 3 | 4 | 8 | 5 | 6 | D3 |
| 3 | 5 | 8 | 5 | 6 | Z |
| 3 | 6 | 8 | 5 | 6 | B5 |
| 3 | 7 | 8 | 5 | 6 | E8 |
| 3 | 8 | 8 | 5 | 6 | B2... |
| 4 | 1 | 8 | 5 | 6 | Z |
| 4 | 2 | 8 | 5 | 6 | B3 |
| 4 | 3 | 8 | 5 | 6 | B6 |

| R1 | R2 | R3 | R4 | Plate | Loc. |
|---|---|---|---|---|---|
| 1 | 3 | 8 | 7 | 6 | J11 |
| 1 | 4 | 8 | 7 | 6 | L8 |
| 1 | 5 | 8 | 7 | 6 | M10 |
| 1 | 6 | 8 | 7 | 6 | Z |
| 1 | 7 | 8 | 7 | 6 | O10* |
| 1 | 8 | 8 | 7 | 6 | O8 |
| 2 | 1 | 8 | 7 | 6 | N3 |
| 2 | 2 | 8 | 7 | 6 | M5 |
| 2 | 3 | 8 | 7 | 6 | K10 |
| 2 | 4 | 8 | 7 | 6 | L7 |
| 2 | 5 | 8 | 7 | 6 | K11 |
| 2 | 6 | 8 | 7 | 6 | J3 |
| 2 | 7 | 8 | 7 | 6 | L5 |
| 2 | 8 | 8 | 7 | 6 | J2 |
| 3 | 1 | 8 | 7 | 6 | L2 |
| 3 | 2 | 8 | 7 | 6 | N6 |
| 3 | 3 | 8 | 7 | 6 | N5 |
| 3 | 4 | 8 | 7 | 6 | K6 |
| 3 | 5 | 8 | 7 | 6 | M4* |
| 3 | 6 | 8 | 7 | 6 | K4 |
| 3 | 7 | 8 | 7 | 6 | L3 |
| 3 | 8 | 8 | 7 | 6 | L11 |
| 4 | 1 | 8 | 7 | 6 | K2 |
| 4 | 2 | 8 | 7 | 6 | J9 |
| 4 | 3 | 8 | 7 | 6 | K3 |

| R1 | R2 | R3 | R4 | Plate | Loc. |
|---|---|---|---|---|---|
| 1 | 3 | 8 | 6 | 6 | E22* |
| 1 | 4 | 8 | 6 | 6 | B18 |
| 1 | 5 | 8 | 6 | 6 | E16 |
| 1 | 6 | 8 | 6 | 6 | Z |
| 1 | 7 | 8 | 6 | 6 | D17 |
| 1 | 8 | 8 | 6 | 6 | F21 |
| 2 | 1 | 8 | 6 | 6 | C23 |
| 2 | 2 | 8 | 6 | 6 | B22 |
| 2 | 3 | 8 | 6 | 6 | E15 |
| 2 | 4 | 8 | 6 | 6 | G15 |
| 2 | 5 | 8 | 6 | 6 | B15 |
| 2 | 6 | 8 | 6 | 6 | E18 |
| 2 | 7 | 8 | 6 | 6 | E23 |
| 2 | 8 | 8 | 6 | 6 | E19 |
| 3 | 1 | 8 | 6 | 6 | G17 |
| 3 | 2 | 8 | 6 | 6 | B16 |
| 3 | 3 | 8 | 6 | 6 | B23 |
| 3 | 4 | 8 | 6 | 6 | F18 |
| 3 | 5 | 8 | 6 | 6 | D21 |
| 3 | 6 | 8 | 6 | 6 | C17 |
| 3 | 7 | 8 | 6 | 6 | C16 |
| 3 | 8 | 8 | 6 | 6 | G22 |
| 4 | 1 | 8 | 6 | 6 | E17 |
| 4 | 2 | 8 | 6 | 6 | C20 |
| 4 | 3 | 8 | 6 | 6 | B19 |

| R1 | R2 | R3 | R4 | Plate | Loc. |
|---|---|---|---|---|---|
| 1 | 3 | 1 | 1 | 6 | L17 |
| 1 | 4 | 1 | 1 | 6 | Z |
| 1 | 5 | 1 | 1 | 6 | M20 |
| 1 | 6 | 1 | 1 | 6 | Z |
| 1 | 7 | 1 | 1 | 6 | M22 |
| 1 | 8 | 1 | 1 | 6 | L15 |
| 2 | 1 | 1 | 1 | 6 | O17 |
| 2 | 2 | 1 | 1 | 6 | L23 |
| 2 | 3 | 1 | 1 | 6 | N17 |
| 2 | 4 | 1 | 1 | 6 | Z |
| 2 | 5 | 1 | 1 | 6 | N18 |
| 2 | 6 | 1 | 1 | 6 | N20 |
| 2 | 7 | 1 | 1 | 6 | K23 |
| 2 | 8 | 1 | 1 | 6 | L21 |
| 3 | 1 | 1 | 1 | 6 | Z |
| 3 | 2 | 1 | 1 | 6 | O14 |
| 3 | 3 | 1 | 1 | 6 | M17 |
| 3 | 4 | 1 | 1 | 6 | M18* |
| 3 | 5 | 1 | 1 | 6 | K21 |
| 3 | 6 | 1 | 1 | 6 | K16 |
| 3 | 7 | 1 | 1 | 6 | Z |
| 3 | 8 | 1 | 1 | 6 | O21 |
| 4 | 1 | 1 | 1 | 6 | M19 |
| 4 | 2 | 1 | 1 | 6 | M15 |
| 4 | 3 | 1 | 1 | 6 | N16 |

FIG. 10B

| | | | | |
|---|---|---|---|---|
| 4 | 4 | 8 | 5 | 6C2 |
| 4 | 5 | 8 | 5 | 6F7 |
| 4 | 6 | 8 | 5 | 6B9 |
| 4 | 7 | 8 | 5 | 6B10 |
| 4 | 8 | 8 | 5 | 6D9 |
| 5 | 1 | 8 | 5 | 6D6 |
| 5 | 2 | 8 | 5 | 6F4 |
| 5 | 3 | 8 | 5 | 6C3 |
| 5 | 4 | 8 | 5 | 6D10 |
| 5 | 5 | 8 | 5 | 6D5 |
| 5 | 6 | 8 | 5 | 6B4* |
| 5 | 7 | 8 | 5 | 6D2 |
| 5 | 8 | 8 | 5 | 6Z |
| 6 | 1 | 8 | 5 | 6E10 |
| 6 | 2 | 8 | 5 | 6E4 |
| 6 | 3 | 8 | 5 | 6B11 |
| 6 | 4 | 8 | 5 | 6C10 |
| 6 | 5 | 8 | 5 | 6D8 |
| 6 | 6 | 8 | 5 | 6C4 |
| 6 | 7 | 8 | 5 | 6F5 |
| 6 | 8 | 8 | 5 | 6F3 |

| | | | | |
|---|---|---|---|---|
| 4 | 4 | 8 | 7 | 6M3 |
| 4 | 5 | 8 | 7 | 6M6 |
| 4 | 6 | 8 | 7 | 6M11 |
| 4 | 7 | 8 | 7 | 6Z |
| 4 | 8 | 8 | 7 | 6M9 |
| 5 | 1 | 8 | 7 | 6Z |
| 5 | 2 | 8 | 7 | 6J10 |
| 5 | 3 | 8 | 7 | 6O11 |
| 5 | 4 | 8 | 7 | 6J4 |
| 5 | 5 | 8 | 7 | 6N4 |
| 5 | 6 | 8 | 7 | 6J7 |
| 5 | 7 | 8 | 7 | 6M8 |
| 5 | 8 | 8 | 7 | 6L9 |
| 6 | 1 | 8 | 7 | 6N7 |
| 6 | 2 | 8 | 7 | 6K9 |
| 6 | 3 | 8 | 7 | 6K8 |
| 6 | 4 | 8 | 7 | 6L6 |
| 6 | 5 | 8 | 7 | 6O6 |
| 6 | 6 | 8 | 7 | 6N8 |
| 6 | 7 | 8 | 7 | 6K5 |
| 6 | 8 | 8 | 7 | 6Z |

| | | | | |
|---|---|---|---|---|
| 4 | 4 | 8 | 6 | 6C15 |
| 4 | 5 | 8 | 6 | 6D18 |
| 4 | 6 | 8 | 6 | 6C19 |
| 4 | 7 | 8 | 6 | 6F20 |
| 4 | 8 | 8 | 6 | 6B21 |
| 5 | 1 | 8 | 6 | 6D19* |
| 5 | 2 | 8 | 6 | 6C21 |
| 5 | 3 | 8 | 6 | 6D20 |
| 5 | 4 | 8 | 6 | 6Z |
| 5 | 5 | 8 | 6 | 6B17 |
| 5 | 6 | 8 | 6 | 6F23 |
| 5 | 7 | 8 | 6 | 6D16 |
| 5 | 8 | 8 | 6 | 6Z |
| 6 | 1 | 8 | 6 | 6B20 |
| 6 | 2 | 8 | 6 | 6F22 |
| 6 | 3 | 8 | 6 | 6F19 |
| 6 | 4 | 8 | 6 | 6D15 |
| 6 | 5 | 8 | 6 | 6F15 |
| 6 | 6 | 8 | 6 | 6C18 |
| 6 | 7 | 8 | 6 | 6F17 |
| 6 | 8 | 8 | 6 | 6E21 |

| | | | | |
|---|---|---|---|---|
| 4 | 4 | 1 | 1 | 6K20 |
| 4 | 5 | 1 | 1 | 6N15 |
| 4 | 6 | 1 | 1 | 6K19 |
| 4 | 7 | 1 | 1 | 6L18 |
| 4 | 8 | 1 | 1 | 6M21 |
| 5 | 1 | 1 | 1 | 6L22 |
| 5 | 2 | 1 | 1 | 6L14 |
| 5 | 3 | 1 | 1 | 6M16 |
| 5 | 4 | 1 | 1 | 6O18 |
| 5 | 5 | 1 | 1 | 6K18 |
| 5 | 6 | 1 | 1 | 6O19 |
| 5 | 7 | 1 | 1 | 6K17 |
| 5 | 8 | 1 | 1 | 6L19 |
| 6 | 1 | 1 | 1 | 6N14* |
| 6 | 2 | 1 | 1 | 6K15 |
| 6 | 3 | 1 | 1 | 6O16 |
| 6 | 4 | 1 | 1 | 6Z |
| 6 | 5 | 1 | 1 | 6M14 |
| 6 | 6 | 1 | 1 | 6M21 |
| 6 | 7 | 1 | 1 | 6N19 |
| 6 | 8 | 1 | 1 | 6K22 |

| R1 | R2 | R3 | R4 | Plate | Loc. |
|---|---|---|---|---|---|
| 1 | 3 | 1 | 2 | 7 | C3 |
| 1 | 4 | 1 | 2 | 7 | C6 |
| 1 | 5 | 1 | 2 | 7 | C5 |
| 1 | 6 | 1 | 2 | 7 | C4 |
| 1 | 7 | 1 | 2 | 7 | D8* |
| 1 | 8 | 1 | 2 | 7 | C7 |
| 2 | 1 | 1 | 2 | 7 | B10 |
| 2 | 2 | 1 | 2 | 7 | E3 |
| 2 | 3 | 1 | 2 | 7 | C11 |
| 2 | 4 | 1 | 2 | 7 | D9 |
| 2 | 5 | 1 | 2 | 7 | F4 |
| 2 | 6 | 1 | 2 | 7 | G6 |
| 2 | 7 | 1 | 2 | 7 | E6 |
| 2 | 8 | 1 | 2 | 7 | F8 |
| 3 | 1 | 1 | 2 | 7 | D11 |
| 3 | 2 | 1 | 2 | 7 | B2 |
| 3 | 3 | 1 | 2 | 7 | C8 |
| 3 | 4 | 1 | 2 | 7 | B5 |
| 3 | 5 | 1 | 2 | 7 | B8 |
| 3 | 6 | 1 | 2 | 7 | D5 |
| 3 | 7 | 1 | 2 | 7 | E2 |
| 3 | 8 | 1 | 2 | 7 | D3 |
| 4 | 1 | 1 | 2 | 7 | E5 |
| 4 | 2 | 1 | 2 | 7 | D7 |
| 4 | 3 | 1 | 2 | 7 | E7 |

| R1 | R2 | R3 | R4 | Plate | Loc. |
|---|---|---|---|---|---|
| 1 | 3 | 1 | 4 | 7 | K9 |
| 1 | 4 | 1 | 4 | 7 | N5 |
| 1 | 5 | 1 | 4 | 7 | K4 |
| 1 | 6 | 1 | 4 | 7 | M4 |
| 1 | 7 | 1 | 4 | 7 | L6 |
| 1 | 8 | 1 | 4 | 7 | K6 |
| 2 | 1 | 1 | 4 | 7 | K3 |
| 2 | 2 | 1 | 4 | 7 | O4 |
| 2 | 3 | 1 | 4 | 7 | M10 |
| 2 | 4 | 1 | 4 | 7 | M8 |
| 2 | 5 | 1 | 4 | 7 | O9* |
| 2 | 6 | 1 | 4 | 7 | M3 |
| 2 | 7 | 1 | 4 | 7 | O3 |
| 2 | 8 | 1 | 4 | 7 | O10 |
| 3 | 1 | 1 | 4 | 7 | K11 |
| 3 | 2 | 1 | 4 | 7 | M6 |
| 3 | 3 | 1 | 4 | 7 | Z |
| 3 | 4 | 1 | 4 | 7 | K7 |
| 3 | 5 | 1 | 4 | 7 | L2 |
| 3 | 6 | 1 | 4 | 7 | L3 |
| 3 | 7 | 1 | 4 | 7 | L7* |
| 3 | 8 | 1 | 4 | 7 | L9 |
| 4 | 1 | 1 | 4 | 7 | N7 |
| 4 | 2 | 1 | 4 | 7 | N4 |
| 4 | 3 | 1 | 4 | 7 | K8 |

| R1 | R2 | R3 | R4 | Plate | Loc. |
|---|---|---|---|---|---|
| 1 | 3 | 1 | 3 | 7 | E16 |
| 1 | 4 | 1 | 3 | 7 | D22 |
| 1 | 5 | 1 | 3 | 7 | B21 |
| 1 | 6 | 1 | 3 | 7 | Z |
| 1 | 7 | 1 | 3 | 7 | C16 |
| 1 | 8 | 1 | 3 | 7 | D21 |
| 2 | 1 | 1 | 3 | 7 | F22 |
| 2 | 2 | 1 | 3 | 7 | F16 |
| 2 | 3 | 1 | 3 | 7 | B18 |
| 2 | 4 | 1 | 3 | 7 | D23 |
| 2 | 5 | 1 | 3 | 7 | F21 |
| 2 | 6 | 1 | 3 | 7 | E17 |
| 2 | 7 | 1 | 3 | 7 | D15 |
| 2 | 8 | 1 | 3 | 7 | Z |
| 3 | 1 | 1 | 3 | 7 | D16 |
| 3 | 2 | 1 | 3 | 7 | F14 |
| 3 | 3 | 1 | 3 | 7 | C19 |
| 3 | 4 | 1 | 3 | 7 | C14* |
| 3 | 5 | 1 | 3 | 7 | C22 |
| 3 | 6 | 1 | 3 | 7 | B15 |
| 3 | 7 | 1 | 3 | 7 | E19 |
| 3 | 8 | 1 | 3 | 7 | B19 |
| 4 | 1 | 1 | 3 | 7 | D20 |
| 4 | 2 | 1 | 3 | 7 | F19 |
| 4 | 3 | 1 | 3 | 7 | E20 |

| R1 | R2 | R3 | R4 | Plate | Loc. |
|---|---|---|---|---|---|
| 2 | 8 | 1 | 5 | 7 | N23 |
| 5 | 8 | 1 | 5 | 7 | K15 |
| 6 | 8 | 1 | 5 | 7 | M16 |
| 4 | 8 | 1 | 5 | 7 | O16 |
| 2 | 6 | 1 | 5 | 7 | O18 |
| 3 | 8 | 1 | 5 | 7 | L19* |
| 1 | 8 | 1 | 5 | 7 | M20 |
| 2 | 7 | 1 | 5 | 7 | O17 |
| 2 | 3 | 1 | 5 | 7 | M23 |
| 5 | 6 | 1 | 5 | 7 | N22 |
| 2 | 1 | 1 | 5 | 7 | K14 |
| 2 | 5 | 1 | 5 | 7 | K21 |
| 6 | 6 | 1 | 5 | 7 | M21 |
| 5 | 7 | 1 | 5 | 7 | L16 |
| 5 | 3 | 1 | 5 | 7 | L21 |
| 4 | 6 | 1 | 5 | 7 | N15 |
| 5 | 1 | 1 | 5 | 7 | Z |
| 6 | 7 | 1 | 5 | 7 | Z |
| 5 | 5 | 1 | 5 | 7 | L17 |
| 5 | 3 | 1 | 5 | 7 | L18 |
| 6 | 3 | 1 | 5 | 7 | O21 |
| 2 | 4 | 1 | 5 | 7 | K16 |
| 3 | 6 | 1 | 5 | 7 | M17 |
| 4 | 7 | 1 | 5 | 7 | L20 |
| 1 | 6 | 1 | 5 | 7 | N18 |
| 4 | 3 | 1 | 5 | 7 | N18 |

| | | | | | |
|---|---|---|---|---|---|
| 6 | 1 | 1 | 5 | 7 | K22* |
| 4 | 1 | 1 | 5 | 7 | K20 |
| 6 | 5 | 1 | 5 | 7 | M18 |
| 4 | 5 | 1 | 5 | 7 | N17 |
| 5 | 4 | 1 | 5 | 7 | L15 |
| 3 | 7 | 1 | 5 | 7 | O19 |
| 1 | 7 | 1 | 5 | 7 | Z |
| 3 | 3 | 1 | 5 | 7 | L23 |
| 1 | 3 | 1 | 5 | 7 | M15 |
| 2 | 2 | 1 | 5 | 7 | K18 |
| 3 | 1 | 1 | 5 | 7 | M22 |
| 6 | 4 | 1 | 5 | 7 | N21 |
| 3 | 5 | 1 | 5 | 7 | M19 |
| 1 | 5 | 1 | 5 | 7 | O22 |
| 4 | 4 | 1 | 5 | 7 | K19 |
| 5 | 2 | 1 | 5 | 7 | K23 |
| 3 | 4 | 1 | 5 | 7 | N19 |
| 1 | 4 | 1 | 5 | 7 | Z |
| 6 | 2 | 1 | 5 | 7 | N20 |
| 4 | 2 | 1 | 5 | 7 | L22 |
| 3 | 2 | 1 | 5 | 7 | O23 |

| | | | | | |
|---|---|---|---|---|---|
| 4 | 4 | 1 | 3 | 7 | E22 |
| 4 | 5 | 1 | 3 | 7 | C17 |
| 4 | 6 | 1 | 3 | 7 | D17 |
| 4 | 7 | 1 | 3 | 7 | B17 |
| 4 | 8 | 1 | 3 | 7 | C18 |
| 5 | 1 | 1 | 3 | 7 | Z |
| 5 | 2 | 1 | 3 | 7 | C15 |
| 5 | 3 | 1 | 3 | 7 | D19 |
| 5 | 4 | 1 | 3 | 7 | F15 |
| 5 | 5 | 1 | 3 | 7 | B20 |
| 5 | 6 | 1 | 3 | 7 | F23 |
| 5 | 7 | 1 | 3 | 7 | E21 |
| 5 | 8 | 1 | 3 | 7 | C23 |
| 6 | 1 | 1 | 3 | 7 | F17 |
| 6 | 2 | 1 | 3 | 7 | C21 |
| 6 | 3 | 1 | 3 | 7 | F18 |
| 6 | 4 | 1 | 3 | 7 | F20 |
| 6 | 5 | 1 | 3 | 7 | B16* |
| 6 | 6 | 1 | 3 | 7 | E23 |
| 6 | 7 | 1 | 3 | 7 | E18 |
| 6 | 8 | 1 | 3 | 7 | E15 |

| | | | | | |
|---|---|---|---|---|---|
| 4 | 4 | 1 | 4 | 7 | M9 |
| 4 | 5 | 1 | 4 | 7 | O5 |
| 4 | 6 | 1 | 4 | 7 | L10 |
| 4 | 7 | 1 | 4 | 7 | K10 |
| 4 | 8 | 1 | 4 | 7 | K5 |
| 5 | 1 | 1 | 4 | 7 | N8 |
| 5 | 2 | 1 | 4 | 7 | M2 |
| 5 | 3 | 1 | 4 | 7 | K2... |
| 5 | 4 | 1 | 4 | 7 | Z |
| 5 | 5 | 1 | 4 | 7 | N11 |
| 5 | 6 | 1 | 4 | 7 | M7 |
| 5 | 7 | 1 | 4 | 7 | L11 |
| 5 | 8 | 1 | 4 | 7 | N2 |
| 6 | 1 | 1 | 4 | 7 | N9 |
| 6 | 2 | 1 | 4 | 7 | L4 |
| 6 | 3 | 1 | 4 | 7 | N3 |
| 6 | 4 | 1 | 4 | 7 | L8 |
| 6 | 5 | 1 | 4 | 7 | J2 |
| 6 | 6 | 1 | 4 | 7 | O11 |
| 6 | 7 | 1 | 4 | 7 | M5 |
| 6 | 8 | 1 | 4 | 7 | Z |

| | | | | | |
|---|---|---|---|---|---|
| 4 | 4 | 1 | 2 | 7 | E9 |
| 4 | 5 | 1 | 2 | 7 | F3 |
| 4 | 6 | 1 | 2 | 7 | E4 |
| 4 | 7 | 1 | 2 | 7 | D6 |
| 4 | 8 | 1 | 2 | 7 | E11 |
| 5 | 1 | 1 | 2 | 7 | B4* |
| 5 | 2 | 1 | 2 | 7 | D4 |
| 5 | 3 | 1 | 2 | 7 | C10 |
| 5 | 4 | 1 | 2 | 7 | F2 |
| 5 | 5 | 1 | 2 | 7 | F11 |
| 5 | 6 | 1 | 2 | 7 | E10 |
| 5 | 7 | 1 | 2 | 7 | F10 |
| 5 | 8 | 1 | 2 | 7 | B7 |
| 6 | 1 | 1 | 2 | 7 | B9 |
| 6 | 2 | 1 | 2 | 7 | C2 |
| 6 | 3 | 1 | 2 | 7 | E8 |
| 6 | 4 | 1 | 2 | 7 | B6 |
| 6 | 5 | 1 | 2 | 7 | B3 |
| 6 | 6 | 1 | 2 | 7 | F7 |
| 6 | 7 | 1 | 2 | 7 | C9 |
| 6 | 8 | 1 | 2 | 7 | B11 |

| R1 | R2 | R3 | R4 | Plate | Loc. |
|---|---|---|---|---|---|
| 1 | 3 | 1 | 6 | 8 | C10 |
| 1 | 4 | 1 | 6 | 8 | C4 |
| 1 | 5 | 1 | 6 | 8 | C3 |
| 1 | 6 | 1 | 6 | 8 | Z |
| 1 | 7 | 1 | 6 | 8 | E4 |
| 1 | 8 | 1 | 6 | 8 | Z |
| 2 | 1 | 1 | 6 | 8 | E8 |
| 2 | 2 | 1 | 6 | 8 | B4 |
| 2 | 3 | 1 | 6 | 8 | F8 |
| 2 | 4 | 1 | 6 | 8 | C11 |
| 2 | 5 | 1 | 6 | 8 | F4 |
| 2 | 6 | 1 | 6 | 8 | D8 |
| 2 | 7 | 1 | 6 | 8 | B6 |
| 2 | 8 | 1 | 6 | 8 | B7 |
| 3 | 1 | 1 | 6 | 8 | C9* |
| 3 | 2 | 1 | 6 | 8 | E7 |
| 3 | 3 | 1 | 6 | 8 | B5 |
| 3 | 4 | 1 | 6 | 8 | B11 |
| 3 | 5 | 1 | 6 | 8 | D6 |
| 3 | 6 | 1 | 6 | 8 | D7 |
| 3 | 7 | 1 | 6 | 8 | D5 |
| 3 | 8 | 1 | 6 | 8 | F5 |
| 4 | 1 | 1 | 6 | 8 | F2 |
| 4 | 2 | 1 | 6 | 8 | D3 |
| 4 | 3 | 1 | 6 | 8 | D11 |

| R1 | R2 | R3 | R4 | Plate | Loc. |
|---|---|---|---|---|---|
| 1 | 3 | 4 | 1 | 8 | N9 |
| 1 | 4 | 4 | 1 | 8 | L11 |
| 1 | 5 | 4 | 1 | 8 | K3 |
| 1 | 6 | 4 | 1 | 8 | Z |
| 1 | 7 | 4 | 1 | 8 | N3 |
| 1 | 8 | 4 | 1 | 8 | M11 |
| 2 | 1 | 4 | 1 | 8 | O2 |
| 2 | 2 | 4 | 1 | 8 | L2 |
| 2 | 3 | 4 | 1 | 8 | L10 |
| 2 | 4 | 4 | 1 | 8 | L6 |
| 2 | 5 | 4 | 1 | 8 | M7 |
| 2 | 6 | 4 | 1 | 8 | M9* |
| 2 | 7 | 4 | 1 | 8 | Z |
| 2 | 8 | 4 | 1 | 8 | M5 |
| 3 | 1 | 4 | 1 | 8 | N10 |
| 3 | 2 | 4 | 1 | 8 | Z |
| 3 | 3 | 4 | 1 | 8 | N7 |
| 3 | 4 | 4 | 1 | 8 | L9 |
| 3 | 5 | 4 | 1 | 8 | Z |
| 3 | 6 | 4 | 1 | 8 | M2 |
| 3 | 7 | 4 | 1 | 8 | K11* |
| 3 | 8 | 4 | 1 | 8 | M4 |
| 4 | 1 | 4 | 1 | 8 | M3 |
| 4 | 2 | 4 | 1 | 8 | K2 |
| 4 | 3 | 4 | 1 | 8 | |

| R1 | R2 | R3 | R4 | Plate | Loc. |
|---|---|---|---|---|---|
| 1 | 3 | 1 | 7 | 8 | B22 |
| 1 | 4 | 1 | 7 | 8 | D15* |
| 1 | 5 | 1 | 7 | 8 | G14 |
| 1 | 6 | 1 | 7 | 8 | Z |
| 1 | 7 | 1 | 7 | 8 | E14 |
| 1 | 8 | 1 | 7 | 8 | Z |
| 2 | 1 | 1 | 7 | 8 | F22 |
| 2 | 2 | 1 | 7 | 8 | Z |
| 2 | 3 | 1 | 7 | 8 | C16 |
| 2 | 4 | 1 | 7 | 8 | E16 |
| 2 | 5 | 1 | 7 | 8 | D14 |
| 2 | 6 | 1 | 7 | 8 | D21 |
| 2 | 7 | 1 | 7 | 8 | B16 |
| 2 | 8 | 1 | 7 | 8 | D16 |
| 3 | 1 | 1 | 7 | 8 | C18 |
| 3 | 2 | 1 | 7 | 8 | E23 |
| 3 | 3 | 1 | 7 | 8 | B14 |
| 3 | 4 | 1 | 7 | 8 | B15 |
| 3 | 5 | 1 | 7 | 8 | F17 |
| 3 | 6 | 1 | 7 | 8 | D18 |
| 3 | 7 | 1 | 7 | 8 | C17 |
| 3 | 8 | 1 | 7 | 8 | E21 |
| 4 | 1 | 1 | 7 | 8 | C19 |
| 4 | 2 | 1 | 7 | 8 | B21 |
| 4 | 3 | 1 | 7 | 8 | E15 |

| R1 | R2 | R3 | R4 | Plate | Loc. |
|---|---|---|---|---|---|
| 1 | 3 | 4 | 2 | 8 | M16 |
| 1 | 4 | 4 | 2 | 8 | Z |
| 1 | 5 | 4 | 2 | 8 | K16 |
| 1 | 6 | 4 | 2 | 8 | O18 |
| 1 | 7 | 4 | 2 | 8 | M21 |
| 1 | 8 | 4 | 2 | 8 | L18 |
| 2 | 1 | 4 | 2 | 8 | K15 |
| 2 | 2 | 4 | 2 | 8 | Z |
| 2 | 3 | 4 | 2 | 8 | N19 |
| 2 | 4 | 4 | 2 | 8 | M14 |
| 2 | 5 | 4 | 2 | 8 | Z |
| 2 | 6 | 4 | 2 | 8 | L19 |
| 2 | 7 | 4 | 2 | 8 | M22* |
| 2 | 8 | 4 | 2 | 8 | O15 |
| 3 | 1 | 4 | 2 | 8 | O21 |
| 3 | 2 | 4 | 2 | 8 | L16 |
| 3 | 3 | 4 | 2 | 8 | L20 |
| 3 | 4 | 4 | 2 | 8 | K18 |
| 3 | 5 | 4 | 2 | 8 | M18 |
| 3 | 6 | 4 | 2 | 8 | L15 |
| 3 | 7 | 4 | 2 | 8 | O17 |
| 3 | 8 | 4 | 2 | 8 | N17 |
| 4 | 1 | 4 | 2 | 8 | N18 |
| 4 | 2 | 4 | 2 | 8 | N16 |
| 4 | 3 | 4 | 2 | 8 | M20 |

| R1 | R2 | R3 | R4 | Plate | Loc. |
|----|----|----|----|-------|------|
| 1 | 3 | 4 | 3 | 9 | D05 |
| 1 | 4 | 4 | 3 | 9 | B08 |
| 1 | 5 | 4 | 3 | 9 | D02 |
| 1 | 6 | 4 | 3 | 9 | F07 |
| 1 | 7 | 4 | 3 | 9 | D10 |
| 1 | 8 | 4 | 3 | 9 | B06 |
| 2 | 1 | 4 | 3 | 9 | F04 |
| 2 | 2 | 4 | 3 | 9 | F06 |
| 2 | 3 | 4 | 3 | 9 | B11 |
| 2 | 4 | 4 | 3 | 9 | E07 |
| 2 | 5 | 4 | 3 | 9 | C02 |
| 2 | 6 | 4 | 3 | 9 | F03 |
| 2 | 7 | 4 | 3 | 9 | D03 |
| 2 | 8 | 4 | 3 | 9 | C07 |
| 3 | 1 | 4 | 3 | 9 | D08 |
| 3 | 2 | 4 | 3 | 9 | D06 |
| 3 | 3 | 4 | 3 | 9 | F09 |
| 3 | 4 | 4 | 3 | 9 | F08 |
| 3 | 5 | 4 | 3 | 9 | E10 |
| 3 | 6 | 4 | 3 | 9 | E06 |
| 3 | 7 | 4 | 3 | 9 | D07 |
| 3 | 8 | 4 | 3 | 9 | D11 |
| 4 | 1 | 4 | 3 | 9 | B02 |
| 4 | 2 | 4 | 3 | 9 | B07 |
| 4 | 3 | 4 | 3 | 9 | D04 |

| R1 | R2 | R3 | R4 | Plate | Loc. |
|----|----|----|----|-------|------|
| 1 | 3 | 4 | 5 | 9 | O07 |
| 1 | 4 | 4 | 5 | 9 | O03 |
| 1 | 5 | 4 | 5 | 9 | M06* |
| 1 | 6 | 4 | 5 | 9 | N11 |
| 1 | 7 | 4 | 5 | 9 | N03 |
| 1 | 8 | 4 | 5 | 9 | Z |
| 2 | 1 | 4 | 5 | 9 | K11 |
| 2 | 2 | 4 | 5 | 9 | L06 |
| 2 | 3 | 4 | 5 | 9 | L11 |
| 2 | 4 | 4 | 5 | 9 | N09 |
| 2 | 5 | 4 | 5 | 9 | O02 |
| 2 | 6 | 4 | 5 | 9 | M09 |
| 2 | 7 | 4 | 5 | 9 | O10 |
| 2 | 8 | 4 | 5 | 9 | K08 |
| 3 | 1 | 4 | 5 | 9 | N04 |
| 3 | 2 | 4 | 5 | 9 | K10 |
| 3 | 3 | 4 | 5 | 9 | O06 |
| 3 | 4 | 4 | 5 | 9 | K06 |
| 3 | 5 | 4 | 5 | 9 | L10 |
| 3 | 6 | 4 | 5 | 9 | L09 |
| 3 | 7 | 4 | 5 | 9 | N02 |
| 3 | 8 | 4 | 5 | 9 | J02 |
| 4 | 1 | 4 | 5 | 9 | K03 |
| 4 | 2 | 4 | 5 | 9 | M05 |
| 4 | 3 | 4 | 5 | 9 | O09 |

| R1 | R2 | R3 | R4 | Plate | Loc. |
|----|----|----|----|-------|------|
| 1 | 3 | 4 | 4 | 9 | E15 |
| 1 | 4 | 4 | 4 | 9 | B17 |
| 1 | 5 | 4 | 4 | 9 | B21 |
| 1 | 6 | 4 | 4 | 9 | Z |
| 1 | 7 | 4 | 4 | 9 | C14 |
| 1 | 8 | 4 | 4 | 9 | F17 |
| 2 | 1 | 4 | 4 | 9 | F21 |
| 2 | 2 | 4 | 4 | 9 | D19 |
| 2 | 3 | 4 | 4 | 9 | F19 |
| 2 | 4 | 4 | 4 | 9 | D15 |
| 2 | 5 | 4 | 4 | 9 | C16 |
| 2 | 6 | 4 | 4 | 9 | F18* |
| 2 | 7 | 4 | 4 | 9 | B15 |
| 2 | 8 | 4 | 4 | 9 | C21 |
| 3 | 1 | 4 | 4 | 9 | C20 |
| 3 | 2 | 4 | 4 | 9 | D21 |
| 3 | 3 | 4 | 4 | 9 | E19 |
| 3 | 4 | 4 | 4 | 9 | B14 |
| 3 | 5 | 4 | 4 | 9 | F23 |
| 3 | 6 | 4 | 4 | 9 | B19 |
| 3 | 7 | 4 | 4 | 9 | E18 |
| 3 | 8 | 4 | 4 | 9 | E21 |
| 4 | 1 | 4 | 4 | 9 | B23 |
| 4 | 2 | 4 | 4 | 9 | B18 |
| 4 | 3 | 4 | 4 | 9 | E14 |

FIG. 13B

| R1 | R2 | R3 | R4 | Plate | Loc. |
|----|----|----|----|-------|------|
| 1 | 3 | 4 | 6 | 9 | Z |
| 1 | 4 | 4 | 6 | 9 | M16 |
| 1 | 5 | 4 | 6 | 9 | Z |
| 1 | 6 | 4 | 6 | 9 | Z |
| 1 | 7 | 4 | 6 | 9 | N17 |
| 1 | 8 | 4 | 6 | 9 | N18 |
| 2 | 1 | 4 | 6 | 9 | N14* |
| 2 | 2 | 4 | 6 | 9 | O15 |
| 2 | 3 | 4 | 6 | 9 | K14 |
| 2 | 4 | 4 | 6 | 9 | L22 |
| 2 | 5 | 4 | 6 | 9 | N22 |
| 2 | 6 | 4 | 6 | 9 | N23 |
| 2 | 7 | 4 | 6 | 9 | J20 |
| 2 | 8 | 4 | 6 | 9 | M23 |
| 3 | 1 | 4 | 6 | 9 | O17 |
| 3 | 2 | 4 | 6 | 9 | L18 |
| 3 | 3 | 4 | 6 | 9 | K18 |
| 3 | 4 | 4 | 6 | 9 | L21* |
| 3 | 5 | 4 | 6 | 9 | L19 |
| 3 | 6 | 4 | 6 | 9 | O21 |
| 3 | 7 | 4 | 6 | 9 | M21 |
| 3 | 8 | 4 | 6 | 9 | O18 |
| 4 | 1 | 4 | 6 | 9 | M17 |
| 4 | 2 | 4 | 6 | 9 | K16 |

| R1 | R2 | R3 | R4 | Plate | Loc. |
|----|----|----|----|-------|------|
| 1 | 3 | 4 | 7 | 10 | Z |
| 1 | 4 | 4 | 7 | 10 | B02 |
| 1 | 5 | 4 | 7 | 10 | D09* |
| 1 | 6 | 4 | 7 | 10 | D07 |
| 1 | 7 | 4 | 7 | 10 | Z |
| 1 | 8 | 4 | 7 | 10 | D10 |
| 2 | 1 | 4 | 7 | 10 | B07 |
| 2 | 2 | 4 | 7 | 10 | Z |
| 2 | 3 | 4 | 7 | 10 | B08 |
| 2 | 4 | 4 | 7 | 10 | E07 |
| 2 | 5 | 4 | 7 | 10 | B03 |
| 2 | 6 | 4 | 7 | 10 | F05 |
| 2 | 7 | 4 | 7 | 10 | C05 |
| 2 | 8 | 4 | 7 | 10 | E06 |
| 3 | 1 | 4 | 7 | 10 | E05 |
| 3 | 2 | 4 | 7 | 10 | F10 |
| 3 | 3 | 4 | 7 | 10 | Z |
| 3 | 4 | 4 | 7 | 10 | D02 |
| 3 | 5 | 4 | 7 | 10 | F07 |
| 3 | 6 | 4 | 7 | 10 | C02 |
| 3 | 7 | 4 | 7 | 10 | C04* |
| 3 | 8 | 4 | 7 | 10 | E04 |
| 4 | 1 | 4 | 7 | 10 | C03 |
| 4 | 2 | 4 | 7 | 10 | D03 |

FIG. 13C

| 4 | 3 | 4 | 4 | 9 | M18 |
|---|---|---|---|---|---|
| 4 | 4 | 4 | 6 | 9 | M22 |
| 4 | 5 | 4 | 6 | 9 | K15 |
| 4 | 6 | 4 | 6 | 9 | M14 |
| 4 | 7 | 4 | 6 | 9 | L20 |
| 4 | 8 | 4 | 6 | 9 | O16 |
| 5 | 1 | 4 | 6 | 9 | L16 |
| 5 | 2 | 4 | 6 | 9 | N20 |
| 5 | 3 | 4 | 6 | 9 | L23 |
| 5 | 4 | 4 | 6 | 9 | L14 |
| 5 | 5 | 4 | 6 | 9 | K22 |
| 5 | 6 | 4 | 6 | 9 | K17 |
| 5 | 7 | 4 | 6 | 9 | O14 |
| 5 | 8 | 4 | 6 | 9 | K17 |
| 6 | 1 | 4 | 6 | 9 | M19 |
| 6 | 2 | 4 | 6 | 9 | N19 |
| 6 | 3 | 4 | 6 | 9 | M20 |
| 6 | 4 | 4 | 6 | 9 | K21 |
| 6 | 5 | 4 | 6 | 9 | Z |
| 6 | 6 | 4 | 6 | 9 | M15 |
| 6 | 7 | 4 | 6 | 9 | K19 |
| 6 | 8 | 4 | 6 | 9 | Z |

| 4 | 3 | 4 | 7 | 10 | B09 |
|---|---|---|---|----|-----|
| 4 | 4 | 4 | 7 | 10 | B06 |
| 4 | 5 | 4 | 7 | 10 | D06 |
| 4 | 6 | 4 | 7 | 10 | B05 |
| 4 | 7 | 4 | 7 | 10 | E03 |
| 4 | 8 | 4 | 7 | 10 | C11 |
| 5 | 1 | 4 | 7 | 10 | F02 |
| 5 | 2 | 4 | 7 | 10 | D11 |
| 5 | 3 | 4 | 7 | 10 | F04 |
| 5 | 4 | 4 | 7 | 10 | B04 |
| 5 | 5 | 4 | 7 | 10 | E09 |
| 5 | 6 | 4 | 7 | 10 | C10 |
| 5 | 7 | 4 | 7 | 10 | C08 |
| 5 | 8 | 4 | 7 | 10 | C09 |
| 6 | 1 | 4 | 7 | 10 | D08 |
| 6 | 2 | 4 | 7 | 10 | F03 |
| 6 | 3 | 4 | 7 | 10 | Z |
| 6 | 4 | 4 | 7 | 10 | D05 |
| 6 | 5 | 4 | 7 | 10 | Z |
| 6 | 6 | 4 | 7 | 10 | F06 |
| 6 | 7 | 4 | 7 | 10 | Z |
| 6 | 8 | 4 | 7 | 10 | E08 |

FIG. 13D

| R1 | R2 | R3 | R4 | Plate | Loc. |
|---|---|---|---|---|---|
| 1 | 3 | 2 | 1 | 11 | L6 |
| 1 | 4 | 2 | 1 | 11 | L10 |
| 1 | 5 | 2 | 1 | 11 | L3 |
| 1 | 6 | 2 | 1 | 11 | N4 |
| 1 | 7 | 2 | 1 | 11 | O8 |
| 1 | 8 | 2 | 1 | 11 | L4 |
| 2 | 1 | 2 | 1 | 11 | M3 |
| 2 | 2 | 2 | 1 | 11 | K7 |
| 2 | 3 | 2 | 1 | 11 | M2 |
| 2 | 4 | 2 | 1 | 11 | Z |
| 2 | 5 | 2 | 1 | 11 | K9 |
| 2 | 6 | 2 | 1 | 11 | L7 |
| 2 | 7 | 2 | 1 | 11 | N11 |
| 2 | 8 | 2 | 1 | 11 | O3 |
| 3 | 1 | 2 | 1 | 11 | O7 |
| 3 | 2 | 2 | 1 | 11 | O6 |
| 3 | 3 | 2 | 1 | 11 | M4 |
| 3 | 4 | 2 | 1 | 11 | N6 |
| 3 | 5 | 2 | 1 | 11 | Z |
| 3 | 6 | 2 | 1 | 11 | K4 |
| 3 | 7 | 2 | 1 | 11 | N9 |
| 3 | 8 | 2 | 1 | 11 | K10 |
| 4 | 1 | 2 | 1 | 11 | M5 |
| 4 | 2 | 2 | 1 | 11 | M9 |
| 4 | 3 | 2 | 1 | 11 | L2 |

| R1 | R2 | R3 | R4 | Plate | Loc. |
|---|---|---|---|---|---|
| 1 | 3 | 2 | 2 | 11 | O18 |
| 1 | 4 | 2 | 2 | 11 | K22 |
| 1 | 5 | 2 | 2 | 11 | N16 |
| 1 | 6 | 2 | 2 | 11 | N20 |
| 1 | 7 | 2 | 2 | 11 | L23 |
| 1 | 8 | 2 | 2 | 11 | K17 |
| 2 | 1 | 2 | 2 | 11 | N14 |
| 2 | 2 | 2 | 2 | 11 | K18 |
| 2 | 3 | 2 | 2 | 11 | L21 |
| 2 | 4 | 2 | 2 | 11 | O15 |
| 2 | 5 | 2 | 2 | 11 | M15 |
| 2 | 6 | 2 | 2 | 11 | M21 |
| 2 | 7 | 2 | 2 | 11 | M19 |
| 2 | 8 | 2 | 2 | 11 | Z |
| 3 | 1 | 2 | 2 | 11 | L22 |
| 3 | 2 | 2 | 2 | 11 | N21 |
| 3 | 3 | 2 | 2 | 11 | N22 |
| 3 | 4 | 2 | 2 | 11 | N17 |
| 3 | 5 | 2 | 2 | 11 | O14 |
| 3 | 6 | 2 | 2 | 11 | N15 |
| 3 | 7 | 2 | 2 | 11 | N19 |
| 3 | 8 | 2 | 2 | 11 | L16 |
| 4 | 1 | 2 | 2 | 11 | N23 |
| 4 | 2 | 2 | 2 | 11 | M22 |
| 4 | 3 | 2 | 2 | 11 | L18 |

FIG. 14A

| | | | |
|---|---|---|---|
| Z | 11 | 1 | 2 | 4 | 4 |
| O9 | 11 | 1 | 2 | 5 | 4 |
| L5 | 11 | 1 | 2 | 6 | 4 |
| K6 | 11 | 1 | 2 | 7 | 4 |
| M8 | 11 | 1 | 2 | 8 | 4 |
| K5 | 11 | 1 | 2 | 1 | 5 |
| M11 | 11 | 1 | 2 | 2 | 5 |
| K8 | 11 | 1 | 2 | 3 | 5 |
| M6 | 11 | 1 | 2 | 4 | 5 |
| Z | 11 | 1 | 2 | 5 | 5 |
| L11 | 11 | 1 | 2 | 6 | 5 |
| N7 | 11 | 1 | 2 | 7 | 5 |
| L8 | 11 | 1 | 2 | 8 | 5 |
| O5 | 11 | 1 | 2 | 1 | 6 |
| M7 | 11 | 1 | 2 | 2 | 6 |
| N3 | 11 | 1 | 2 | 3 | 6 |
| K2 | 11 | 1 | 2 | 4 | 6 |
| K11 | 11 | 1 | 2 | 5 | 6 |
| N5 | 11 | 1 | 2 | 6 | 6 |
| N8 | 11 | 1 | 2 | 7 | 6 |
| L9 | 11 | 1 | 2 | 8 | 6 |

| | | | |
|---|---|---|---|
| L14 | 11 | 2 | 2 | 4 | 4 |
| O16 | 11 | 2 | 2 | 5 | 4 |
| Z | 11 | 2 | 2 | 6 | 4 |
| K15 | 11 | 2 | 2 | 7 | 4 |
| K16 | 11 | 2 | 2 | 8 | 4 |
| K23 | 11 | 2 | 2 | 1 | 5 |
| L20 | 11 | 2 | 2 | 2 | 5 |
| L17 | 11 | 2 | 2 | 3 | 5 |
| M18 | 11 | 2 | 2 | 4 | 5 |
| K20 | 11 | 2 | 2 | 5 | 5 |
| N18 | 11 | 2 | 2 | 6 | 5 |
| K14 | 11 | 2 | 2 | 7 | 5 |
| M16 | 11 | 2 | 2 | 8 | 5 |
| Z | 11 | 2 | 2 | 1 | 6 |
| M14 | 11 | 2 | 2 | 2 | 6 |
| M17 | 11 | 2 | 2 | 3 | 6 |
| M20 | 11 | 2 | 2 | 4 | 6 |
| K21 | 11 | 2 | 2 | 5 | 6 |
| K19 | 11 | 2 | 2 | 6 | 6 |
| L19 | 11 | 2 | 2 | 7 | 6 |
| M23 | 11 | 2 | 2 | 8 | 6 |

FIG. 14B

| R1 | R2 | R3 | R4 | Plate | Loc. | R1 | R2 | R3 | R4 | Plate | Loc. | R1 | R2 | R3 | R4 | Plate | Loc. | R1 | R2 | R3 | R4 | Plate | Loc. |
|---|---|---|---|---|---|---|---|---|---|---|---|---|---|---|---|---|---|---|---|---|---|---|---|
| 1 | 3 | 2 | 3 | 12 | B9 | 1 | 3 | 2 | 5 | 12 | K6 | 1 | 3 | 2 | 4 | 12 | D18 | 1 | 3 | 2 | 6 | 12 | N16 |
| 1 | 4 | 2 | 3 | 12 | D2 | 1 | 4 | 2 | 5 | 12 | L11 | 1 | 4 | 2 | 4 | 12 | Z | 1 | 4 | 2 | 6 | 12 | Z |
| 1 | 5 | 2 | 3 | 12 | F3 | 1 | 5 | 2 | 5 | 12 | Z | 1 | 5 | 2 | 4 | 12 | E23 | 1 | 5 | 2 | 6 | 12 | N14 |
| 1 | 6 | 2 | 3 | 12 | D10 | 1 | 6 | 2 | 5 | 12 | K11 | 1 | 6 | 2 | 4 | 12 | D22 | 1 | 6 | 2 | 6 | 12 | L14 |
| 1 | 7 | 2 | 3 | 12 | Z | 1 | 7 | 2 | 5 | 12 | M5 | 1 | 7 | 2 | 4 | 12 | Z | 1 | 7 | 2 | 6 | 12 | L22 |
| 1 | 8 | 2 | 3 | 12 | B5 | 1 | 8 | 2 | 5 | 12 | K10 | 1 | 8 | 2 | 4 | 12 | E20 | 1 | 8 | 2 | 6 | 12 | N21 |
| 2 | 1 | 2 | 3 | 12 | Z | 2 | 1 | 2 | 5 | 12 | L5 | 2 | 1 | 2 | 4 | 12 | E21 | 2 | 1 | 2 | 6 | 12 | L16 |
| 2 | 2 | 2 | 3 | 12 | B8 | 2 | 2 | 2 | 5 | 12 | L2 | 2 | 2 | 2 | 4 | 12 | Z | 2 | 2 | 2 | 6 | 12 | L15 |
| 2 | 3 | 2 | 3 | 12 | Z | 2 | 3 | 2 | 5 | 12 | Z | 2 | 3 | 2 | 4 | 12 | Z | 2 | 3 | 2 | 6 | 12 | M15* |
| 2 | 4 | 2 | 3 | 12 | Z | 2 | 4 | 2 | 5 | 12 | N6 | 2 | 4 | 2 | 4 | 12 | B20 | 2 | 4 | 2 | 6 | 12 | O17 |
| 2 | 5 | 2 | 3 | 12 | F7 | 2 | 5 | 2 | 5 | 12 | M6 | 2 | 5 | 2 | 4 | 12 | E19 | 2 | 5 | 2 | 6 | 12 | K18 |
| 2 | 6 | 2 | 3 | 12 | Z | 2 | 6 | 2 | 5 | 12 | Z | 2 | 6 | 2 | 4 | 12 | Z | 2 | 6 | 2 | 6 | 12 | N19 |
| 2 | 7 | 2 | 3 | 12 | Z | 2 | 7 | 2 | 5 | 12 | N2 | 2 | 7 | 2 | 4 | 12 | B23 | 2 | 7 | 2 | 6 | 12 | K17 |
| 2 | 8 | 2 | 3 | 12 | C10 | 2 | 8 | 2 | 5 | 12 | K9 | 2 | 8 | 2 | 4 | 12 | Z | 2 | 8 | 2 | 6 | 12 | L18 |
| 3 | 1 | 2 | 3 | 12 | Z | 3 | 1 | 2 | 5 | 12 | M4 | 3 | 1 | 2 | 4 | 12 | C22 | 3 | 1 | 2 | 6 | 12 | M21 |
| 3 | 2 | 2 | 3 | 12 | Z | 3 | 2 | 2 | 5 | 12 | L9 | 3 | 2 | 2 | 4 | 12 | Z | 3 | 2 | 2 | 6 | 12 | Z |
| 3 | 3 | 2 | 3 | 12 | Z | 3 | 3 | 2 | 5 | 12 | K2 | 3 | 3 | 2 | 4 | 12 | Z | 3 | 3 | 2 | 6 | 12 | N20 |
| 3 | 4 | 2 | 3 | 12 | Z | 3 | 4 | 2 | 5 | 12 | Z | 3 | 4 | 2 | 4 | 12 | Z | 3 | 4 | 2 | 6 | 12 | Z |
| 3 | 5 | 2 | 3 | 12 | Z | 3 | 5 | 2 | 5 | 12 | O7 | 3 | 5 | 2 | 4 | 12 | C16 | 3 | 5 | 2 | 6 | 12 | O21 |
| 3 | 6 | 2 | 3 | 12 | Z | 3 | 6 | 2 | 5 | 12 | N10 | 3 | 6 | 2 | 4 | 12 | Z | 3 | 6 | 2 | 6 | 12 | Z |
| 3 | 7 | 2 | 3 | 12 | Z | 3 | 7 | 2 | 5 | 12 | M3* | 3 | 7 | 2 | 4 | 12 | Z | 3 | 7 | 2 | 6 | 12 | K16 |
| 3 | 8 | 2 | 3 | 12 | C2 | 3 | 8 | 2 | 5 | 12 | M11 | 3 | 8 | 2 | 4 | 12 | Z | 3 | 8 | 2 | 6 | 12 | M20 |
| 4 | 1 | 2 | 3 | 12 | Z | 4 | 1 | 2 | 5 | 12 | L3 | 4 | 1 | 2 | 4 | 12 | C21 | 4 | 1 | 2 | 6 | 12 | M23 |
| 4 | 2 | 2 | 3 | 12 | Z | 4 | 2 | 2 | 5 | 12 | L7 | 4 | 2 | 2 | 4 | 12 | Z | 4 | 2 | 2 | 6 | 12 | K20 |
| 4 | 3 | 2 | 3 | 12 | Z | 4 | 3 | 2 | 5 | 12 | M8 | 4 | 3 | 2 | 4 | 12 | Z | 4 | 3 | 2 | 6 | 12 | L17 |

| R1 | R2 | R3 | R4 | Plate | Loc. | R1 | R2 | R3 | R4 | Plate | Loc. | R1 | R2 | R3 | R4 | Plate | Loc. | R1 | R2 | R3 | R4 | Plate | Loc. |
|---|---|---|---|---|---|---|---|---|---|---|---|---|---|---|---|---|---|---|---|---|---|---|---|
| 1 | 3 | 2 | 7 | 13 | C11 | 1 | 3 | 3 | 2 | 13 | M06 | 1 | 3 | 3 | 1 | 13 | E14 | 1 | 3 | 3 | 3 | 13 | Z |
| 1 | 4 | 2 | 7 | 13 | B05 | 1 | 4 | 3 | 2 | 13 | N03 | 1 | 4 | 3 | 1 | 13 | D23 | 1 | 4 | 3 | 3 | 13 | Z |
| 1 | 5 | 2 | 7 | 13 | B06 | 1 | 5 | 3 | 2 | 13 | Z | 1 | 5 | 3 | 1 | 13 | B21 | 1 | 5 | 3 | 3 | 13 | Z |
| 1 | 6 | 2 | 7 | 13 | B09* | 1 | 6 | 3 | 2 | 13 | Z | 1 | 6 | 3 | 1 | 13 | F18 | 1 | 6 | 3 | 3 | 13 | Z |
| 1 | 7 | 2 | 7 | 13 | Z | 1 | 7 | 3 | 2 | 13 | L03 | 1 | 7 | 3 | 1 | 13 | E15 | 1 | 7 | 3 | 3 | 13 | Z |
| 1 | 8 | 2 | 7 | 13 | F04 | 1 | 8 | 3 | 2 | 13 | L11 | 1 | 8 | 3 | 1 | 13 | D19 | 1 | 8 | 3 | 3 | 13 | Z |
| 2 | 1 | 2 | 7 | 13 | E07 | 2 | 1 | 3 | 2 | 13 | K02 | 2 | 1 | 3 | 1 | 13 | B18* | 2 | 1 | 3 | 3 | 13 | K21 |
| 2 | 2 | 2 | 7 | 13 | C07 | 2 | 2 | 3 | 2 | 13 | O03 | 2 | 2 | 3 | 1 | 13 | F14 | 2 | 2 | 3 | 3 | 13 | Z |
| 2 | 3 | 2 | 7 | 13 | C04 | 2 | 3 | 3 | 2 | 13 | N02* | 2 | 3 | 3 | 1 | 13 | D21 | 2 | 3 | 3 | 3 | 13 | Z |
| 2 | 4 | 2 | 7 | 13 | F05 | 2 | 4 | 3 | 2 | 13 | O05 | 2 | 4 | 3 | 1 | 13 | B17 | 2 | 4 | 3 | 3 | 13 | Z |
| 2 | 5 | 2 | 7 | 13 | E05 | 2 | 5 | 3 | 2 | 13 | N05 | 2 | 5 | 3 | 1 | 13 | D15 | 2 | 5 | 3 | 3 | 13 | Z |
| 2 | 6 | 2 | 7 | 13 | B10 | 2 | 6 | 3 | 2 | 13 | L02 | 2 | 6 | 3 | 1 | 13 | B16 | 2 | 6 | 3 | 3 | 13 | Z |
| 2 | 7 | 2 | 7 | 13 | D02* | 2 | 7 | 3 | 2 | 13 | K06 | 2 | 7 | 3 | 1 | 13 | E19 | 2 | 7 | 3 | 3 | 13 | Z |
| 2 | 8 | 2 | 7 | 13 | E02 | 2 | 8 | 3 | 2 | 13 | N04 | 2 | 8 | 3 | 1 | 13 | D20 | 2 | 8 | 3 | 3 | 13 | Z |
| 3 | 1 | 2 | 7 | 13 | D08 | 3 | 1 | 3 | 2 | 13 | L08 | 3 | 1 | 3 | 1 | 13 | F19 | 3 | 1 | 3 | 3 | 13 | Z |
| 3 | 2 | 2 | 7 | 13 | C03 | 3 | 2 | 3 | 2 | 13 | K10 | 3 | 2 | 3 | 1 | 13 | C21 | 3 | 2 | 3 | 3 | 13 | Z |
| 3 | 3 | 2 | 7 | 13 | E08 | 3 | 3 | 3 | 2 | 13 | O02 | 3 | 3 | 3 | 1 | 13 | E18 | 3 | 3 | 3 | 3 | 13 | Z |
| 3 | 4 | 2 | 7 | 13 | B03 | 3 | 4 | 3 | 2 | 13 | N09 | 3 | 4 | 3 | 1 | 13 | B15 | 3 | 4 | 3 | 3 | 13 | Z |
| 3 | 5 | 2 | 7 | 13 | D06 | 3 | 5 | 3 | 2 | 13 | K05 | 3 | 5 | 3 | 1 | 13 | C14* | 3 | 5 | 3 | 3 | 13 | N21 |
| 3 | 6 | 2 | 7 | 13 | C02 | 3 | 6 | 3 | 2 | 13 | Z | 3 | 6 | 3 | 1 | 13 | B23 | 3 | 6 | 3 | 3 | 13 | Z |
| 3 | 7 | 2 | 7 | 13 | C09 | 3 | 7 | 3 | 2 | 13 | N08 | 3 | 7 | 3 | 1 | 13 | B19 | 3 | 7 | 3 | 3 | 13 | Z |
| 3 | 8 | 2 | 7 | 13 | B02 | 3 | 8 | 3 | 2 | 13 | No7* | 3 | 8 | 3 | 1 | 13 | F21 | 3 | 8 | 3 | 3 | 13 | Z |
| 4 | 1 | 2 | 7 | 13 | B04 | 4 | 1 | 3 | 2 | 13 | M08 | 4 | 1 | 3 | 1 | 13 | D16 | 4 | 1 | 3 | 3 | 13 | Z |
| 4 | 2 | 2 | 7 | 13 | C08 | 4 | 2 | 3 | 2 | 13 | P04 | 4 | 2 | 3 | 1 | 13 | C16 | 4 | 2 | 3 | 3 | 13 | K23 |
| 4 | 3 | 2 | 7 | 13 | D05 | 4 | 3 | 3 | 2 | 13 | M04 | 4 | 3 | 3 | 1 | 13 | D14 | 4 | 3 | 3 | 3 | 13 | Z |
| 4 | 4 | 2 | 7 | 13 | C10 | 4 | 4 | 3 | 2 | 13 | N10 | 4 | 4 | 3 | 1 | 13 | F16 | 4 | 4 | 3 | 3 | 13 | Z |

FIG. 16B

| R1 | R2 | R3 | R4 | Plate | Loc. | R1 | R2 | R3 | R4 | Plate | Loc. | R1 | R2 | R3 | R4 | Plate | Loc. | R1 | R2 | R3 | R4 | Plate | Loc. |
|---|---|---|---|---|---|---|---|---|---|---|---|---|---|---|---|---|---|---|---|---|---|---|---|
| 1 | 3 | 3 | 4 | 14 | Z   | 1 | 3 | 3 | 6 | 14 | L11   | 1 | 3 | 3 | 5 | 14 | F17   | 1 | 3 | 3 | 7 | 14 | M19 |
| 1 | 4 | 3 | 4 | 14 | Z   | 1 | 4 | 3 | 6 | 14 | K02   | 1 | 4 | 3 | 5 | 14 | Z     | 1 | 4 | 3 | 7 | 14 | K15 |
| 1 | 5 | 3 | 4 | 14 | B11 | 1 | 5 | 3 | 6 | 14 | L02   | 1 | 5 | 3 | 5 | 14 | C18   | 1 | 5 | 3 | 7 | 14 | K16 |
| 1 | 6 | 3 | 4 | 14 | Z   | 1 | 6 | 3 | 6 | 14 | L09   | 1 | 6 | 3 | 5 | 14 | Z     | 1 | 6 | 3 | 7 | 14 | Z   |
| 1 | 7 | 3 | 4 | 14 | Z   | 1 | 7 | 3 | 6 | 14 | N10   | 1 | 7 | 3 | 5 | 14 | E20   | 1 | 7 | 3 | 7 | 14 | M20 |
| 1 | 8 | 3 | 4 | 14 | Z   | 1 | 8 | 3 | 6 | 14 | N08   | 1 | 8 | 3 | 5 | 14 | D19   | 1 | 8 | 3 | 7 | 14 | M14 |
| 2 | 1 | 3 | 4 | 14 | Z   | 2 | 1 | 3 | 6 | 14 | M07   | 2 | 1 | 3 | 5 | 14 | D15   | 2 | 1 | 3 | 7 | 14 | L15 |
| 2 | 2 | 3 | 4 | 14 | B7  | 2 | 2 | 3 | 6 | 14 | L08   | 2 | 2 | 3 | 5 | 14 | G14   | 2 | 2 | 3 | 7 | 14 | M22 |
| 2 | 3 | 3 | 4 | 14 | Z   | 2 | 3 | 3 | 6 | 14 | M04   | 2 | 3 | 3 | 5 | 14 | Z     | 2 | 3 | 3 | 7 | 14 | M23 |
| 2 | 4 | 3 | 4 | 14 | Z   | 2 | 4 | 3 | 6 | 14 | L10   | 2 | 4 | 3 | 5 | 14 | B23   | 2 | 4 | 3 | 7 | 14 | J14 |
| 2 | 5 | 3 | 4 | 14 | Z   | 2 | 5 | 3 | 6 | 14 | L05*  | 2 | 5 | 3 | 5 | 14 | D17   | 2 | 5 | 3 | 7 | 14 | O17 |
| 2 | 6 | 3 | 4 | 14 | Z   | 2 | 6 | 3 | 6 | 14 | K03   | 2 | 6 | 3 | 5 | 14 | F22   | 2 | 6 | 3 | 7 | 14 | L22 |
| 2 | 7 | 3 | 4 | 14 | Z   | 2 | 7 | 3 | 6 | 14 | M09   | 2 | 7 | 3 | 5 | 14 | B22   | 2 | 7 | 3 | 7 | 14 | J16 |
| 2 | 8 | 3 | 4 | 14 | Z   | 2 | 8 | 3 | 6 | 14 | Z     | 2 | 8 | 3 | 5 | 14 | E15   | 2 | 8 | 3 | 7 | 14 | L21 |
| 3 | 1 | 3 | 4 | 14 | B10 | 3 | 1 | 3 | 6 | 14 | M10   | 3 | 1 | 3 | 5 | 14 | F15   | 3 | 1 | 3 | 7 | 14 | O18 |
| 3 | 2 | 3 | 4 | 14 | Z   | 3 | 2 | 3 | 6 | 14 | L06   | 3 | 2 | 3 | 5 | 14 | D23*  | 3 | 2 | 3 | 7 | 14 | M15 |
| 3 | 3 | 3 | 4 | 14 | Z   | 3 | 3 | 3 | 6 | 14 | M11   | 3 | 3 | 3 | 5 | 14 | E20   | 3 | 3 | 3 | 7 | 14 | M18 |
| 3 | 4 | 3 | 4 | 14 | B9  | 3 | 4 | 3 | 6 | 14 | N09   | 3 | 4 | 3 | 5 | 14 | B19   | 3 | 4 | 3 | 7 | 14 | N14 |
| 3 | 5 | 3 | 4 | 14 | B8  | 3 | 5 | 3 | 6 | 14 | M02   | 3 | 5 | 3 | 5 | 14 | E21   | 3 | 5 | 3 | 7 | 14 | O22 |
| 3 | 6 | 3 | 4 | 14 | Z   | 3 | 6 | 3 | 6 | 14 | N03   | 3 | 6 | 3 | 5 | 14 | B16   | 3 | 6 | 3 | 7 | 14 | L18 |
| 3 | 7 | 3 | 4 | 14 | Z   | 3 | 7 | 3 | 6 | 14 | Z     | 3 | 7 | 3 | 5 | 14 | F14   | 3 | 7 | 3 | 7 | 14 | L19 |
| 3 | 8 | 3 | 4 | 14 | Z   | 3 | 8 | 3 | 6 | 14 | O03   | 3 | 8 | 3 | 5 | 14 | D22   | 3 | 8 | 3 | 7 | 14 | L17* |
| 4 | 1 | 3 | 4 | 14 | Z   | 4 | 1 | 3 | 6 | 14 | N07   | 4 | 1 | 3 | 5 | 14 | B20   | 4 | 1 | 3 | 7 | 14 | Z   |
| 4 | 2 | 3 | 4 | 14 | Z   | 4 | 2 | 3 | 6 | 14 | Z     | 4 | 2 | 3 | 5 | 14 | E14   | 4 | 2 | 3 | 7 | 14 | N22 |
| 4 | 3 | 3 | 4 | 14 | Z   | 4 | 3 | 3 | 6 | 14 | K08   | 4 | 3 | 3 | 5 | 14 | Z     | 4 | 3 | 3 | 7 | 14 | N15 |

| R1 | R2 | R3 | R4 | Plate | Loc. |
|---|---|---|---|---|---|
| 1 | 3 | 5 | 1 | 15 | N3 |
| 1 | 4 | 5 | 1 | 15 | K2* |
| 1 | 5 | 5 | 1 | 15 | L4 |
| 1 | 6 | 5 | 1 | 15 | M6 |
| 1 | 7 | 5 | 1 | 15 | Z |
| 1 | 8 | 5 | 1 | 15 | O4 |
| 2 | 1 | 5 | 1 | 15 | O6 |
| 2 | 2 | 5 | 1 | 15 | K9 |
| 2 | 3 | 5 | 1 | 15 | M5 |
| 2 | 4 | 5 | 1 | 15 | N5 |
| 2 | 5 | 5 | 1 | 15 | Z |
| 2 | 6 | 5 | 1 | 15 | L10 |
| 2 | 7 | 5 | 1 | 15 | O7 |
| 2 | 8 | 5 | 1 | 15 | M4 |
| 3 | 1 | 5 | 1 | 15 | N10 |
| 3 | 2 | 5 | 1 | 15 | K4 |
| 3 | 3 | 5 | 1 | 15 | O2 |
| 3 | 4 | 5 | 1 | 15 | K5 |
| 3 | 5 | 5 | 1 | 15 | K8 |
| 3 | 6 | 5 | 1 | 15 | N9* |
| 3 | 7 | 5 | 1 | 15 | M10 |
| 3 | 8 | 5 | 1 | 15 | Z |
| 4 | 1 | 5 | 1 | 15 | M3 |
| 4 | 2 | 5 | 1 | 15 | Z |
| 4 | 3 | 5 | 1 | 15 | N2 |

| R1 | R2 | R3 | R4 | Plate | Loc. |
|---|---|---|---|---|---|
| 1 | 3 | 5 | 2 | 15 | L16* |
| 1 | 4 | 5 | 2 | 15 | K14 |
| 1 | 5 | 5 | 2 | 15 | N17 |
| 1 | 6 | 5 | 2 | 15 | L15 |
| 1 | 7 | 5 | 2 | 15 | O16 |
| 1 | 8 | 5 | 2 | 15 | N18 |
| 2 | 1 | 5 | 2 | 15 | K15 |
| 2 | 2 | 5 | 2 | 15 | L14 |
| 2 | 3 | 5 | 2 | 15 | N22 |
| 2 | 4 | 5 | 2 | 15 | L19 |
| 2 | 5 | 5 | 2 | 15 | K21 |
| 2 | 6 | 5 | 2 | 15 | M20 |
| 2 | 7 | 5 | 2 | 15 | N16 |
| 2 | 8 | 5 | 2 | 15 | M21 |
| 3 | 1 | 5 | 2 | 15 | K15 |
| 3 | 2 | 5 | 2 | 15 | Z |
| 3 | 3 | 5 | 2 | 15 | K18 |
| 3 | 4 | 5 | 2 | 15 | M14 |
| 3 | 5 | 5 | 2 | 15 | M19 |
| 3 | 6 | 5 | 2 | 15 | Z |
| 3 | 7 | 5 | 2 | 15 | K23 |
| 3 | 8 | 5 | 2 | 15 | M16 |
| 4 | 1 | 5 | 2 | 15 | N19 |
| 4 | 2 | 5 | 2 | 15 | Z |
| 4 | 3 | 5 | 2 | 15 | K16 |

FIG. 18A

| 4 | 4 | 5 | 1 | 15 | N4 |
|---|---|---|---|----|-----|
| 4 | 5 | 5 | 1 | 15 | O9 |
| 4 | 6 | 5 | 1 | 15 | L5 |
| 4 | 7 | 5 | 1 | 15 | N8 |
| 4 | 8 | 5 | 1 | 15 | L6 |
| 5 | 1 | 5 | 1 | 15 | L3 |
| 5 | 2 | 5 | 1 | 15 | M7 |
| 5 | 3 | 5 | 1 | 15 | N11 |
| 5 | 4 | 5 | 1 | 15 | L9 |
| 5 | 5 | 5 | 1 | 15 | L7 |
| 5 | 6 | 5 | 1 | 15 | M11 |
| 5 | 7 | 5 | 1 | 15 | M2 |
| 5 | 8 | 5 | 1 | 15 | K6 |
| 6 | 1 | 5 | 1 | 15 | M9 |
| 6 | 2 | 5 | 1 | 15 | O3 |
| 6 | 3 | 5 | 1 | 15 | K11 |
| 6 | 4 | 5 | 1 | 15 | N7 |
| 6 | 5 | 5 | 1 | 15 | O5 |
| 6 | 6 | 5 | 1 | 15 | K10 |
| 6 | 7 | 5 | 1 | 15 | K3 |
| 6 | 8 | 5 | 1 | 15 | K7 |

| 4 | 4 | 5 | 2 | 15 | L18* |
|---|---|---|---|----|------|
| 4 | 5 | 5 | 2 | 15 | Z |
| 4 | 6 | 5 | 2 | 15 | M15 |
| 4 | 7 | 5 | 2 | 15 | M17 |
| 4 | 8 | 5 | 2 | 15 | M22 |
| 5 | 1 | 5 | 2 | 15 | K20 |
| 5 | 2 | 5 | 2 | 15 | L22 |
| 5 | 3 | 5 | 2 | 15 | L17 |
| 5 | 4 | 5 | 2 | 15 | Z |
| 5 | 5 | 5 | 2 | 15 | O15 |
| 5 | 6 | 5 | 2 | 15 | Z |
| 5 | 7 | 5 | 2 | 15 | N14 |
| 5 | 8 | 5 | 2 | 15 | N23 |
| 6 | 1 | 5 | 2 | 15 | L21 |
| 6 | 2 | 5 | 2 | 15 | N15 |
| 6 | 3 | 5 | 2 | 15 | K19 |
| 6 | 4 | 5 | 2 | 15 | K22 |
| 6 | 5 | 5 | 2 | 15 | L20 |
| 6 | 6 | 5 | 2 | 15 | O14 |
| 6 | 7 | 5 | 2 | 15 | M23 |
| 6 | 8 | 5 | 2 | 15 | N20 |

| R1 | R2 | R3 | R4 | Plate | Loc. | R1 | R2 | R3 | R4 | Plate | Loc. | R1 | R2 | R3 | R4 | Plate | Loc. | R1 | R2 | R3 | R4 | Plate | Loc. |
|---|---|---|---|---|---|---|---|---|---|---|---|---|---|---|---|---|---|---|---|---|---|---|---|
| 1 | 3 | 5 | 3 | 16 | F06 | 1 | 3 | 5 | 5 | 16 | O08 | 1 | 3 | 5 | 4 | 16 | Z | 1 | 3 | 5 | 6 | 16 | M18 |
| 1 | 4 | 5 | 3 | 16 | D03 | 1 | 4 | 5 | 5 | 16 | Z | 1 | 4 | 5 | 4 | 16 | C23 | 1 | 4 | 5 | 6 | 16 | L20 |
| 1 | 5 | 5 | 3 | 16 | D02 | 1 | 5 | 5 | 5 | 16 | N07* | 1 | 5 | 5 | 4 | 16 | C22 | 1 | 5 | 5 | 6 | 16 | N18* |
| 1 | 6 | 5 | 3 | 16 | F03 | 1 | 6 | 5 | 5 | 16 | J03 | 1 | 6 | 5 | 4 | 16 | C20 | 1 | 6 | 5 | 6 | 16 | M23 |
| 1 | 7 | 5 | 3 | 16 | B08 | 1 | 7 | 5 | 5 | 16 | M11 | 1 | 7 | 5 | 4 | 16 | C15 | 1 | 7 | 5 | 6 | 16 | K14 |
| 1 | 8 | 5 | 3 | 16 | E02* | 1 | 8 | 5 | 5 | 16 | Z | 1 | 8 | 5 | 4 | 16 | D15 | 1 | 8 | 5 | 6 | 16 | N23 |
| 2 | 1 | 5 | 3 | 16 | B02 | 2 | 1 | 5 | 5 | 16 | N03 | 2 | 1 | 5 | 4 | 16 | Z | 2 | 1 | 5 | 6 | 16 | Z |
| 2 | 2 | 5 | 3 | 16 | E09 | 2 | 2 | 5 | 5 | 16 | K10 | 2 | 2 | 5 | 4 | 16 | D18 | 2 | 2 | 5 | 6 | 16 | Z |
| 2 | 3 | 5 | 3 | 16 | E05 | 2 | 3 | 5 | 5 | 16 | L08 | 2 | 3 | 5 | 4 | 16 | B17 | 2 | 3 | 5 | 6 | 16 | M19 |
| 2 | 4 | 5 | 3 | 16 | D07 | 2 | 4 | 5 | 5 | 16 | L03 | 2 | 4 | 5 | 4 | 16 | Z | 2 | 4 | 5 | 6 | 16 | K20 |
| 2 | 5 | 5 | 3 | 16 | D04 | 2 | 5 | 5 | 5 | 16 | O07 | 2 | 5 | 5 | 4 | 16 | D19 | 2 | 5 | 5 | 6 | 16 | N16 |
| 2 | 6 | 5 | 3 | 16 | C10 | 2 | 6 | 5 | 5 | 16 | O02 | 2 | 6 | 5 | 4 | 16 | C17 | 2 | 6 | 5 | 6 | 16 | O20 |
| 2 | 7 | 5 | 3 | 16 | F08 | 2 | 7 | 5 | 5 | 16 | M3 | 2 | 7 | 5 | 4 | 16 | Z | 2 | 7 | 5 | 6 | 16 | M14 |
| 2 | 8 | 5 | 3 | 16 | B09 | 2 | 8 | 5 | 5 | 16 | N05 | 2 | 8 | 5 | 4 | 16 | E19 | 2 | 8 | 5 | 6 | 16 | O17 |
| 3 | 1 | 5 | 3 | 16 | D05 | 3 | 1 | 5 | 5 | 16 | M06* | 3 | 1 | 5 | 4 | 16 | Z | 3 | 1 | 5 | 6 | 16 | K16 |
| 3 | 2 | 5 | 3 | 16 | E11 | 3 | 2 | 5 | 5 | 16 | K04 | 3 | 2 | 5 | 4 | 16 | Z | 3 | 2 | 5 | 6 | 16 | O22 |
| 3 | 3 | 5 | 3 | 16 | C08 | 3 | 3 | 5 | 5 | 16 | M09 | 3 | 3 | 5 | 4 | 16 | Z | 3 | 3 | 5 | 6 | 16 | J18 |
| 3 | 4 | 5 | 3 | 16 | D11 | 3 | 4 | 5 | 5 | 16 | L05 | 3 | 4 | 5 | 4 | 16 | D16 | 3 | 4 | 5 | 6 | 16 | L22 |
| 3 | 5 | 5 | 3 | 16 | B04 | 3 | 5 | 5 | 5 | 16 | N08 | 3 | 5 | 5 | 4 | 16 | E14 | 3 | 5 | 5 | 6 | 16 | M20 |
| 3 | 6 | 5 | 3 | 16 | B10 | 3 | 6 | 5 | 5 | 16 | J02 | 3 | 6 | 5 | 4 | 16 | D17 | 3 | 6 | 5 | 6 | 16 | N21 |
| 3 | 7 | 5 | 3 | 16 | F04 | 3 | 7 | 5 | 5 | 16 | M02 | 3 | 7 | 5 | 4 | 16 | D14* | 3 | 7 | 5 | 6 | 16 | K22 |
| 3 | 8 | 5 | 3 | 16 | B11 | 3 | 8 | 5 | 5 | 16 | J08 | 3 | 8 | 5 | 4 | 16 | E16 | 3 | 8 | 5 | 6 | 16 | L19 |
| 4 | 1 | 5 | 3 | 16 | F05 | 4 | 1 | 5 | 5 | 16 | K11 | 4 | 1 | 5 | 4 | 16 | C19 | 4 | 1 | 5 | 6 | 16 | O14 |
| 4 | 2 | 5 | 3 | 16 | Z | 4 | 2 | 5 | 5 | 16 | Z | 4 | 2 | 5 | 4 | 16 | Z | 4 | 2 | 5 | 6 | 16 | Z |

FIG. 19B

| 4 | 3 | 5 | 5 | 6 | | 4 | 3 | 5 | 5 | 6 | | 4 | 3 | 5 | 5 | 6 | | 4 | 3 | 5 | 5 | 6 | |
|---|---|---|---|---|---|---|---|---|---|---|---|---|---|---|---|---|---|---|---|---|---|---|---|
| 4 | 3 | 5 | 5 | 16 E08 | | 4 | 3 | 5 | 5 | 16 L02 | | 4 | 4 | 5 | 4 | 16 C21 | | 4 | 3 | 5 | 6 | 16 N14 |
| 4 | 4 | 5 | 5 | 16 E03 | | 4 | 4 | 5 | 5 | 16 M10 | | 4 | 4 | 5 | 4 | 16 D21 | | 4 | 4 | 5 | 6 | 16 K15 |
| 4 | 5 | 5 | 5 | 16 Z | | 4 | 5 | 5 | 5 | 16 J07 | | 4 | 5 | 5 | 4 | 16 Z | | 4 | 5 | 5 | 6 | 16 K17 |
| 4 | 6 | 5 | 5 | 16 B07 | | 4 | 6 | 5 | 5 | 16 O05 | | 4 | 6 | 5 | 4 | 16 C16 | | 4 | 6 | 5 | 6 | 16 O18 |
| 4 | 7 | 5 | 5 | 16 Z | | 4 | 7 | 5 | 5 | 16 M07 | | 4 | 7 | 5 | 4 | 16 E18* | | 4 | 7 | 5 | 6 | 16 Z |
| 4 | 8 | 5 | 5 | 16 C06 | | 4 | 8 | 5 | 5 | 16 N02 | | 4 | 8 | 5 | 4 | 16 B18 | | 4 | 8 | 5 | 6 | 16 L17 |
| 5 | 1 | 5 | 5 | 16 B03 | | 5 | 1 | 5 | 5 | 16 K03 | | 5 | 1 | 5 | 4 | 16 B14 | | 5 | 1 | 5 | 6 | 16 L14 |
| 5 | 2 | 5 | 5 | 16 D08* | | 5 | 2 | 5 | 5 | 16 K05 | | 5 | 2 | 5 | 4 | 16 C18 | | 5 | 2 | 5 | 6 | 16 N20* |
| 5 | 3 | 5 | 5 | 16 F02 | | 5 | 3 | 5 | 5 | 16 N04 | | 5 | 3 | 5 | 4 | 16 D23 | | 5 | 3 | 5 | 6 | 16 K21 |
| 5 | 4 | 5 | 5 | 16 Z | | 5 | 4 | 5 | 5 | 16 K02 | | 5 | 4 | 5 | 4 | 16 E21 | | 5 | 4 | 5 | 6 | 16 J19 |
| 5 | 5 | 5 | 5 | 16 B06 | | 5 | 5 | 5 | 5 | 16 L09 | | 5 | 5 | 5 | 4 | 16 B16 | | 5 | 5 | 5 | 6 | 16 L23 |
| 5 | 6 | 5 | 5 | 16 D06 | | 5 | 6 | 5 | 5 | 16 N11 | | 5 | 6 | 5 | 4 | 16 B15 | | 5 | 6 | 5 | 6 | 16 Z |
| 5 | 7 | 5 | 5 | 16 E10 | | 5 | 7 | 5 | 5 | 16 Z | | 5 | 7 | 5 | 4 | 16 E20 | | 5 | 7 | 5 | 6 | 16 K19 |
| 5 | 8 | 5 | 5 | 16 F07 | | 5 | 8 | 5 | 5 | 16 N10 | | 5 | 8 | 5 | 4 | 16 E23 | | 5 | 8 | 5 | 6 | 16 M17 |
| 6 | 1 | 5 | 5 | 16 C05 | | 6 | 1 | 5 | 5 | 16 Z | | 6 | 1 | 5 | 4 | 16 D22 | | 6 | 1 | 5 | 6 | 16 M15 |
| 6 | 2 | 5 | 5 | 16 E04 | | 6 | 2 | 5 | 5 | 16 K06 | | 6 | 2 | 5 | 4 | 16 B20 | | 6 | 2 | 5 | 6 | 16 O15 |
| 6 | 3 | 5 | 5 | 16 C04 | | 6 | 3 | 5 | 5 | 16 N09 | | 6 | 3 | 5 | 4 | 16 E17 | | 6 | 3 | 5 | 6 | 16 L21 |
| 6 | 4 | 5 | 5 | 16 D10 | | 6 | 4 | 5 | 5 | 16 M08 | | 6 | 4 | 5 | 4 | 16 B21 | | 6 | 4 | 5 | 6 | 16 N19 |
| 6 | 5 | 5 | 5 | 16 D09 | | 6 | 5 | 5 | 5 | 16 M05 | | 6 | 5 | 5 | 4 | 16 B22 | | 6 | 5 | 5 | 6 | 16 N15 |
| 6 | 6 | 5 | 5 | 16 B05 | | 6 | 6 | 5 | 5 | 16 L06 | | 6 | 6 | 5 | 4 | 16 D20 | | 6 | 6 | 5 | 6 | 16 K18 |
| 6 | 7 | 5 | 5 | 16 C11 | | 6 | 7 | 5 | 5 | 16 L04 | | 6 | 7 | 5 | 4 | 16 C14 | | 6 | 7 | 5 | 6 | 16 Z |
| 6 | 8 | 5 | 5 | 16 C07 | | 6 | 8 | 5 | 5 | 16 L04 | | 6 | 8 | 5 | 4 | 16 E15 | | 6 | 8 | 5 | 6 | 16 M21 |

FIG. 20A

| R1 | R2 | R3 | R4 | Plate | Loc. |
|---|---|---|---|---|---|
| 1 | 3 | 5 | 7 | 17 | F5 |
| 1 | 4 | 5 | 7 | 17 | Z |
| 1 | 5 | 5 | 7 | 17 | F8 |
| 1 | 6 | 5 | 7 | 17 | B5 |
| 1 | 7 | 5 | 7 | 17 | B6 |
| 1 | 8 | 5 | 7 | 17 | C9 |
| 2 | 1 | 5 | 7 | 17 | E9 |
| 2 | 2 | 5 | 7 | 17 | E2 |
| 2 | 3 | 5 | 7 | 17 | E3 |
| 2 | 4 | 5 | 7 | 17 | B9 |
| 2 | 5 | 5 | 7 | 17 | C6 |
| 2 | 6 | 5 | 7 | 17 | E8 |
| 2 | 7 | 5 | 7 | 17 | Z |
| 2 | 8 | 5 | 7 | 17 | B11 |
| 3 | 1 | 5 | 7 | 17 | D3 |
| 3 | 2 | 5 | 7 | 17 | D2 |
| 3 | 3 | 5 | 7 | 17 | F7 |
| 3 | 4 | 5 | 7 | 17 | C8 |
| 3 | 5 | 5 | 7 | 17 | C10 |
| 3 | 6 | 5 | 7 | 17 | E11 |
| 3 | 7 | 5 | 7 | 17 | F3 |
| 3 | 8 | 5 | 7 | 17 | E7 |
| 4 | 1 | 5 | 7 | 17 | C2 |
| 4 | 2 | 5 | 7 | 17 | Z |
| 4 | 3 | 5 | 7 | 17 | C4 |

| R1 | R2 | R3 | R4 | Plate | Loc. |
|---|---|---|---|---|---|
| 1 | 3 | 6 | 2 | 17 | K2 |
| 1 | 4 | 6 | 2 | 17 | L3 |
| 1 | 5 | 6 | 2 | 17 | M7 |
| 1 | 6 | 6 | 2 | 17 | M8 |
| 1 | 7 | 6 | 2 | 17 | O6 |
| 1 | 8 | 6 | 2 | 17 | M3 |
| 2 | 1 | 6 | 2 | 17 | M9 |
| 2 | 2 | 6 | 2 | 17 | L6 |
| 2 | 3 | 6 | 2 | 17 | M11 |
| 2 | 4 | 6 | 2 | 17 | L8 |
| 2 | 5 | 6 | 2 | 17 | N10 |
| 2 | 6 | 6 | 2 | 17 | O4 |
| 2 | 7 | 6 | 2 | 17 | O8 |
| 2 | 8 | 6 | 2 | 17 | N8 |
| 3 | 1 | 6 | 2 | 17 | O5 |
| 3 | 2 | 6 | 2 | 17 | K5 |
| 3 | 3 | 6 | 2 | 17 | N6 |
| 3 | 4 | 6 | 2 | 17 | K4 |
| 3 | 5 | 6 | 2 | 17 | L2 |
| 3 | 6 | 6 | 2 | 17 | K7 |
| 3 | 7 | 6 | 2 | 17 | J3 |
| 3 | 8 | 6 | 2 | 17 | K10 |
| 4 | 1 | 6 | 2 | 17 | L11 |
| 4 | 2 | 6 | 2 | 17 | Z |
| 4 | 3 | 6 | 2 | 17 | M2 |

| R1 | R2 | R3 | R4 | Plate | Loc. |
|---|---|---|---|---|---|
| 1 | 3 | 6 | 1 | 17 | B14 |
| 1 | 4 | 6 | 1 | 17 | C22 |
| 1 | 5 | 6 | 1 | 17 | Z |
| 1 | 6 | 6 | 1 | 17 | D19 |
| 1 | 7 | 6 | 1 | 17 | Z |
| 1 | 8 | 6 | 1 | 17 | E23 |
| 2 | 1 | 6 | 1 | 17 | E18 |
| 2 | 2 | 6 | 1 | 17 | B14 |
| 2 | 3 | 6 | 1 | 17 | E20 |
| 2 | 4 | 6 | 1 | 17 | B18 |
| 2 | 5 | 6 | 1 | 17 | C19 |
| 2 | 6 | 6 | 1 | 17 | F16 |
| 2 | 7 | 6 | 1 | 17 | D17 |
| 2 | 8 | 6 | 1 | 17 | E19 |
| 3 | 1 | 6 | 1 | 17 | B21 |
| 3 | 2 | 6 | 1 | 17 | D16 |
| 3 | 3 | 6 | 1 | 17 | F15 |
| 3 | 4 | 6 | 1 | 17 | Z |
| 3 | 5 | 6 | 1 | 17 | D22 |
| 3 | 6 | 6 | 1 | 17 | C17 |
| 3 | 7 | 6 | 1 | 17 | B16 |
| 3 | 8 | 6 | 1 | 17 | F21 |
| 4 | 1 | 6 | 1 | 17 | D15 |
| 4 | 2 | 6 | 1 | 17 | F20 |
| 4 | 3 | 6 | 1 | 17 | F18 |

| R1 | R2 | R3 | R4 | Plate | Loc. |
|---|---|---|---|---|---|
| 1 | 3 | 6 | 3 | 17 | K19 |
| 1 | 4 | 6 | 3 | 17 | N14 |
| 1 | 5 | 6 | 3 | 17 | M21 |
| 1 | 6 | 6 | 3 | 17 | K16 |
| 1 | 7 | 6 | 3 | 17 | L16 |
| 1 | 8 | 6 | 3 | 17 | N17 |
| 2 | 1 | 6 | 3 | 17 | K18 |
| 2 | 2 | 6 | 3 | 17 | K17 |
| 2 | 3 | 6 | 3 | 17 | M17 |
| 2 | 4 | 6 | 3 | 17 | N18 |
| 2 | 5 | 6 | 3 | 17 | N23 |
| 2 | 6 | 6 | 3 | 17 | K15 |
| 2 | 7 | 6 | 3 | 17 | O23 |
| 2 | 8 | 6 | 3 | 17 | N15 |
| 3 | 1 | 6 | 3 | 17 | O21 |
| 3 | 2 | 6 | 3 | 17 | J15 |
| 3 | 3 | 6 | 3 | 17 | J16 |
| 3 | 4 | 6 | 3 | 17 | O16 |
| 3 | 5 | 6 | 3 | 17 | K21 |
| 3 | 6 | 6 | 3 | 17 | M22 |
| 3 | 7 | 6 | 3 | 17 | M20 |
| 3 | 8 | 6 | 3 | 17 | M14 |
| 4 | 1 | 6 | 3 | 17 | M19 |
| 4 | 2 | 6 | 3 | 17 | Z |
| 4 | 3 | 6 | 3 | 17 | L14 |

| R1 | R2 | R3 | R4 | Plate | Loc. |
|---|---|---|---|---|---|
| 1 | 3 | 6 | 4 | 18 | E7 |
| 1 | 4 | 6 | 4 | 18 | C10 |
| 1 | 5 | 6 | 4 | 18 | Z |
| 1 | 6 | 6 | 4 | 18 | D11 |
| 1 | 7 | 6 | 4 | 18 | D3 |
| 1 | 8 | 6 | 4 | 18 | C5 |
| 2 | 1 | 6 | 4 | 18 | F4 |
| 2 | 2 | 6 | 4 | 18 | E8 |
| 2 | 3 | 6 | 4 | 18 | B7 |
| 2 | 4 | 6 | 4 | 18 | Z |
| 2 | 5 | 6 | 4 | 18 | C2 |
| 2 | 6 | 6 | 4 | 18 | B10 |
| 2 | 7 | 6 | 4 | 18 | E2 |
| 2 | 8 | 6 | 4 | 18 | C6 |
| 3 | 1 | 6 | 4 | 18 | F3 |
| 3 | 2 | 6 | 4 | 18 | F5 |
| 3 | 3 | 6 | 4 | 18 | Z |
| 3 | 4 | 6 | 4 | 18 | D4 |
| 3 | 5 | 6 | 4 | 18 | D8 |
| 3 | 6 | 6 | 4 | 18 | Z |
| 3 | 7 | 6 | 4 | 18 | D9 |
| 3 | 8 | 6 | 4 | 18 | D2 |
| 4 | 1 | 6 | 4 | 18 | B2 |
| 4 | 2 | 6 | 4 | 18 | Z |
| 4 | 3 | 6 | 4 | 18 | B8 |

| R1 | R2 | R3 | R4 | Plate | Loc. |
|---|---|---|---|---|---|
| 1 | 3 | 6 | 6 | 18 | K7 |
| 1 | 4 | 6 | 6 | 18 | K8 |
| 1 | 5 | 6 | 6 | 18 | K2 |
| 1 | 6 | 6 | 6 | 18 | M7 |
| 1 | 7 | 6 | 6 | 18 | L2 |
| 1 | 8 | 6 | 6 | 18 | K6 |
| 2 | 1 | 6 | 6 | 18 | M4 |
| 2 | 2 | 6 | 6 | 18 | N5 |
| 2 | 3 | 6 | 6 | 18 | M3 |
| 2 | 4 | 6 | 6 | 18 | M11 |
| 2 | 5 | 6 | 6 | 18 | L6 |
| 2 | 6 | 6 | 6 | 18 | L10 |
| 2 | 7 | 6 | 6 | 18 | N6 |
| 2 | 8 | 6 | 6 | 18 | M2 |
| 3 | 1 | 6 | 6 | 18 | Z |
| 3 | 2 | 6 | 6 | 18 | O4 |
| 3 | 3 | 6 | 6 | 18 | K11 |
| 3 | 4 | 6 | 6 | 18 | N2 |
| 3 | 5 | 6 | 6 | 18 | N8 |
| 3 | 6 | 6 | 6 | 18 | M5 |
| 3 | 7 | 6 | 6 | 18 | Z |
| 3 | 8 | 6 | 6 | 18 | N4 |
| 4 | 1 | 6 | 6 | 18 | K3 |
| 4 | 2 | 6 | 6 | 18 | Z |
| 4 | 3 | 6 | 6 | 18 | N10 |

| R1 | R2 | R3 | R4 | Plate | Loc. |
|---|---|---|---|---|---|
| 1 | 3 | 6 | 5 | 18 | D15 |
| 1 | 4 | 6 | 5 | 18 | B23 |
| 1 | 5 | 6 | 5 | 18 | C17 |
| 1 | 6 | 6 | 5 | 18 | B22 |
| 1 | 7 | 6 | 5 | 18 | B19 |
| 1 | 8 | 6 | 5 | 18 | B18 |
| 2 | 1 | 6 | 5 | 18 | C23 |
| 2 | 2 | 6 | 5 | 18 | D23 |
| 2 | 3 | 6 | 5 | 18 | B16 |
| 2 | 4 | 6 | 5 | 18 | D17 |
| 2 | 5 | 6 | 5 | 18 | E15 |
| 2 | 6 | 6 | 5 | 18 | E14 |
| 2 | 7 | 6 | 5 | 18 | C20 |
| 2 | 8 | 6 | 5 | 18 | B15 |
| 3 | 1 | 6 | 5 | 18 | E18 |
| 3 | 2 | 6 | 5 | 18 | E16 |
| 3 | 3 | 6 | 5 | 18 | D16 |
| 3 | 4 | 6 | 5 | 18 | Z |
| 3 | 5 | 6 | 5 | 18 | F14 |
| 3 | 6 | 6 | 5 | 18 | Z |
| 3 | 7 | 6 | 5 | 18 | F15 |
| 3 | 8 | 6 | 5 | 18 | F16 |
| 4 | 1 | 6 | 5 | 18 | D20 |
| 4 | 2 | 6 | 5 | 18 | F23 |
| 4 | 3 | 6 | 5 | 18 | D22 |

| R1 | R2 | R3 | R4 | Plate | Loc. |
|---|---|---|---|---|---|
| 1 | 3 | 6 | 7 | 18 | K14 |
| 1 | 4 | 6 | 7 | 18 | Z |
| 1 | 5 | 6 | 7 | 18 | L15 |
| 1 | 6 | 6 | 7 | 18 | Z |
| 1 | 7 | 6 | 7 | 18 | M21 |
| 1 | 8 | 6 | 7 | 18 | M22 |
| 2 | 1 | 6 | 7 | 18 | O15 |
| 2 | 2 | 6 | 7 | 18 | M23 |
| 2 | 3 | 6 | 7 | 18 | M18 |
| 2 | 4 | 6 | 7 | 18 | M16 |
| 2 | 5 | 6 | 7 | 18 | N18 |
| 2 | 6 | 6 | 7 | 18 | Z |
| 2 | 7 | 6 | 7 | 18 | K22 |
| 2 | 8 | 6 | 7 | 18 | K19 |
| 3 | 1 | 6 | 7 | 18 | N15 |
| 3 | 2 | 6 | 7 | 18 | N16 |
| 3 | 3 | 6 | 7 | 18 | O17 |
| 3 | 4 | 6 | 7 | 18 | K23 |
| 3 | 5 | 6 | 7 | 18 | L23 |
| 3 | 6 | 6 | 7 | 18 | K18 |
| 3 | 7 | 6 | 7 | 18 | K20 |
| 3 | 8 | 6 | 7 | 18 | N17 |
| 4 | 1 | 6 | 7 | 18 | L17 |
| 4 | 2 | 6 | 7 | 18 | Z |
| 4 | 3 | 6 | 7 | 18 | O16 |

| R1 | R2 | R3 | R4 | MW | Plate | Loc. |
|---|---|---|---|---|---|---|
| 1 | 3 | 8 | 8 | 604.2 | 4 | L20 |
| 1 | 4 | 8 | 8 | 654.2 | 4 | O15 |
| 1 | 5 | 8 | 8 | 624.2 | 4 | L19 |
| 1 | 6 | 8 | 8 | 578.2 | 4 | N18 |
| 1 | 7 | 8 | 8 | 602.2 | 4 | N22 |
| 1 | 8 | 8 | 8 | 500.2 | 4 | N16 |
| 2 | 1 | 8 | 8 | 533.2 | 4 | N21 |
| 2 | 2 | 8 | 8 | 611.2 | 4 | M23 |
| 2 | 3 | 8 | 8 | 523.2 | 4 | K22 |
| 2 | 4 | 8 | 8 | 573.2 | 4 | N15 |
| 2 | 5 | 8 | 8 | 543.2 | 4 | L17 |
| 2 | 6 | 8 | 8 | 497.2 | 4 | K21 |
| 2 | 7 | 8 | 8 | 521.2 | 19 | D8 |
| 2 | 8 | 8 | 8 | 419.1 | 4 | M21 |
| 3 | 1 | 8 | 8 | 613.2 | 4 | L14 |
| 3 | 2 | 8 | 8 | 691.2 | 4 | N14 |
| 3 | 3 | 8 | 8 | 603.3 | 4 | L21 |
| 3 | 4 | 8 | 8 | 653.3 | 4 | M17 |
| 3 | 5 | 8 | 8 | 623.3 | 4 | N20 |
| 3 | 6 | 8 | 8 | 577.2 | 4 | N17 |
| 3 | 7 | 8 | 8 | 601.3 | 4 | K16 |
| 3 | 8 | 8 | 8 | 499.2 | 4 | K20 |

| R1 | R2 | R3 | R4 | MW | Plate | Loc. |
|---|---|---|---|---|---|---|
| 4 | 1 | 8 | 8 | 589.3 | 4 | K23 |
| 4 | 2 | 8 | 8 | 667.3 | 19 | B10 |
| 4 | 3 | 8 | 8 | 579.3 | 4 | K19 |
| 4 | 4 | 8 | 8 | 629.3 | 4 | N19 |
| 4 | 5 | 8 | 8 | 599.3 | 4 | O16 |
| 4 | 6 | 8 | 8 | 553.3 | 4 | M18 |
| 4 | 7 | 8 | 8 | 577.3 | 4 | L16 |
| 4 | 8 | 8 | 8 | 475.2 | 4 | L15 |
| 5 | 1 | 8 | 8 | 561.2 | 4 | L23 |
| 5 | 2 | 8 | 8 | 639.2 | 4 | M22 |
| 5 | 3 | 8 | 8 | 551.3 | 4 | M14 |
| 5 | 4 | 8 | 8 | 601.2 | 4 | N23 |
| 5 | 5 | 8 | 8 | 571.2 | 4 | M16 |
| 5 | 6 | 8 | 8 | 525.2 | 4 | O14 |
| 5 | 7 | 8 | 8 | 549.2 | 4 | L18 |
| 5 | 8 | 8 | 8 | 447.2 | 4 | K14 |
| 6 | 1 | 8 | 8 | 479 | 4 | M20 |
| 6 | 2 | 8 | 8 | 557.1 | 4 | M19 |
| 6 | 3 | 8 | 8 | 469.1 | 4 | K15 |
| 6 | 4 | 8 | 8 | 519.1 | 4 | L22 |
| 6 | 5 | 8 | 8 | 489.1 | 4 | M15 |
| 6 | 6 | 8 | 8 | 443 | 4 | K18 |
| 6 | 7 | 8 | 8 | 467.1 | 4 | O17 |
| 6 | 8 | 8 | 8 | 365 | 19 | E5 |

| R1 | R2 | R3 | R4 | Plate | Loc |
|---|---|---|---|---|---|
| 1 | 3 | 1 | 8 | 1 | K02 |
| 1 | 4 | 1 | 8 | 1 | K03 |
| 1 | 5 | 1 | 8 | 1 | K07 |
| 1 | 6 | 1 | 8 | 1 | O05 |
| 1 | 7 | 1 | 8 | 1 | L05 |
| 1 | 8 | 1 | 8 | 1 | N04 |
| 2 | 1 | 1 | 8 | 1 | K04 |
| 2 | 2 | 1 | 8 | 1 | K09 |
| 2 | 3 | 1 | 8 | 1 | L06 |
| 2 | 4 | 1 | 8 | 1 | L08 |
| 2 | 5 | 1 | 8 | 1 | M08 |
| 2 | 6 | 1 | 8 | 1 | N02 |
| 2 | 7 | 1 | 8 | 1 | L09 |
| 2 | 8 | 1 | 8 | 1 | M11 |
| 3 | 1 | 1 | 8 | 1 | N09 |
| 3 | 2 | 1 | 8 | 1 | Z |
| 3 | 3 | 1 | 8 | 1 | Z |
| 3 | 4 | 1 | 8 | 1 | O09 |
| 3 | 5 | 1 | 8 | 1 | Z |
| 3 | 6 | 1 | 8 | 1 | M02 |
| 3 | 7 | 1 | 8 | 1 | M07 |
| 3 | 8 | 1 | 8 | 1 | Z |
| 4 | 1 | 1 | 8 | 1 | L07 |
| 4 | 2 | 1 | 8 | 1 | K11 |

Figs VI.3.2.7-12

| R1 | R2 | R3 | R4 | Plate | Loc |
|---|---|---|---|---|---|
| 1 | 3 | 2 | 8 | 11 | C11 |
| 1 | 4 | 2 | 8 | 11 | F11 |
| 1 | 5 | 2 | 8 | 11 | E11 |
| 1 | 6 | 2 | 8 | 11 | D6 |
| 1 | 7 | 2 | 8 | 11 | C5 |
| 1 | 8 | 2 | 8 | 11 | E9 |
| 2 | 1 | 2 | 8 | 11 | D11 |
| 2 | 2 | 2 | 8 | 11 | C2 |
| 2 | 3 | 2 | 8 | 11 | Z |
| 2 | 4 | 2 | 8 | 11 | F4 |
| 2 | 5 | 2 | 8 | 11 | B3 |
| 2 | 6 | 2 | 8 | 11 | B11 |
| 2 | 7 | 2 | 8 | 11 | F9 |
| 2 | 8 | 2 | 8 | 11 | B9 |
| 3 | 1 | 2 | 8 | 11 | D8 |
| 3 | 2 | 2 | 8 | 11 | F7 |
| 3 | 3 | 2 | 8 | 11 | B7 |
| 3 | 4 | 2 | 8 | 11 | B8 |
| 3 | 5 | 2 | 8 | 11 | D10 |
| 3 | 6 | 2 | 8 | 11 | E4 |
| 3 | 7 | 2 | 8 | 11 | E7 |
| 3 | 8 | 2 | 8 | 11 | Z |
| 4 | 1 | 2 | 8 | 11 | D9 |
| 4 | 2 | 2 | 8 | 11 | C10 |

Table 1:

| | | | | |
|---|---|---|---|---|
| 4 | 3 | 2 | 8 | 11F3 |
| 4 | 4 | 2 | 8 | 11E3 |
| 4 | 5 | 2 | 8 | 11Z |
| 4 | 6 | 2 | 8 | 11Z |
| 4 | 7 | 2 | 8 | 11C9 |
| 4 | 8 | 2 | 8 | 11Z |
| 5 | 1 | 2 | 8 | 11B2 |
| 5 | 2 | 2 | 8 | 11B4 |
| 5 | 3 | 2 | 8 | 11F10 |
| 5 | 4 | 2 | 8 | 11E2 |
| 5 | 5 | 2 | 8 | 11C4 |
| 5 | 6 | 2 | 8 | 11D7 |
| 5 | 7 | 2 | 8 | 11F2 |
| 5 | 8 | 2 | 8 | 11E5 |
| 6 | 1 | 2 | 8 | 11F6 |
| 6 | 2 | 2 | 8 | 11C6 |
| 6 | 3 | 2 | 8 | 11F8 |
| 6 | 4 | 2 | 8 | 11D5 |
| 6 | 5 | 2 | 8 | 11E10 |
| 6 | 6 | 2 | 8 | 11E6 |
| 6 | 7 | 2 | 8 | 11D3 |
| 6 | 8 | 2 | 8 | 11B5 |

Table 2:

| | | | | |
|---|---|---|---|---|
| 4 | 3 | 1 | 8 | 1O02 |
| 4 | 4 | 1 | 8 | 1M03 |
| 4 | 5 | 1 | 8 | 1Z |
| 4 | 6 | 1 | 8 | 1Z |
| 4 | 7 | 1 | 8 | 1N11 |
| 4 | 8 | 1 | 8 | 1K06 |
| 5 | 1 | 1 | 8 | 1K05 |
| 5 | 2 | 1 | 8 | 1L03 |
| 5 | 3 | 1 | 8 | 1Z |
| 5 | 4 | 1 | 8 | 1L10 |
| 5 | 5 | 1 | 8 | 1Z |
| 5 | 6 | 1 | 8 | 1Z |
| 5 | 7 | 1 | 8 | 1N06 |
| 5 | 8 | 1 | 8 | 1K10 |
| 6 | 1 | 1 | 8 | 1N07 |
| 6 | 2 | 1 | 8 | 1L02 |
| 6 | 3 | 1 | 8 | 1M10 |
| 6 | 4 | 1 | 8 | 1O03 |
| 6 | 5 | 1 | 8 | 1N10 |
| 6 | 6 | 1 | 8 | 1M04 |
| 6 | 7 | 1 | 8 | 1M06 |
| 6 | 8 | 1 | 8 | 1N05 |

| Figs VI.3.2.13-18 | | | | | | Figs VI.3.2.19-24 | | | | | |
|---|---|---|---|---|---|---|---|---|---|---|---|
| R1 | R2 | R3 | R4 | Plate | Loc | R1 | R2 | R3 | R4 | Plate | Loc |
| 1 | 3 | 3 | 8 | 11 | D23 | 1 | 3 | 4 | 8 | 1 | L17 |
| 1 | 4 | 3 | 8 | 11 | D21 | 1 | 4 | 4 | 8 | 1 | M23 |
| 1 | 5 | 3 | 8 | 11 | E23 | 1 | 5 | 4 | 8 | 1 | L22 |
| 1 | 6 | 3 | 8 | 11 | Z | 1 | 6 | 4 | 8 | 1 | L16 |
| 1 | 7 | 3 | 8 | 11 | F17 | 1 | 7 | 4 | 8 | 1 | N17 |
| 1 | 8 | 3 | 8 | 11 | D18 | 1 | 8 | 4 | 8 | 1 | O15 |
| 2 | 1 | 3 | 8 | 11 | E16 | 2 | 1 | 4 | 8 | 1 | K16 |
| 2 | 2 | 3 | 8 | 11 | F15 | 2 | 2 | 4 | 8 | 1 | K18 |
| 2 | 3 | 3 | 8 | 11 | Z | 2 | 3 | 4 | 8 | 1 | L15 |
| 2 | 4 | 3 | 8 | 11 | C21 | 2 | 4 | 4 | 8 | 1 | N15 |
| 2 | 5 | 3 | 8 | 11 | C15 | 2 | 5 | 4 | 8 | 1 | O16 |
| 2 | 6 | 3 | 8 | 11 | E20 | 2 | 6 | 4 | 8 | 1 | K17 |
| 2 | 7 | 3 | 8 | 11 | G22 | 2 | 7 | 4 | 8 | 1 | L21 |
| 2 | 8 | 3 | 8 | 11 | B14 | 2 | 8 | 4 | 8 | 1 | K20 |
| 3 | 1 | 3 | 8 | 11 | C14 | 3 | 1 | 4 | 8 | 1 | Z |
| 3 | 2 | 3 | 8 | 11 | B18 | 3 | 2 | 4 | 8 | 1 | Z |
| 3 | 3 | 3 | 8 | 11 | F23 | 3 | 3 | 4 | 8 | 1 | N16 |
| 3 | 4 | 3 | 8 | 11 | C19 | 3 | 4 | 4 | 8 | 1 | M16 |
| 3 | 5 | 3 | 8 | 11 | D20 | 3 | 5 | 4 | 8 | 1 | Z |
| 3 | 6 | 3 | 8 | 11 | C23 | 3 | 6 | 4 | 8 | 1 | M14 |
| 3 | 7 | 3 | 8 | 11 | C16 | 3 | 7 | 4 | 8 | 1 | N14 |
| 3 | 8 | 3 | 8 | 11 | F19 | 3 | 8 | 4 | 8 | 1 | Z |
| 4 | 1 | 3 | 8 | 11 | B17 | 4 | 1 | 4 | 8 | 1 | N21 |
| 4 | 2 | 3 | 8 | 11 | G17 | 4 | 2 | 4 | 8 | 1 | L14 |

FIG. 24A

| 4 | 3 | 3 | 8 | 11 | Z |
|---|---|---|---|---|---|
| 4 | 4 | 3 | 8 | 11 | F18 |
| 4 | 5 | 3 | 8 | 11 | G18 |
| 4 | 6 | 3 | 8 | 11 | E22 |
| 4 | 7 | 3 | 8 | 11 | H16 |
| 4 | 8 | 3 | 8 | 11 | G15 |
| 5 | 1 | 3 | 8 | 11 | G21 |
| 5 | 2 | 3 | 8 | 11 | F20 |
| 5 | 3 | 3 | 8 | 11 | G20 |
| 5 | 4 | 3 | 8 | 11 | G19 |
| 5 | 5 | 3 | 8 | 11 | G23 |
| 5 | 6 | 3 | 8 | 11 | D15 |
| 5 | 7 | 3 | 8 | 11 | B20 |
| 5 | 8 | 3 | 8 | 11 | B23 |
| 6 | 1 | 3 | 8 | 11 | D19 |
| 6 | 2 | 3 | 8 | 11 | C22 |
| 6 | 3 | 3 | 8 | 11 | H14 |
| 6 | 4 | 3 | 8 | 11 | B22 |
| 6 | 5 | 3 | 8 | 11 | D16 |
| 6 | 6 | 3 | 8 | 11 | B16 |
| 6 | 7 | 3 | 8 | 11 | E15 |
| 6 | 8 | 3 | 8 | 11 | H15 |

| 4 | 3 | 4 | 8 | 1 | L23 |
|---|---|---|---|---|---|
| 4 | 4 | 4 | 8 | 1 | O17 |
| 4 | 5 | 4 | 8 | 1 | O18 |
| 4 | 6 | 4 | 8 | 1 | K14 |
| 4 | 7 | 4 | 8 | 1 | N23 |
| 4 | 8 | 4 | 8 | 1 | M20 |
| 5 | 1 | 4 | 8 | 1 | M18 |
| 5 | 2 | 4 | 8 | 1 | K15 |
| 5 | 3 | 4 | 8 | 1 | K19 |
| 5 | 4 | 4 | 8 | 1 | L18 |
| 5 | 5 | 4 | 8 | 1 | M17 |
| 5 | 6 | 4 | 8 | 1 | L19 |
| 5 | 7 | 4 | 8 | 1 | M19 |
| 5 | 8 | 4 | 8 | 1 | K22 |
| 6 | 1 | 4 | 8 | 1 | M21 |
| 6 | 2 | 4 | 8 | 1 | K21 |
| 6 | 3 | 4 | 8 | 1 | M15 |
| 6 | 4 | 4 | 8 | 1 | M22 |
| 6 | 5 | 4 | 8 | 1 | Z |
| 6 | 6 | 4 | 8 | 1 | K23 |
| 6 | 7 | 4 | 8 | 1 | L20 |
| 6 | 8 | 4 | 8 | 1 | Z |

| R1 | R2 | R3 | R4 | Plate | Loc |
|----|----|----|----|-------|-----|
| 1 | 3 | 5 | 8 | 15 | Z |
| 1 | 4 | 5 | 8 | 15 | B2 |
| 1 | 5 | 5 | 8 | 15 | B7 |
| 1 | 6 | 5 | 8 | 15 | Z |
| 1 | 7 | 5 | 8 | 15 | B5 |
| 1 | 8 | 5 | 8 | 15 | F9 |
| 2 | 1 | 5 | 8 | 15 | B3 |
| 2 | 2 | 5 | 8 | 15 | D9 |
| 2 | 3 | 5 | 8 | 15 | E6 |
| 2 | 4 | 5 | 8 | 15 | B6 |
| 2 | 5 | 5 | 8 | 15 | F5 |
| 2 | 6 | 5 | 8 | 15 | C6 |
| 2 | 7 | 5 | 8 | 15 | F7 |
| 2 | 8 | 5 | 8 | 15 | F6 |
| 3 | 1 | 5 | 8 | 15 | Z |
| 3 | 2 | 5 | 8 | 15 | C10 |
| 3 | 3 | 5 | 8 | 15 | E8 |
| 3 | 4 | 5 | 8 | 15 | D3 |
| 3 | 5 | 5 | 8 | 15 | D4 |
| 3 | 6 | 5 | 8 | 15 | F4 |
| 3 | 7 | 5 | 8 | 15 | Z |
| 3 | 8 | 5 | 8 | 15 | E9 |
| 4 | 1 | 5 | 8 | 15 | D6 |
| 4 | 2 | 5 | 8 | 15 | Z |

Figs VI.3.2.31-36

| R1 | R2 | R3 | R4 | Plate | Loc |
|----|----|----|----|-------|-----|
| 1 | 3 | 6 | 8 | 15 | C20 |
| 1 | 4 | 6 | 8 | 15 | D18 |
| 1 | 5 | 6 | 8 | 15 | B19 |
| 1 | 6 | 6 | 8 | 15 | F20 |
| 1 | 7 | 6 | 8 | 15 | E19 |
| 1 | 8 | 6 | 8 | 15 | E17 |
| 2 | 1 | 6 | 8 | 15 | B16 |
| 2 | 2 | 6 | 8 | 15 | F15 |
| 2 | 3 | 6 | 8 | 15 | E14 |
| 2 | 4 | 6 | 8 | 15 | E16 |
| 2 | 5 | 6 | 8 | 15 | E22 |
| 2 | 6 | 6 | 8 | 15 | C22 |
| 2 | 7 | 6 | 8 | 15 | E23 |
| 2 | 8 | 6 | 8 | 15 | B15 |
| 3 | 1 | 6 | 8 | 15 | B22 |
| 3 | 2 | 6 | 8 | 15 | D23 |
| 3 | 3 | 6 | 8 | 15 | F14 |
| 3 | 4 | 6 | 8 | 15 | B18 |
| 3 | 5 | 6 | 8 | 15 | E18 |
| 3 | 6 | 6 | 8 | 15 | B17 |
| 3 | 7 | 6 | 8 | 15 | B21 |
| 3 | 8 | 6 | 8 | 15 | D20 |
| 4 | 1 | 6 | 8 | 15 | B20 |
| 4 | 2 | 6 | 8 | 15 | Z |

| | | | | | |
|---|---|---|---|---|---|
| 4 | 3 | 5 | 8 | 15 | B9 |
| 4 | 4 | 5 | 8 | 15 | D11 |
| 4 | 5 | 5 | 8 | 15 | D7 |
| 4 | 6 | 5 | 8 | 15 | E2 |
| 4 | 7 | 5 | 8 | 15 | C3 |
| 4 | 8 | 5 | 8 | 15 | C8 |
| 5 | 1 | 5 | 8 | 15 | B10 |
| 5 | 2 | 5 | 8 | 15 | B11 |
| 5 | 3 | 5 | 8 | 15 | C5 |
| 5 | 4 | 5 | 8 | 15 | Z |
| 5 | 5 | 5 | 8 | 15 | C4 |
| 5 | 6 | 5 | 8 | 15 | D5 |
| 5 | 7 | 5 | 8 | 15 | B8 |
| 5 | 8 | 5 | 8 | 15 | F3 |
| 6 | 1 | 5 | 8 | 15 | Z |
| 6 | 2 | 5 | 8 | 15 | C11 |
| 6 | 3 | 5 | 8 | 15 | E3 |
| 6 | 4 | 5 | 8 | 15 | C9 |
| 6 | 5 | 5 | 8 | 15 | E4 |
| 6 | 6 | 5 | 8 | 15 | Z |
| 6 | 7 | 5 | 8 | 15 | B4 |
| 6 | 8 | 5 | 8 | 15 | D2 |

| | | | | | |
|---|---|---|---|---|---|
| 4 | 3 | 6 | 8 | 15 | C17 |
| 4 | 4 | 6 | 8 | 15 | F19 |
| 4 | 5 | 6 | 8 | 15 | F16 |
| 4 | 6 | 6 | 8 | 15 | D19 |
| 4 | 7 | 6 | 8 | 15 | C23 |
| 4 | 8 | 6 | 8 | 15 | D15 |
| 5 | 1 | 6 | 8 | 15 | C19 |
| 5 | 2 | 6 | 8 | 15 | B14 |
| 5 | 3 | 6 | 8 | 15 | C14 |
| 5 | 4 | 6 | 8 | 15 | E21 |
| 5 | 5 | 6 | 8 | 15 | E15 |
| 5 | 6 | 6 | 8 | 15 | F18 |
| 5 | 7 | 6 | 8 | 15 | F17 |
| 5 | 8 | 6 | 8 | 15 | D17 |
| 6 | 1 | 6 | 8 | 15 | C15 |
| 6 | 2 | 6 | 8 | 15 | C16 |
| 6 | 3 | 6 | 8 | 15 | E20 |
| 6 | 4 | 6 | 8 | 15 | D14 |
| 6 | 5 | 6 | 8 | 15 | B23 |
| 6 | 6 | 6 | 8 | 15 | C18 |
| 6 | 7 | 6 | 8 | 15 | D16 |
| 6 | 8 | 6 | 8 | 15 | C21 |

Figs VI.3.2.37-42

| R1 | R2 | R3 | R4 | Plate | Loc |
|---|---|---|---|---|---|
| 1 | 3 | 7 | 8 | 1 | D07 |
| 1 | 4 | 7 | 8 | 1 | C06 |
| 1 | 5 | 7 | 8 | 1 | F03 |
| 1 | 6 | 7 | 8 | 1 | E07 |
| 1 | 7 | 7 | 8 | 1 | E10 |
| 1 | 8 | 7 | 8 | 1 | C03 |
| 2 | 1 | 7 | 8 | 1 | D11 |
| 2 | 2 | 7 | 8 | 1 | Z |
| 2 | 3 | 7 | 8 | 1 | Z |
| 2 | 4 | 7 | 8 | 1 | E09 |
| 2 | 5 | 7 | 8 | 1 | Z |
| 2 | 6 | 7 | 8 | 1 | E05 |
| 2 | 7 | 7 | 8 | 1 | D05 |
| 2 | 8 | 7 | 8 | 1 | D06 |
| 3 | 1 | 7 | 8 | 1 | E11 |
| 3 | 2 | 7 | 8 | 1 | Z |
| 3 | 3 | 7 | 8 | 1 | B06 |
| 3 | 4 | 7 | 8 | 1 | C02 |
| 3 | 5 | 7 | 8 | 1 | Z |
| 3 | 6 | 7 | 8 | 1 | E04 |
| 3 | 7 | 7 | 8 | 1 | D04 |
| 3 | 8 | 7 | 8 | 1 | B08 |
| 4 | 1 | 7 | 8 | 1 | B07 |
| 4 | 2 | 7 | 8 | 1 | E08 |

FIG. 26A

| | 1D08 | 1D09 | 1F04 | 1C07 | 1D10 | 1F02 | 1B04 | 1F06 | 1C04 | 1C05 | 1C08 | 1E03 | 1D02 | 1C11 | 1B09 | 1B02 | 1B03 | 1E02 | 1C10 | 1B10 | 1B11 | 1B05 |
|---|---|---|---|---|---|---|---|---|---|---|---|---|---|---|---|---|---|---|---|---|---|---|
| | 8 | 8 | 8 | 8 | 8 | 8 | 8 | 8 | 8 | 8 | 8 | 8 | 8 | 8 | 8 | 8 | 8 | 8 | 8 | 8 | 8 | 8 |
| | 7 | 7 | 7 | 7 | 7 | 7 | 7 | 7 | 7 | 7 | 7 | 7 | 7 | 7 | 7 | 7 | 7 | 7 | 7 | 7 | 7 | 7 |
| | 3 | 4 | 5 | 6 | 7 | 8 | 1 | 2 | 3 | 4 | 5 | 6 | 7 | 8 | 1 | 2 | 3 | 4 | 5 | 6 | 7 | 8 |
| | 4 | 4 | 4 | 4 | 4 | 4 | 5 | 5 | 5 | 5 | 5 | 5 | 5 | 5 | 6 | 6 | 6 | 6 | 6 | 6 | 6 | 6 |

FIG. 26B

Rotating Vacuum Cups for Lid Removal    Pin Array (built by Jeff Tong and James Hardwick)

1L19

$C_{29}H_{34}BrNO_6S_2$
Exact Mass: 635.10
Mol. Wt.: 636.62
C, 54.71; H, 5.38; Br, 12.55; N, 2.20; O, 15.08; S, 10.07

1L17
1N22

$C_{33}H_{35}BrN_2O_7S_2$
Exact Mass: 714.11
Mol. Wt.: 715.68
C, 55.38; H, 4.93; Br, 11.16; N, 3.91; O, 15.65; S, 8.96

2F15

$C_{36}H_{46}BrNO_7S$
Exact Mass: 715.22
Mol. Wt.: 716.72
C, 60.33; H, 6.47; Br, 11.15; N, 1.95; O, 15.63; S, 4.47

2C18

C₃₀H₄₀BrNO₆
Exact Mass: 589.20
Mol. Wt.: 590.55
C, 61.01; H, 6.83; Br, 13.53; N, 2.37; O, 16.26

2B21
2B22

C₃₀H₄₂BrNO₉S
Exact Mass: 671.18
Mol. Wt.: 672.63
C, 53.57; H, 6.29; Br, 11.88; N, 2.08; O, 21.41; S, 4.77

4E09
4D02

C₃₅H₅₁BrN₂O₆S
Exact Mass: 706.27
Mol. Wt.: 707.76
C, 59.40; H, 7.26; Br, 11.29; N, 3.96; O, 13.56; S, 4.53

11D20

$C_{35}H_{39}BrN_2O_6S$
Exact Mass: 694.17
Mol. Wt.: 695.66
C, 60.43; H, 5.65; Br, 11.49; N, 4.03; O, 13.80; S, 4.61

9B21

$C_{42}H_{38}BrN_3O_7S_2$
Exact Mass: 839.13
Mol. Wt.: 840.80
C, 60.00; H, 4.56; Br, 9.50; N, 5.00; O, 13.32; S, 7.63

13B20

$C_{40}H_{46}BrF_3N_4O_6S_2$
Exact Mass: 878.20
Mol. Wt.: 879.85
C, 54.60; H, 5.27; Br, 9.08; F, 6.48; N, 6.37; O, 10.91; S, 7.29

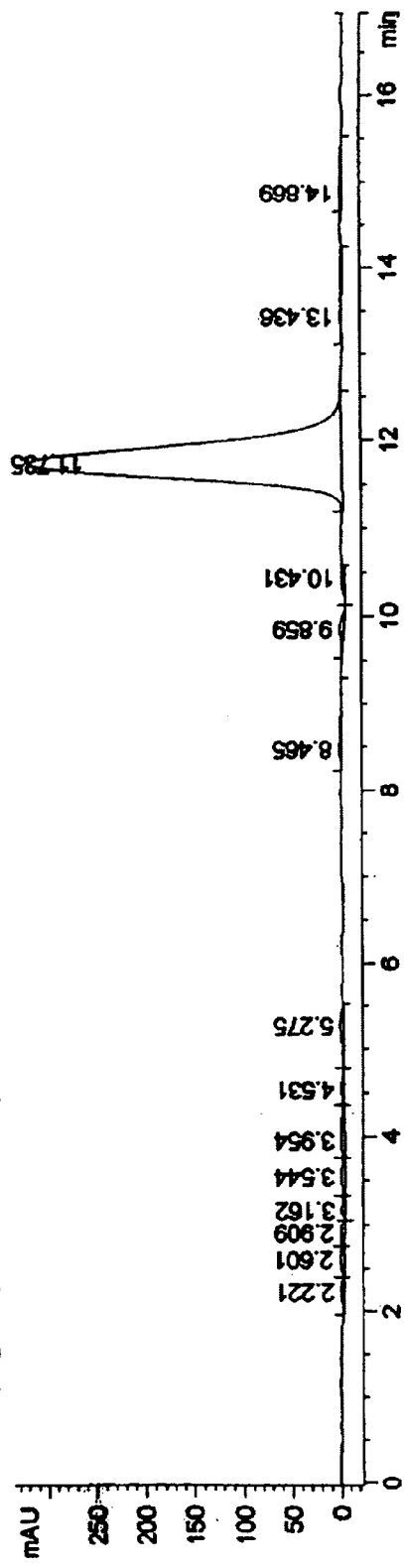
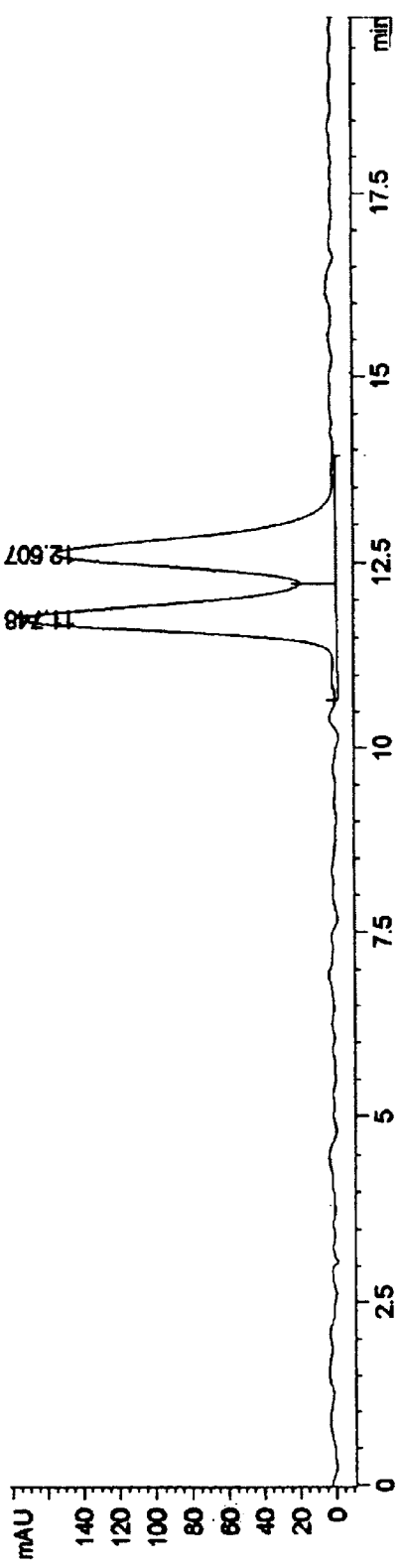
FIG. 44A
FIG. 44B

ALKALOIDS

PRIORITY INFORMATION

The present application is a continuation-in-part application of U.S. patent application Ser. No. 09/838,760, filed Apr. 19, 2001 entitled "Biomimetic Combinatorial Synthesis", which application is a continuation application of U.S. patent application Ser. No. 09/329,970, filed Jun. 10, 1999, entitled "Biomimetic Combinatorial Synthesis", now abandoned, which application claims priority to provisional application No. 60/089,124, filed Jun. 11, 1998, entitled "Biomimetic Combinatorial Synthesis", and the entire contents of each of these applications are hereby incorporated by reference in their entirety.

BACKGROUND OF THE INVENTION

The identification of small organic molecules that affect specific biological functions is an endeavor that impacts both biology and medicine. Such molecules are useful as therapeutic agents and as probes of biological function. In but one example from the emerging field of chemical genetics, in which small molecules can be used to alter the function of biological molecules to which they bind, these molecules have been useful at elucidating signal transduction pathways by acting as chemical protein knockouts, thereby causing a loss of protein function. (Schreiber et al., *J. Am. Chem. Soc.,* 1990, 112, 5583; Mitchison, *Chem. and Biol.,* 1994, 1, 3) Additionally, due to the interaction of these small molecules with particular biological targets and their ability to affect specific biological function, they may also serve as candidates for the development of therapeutics. One important class of small molecules, natural products, which are small molecules obtained from nature, clearly have played an important role in the development of biology and medicine, serving as pharmaceutical leads, drugs (Newman et al., *Nat. Prod. Rep.* 2000, 17, 215–234), and powerful reagents for studying cell biology (Schreiber, S. L. *Chem. and Eng. News* 1992 (Oct. 26), 22–32).

Because it is difficult to predict which small molecules will interact with a biological target, intense efforts have been directed towards the generation of large numbers, or libraries, of small organic compounds. These libraries can then be linked to sensitive screens to identify the active molecules. Of particular interest has been the development of libraries based upon existing natural products. To date, however, libraries based on natural products have been synthesized primarily for the purpose of improving the known biological and pharmacokinetic properties of the parent natural products (Hall, D. G.; Manku, S.; Wang, F. *J. Comb. Chem.* 2001, 3(2), 125–150; Nicolaou, K. C.; Vourloumis, D.; Li, T.; Pastor, J.; Winssinger, N.; He, Y.; Ninkovis, S.; Sarabia, F.; Vallberg, H.; Roschanger, F.; King, N. P.; Finlay, R. V.; Giannakakou, P.; Verdier-Pinard, P.; Hamel, E. *Angew. Chem., Int. Ed. Engl.* 1997, 36, 2097–2103; Nicolaou, K. C.; Winssinger, D.; Vourloumis, D.; Ohshima, T.; Kim, S.; Pfefferkoth, J.; Xu, J.-Y.; Li, T. *J. Am. Chem. Soc.* 1998, 120, 10814–10826; Lee, K. J.; Angulo, A.; Ghazal, P.; Janda, K. D. *Org. Lett.* 1999, 1, 1859–1862; Xu, R.; Greiveldinger, G.; Marenus, L. E.; Cooper, A.; Ellman, J. A. *J. Am. Chem. Soc.* 1999,121, 4898–4899; Wipf, P.; Reeves, J. T.; Balachandran, R.; Giuliano, K. A.; Hamel, E.; Day, B. W. *J. Am. Chem. Soc.* 2000, 122, 9391–9395; Boger, D. L.; Fink, B. E.; Hedrick, M. P. *J. Am. Chem. Soc.* 2000, 122, 6382–6394; Nicolaou, K. C.; Pfefferkorn, J. A.; Barluenga, S.; Mitchell, H. J.; Roecker, A. J.; Cao, G.-Q. *J. Am. Chem. Soc.* 2000, 122, 9968–9976 and references cited therein).

Clearly, as detailed above, a great deal of research has been conducted to optimize existing natural product leads, the development of compounds and libraries of compounds based upon natural products and/or emulating the structural and stereochemical diversity of natural products, but having different biological activities than the parent natural product, would also be useful. Additionally, the development of novel synthetic methodologies would assist in the development of new classes of complex compounds and libraries of compound. In order achieve greater diversity and complexity in the synthesis of compounds and particularly libraries of compounds, it would be desirable to develop such methods by either utilizing or emulating the rapid and stereoselective pathways that nature uses in the synthesis of natural products for the efficient production of complex compounds and libraries of compounds. Any resultant novel complex compounds and libraries based on biomimetic pathways will certainly be useful in the quest to discover either non-natural compounds having the binding affinities and specific characteristics of natural products, themselves the products of genetic recombination and natural selection, or will be particularly useful in the quest to discover compounds based upon natural products that exhibit novel biological properties.

SUMMARY OF THE INVENTION

In one aspect of the invention, novel compounds having the structure (I) are provided:

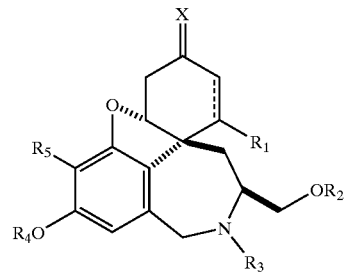

(I)

wherein $R_1$ is hydrogen or halogen, or is an aliphatic, heteroaliphatic, aryl, heteroaryl, alkylaryl, alkylheteroaryl moiety or is $SR_A$, $N(R_A)_2$, or $OR_A$, wherein $R_A$ is hydrogen or is an aliphatic, heteroaliphatic, aryl, heteroaryl, alkylaryl, or alkylheteroaryl moiety, and wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein $R_2$ is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted, or $R_2$ is a solid support optionally attached through a linker moiety;

wherein $R_3$ is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl, or alkylheteroaryl moieties may be substituted or unsubstituted; or wherein $R_3$ is —CN; —O(CN)$R_x$; —C(O)$R_x$; —CO$_2$ ($R_x$); —CON($R_x$)$_2$; —OC(O)$R_x$; —OCO$_2R_x$; —OCON($R_x$)$_2$; —N($R_x$)$_2$; —S(O)$_2R_x$; wherein each occurrence of $R_1$ is aliphatic, heteroaliphatic, aryl, heteroaryl, alkylaryl, or alkylheteroaryl, wherein any of the aliphatic, heteroaliphatic, alkylaryl, or alkylheteroaryl substituents may be substituted or unsubstituted, branched or unbranched, cyclic or acyclic, and wherein any of the aryl or heteroaryl substituents may be substituted or unsubstituted;

wherein $R_4$ is is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein $R_5$ is hydrogen, halogen, —NO$_2$, —CN, —C(O)$R_x$, —CO$_2$($R_x$), —CON($R_x$)$_2$, —OC(O)$R_x$, —OCO$_2R_x$, —OCON($R_x$)$_2$, —N($R_x$)$_2$, —S(O)$_2R_x$, wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted; or $R_5$ is an aliphatic, heteroaliphatic, aryl, heteroaryl, alkylaryl, alkylheteroaryl moiety, or is $SR_A$, $N(R_A)_2$, or $OR_A$, wherein $R_A$ is an aliphatic, heteroaliphatic, aryl, heteroaryl, alkylaryl, or alkylheteroaryl moiety, and wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein X is O, S or NR$_6$, wherein R$_6$ is OR$_7$, NHR$_7$, or NH(S(=O)$_2$)R$_7$, wherein R$_7$ is aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted; and wherein the dotted line indicates the absence of a bond or indicates a bond, whereby a single bond or double bond is present, respectively.

In certain embodiments, compounds having the structure (II) are provided:

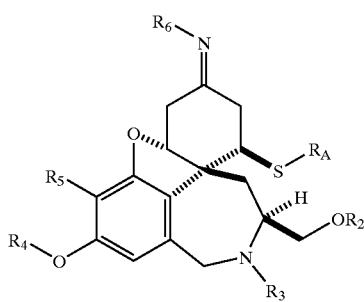

(II)

wherein $R_A$ is hydrogen or is an aliphatic, heteroaliphatic, aryl, heteroaryl, alkylaryl, or alkylheteroaryl moiety, and wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein $R_2$ is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted, or $R_2$ is a solid support optionally attached through a linker moiety;

wherein $R_3$ is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl, or alkylheteroaryl moieties may be substituted or unsubstituted; or wherein $R_3$ is —CN; —O(CN)$R_x$; —C(O)$R_x$; —CO$_2$($R_x$); —CON($R_x$)$_2$; —OC(O)$R_x$; —OCO$_2R_x$; —OCON($R_x$)$_2$; —N($R_x$); —S(O)$_2R_x$; wherein each occurrence of $R_x$ is aliphatic, heteroaliphatic, aryl, heteroaryl, alkylaryl, or alkylheteroaryl, wherein any of the aliphatic, heteroaliphatic, alkylaryl, or alkylheteroaryl substituents may be substituted or unsubstituted, branched or unbranched; cyclic or acyclic, and wherein any of the aryl or heteroaryl substituents may be substituted or unsubstituted;

wherein $R_4$ is is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein $R_5$ is hydrogen, halogen, —NO$_2$, —CN, —C(O)$R_x$, —CO$_2$($R_x$), —CON($R_x$)$_2$, —OC(O)$R_x$, —OCO$_2R_x$, —OCON($R_x$)$_2$, —N($R_x$)$_2$, —S(O)$_2R_x$, wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted; or $R_5$ is an aliphatic, heteroaliphatic, aryl, heteroaryl, alkylaryl, alkylheteroaryl moiety, or is $SR_A$, $N(R_A)_2$, or $OR_A$, wherein $R_A$ is an aliphatic, heteroaliphatic, aryl, heteroaryl, alkylaryl, or alkylheteroaryl moiety, and wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted; and wherein $R_6$ is OR$_7$, NHR$_7$, or NH(S(=O)$_2$)R$_7$, wherein R$_7$ is aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted.

In yet other embodiments, collection of compounds comprising two or more of the compounds of structures (I) or (II) are provided. In certain embodiments, the collection is provided in array format. In yet other embodiments, the collection is provided in array format on a glass slide. In still other embodiments, the collection comprises at least 100 compounds. In yet other embodiments, the collection comprises at least 1,000 compounds. In still further embodiments, the collection comprises at least 2,000 compounds. In yet other embodiments, the collection comprises at least 10,000 compounds.

In another aspect of the invention, a method for the synthesis of the core structure (III) is provided, said method comprising:

providing two phenolic precursors having the structures:

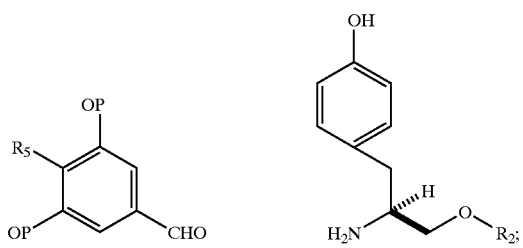

subjecting the two phenolic precursors to suitable conditions to generate an intermediate having the structure:

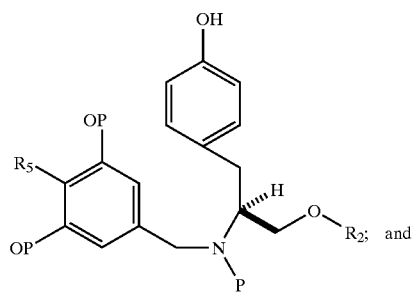

subjecting the intermediate to suitable conditions to effect oxidation and subsequent cyclization to generate a scaffold having the core structure (III):

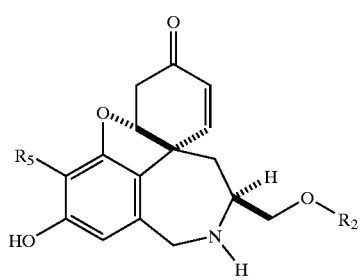

wherein $R_2$ is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted, or $R_2$ is a solid support optionally attached through a linker moiety wherein $R_5$ is hydrogen, halogen, $-NO_2$, $-CN$, $-C(O)R_x$, $-CO_2(R_x)$, $-CON(R_x)_2$, $-OC(O)R_x$, $-OCO_2R_x$, $-OCON(R_x)_2$, $-N(R_x)_2$, $-S(O)_2R_x$, wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted; or $R_5$ is an aliphatic, heteroaliphatic, aryl, heteroaryl, alkylaryl, alkylheteroaryl moiety, or is $SR_A$, $N(R_A)_2$, or $OR_A$, wherein $R_A$ is an aliphatic, heteroaliphatic, aryl, heteroaryl, alkylaryl, or alkylheteroaryl moiety, and wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted; and wherein P is an oxygen protecting group.

In certain embodiments, the method further comprises subjecting the core structure (III) to one or more diversification reactions to generate one or more compounds having the structure (I):

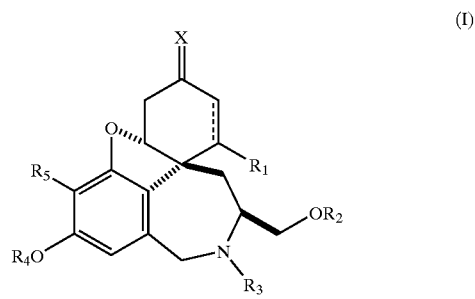

wherein $R_1$ is hydrogen or halogen, or is an aliphatic, heteroaliphatic, aryl, heteroaryl, alkylaryl, alkylheteroaryl moiety or is $SR_A$, $N(R_A)_2$, or $OR_A$, wherein $R_A$ is hydrogen or is an aliphatic, heteroaliphatic, aryl, heteroaryl, alkylaryl, or alkylheteroaryl moiety, and wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein $R_2$ is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted, or $R_2$ is a solid support optionally attached through a linker moiety;

wherein $R_3$ is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl, or alkylheteroaryl moieties may be substituted or unsubstituted; or wherein $R_3$ is —CN; —O(CN)$R_x$; —C(O)$R_x$; —CO$_2$($R_x$); —CON($R_x$)$_2$; —OC(O)$R_x$; —OCO$_2$$R_x$; —OCON($R_x$)$_2$; —N($R_x$)$_2$; —S(O)$_2$$R_x$; wherein each occurrence of $R_x$ is aliphatic, heteroaliphatic, aryl, heteroaryl, alkylaryl, or alkylheteroaryl, wherein any of the aliphatic, heteroaliphatic, alkylaryl, or alkylheteroaryl substituents may be substituted or unsubstituted, branched or unbranched, cyclic or acyclic, and wherein any of the aryl or heteroaryl substituents may be substituted or unsubstituted;

wherein $R_4$ is is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein $R_5$ is hydrogen, halogen, —NO$_2$, —CN, —C(O)$R_x$, —CO$_2$($R_x$), —CON($R_x$)$_2$, —OC(O)$R_x$, —OCO$_2$$R_x$, —OCON($R_x$)$_2$, —N($R_x$)$_2$, —S(O)$_2$$R_x$, wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted; or $R_5$ is an aliphatic, heteroaliphatic, aryl, heteroaryl, alkylaryl, alkylheteroaryl moiety, or is $SR_A$, $N(R_A)_2$, or $OR_A$, wherein $R_A$ is an aliphatic, heteroaliphatic, aryl, heteroaryl, alkylaryl, or alkylheteroaryl moiety, and wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein X is O, S or $NR_6$, wherein $R_6$ is $OR_7$, $NHR_7$, or $NH(S(=O)_2)R_7$, wherein $R_7$ is aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted; and wherein the dotted line indicates the absence of a bond or indicates a bond, whereby a single bond or double bond is present, respectively.

In yet another embodiment, the method further comprises subjecting the core structure (III) to one or more diversification reactions to generate one or more compounds having the structure (II):

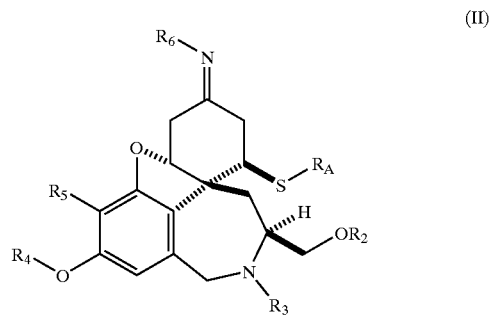

wherein $R_A$ is hydrogen or is an aliphatic, heteroaliphatic, aryl, heteroaryl, alkylaryl, or alkylheteroaryl moiety, and wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein $R_2$ is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted, or $R_2$ is a solid support optionally attached through a linker moiety;

wherein $R_3$ is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl, or alkylheteroaryl moieties may be substituted or unsubstituted; or wherein $R_3$ is —CN; —O(CN)$R_x$; —C(O)$R_x$; —CO$_2$($R_x$); CON($R_x$)$_2$; —OC(O)$R_x$; —OCO$_2$$R_x$; —OCON($R_x$)$_2$; —N($R_x$)$_2$; —S(O)$_2$$R_x$; wherein each occurrence of $R_x$ is aliphatic, heteroaliphatic, aryl, heteroaryl, alkylaryl, or alkylheteroaryl, wherein any of the aliphatic, heteroaliphatic, alkylaryl, or alkylheteroaryl substituents may be substituted or unsubstituted, branched or unbranched, cyclic or acyclic, and wherein any of the aryl or heteroaryl substituents may be substituted or unsubstituted;

wherein $R_4$ is is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein $R_5$ is hydrogen, halogen, —NO$_2$, —CN, —C(O)$R_x$, —CO$_2$($R_x$), —CON($R_x$)$_2$, —OC(O)$R_x$, —OCO$_2$$R_x$, —OCON($R_x$)$_2$, —N($R_x$)$_2$, —S(O)$_2$$R_x$, wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted; or $R_5$ is an aliphatic, heteroaliphatic, aryl, heteroaryl, alkylaryl, alkylheteroaryl moiety, or is $SR_A$, $N(R_A)_2$, or $OR_A$, wherein $R_A$ is an aliphatic, heteroaliphatic, aryl, heteroaryl, alkylaryl, or alkylheteroaryl moiety, and wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted; and wherein $R_6$ is $OR_7$, $NHR_7$, or $NH(S(=O)_2)R_7$, wherein $R_7$ is aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted.

In yet another aspect of the invention, pharmaceutical compositions are provided comprising any one of the compounds described above and herein; and a pharmaceutically acceptable carrier or diluent.

In still another aspect of the invention, methods of treating a variety of disorders are provided comprising administering a therapeutically effective compound or composition thereof to a subject in need thereof. In certain embodiments, the inventive compounds are utilized to effect wound healing. In certain other embodiments, the inventive compounds are utilized to treat proliferative disorders, including, but not limited to cancer. In certain other embodiments, the inventive compounds are utilized to treat reproductive disorders. In still other embodiments, the inventive compounds are utilized to treat bacterial or protozoal infections.

Definitions

This invention provides a new family of compounds with a range of biological properties. Compounds of this invention have biological activities relevant for the treatment of diseases including proliferative diseases such as cancer, wound healing, and bacterial infections to name a few. Compounds of this invention include those specifically set forth above and described herein, and are illustrated in part by the various classes, subgenera and species disclosed elsewhere herein.

It will be appreciated by one of ordinary skill in the art that asymmetric centers may exist in the compounds of the present invention. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, a mixtures of stereoisomers or diastereomers are provided.

Additionally, the present invention provides pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative disorders, cancer, wound healing, infectious diseases, and immunological diseases. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes both straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups.

In certain embodiments, the alkyl, alkenyl and alkynyl groups employed in the invention contain 1–20 aliphatic carbon atoms. In certain other embodiments, the alkyl, alkenyl, and alkynyl groups employed in the invention contain 1–10 aliphatic carbon atoms. In still other embodiments, the alkyl, alkenyl, and alkynyl groups employed in the invention contain 1–6 aliphatic carbon atoms. In yet other embodiments, the alkyl, alkenyl, and alkynyl groups employed in the invention contain 1–4 aliphatic carbon atoms. Illustrative aliphatic groups thus include, but are not limited to, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alkoxy", or "thioalkyl" as used herein refers to an alkyl group, as previously defined, attached to the parent molecular moiety through an oxygen atom or through a sulfur atom. In certain embodiments, the alkyl group contains 1–20 alipahtic carbon atoms. In certain other embodiments, the alkyl group contains 1–10 aliphatic carbon atoms. In still other embodiments, the alkyl group contains 1–6 aliphatic carbon atoms. In yet other embodiments, the alkyl group contains 1–4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. In certain embodiments, the alkyl group contains 1–20 aliphatic carbon atoms. In certain other embodiments, the alkyl group contains 1–10 aliphatic carbon atoms. In still other embodiments, the alkyl group contains 1–6 aliphatic carbon atoms. In yet other embodiments, the alkyl group contains 1–4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples which are described herein.

In general, the terms "aryl" and "heteroaryl", as used herein, refer to stable mono- or polycyclic, heterocyclic, polycyclic, and polyheterocyclic unsaturated moieties having preferably 3–14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R)_2$; —$S(O)_2R_x$; wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or hetercyclic moieties, may optionally be substituted with substituents including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

The term "heteroaliphatic", as used herein, refers to aliphatic moieties which contain one or more oxygen, sulfur, nitrogen, phosphorous or silicon atoms, e.g., in place of carbon atoms. Heteroaliphatic moieties may be branched, unbranched or cyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

The term "solid support", as used herein, refers to a material having a rigid or semi-rigid surface. Such materials will preferably take the form of small beads, pellets, disks, chips, dishes, multi-well plates, glass slides, wafers, or the like, although other forms may be used. In some embodiments, at least one surface of the substrate will be substantially flat. The term "surface" refers to any generally two-dimensional structure on a solid substrate and may have steps, ridges, kinks, terraces, and the like without ceasing to be a surface.

The term "polymeric support", as used herein, refers to a soluble or insoluble polymer to which an amino acid or other chemical moiety can be covalently bonded by reaction with a functional group of the polymeric support. Many suitable polymeric supports are known, and include soluble polymers such as polyethylene glycols or polyvinyl alcohols, as well as insoluble polymers such as polystyrene resins. A suitable polymeric support includes functional groups such as those described below. A polymeric support is termed "soluble" if a polymer, or a polymer-supported compound, is soluble under the conditions employed. However, in general, a soluble polymer can be rendered insoluble under defined conditions. Accordingly, a polymeric support can be soluble under certain conditions and insoluble under other conditions.

The term "linker", as used herein, refers to a chemical moiety utilized to, attach a compound of interest to a solid support to facilitate synthesis of inventive compounds. Exemplary linkers are described in Example 2, as described herein. It will be appreciated that other linkers (including silicon-based linkers and other linkers) that are known in the art can also be employed for the synthesis of the compounds of the invention.

DESCRIPTION OF THE DRAWING

FIGS. 7–22 depict compound locations, as detailed in Example 1.

FIGS. 23–26 depict compound locations, as detailed in Example 1.

FIG. 44 depicts evaluation of the enantiomeric purity of compound 20 by chiral HPLC. (A) HPLC of 20 @230 nm, major peak retention time=11.7 minutes; (B) HPLC of rac-20 @ 230 nm, major peaks retention time=11.7 minutes and 12.6 minutes.

DETAILED DESCRIPTION OF THE INVENTION

As stated above, natural products are central to biology and medicine, serving as pharmaceutical leads, drugs, and powerful reagents for studying cell biology. Although many studies have been directed to the development of compounds and libraries of compounds that are based upon natural products (e.g., cytotoxicity, antibacterial activity), it would also be beneficial to develop compounds and libraries of compounds that are either based upon natural products, or that emulate certain properties of natural products (e.g., diversity and density of functionalization, or rich stereochemistry, to name a few), but that would exhibit novel and different biological properties. It would additionally be beneficial to develop facile routes to those compounds that would enable rapid construction of detailed core structures and that would enable diversification.

Figure 1:
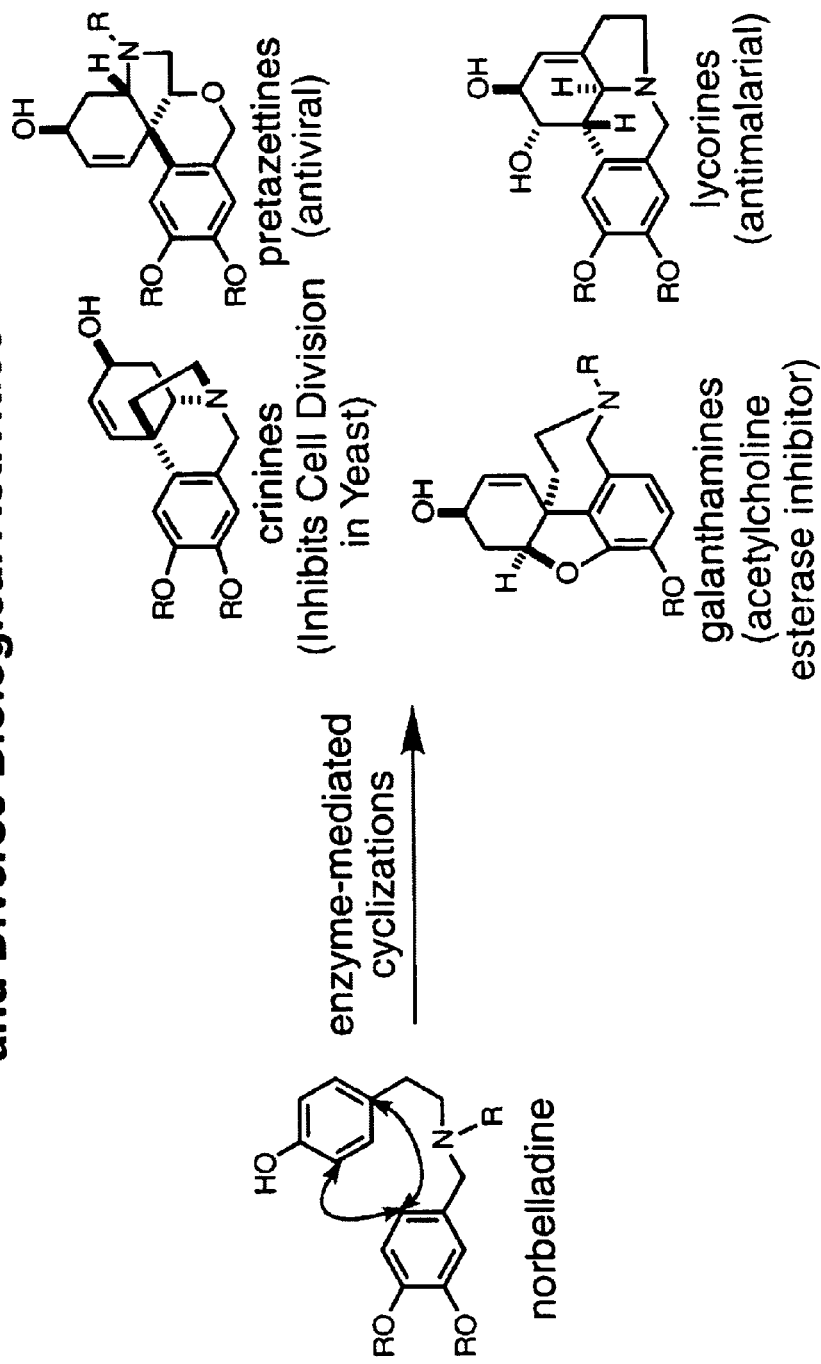
FIG. 1 depicts structures of amaryllidacaeae alkaloids.

Thus, in one aspect of the invention, novel and structurally diverse compounds and libraries of compounds are provided which exhibit a diverse range of biological activity. Another aspect of the invention is the recognition that, in nature, elegant and powerful synthetic pathways are often employed to produce complex biological molecules (See, FIG. 1). Chemical synthesis strategies can sometimes be designed to recreate a biological reaction process in a solid phase (or solution phase) reaction process. Furthermore, in addition to the reaction of exact biological reaction processes, chemical synthesis strategies can also sometimes be designed to improve upon or change a biological reaction process thus gaining efficient access to reaction pathways or stereospecificities previously unavailable in natural products. Certain exemplary compounds and methods are described in more detail below; however, it will be appreciated that the specific examples as described herein are not intended to limit the scope of the invention.

General Description of Compounds of the Invention

As detailed above, in one aspect of the invention, novel alkaloids having the following structure (I) are provided:

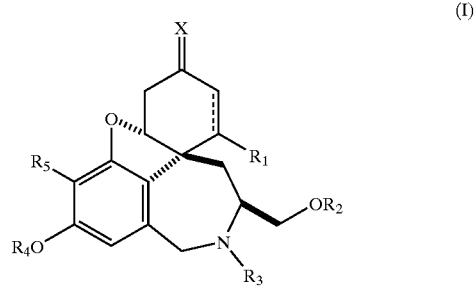

(I)

wherein R$_1$ is hydrogen or halogen, or is an aliphatic, heteroaliphatic, aryl, heteroaryl, alkylaryl, alkylheteroaryl moiety or is SR$_A$, N(R$_A$)$_2$, or OR$_A$, wherein R$_A$ is hydrogen or is an aliphatic, heteroaliphatic, aryl, heteroaryl, alkylaryl, or alkylheteroaryl moiety, and wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein $R_2$ is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted, or $R_2$ is a solid support optionally attached through a linker moiety;

wherein $R_3$ is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl, or alkylheteroaryl moieties may be substituted or unsubstituted; or wherein $R_3$ is —CN; —O(CN)$R_x$; —C(O)$R_x$; —CO$_2$ ($R_x$); —CON($R_x$)$_2$; —OC(O)$R_x$; —OCO$_2R_x$; —OCON($R_x$)$_2$; —N($R_x$)$_2$; —S(O)$_2R_x$; wherein each occurrence of $R_x$ is aliphatic, heteroaliphatic, aryl, heteroaryl, alkylaryl, or alkylheteroaryl, wherein any of the aliphatic, heteroaliphatic, alkylaryl, or alkylheteroaryl substituents may be substituted or unsubstituted, branched or unbranched, cyclic or acyclic, and wherein any of the aryl or heteroaryl substituents may be substituted or unsubstituted;

wherein $R_4$ is is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein $R_5$ is hydrogen, halogen, —NO$_2$, —CN, —C(O)$R_x$, —CO$_2(R_x)$, —CON($R_x$)$_2$, —OC(O)$R_x$, —OCO$_2R_x$, —OCON($R_x$)$_2$, —N($R_x$)$_2$, —S(O)$_2R_x$, wherein each occurrence of $R_x$ independently includes, but is not limited to, aliphatic, heteroaliphatic, aryl, heteroaryl, alkylaryl, or alkylheteroaryl, wherein any of the aliphatic; heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted; or $R_5$ is an aliphatic, heteroaliphatic, aryl, heteroaryl, alkylaryl, alkylheteroaryl moiety, or is $SR_A$, $N(R_A)_2$; or $OR_A$, wherein $R_A$ is an aliphatic, heteroaliphatic, aryl, heteroaryl, alkylaryl, or alkylheteroaryl moiety, and wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein X is O, S or NR$_6$, wherein R$_6$ is OR$_7$, NHR$_7$, or NH(S(=O)$_2$)R$_7$, wherein R$_7$ is aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted; and wherein the dotted line indicates the absence of a bond or indicates a bond, whereby a single bond or double bond is present, respectively.

In one exemplary subset of the invention, compounds having the following structure (II) are provided:

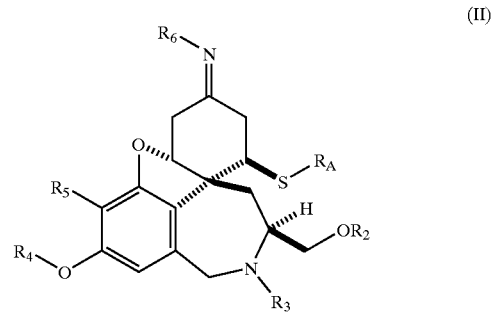

(II)

wherein $R_A$ is hydrogen or is an aliphatic, heteroaliphatic, aryl, heteroaryl, alkylaryl, or alkylheteroaryl moiety, and wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein $R_2$ is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted, or $R_2$ is a solid support optionally attached through a linker moiety;

wherein $R_3$ is hydrogen or is an aliphatic, heteroaliphatic, aryl; heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl, or alkylheteroaryl moieties may be substituted or unsubstituted; or wherein $R_3$ is —CN; —O(CN)$R_x$; —C(O)$R_x$; —CO$_2$ ($R_x$); —CON($R_x$)$_2$; —OC(O)$R_x$; —OCO$_2R_x$; —OCON($R_x$)$_2$; —N($R_x$)$_2$; —S(O)$_2R_x$; wherein each occurrence of $R_x$ is aliphatic, heteroaliphatic, aryl, heteroaryl, alkylaryl, or alkylheteroaryl, wherein any of the aliphatic, heteroaliphatic, alkylaryl, or alkylheteroaryl substituents may be substituted or unsubstituted, branched or unbranched, cyclic or acyclic, and wherein any of the aryl or heteroaryl substituents may be substituted or unsubstituted;

wherein $R_4$ is is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted;

wherein $R_5$ is hydrogen, halogen, —NO$_2$, —CN, —C(O)$R_x$, —CO$_2(R_x)$, —CON($R_x$)$_2$, —OC(O)$R_x$, —OCO$_2R_x$, —OCON($R_x$)$_2$, —N($R_x$)$_2$, —S(O)$_2R_x$, wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted; or $R_5$ is an aliphatic, heteroaliphatic, aryl, heteroaryl, alkylaryl, alkylheteroaryl moiety, or is $SR_A$, $N(R_A)_2$, or $OR_A$, wherein $R_A$ is an aliphatic, heteroaliphatic, aryl, heteroaryl, alkylaryl, or alkylheteroaryl moiety, and wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted; and wherein $R_6$ is $OR_7$, $NHR_7$, or $NH(S(=O)_2)R_7$, wherein $R_7$ is aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted.

In still other subsets of the invention, compounds are provided in which the phenol ($R_4$) is functionalized. In other subsets of the invention, compounds are provided in which the enone ($R_1$) is functionalized. In still other subsets of the invention, compounds are provided in which the nitrogen ($R_3$) is functionalized. In yet other subsets of the invention, compounds are provided in which X is a ketone and is functionalized. In still other subsets of the invention, compounds are provided in which $R_2$ is a solid support linked through a silyl linker as described in Example 2 herein. In further subsets of the invention, compounds having functionalization at two or more of these sites are provided. In still other subsets of the invention, compounds having functionalization at each of these sites are provided. In certain other subsets of the invention, compounds are provided as described using the reagents detailed in Example 1.

In another embodiment of the invention, the inventive compounds are provided as a collection and thus may be provided as a collection of two or more of any of the compounds as detailed above or as described herein. In certain embodiments, the collection is provided in array format. In certain other embodiments, the collection is provided in array format on a glass slide. In still other embodiments, the collection comprises at least 100 compounds. In yet other embodiments, the collection comprises at least 1,000, 2,000 or 10,000 compounds.

Synthetic Methodology

Figure 2:
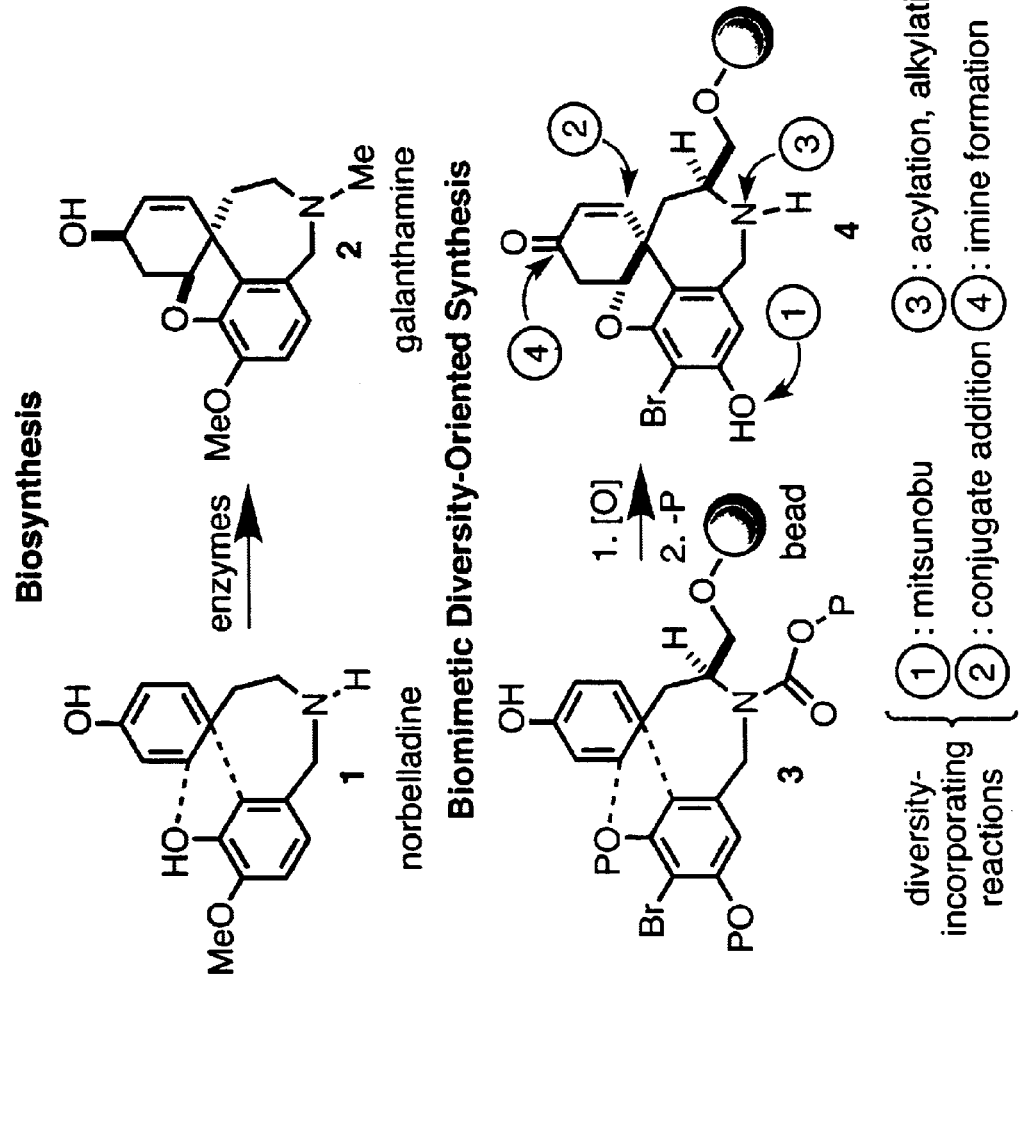
FIG. 2 depicts Biomimetic Diversity Oriented Synthesis.

In yet another aspect of the present invention, novel methods for the synthesis of the novel alkaloids as described herein are provided. In general, the method takes advantage of efficient biomimetic reactions as depicted in FIG. 2 (see also, Biomimetic syntheses of galanthamine: (a) Barton, D. H. R.; Kirby, G. W. J. Chem. Soc. 1962, 806–817. (b) Shimizu, K.; Tomioka, K.; Yamada, S.; Koga, K. Chem. Pharm. Bull. 1978, 26, 3765–3771. (c) Kita, Y.; Arisawa, M.; Gyoten, M.; Nakajima, M.; Hamada, R.; Tohma, H.; Takada, T. J. Org. Chem. 1998, 63, 6625–6633), paralleling the biosynthesis of the natural product, as shown in FIG. 2 (Barton, D. H. R.; Cohen, T. Festschrift A. Stoll; Birkhauser, Basel, 1957). Following biomimetic solid phase synthesis of the core structure (4), as depicted in FIG. 2, four diversity generating reactions were performed to complete the synthesis of each member of the library of compounds.

More generally, according to the method of the present invention, a core structure can be provided which core structure is synthesized by the method comprising:

providing two phenolic precursors having the structures:

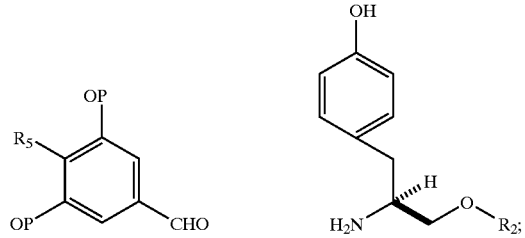

subjecting the two phenolic precursors to suitable conditions to generate an intermediate having the structure:

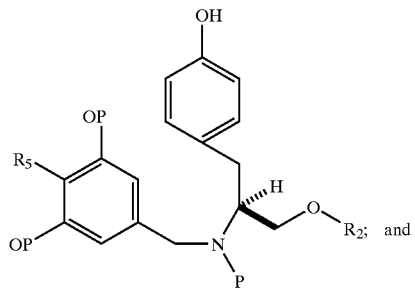

subjecting the intermediate to suitable conditions to effect oxidation and subsequent cyclization to generate a scaffold having the core structure (III):

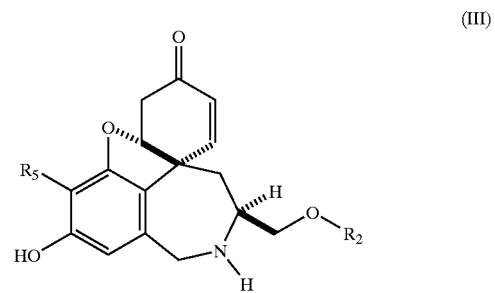

(III)

wherein $R_2$ is hydrogen or is an aliphatic, heteroaliphatic, aryl, heteroaryl, alkylaryl, alkylheteroaryl moiety, wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted, or $R_2$ is a solid support optionally attached through a linker moiety wherein $R_5$ is hydrogen, halogen, —$NO_2$, —CN, —C(O)$R_x$, —$CO_2$($R_x$), —CON($R_x$)$_2$, —OC(O)$R_x$, —$OCO_2R_x$, —OCON($R_x$)$_2$, —N($R_x$)$_2$, —S(O)$_2R_x$, wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted; or $R_5$ is an aliphatic, heteroaliphatic, aryl, heteroaryl, alkylaryl, alkylheteroaryl moiety, or is $SR_A$, $N(R_A)_2$, or $OR_A$, wherein $R_A$ is an aliphatic, heteroaliphatic, aryl, heteroaryl, alkylaryl, or alkylheteroaryl moiety, and wherein each of the aliphatic and heteroaliphatic moieties may be substituted or unsubstituted, cyclic or acyclic, or branched or unbranched, and wherein each of the aryl, heteroaryl, alkylaryl or alkylheteroaryl moieties may be substituted or unsubstituted; and wherein P is an oxygen protecting group. It will be appreciated that, in addition to the specific protecting groups as described in the Examples herein, a variety of well-known protecting groups in the art of organic synthesis can also be utilized as detailed in Greene and Wuts, *Protective Groups in Organic Synthesis*, Third Edition, John Wiley & Sons, New York: 1999, the entire contents of which are hereby incorporated by reference.

Once the core structure is prepared, as detailed above, one or more compounds can be synthesized via combinatorial techniques, or by synthesizing one compound at a time, by diversifying at particular functional groups. Thus, in another embodiment, the method further comprises functionalizing the core structure (III) at one or more sites to generate compounds having the structures (I) or (II). For example, the phenol can be functionalized via Mitsunobu reaction; enone functionalization occurs via conjugate addition and can be diversified using oxygen, sulfur, nitrogen or carbon nucleophiles; the amine can be functionalized via acylation or alkylation; and the ketone can be diversified via imine formation, to name a few. In certain exemplary embodiments, phenol functionalization is achieved using 3-Nitrobenzyl alcohol, cyclopropylmethanol, 3-phenoxy-1-propanol, 3-cyclopentyl-1-propanol, 5-hexen-1-ol, or a skip codon is utilized. In certain exemplary embodiments enone functionalization is achieved using furfuryl mercaptan, 3-(trifluoromethyl)benzyl mercaptan, 3-methyl-1-buranethiol, 4-methoxy-alpha-toluenethiol, benzyl mercaptan, 2-(tert butyldimethylsiloxy)ethylmercaptan, cyclopentanethiol, or a skip codon. In certain embodiments, amine (nitrogen) functionalization is achieved using benzoyl chloride, benzyl isocyanate, ethyl isocyanate, thiophene-2-carbonyl chloride, 3-(methylthio)propionaldehyde, undecanal, cyclopropanecarboxaldehyde, or a skip codon. In certain embodiments, ketone functionalization is achieved using p-toluenesulfonhydrazide, dansyl hydrazine, methoxyamine hydrochloride, o-Benzylhydroxylamine hydrochloride, Carboxymethoxylamine hemihydrochloride, p-Methoxybenzensulfonylhydrazide, 4-Nitrophenylhydrazine or a skip codon.

Although certain exemplary diversification reactions and reagents are described in more detail herein, it will be appreciated that the present invention is intended to encompass equivalent diversification reactions within the arsenal of synthetic organic chemistry that can be utilized to diversify the inventive scaffold as described herein (see, for example, March, J. *Advanced Organic Chemistry*, Fourth Edition, John Wiley & Sons, New York: 1992, the entire contents of which are hereby incorporated by reference). For example, although certain reagents for phenol functionalization are described in the examples (e.g., cyclopropylmethanol), it will be appreciated that other derivatives can be utilized (e.g., cyclopropylethanol, cyclopropylpropanol, etc.), including, but not limited to, homologues and other similarly substituted moieties. In but another example, while cyclopentanethiol is described herein for enone functionalization, it will be appreciated that alkylcyclopentanethiol reagents or cyclohexanethiol reagents can also be utilized to name a few. These additional examples are not intended to limit the scope of the invention; rather they are provided to exemplify the broad utility of the inventive scaffold in the employment of a variety of diversification reactions and reagents.

Figure 3:
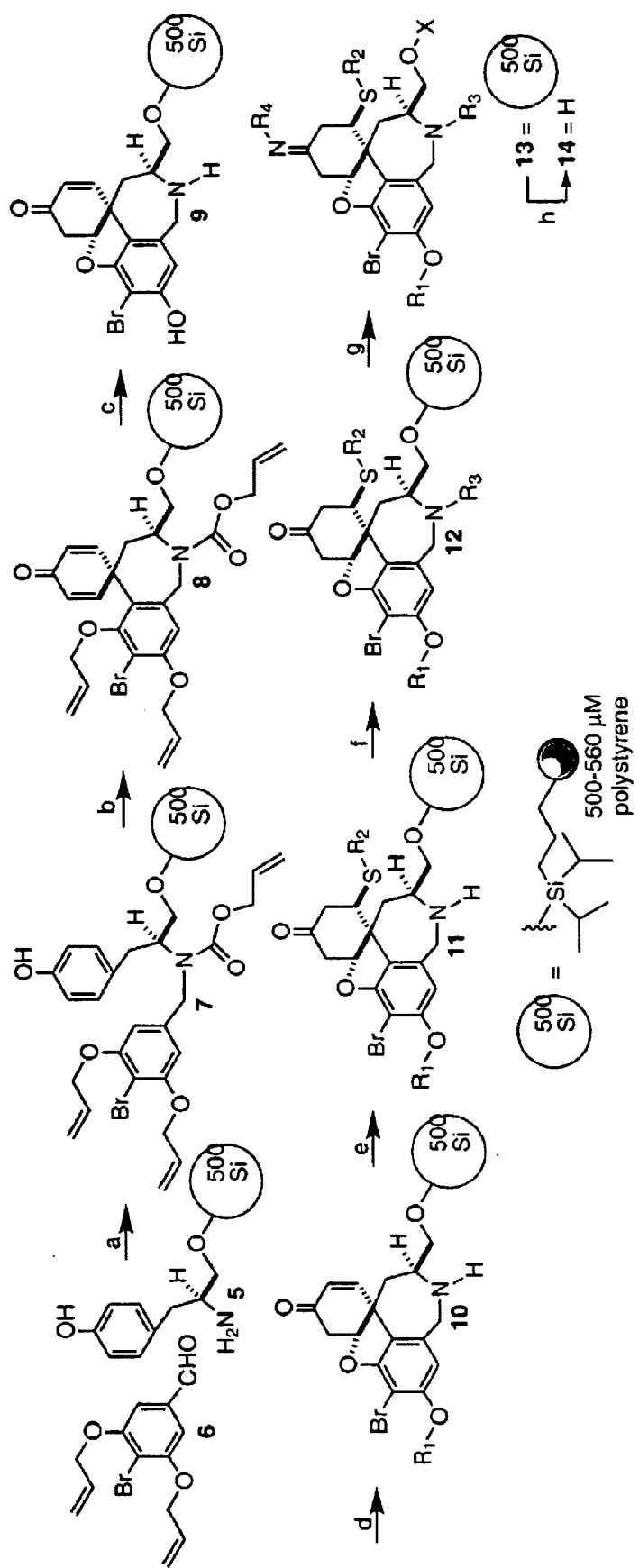
FIG. 3 depicts the synthesis of novel alkaloids.

In one exemplary embodiment, as depicted in FIG. 3, and as described in Example 1, the library synthesis utilized a tyrosine derivative to 500–600 μm high capacity (1.43 mmol/g) polystyrene beads through a Si—O bond to generate 5 upon deprotection (Scheme 1) (Tallarico, J. A.; Depew, K. M.; Pelish, H. E.; Westwood, N. J.; Lindsley, C. W.; Shair, M. D.; Schreiber, S. L.; Foley, M. A. *J. Comb. Chem.*, 2001, 3(3), 312–318; see also Example 2, herein). Reductive amination (Look, G. C.; Murphy, M. M.; Campbell, D. A.; Gallop, M. A. *Tet. Lett.* 1995, 36, 2937–2940) and protecting group adjustments produced 7. Exposure of 7 to $PhI(OAc)_2$ (For the use of hypervalent iodine (III) reagents in similar oxidations, see Krihna, K. V. R.; Sujatha, K.; Kapil, R. S. *Tet. Lett.* 1990, 31, 1351–1352. Kita, Y.; Takada, T.; Gyoten, M.; Tohma, H.; Zenk, M. H.; Eichhorn, J. *J. Org. Chem.* 1996, 61, 5857–5864 and references therein) afforded 8 which was then converted to 9 via Pd-mediated deprotection and spontaneous cyclization.

Pharmaceutical Compositions

As detailed herein, several of the inventive compositions have been determined to have a wide range of biological activities (e.g., inhibition of cell cycle, wound healing, antibacterial effect). Thus, in another aspect of the present invention, pharmaceutical compositions are provided, wherein these compositions include a compound that is useful in treating a "physiological condition," defined herein as any biological or biochemical process that affects the health of an individual, and a pharmaceutically acceptable carrier. It will be appreciated that the inventive pharmaceutical compositions encompasses each of those compounds identified that inhibit or activate any physiological process.

It will also be appreciated that certain of the compounds of the present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences,* 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutical Compositions

In yet another aspect, according to the methods of treatment of the present invention, physiological conditions are treated or prevented in a subject such as a human, lower mammal, or other organism, by administering to the patient a therapeutically effective amount of an inventive compound or pharmaceutical composition thereof, as described in detail above, in such amounts and for such time as is necessary to achieve the desired result. In certain embodiments of the present invention a "therapeutically effective amount" of an inventive compound or pharmaceutical composition is that amount effective for reducing the symptoms associated with the physiological condition. In other preferred embodiments, a "therapeutically effective amount" of an inventive compound or pharmaceutical composition is that amount effective for affecting the secretory pathway of a cell. Other "therapeutically effective amounts" include amounts effective for inhibiting the cell cycle, e.g., inhibiting the growth of cancer cells. In still other embodiments, "therapeutically effective amounts" include amounts effective for antibacterial activity. Alternatively, a "therapeutically effective amount" is an amount that is effective for inhibiting or activating a physiological process of interest, wherein the physiological process is related to improving the health of the individual.

The compounds and compositions, according to the method of the present invention, may be administered using any amount and any route of administration effective for obtaining the physiological result. Thus, the expression "therapeutically effective amount," as used herein, refers to a nontoxic but sufficient amount of an inventive compound to provide the desired treatment. The exact amount required will vary from subject to subject, depending on the species, age, and general condition of the subject, the severity of the physiological condition (e.g., a microbial infection or cancer), the particular compound, its mode of administration, and the like. The compounds of the invention are preferably formulated in dosage unit form for ease of administration and uniformity of dosage. The expression "dosage unit form" as used herein refers to a physically discrete unit of compound appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the condition being treated. In certain embodiments, the compounds of the invention may be administered orally or parenterally at dosage levels of about 0.01 mg/kg to about 50 mg/kg and preferably from about 0.1 mg/kg to about 25 mg/kg, of patient body weight, per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium laurel sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects.

For example, other compounds that may be used in combination with the compounds that can be provided using the structural information of the present invention. For example, if the inventive compound is a chemotherapeutic agent, a second or third chemotherapeutic agent, such as cisplatin, may be administered with the inventive compound to achieve the benefit of their combined effects. As but another example, if the compound were to treat or prevent a reproductive disorder, the inventive compound may be administered with a hormone, such as testosterone or estrogen. For a more comprehensive discussion regarding physiological conditions, symptoms and treatment, see The Merck Manual, Seventeenth Ed. 1999, the entire contents of which are hereby incorporated by reference.

In yet another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

Methods of Treatment

In another embodiment, the compounds of the present invention, e.g., compounds having cell cycle inhibitory activity or cellular trafficking inhibitory activity, may be administered to a subject to treat or prevent cancer including, but are not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, to name a few.

In another embodiment, the compounds of the present invention, e.g., inhibitors of cellular trafficking, may be administered to a subject to prevent or treat a reproductive disorder. Such disorders may include, but are not limited to, disorders or prolactin production; infertility including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; and disruptions of spermatogenesis, abnormal sperm physiology, cancer of the testis, cancer of the prostate, benign prostatic hyperplasia, prostatitis, carcinoma of the male breast, and gynecomastia.

In another embodiment, the identified compounds may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, extracorporeal circulation; viral, bacterial, fungal, parasitic, protozoal, and helminthic infections, and trauma.

In one embodiment, the compounds may be administered to a subject to treat or prevent a developmental disorder. Such disorders may include, but are not limited to, renal tubular acidosis, anemia, Cushing's syndrome, achondroplastic dwarfism, Duchenne and Becker muscular dystrophy, epilepsy, gonadal dysgenesis, WAGR syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss.

In another embodiment, the compounds may be administered to a subject to treat or prevent microbial infections, particularly bacterial infections. Infections by any pathogenic bacteria, including any eubacteria or archaebacteria, are included in this aspect of the invention. Such bacterial infections include, e.g., infection by *Escherichia coli, Vibrio cholera, Staphylococcus aureus, Hemophilus influenzae, Streptococcus spp., Past. multocida, N. catarrhalis, B.*

*subtilis, Staph. aureus, Staph. aureus Russel, Strep. pyogenes,* and *Strep. pneumoniae* Bacteria of veterinary importance include *Bord. bronchiseptica, Past. multocida, Past. haemolytica, Staph. aureus* B4(pen resistant), *Staph. aureus,* (pen sensitive), *Strep. uberis, Strep. dysgalactiae,* and *Strep. agalactiae.* However, those skilled in the art will appreciate that a limitless number of bacterial species could be treated by compounds of the invention, and the invention is not limited only to treatment of the particular bacterial species listed herein.

In yet another embodiment, the compounds may be administered to a subject to treat a wound. For example, the compounds of the present invention may be administered to a subject with a wound or be applied directly to the wound to promote closure of the wound. Without limiting the mechanism of the invention, wound healing may be promoted by the compound stimulating the migration of cells, into the wound to close the wound. In one exemplary embodiment, the compounds stimulate migration of fibroblasts into the wound. Alternatively, the compounds may attract cells, such as macrophages, or immune cells, that assist in the healing of the wound.

Those skilled in the art will appreciate that the invention is by no means limited to the treatment of the above disorders, but can be used to treat any disorder that may be identified by a practicing physician and which symptoms may be decreased by the compounds of the invention.

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance which can be adapted to the practice of this invention in its various embodiments and the equivalents thereof.

EXEMPLIFICATION

Example 1

Synthesis of Inventive Compounds

Our library synthesis strategy took advantage of efficient biomimetic reactions (3→4), paralleling the biosynthesis of the natural product (1→2). Following biomimetic solid-phase synthesis of the core structure 4, four diversity-generating reactions were performed to complete the library synthesis (FIG. 2).

Figure 4:
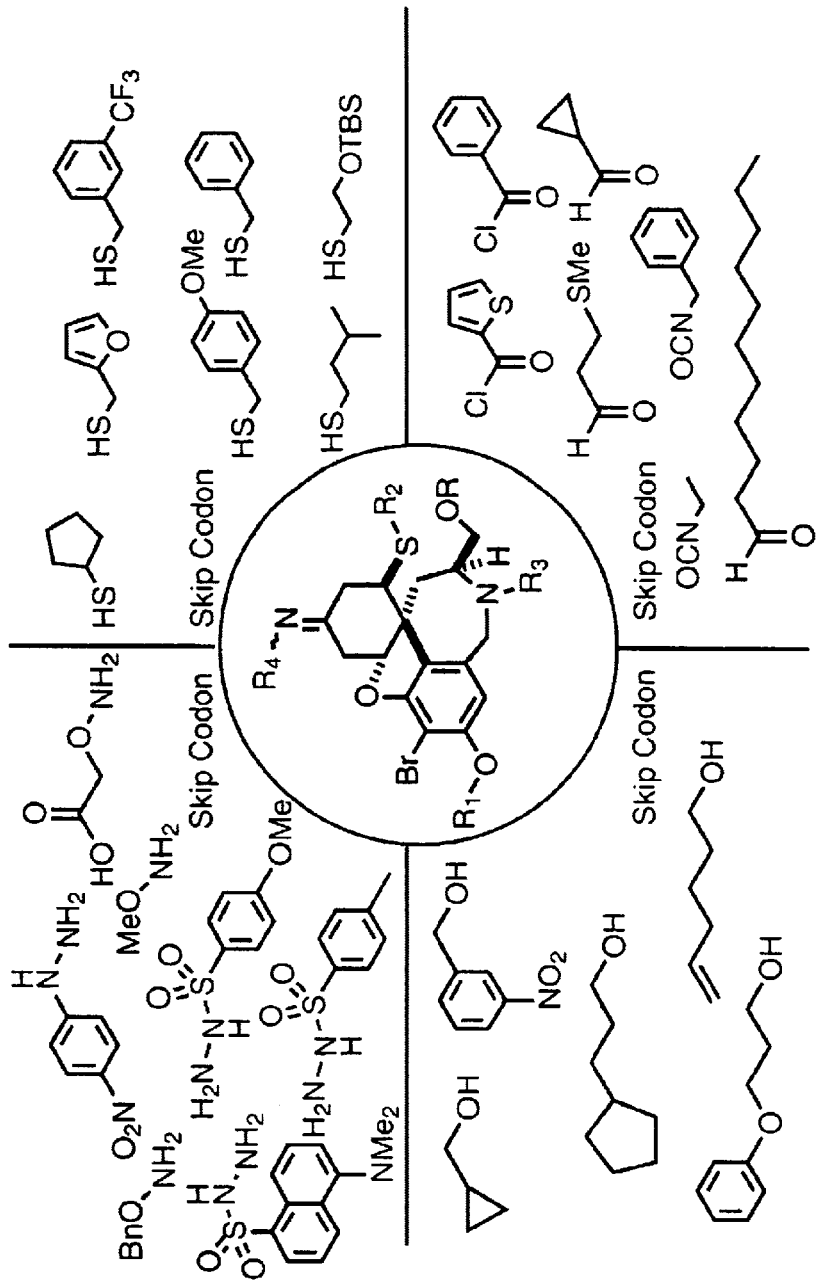
FIG. 4 depicts building blocks for the inventive alkaloid libraries.
Figure 5:
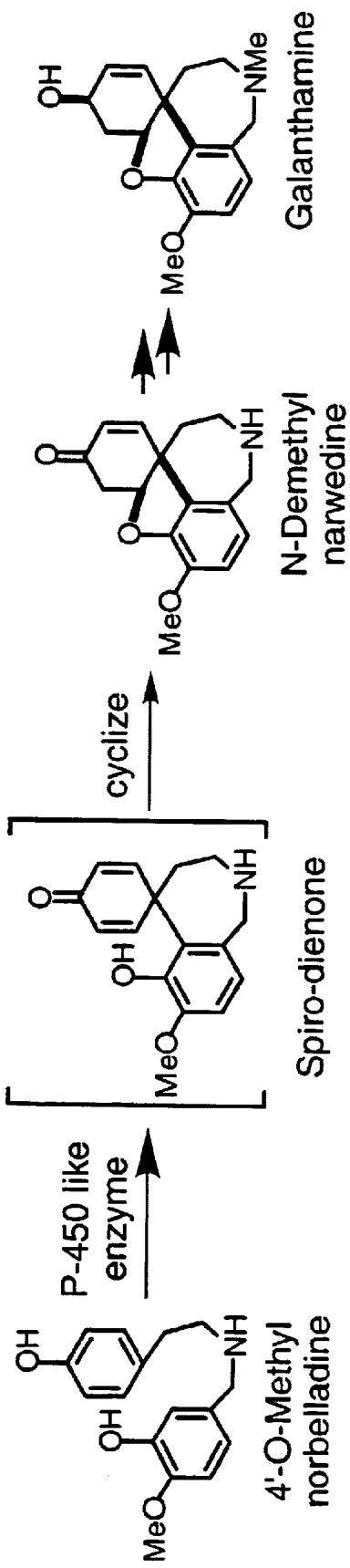
FIG. 5 depicts biomimetic solid phase synthesis.
Figure 5:
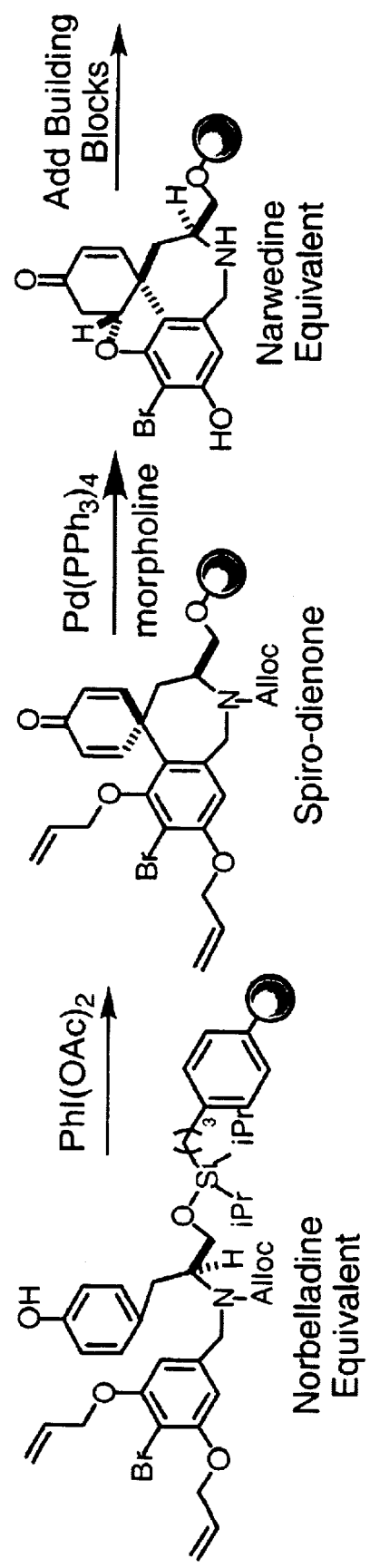
Figure 6:
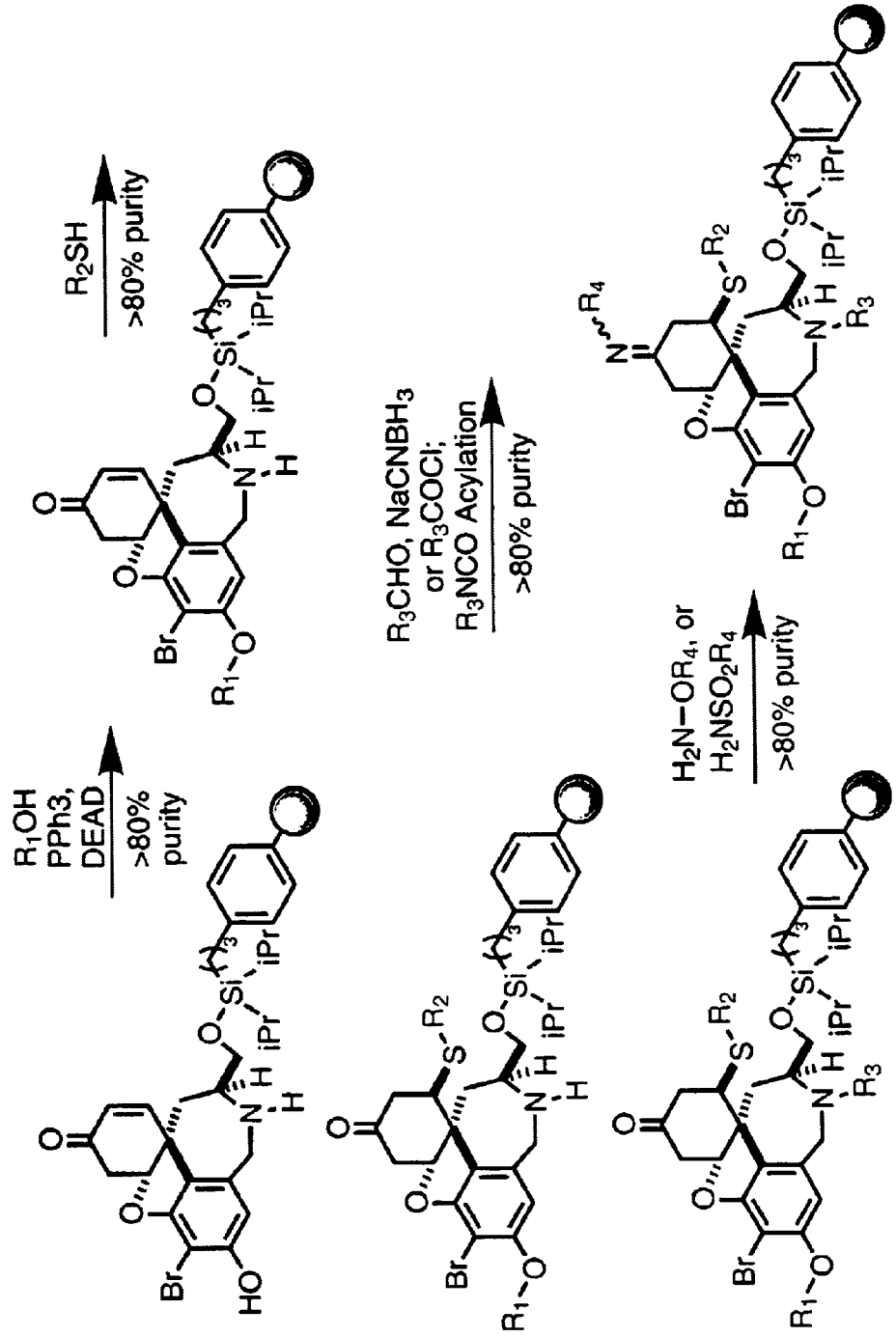
FIG. 6 depicts diversity incorporating reactions.

The library synthesis commenced with attachment of a tyrosine derivative to 500–600 µm high capacity (1.43 mmol/g) polystyrene beads through a Si—O bond to generate 5 upon deprotection (FIG. 3). Reductive amination and protecting group adjustments produced 7. Exposure of 7 to PhI(OAc)$_2$ afforded 8 which was then converted to 9 via Pd-mediated deprotection and spontaneous cyclization. For the library synthesis, building blocks were selected that reacted in >80% yield and as a group possessed diverse physical characteristics. (FIG. 4). The first diversity step was accomplished by coupling the phenol of 9 with five primary alcohols to afford 10 (FIG. 3). Treatment of 10 with thiols in the presence of "BuLi afforded 11 as a single diastereomer. The nitrogen of 11 was either acylated or alkylated providing compounds that would be neutral or positively charged, respectively, at physiological pH. The last diversification step involved treatment of 12 with hydrazines and hydroxylamines, generating 13.

The library was prepared as a single copy (1 bead per library member), arrayed in 384-well plates (1 bead per well), and detached from the solid-support with HF-pyridine (13→14). Following completion of the synthesis, the presence of 2527 out of 2946 (86%) potential compounds was confirmed by mass spectrometry. Evaporation of the cleavage cocktail and resuspension in 7 µl DMSO afforded 2527 stock solutions for biological screening. The reagents utilized for FIG. 3 are as follows: "Reagents: (a) 6, CH(OCH$_3$)$_3$—CH$_2$Cl$_2$, wash then NaBH$_3$CN, AcOH, MeOH-THF, 23 C. (b) allylchloroformate, iPr$_2$EtN, CH$_2$Cl$_2$, 23 C. (c) piperidine, THF, 23 C. (d) PhI(OAc)$_2$, (CF$_3$)$_2$CHOH—CH$_2$Cl$_2$, 23 C. (e) Pd(PPh$_3$)$_4$, morpholine-THF, 23 C. (f) R$_1$OH, PPh$_3$, DIAD, THF, 0 C. (2×). (g) R$_2$SH, 2,6-lutidine, "BuLi, THF 0→40 C. (h) R$_3$CHO, AcOH, MeOH-THF, then NaBH$_3$CN in MeOH, 23 C. or R$_3$COCl, 2,6-lutidine, CH$_2$Cl$_2$, 23 C. or R$_3$NCO, CH$_2$Cl$_2$, 23 C. (i) R$_4$NH$_2$, AcOH-MeOH—CH$_2$Cl$_2$, 23 C. (j) HF-pyridine, THF, 23 C. then TMSOMe.

I. General Methods

General Procedures.

All reactions were performed in oven or flame-dried glassware under a positive pressure of argon unless otherwise noted. Flash chromatography was performed as described by Still et al.[i] employing E. Merck silica gel 60 (230–400 mesh ASTM) unless noted otherwise. All solid phase reactions were performed in either oven-dried glassware under a positive pressure of argon, ChemGlass solid phase reaction vessels (CG-1866) or BioRad Poly-Prep Chromatography Columns. A Lab-Line 3-D Rotator provided agitation. Resin washing was performed with a Promega wash station.

Materials.

Starting materials and reagents were purchased from commercial suppliers and used without further purification unless otherwise noted. Tetrahydrofuran and ethyl ether were distilled under nitrogen from sodium-benzophenone ketyl. Toluene was distilled under nitrogen from sodium. Dichloromethane, triethylamine, N,N-diisopropylamine, 2,6-lutidine, and diisopropylethylamine were distilled under nitrogen from CaH$_2$. Alternatively, tetrahydrofuran, ethyl ether, toluene, N,N-dimethylformamide, and dichloromethane were purchased as dry solvents from Baker, and filtered through a column charged with activated Al$_2$O$_3$.[ii] TLC analyses were performed on 250 µm Silica Gel 60F$_{254}$ plates purchased from EM Science. Wash solvents were used as received. 500–600 µm p-bromopolystyrene was obtained from Polymer Laboratories, Inc. and the linker was attached according to the procedure of Tallarico et. al.[iii]

Instrumentation.

Infrared spectra were recorded using a Nicolet Nexus 400 or a Perkin Elmer Spectrum One FT-IR spectrometer. $^1$H and $^{13}$C NMR, COSY, NOESY, and GOESY spectra were recorded on a Bruker AM500 or AM400, or a Varian INOVA500 or Mercury400 spectrometer. Chemical shifts for proton and carbon resonances are reported in ppm (δ) relative to chloroform (δ7.26, 77.1 respectively), acetone (δ2.05, 29.84 respectively), or DMSO (δ2.50, 39.52 respectively). Tandem high pressure liquid chromatography/ mass spectral (LCMS) analyses were performed on a Micromass Platform II mass spectrometer in atmospheric pressure chemical ionization (APCI) mode or electrospray ionization mode (ES) after separation performed on a Waters Alliance 2690 separations module. A Waters Symmetry® $C_{18}$ column (2.1 mm×50 mm, 3.5 μm, Protocol A) or a Waters YMC ODS-AQ S3 120A column (2.0 mm×60 mm, Protocol B) were used. In protocol A, samples were eluted using a flow rate of 0.4 mL/min and a 12 minute gradient of 15→100% $CH_3CN$ in $H_2O$, constant 0.1% formic acid buffer. In protocol B, samples were eluted using a flow rate of 0.4 mL/min and a 12 minute gradient of 0→100% $CH_3CN$ in $H_2O$, constant 0.1% formic acid buffer. A Waters 996 photodiode array detector was used (scan width 200–450 nm, 1 spectra/sec). Automated mass spectral analyses were performed using the above equipment (with column bypassed) at a flow rate of 0.25 mL/min of 50% $CH_3CN$ in $H_2O$, constant 0.1% formic acid buffer for 1.5 minutes per sample. Chiral HPLC data was obtained on a Hewlet Packard Series 1100 HPLC with a Chiracel OD column.

II. Solution Phase Synthesis of Solid-Phase Precursors

Scheme II.1

Synthesis of 6.

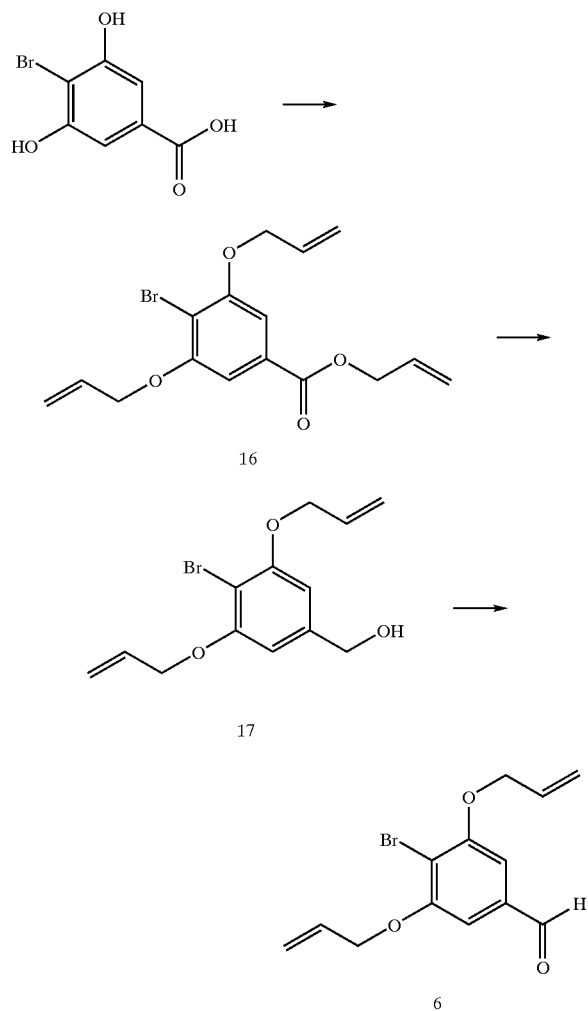

3,5-Bis-allyloxy-4-bromo-benzoic acid allyl ester (16):
To a solution of 4-Bromo-3,5-dihydroxybenzoic acid (20.43 g, 87.5 mmol, 1.0 equiv) in DMF (120 mL) at room temperature was added solid $K_2CO_3$ (60.5 g, 438 mmol, 5 equiv). To the suspension was added allylbromide (31 ml, 358 mmol, 4.1 equiv) dropwise over 25 minutes. After 15 hours, water (150 mL) was added and the slurry was poured into water (300 mL). The precipitate was separated by filtration, washed with water, and dissolved in ether. The solution was washed with brine, dried over $MgSO_4$, filtered, and concentrated to afford 16 as a white powder (30.1 g, 97%). $R_f$=0.52 (15% EtOAc/hexane); FTIR (neat, $cm^{-1}$) 3088, 2900, 1717, 1649, 1582, 1424, 986; $^1$H NMR (400 MHz, $CDCl_3$) δ, 7.24 (s, 2H), 6.12–5.98 (m, 3H), 5.51 (dd, J=17.6, 1.6 Hz, 2H), 5.40 (dd, J=17.2, 1.2 Hz, 1H), 5.32 (dd, J=10.2, 1.2 Hz, 2H), 5.30 (dd, J=8.4, 1.6 Hz, 1H), 4.81 (d, J=6.0 Hz, 2H), 4.66 (d, J=3.4 Hz, 4H); $^{13}$C NMR (100 MHz, $CDCl_3$) δ132.2, 132.0, 129.9, 118.4, 117.9, 107.9, 106.9, 69.9, 65.7; MS EI+ calculated for $C_{16}H_{17}BrO_4$ (M–H$^+$): 351, found: 351.

(3,5-Bis-allyloxy-4-bromo-phenyl)-methanol (17):
To a solution of 16 (30 g, 85 mmol) in THF (600 ml) at 0° C. was added lithium aluminum hydride (1.0M in THF, 175 mL, 2 equiv) dropwise over 45 minutes. The reaction was stirred at 0° C. for 2 hours, after which time saturated aqueous potassium sodium tartrate was added dropwise until bubbling ceased (25 mL, over 45 minutes). To the suspension was added ether (100 mL) and additional saturated aqueous potassium sodium tartrate (30 mL). The suspension was filtered through celite, the THF and ether were removed under reduced pressure, and water (250 mL) was added. The aqueous suspension was extracted into EtOAc (4×250 mL). The organic layer was washed with brine, dried over $MgSO_4$, filtered, and concentrated. Purification by flash chromatography (20→75% EtOAc/hexane) afforded 17 (11.93 g, 47%) as a white oil. $R_f$=0.39 (50% EtOAc/hexane); FTIR (neat, $cm^{-1}$) 3363, 2924, 2869, 1587, 1435, 817; $^1$H NMR (400 MHz, $CDCl_3$) δ, 6.56 (s, 2H), 6.10–6.00 (m, 2H), 5.48 (dd, J=17.4, 1.6 Hz, 2H), 5.29 (dd, J=10.6, 1.6 Hz, 2H), 4.62 (s, 2H), 4.60 (d, J=5.2 Hz, 4H); $^{13}$C NMR (100 MHz, $CDCl_3$) δ156.2, 141.4, 132.6, 117.6, 104.5, 100.9, 69.8, 65.0; MS EI+ calculated for $C_{13}H_{15}BrO_3$ (M–H)$^+$: 298, found: 298.

3,5-Bis-allyloxy-4-bromo-benzaldehyde (6):[iv]
To a suspension of pyridinium chlorochromate (17.02 g, 79.0 mmol, 2 equiv), celite (17 g, 1:1 PCC:Celite), and sodium acetate (1.62 g, 19.7 mmol, 0.5 equiv) in $CH_2Cl_2$ (230 mL) at 0° C. was added 17 (11.82 g, 39.5 mmol, 1 equiv) in $CH_2Cl_2$ (115 mL). The reaction was stirred for 4.5 hours at 0° C., after which time the suspension was decanted into ether (600 mL) at room temperature. The suspension was stirred for 2.5 hours at room temperature, after which time it was filtered through celite and concentrated to afford a brown solid. The solid was dissolved in ether with sonocation and filtered through a short column of Florisil which afforded 6 (11.05 g, 94%) as a white solid upon concentration. Crystallization from hot hexanes (~60 ml/g) prior to solid-phase reductive amination (Section III) afforded 6 as white needles. $R_f$=0.38 (20% EtOAc/hexane); FTIR (neat, $cm^{-1}$) 3079, 2927, 2359, 1699, 1649, 1578, 1436, 1423; $^1$H NMR (400 MHz, $CDCl_3$) δ, 9.88 (s, 1H), 7.02 (s, 2H), 6.18–6.00 (m, 2H), 5.50 (dd, J=17.4, 2.0 Hz, 2H), 5.33 (dd, J=10.6, 1.2 Hz, 2H), 4.70 (ddd, J=5.2, 1.6, 1.6 Hz, 4H); $^{13}$C NMR (100 MHz, $CDCl_3$) δ191.0, 156.7, 136.0, 132.0, 118.1, 109.7, 106.4, 69.9; HRMS (EI$^+$) calculated for $C_{13}H_{13}BrO_3$: 296.0048, found: 296.0055.

Scheme II.2

Synthesis of 20.

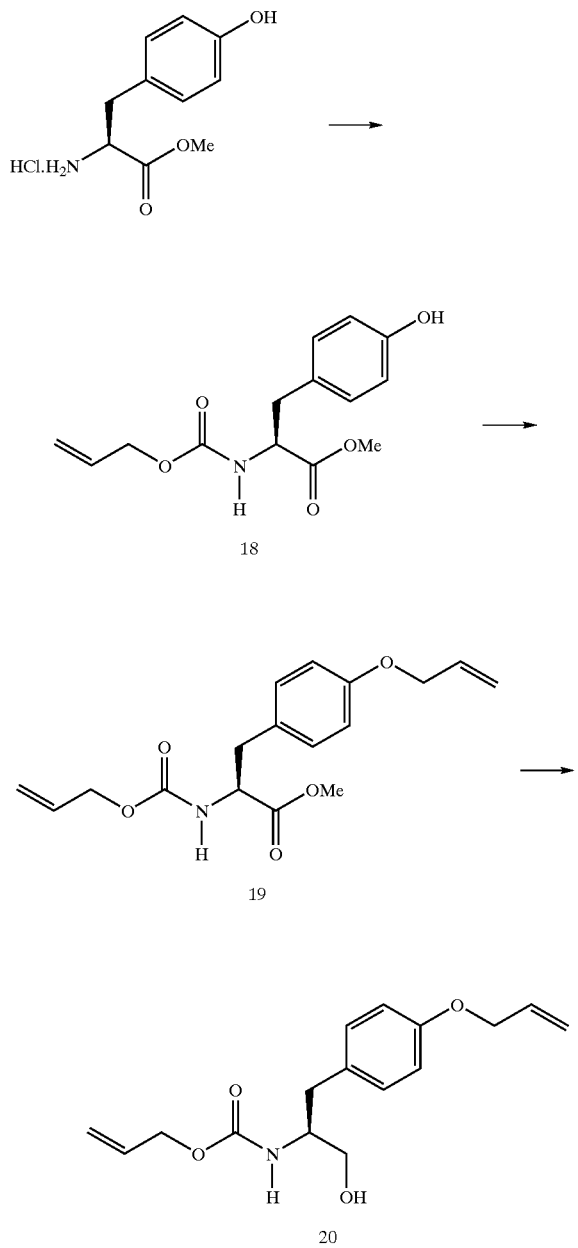

(S)-2-Allyloxycarbonylamino-3-(4-hydroxy-phenyl)-propionic acid methyl ester (18):

To a solution of L-Tyrosine methyl ester hydrochloride (25 g, 107.9 mmol, 1.0 equiv) in THF (500 mL) and $CH_2Cl_2$ (250 mL) at room temperature was added diisopropyl ethylamine (56.5 ml, 322.5 mmol, 3.0 equiv). The solution was cooled to 0° C. and allylchoroformate (11.5 ml, 107.9 mmol, 1.0 equiv) was added dropwise. The reaction was stirred at 0° C. for 1.5 hours, after which time saturated ammonium chloride (100 mL) was added and the THF and $CH_2Cl_2$ were removed under reduced pressure. The aqueous suspension was extracted with ether (4×300 mL). The organics were combined, washed with brine, dried over $MgSO_4$, and concentrated. Purification by flash chromatography (15→60% EtOAc/hexane) afforded 18 (30 g, 96%) as a white solid. $R_f$=0.43 (50% EtOAc/hexane); FTIR (neat, cm$^{-1}$) 3297, 2959, 1734, 1688, 1566, 1518, 1441, 1229; $^1$H NMR (400 MHz, CDCl$_3$) δ6.95 (d, J=7.9 Hz, 2H), 6.71 (d, J=8.0 Hz, 2H), 5.85 (m, 1H), 5.24 (m, 3H), 4.6 (m, 1H), 4.53 (d, J=5.2, 2H), 3.71 (s, 3H), 3.01 (m, 2H); $^{13}$C NMR (100 MHz, CDCl$_3$) δ172.3, 155.8, 155.2, 132.3, 130.3, 127.0, 118.0, 115.5, 66.0, 54.9, 52.9, 52.4, 37.4; HRMS (ES$^+$) calculated for $C_{14}H_{17}NO_5$ (M+H)$^+$: 280.1107, found: 280.1195.

(S)-2-Allyloxycarbonylamino-3-(4-allyloxy-phenyl)-propionic acid methyl ester (19):

To a solution of 18 (30 g, 107.4 mmol, 1.0 equiv) in DMF (170 mL) at room temperature was added solid $K_2CO_3$ (29.6 g, 214.2 mmol, 2.0 equiv) then allylbromide (10.2 mL, 116.3 mmol, 1.1 equiv) dropwise. The suspension was stirred at room temperature for 9 hours, after which time water (500 mL) was added and extracted with ether (4×250 mL). The organics were combined, washed with brine, dried over $MgSO_4$, and concentrated. Purification by flash chromatography (20→60% EtOAc/hexane) afforded 19 (31.6 g, 92%) as a clear oil. $R_f$=0.27 (25% EtOAc/hexane); FTIR (neat, cm$^{-1}$) 3343, 2919, 1721, 1510, 1239, 1215, 1176, 1052, 1017; $^1$H NMR (400 MHz, CDCl$_3$) δ7.00 (d, J=8.4 Hz, 2H), 6.79 (d, J=8.8 Hz, 2H), 5.99 (m, 1H), 5.85 (m, 1H), 5.44 (d, J=8.0 Hz, 1H), 5.36 (dd, J=17.4, 1.2 Hz, 1H), 5.25 (s, 1H), 5.22 (dd, J=10.2, 1.6 Hz, 1H), 5.15 (dd, J=10.4, 1.2 Hz, 1H), 4.56 (dd, J=14.2, 6.0 Hz, 1H), 4.51 (d, J=5.6 Hz, 2H), 4.45 (d, J=5.2 Hz, 2H), 3.66 (s, 3H), 3.03 (dd, J=14.4, 5.2 Hz, 1H), 2.96 (dd, J=14.0, 6.4 Hz, 1H); $^{13}$C NMR (100 MHz, CDCl$_3$) δ172.0, 157.5, 155.4, 133.1, 132.5, 130.0, 127.8, 117.4, 117.3, 114.5, 68.4, 65.5, 54.7, 52.0, 37.0; MS (ES$^+$) calculated for $C_{17}H_{21}NO_5$ (M+H)$^+$: 320.1420, found: 320.2.

[(S)-2-(4-Allyloxy-phenyl)-1-hydroxymethyl-ethyl]-carbamic acid allyl ester (20):

To a solution of 19 (1.17 g, 3.66 mmol, 1.0 equiv) in THF (10 mL) at room temperature was added ground anhydrous lithium chloride (0.31 g, 7.3 mmol, 2.0 equiv), sodium borohydride (0.28 g, 7.3 mmol, 2.0 equiv), and then ethanol (10.2 ml, 176 mmol, 48.0 equiv). The reaction was stirred at room temperature for 19 hours, after which time the mixture was cooled to 0° C. and a 10% aqueous citric acid solution (5 mL) was added to achieve pH 3–4. After concentration under reduced pressure, water (20 ml) was added and the solution was extracted into ethylacetate (3×75 ml). The organics were combined, dried over anhydrous $MgSO_4$, and concentrated. Purification by flash chromatography (30→50% EtOAc/hexane) afforded 20 (0.85 g, 80%) as a white solid. $R_f$=0.24 (50% EtOAc/hexane); $[α]^{25}_D$=−22.3° (c=0.9, $CH_2Cl_2$); FTIR (KBr pellet, cm$^{-1}$) 3324, 2953, 1696, 1613, 1543, 1512, 1240; $^1$H NMR (400 MHz, CDCl$_3$) δ7.11 (d, J=8.8 Hz, 2H), 6.85 (d, J=8.4 Hz, 2H), 6.09–6.00 (m, 1H), 5.92–5.84 (m, 1H), 5.40 (dd, J=15.6, 2.0 Hz, 1 H), 5.28 (dd, J=10.4, 1.2 Hz, 1H), 5.27 (dd, J=17.2, 1.6 Hz, 1H), 5.20 (dd, J=10.0, 1.6 Hz, 1H), 4.97 (d, J=7.2 Hz, 1H), 4.54–4.50 (m, 4H), 3.89–3.86 (m, 1H), 3.68–3.65 (b, 1H), 3.57 (b, 1H), 2.80 (d, J=7.2 Hz, 2H) 2.29 (br-s, 1H); $^{13}$C NMR (100 MHz, CDCl$_3$) δ157.4, 156.4, 133.4, 132.8, 130.3, 129.7, 117.8, 117.7, 114.9, 68.9, 65.7, 64.1, 54.2, 36.5; HRMS (ES$^+$) calculated for $C_{16}H_{21}NO_4$ (M+H)$^+$: 292.1471, found: 292.1551.

Enantiomeric Purity of 20 by Chiral HPLC: rac-20 was sysnthesized as described above starting from DL-tyrosine methyl ester and compared to 20 by Chiral HPLC on Chiracel OD column, 8% isopropanol/hexane at 1 min/mL. Only one enantiomer was observed by Chiral HPLC (See FIGS 44A and 44B).

Scheme II.3

Synthesis of 25.

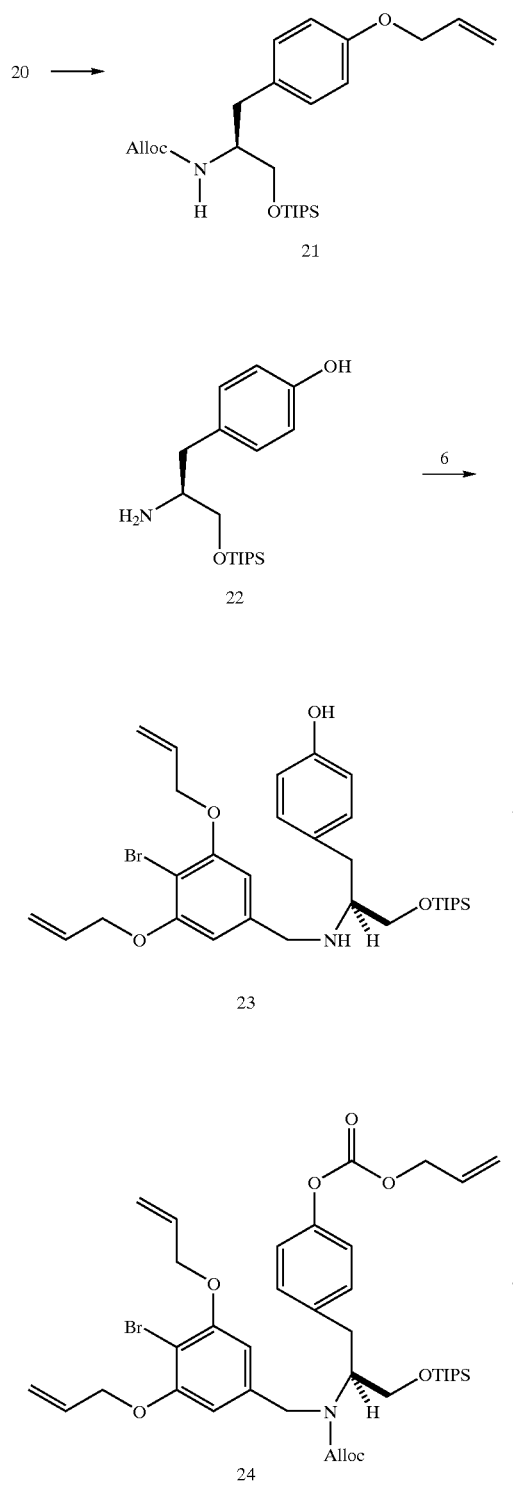

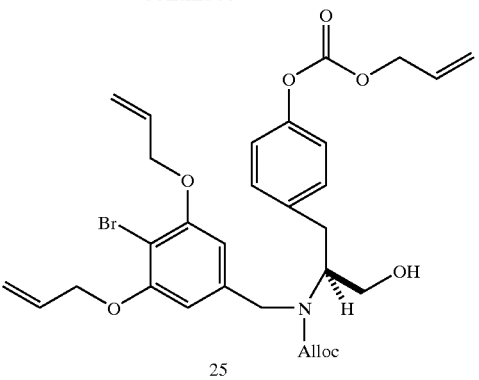

[(S)-1-(4-Allyloxy-benzyl)-2-(triisopropyl-silanyloxy)-ethyl]-carbamic acid allyl ester (21):

To a solution of 20 (4.54 g, 15.6 mmol, 1.0 equiv) in $CH_2Cl_2$ (150 ml) at 0° C. was added diisopropylethylamine (8.1 ml, 46.7 mmol, 3.0 equiv) and triisopropylsilyltriflate (5.2 ml, 19.3 mmol, 1.2 equiv) dropwise with stirring. The reaction was stirred at 0° C. for 1.5 hours, after which time the reaction was warmed to room temperature. The reaction was stirred at room temperature for 30 minutes, after which time saturated aqueous ammonium chloride (50 mL) was added. The mixture was extracted with $CH_2Cl_2$ (3×100 mL). The organics were combined, washed with brine, dried over $MgSO_4$, filtered, and concentrated. Purification by flash chromatography (5→50% EtOAc/hexane) afforded 21 (6.1 g, 88%) as a yellow oil. $R_f$=0.41 (10% EtOAc/hexane); FTIR (neat, cm$^{-1}$) 3446, 3340, 2943, 2866, 1725, 1612, 1511, 1243; $^1$H NMR (400 MHz, CDCl$_3$) δ7.11 (d, J=8 Hz, 2H), 6.82 (d, J=8.8 Hz, 2H), 6.08–5.99 (m, 1H), 5.92–5.82 (m, 1H), 5.39 (dd, J=17.2, 1.6 Hz, 1H), 5.27–5.22 (m, 2H), 5.17 (dd, J=10.0, 0.8 Hz, 1H), 4.95 (d, J=8.4 Hz, 1H), 4.52–4.48 (m, 4H), 3.8 (br s, 1H), 3.60 (d, J=3.6 Hz, 2H), 2.81 (d, J=7.2 Hz, 2H), 1.1–1.0 (m, 21H); $^{13}$C NMR (100 MHz, CDCl$_3$) δ157.1, 155.7, 133.3, 133.0, 130.3, 130.2, 117.6, 117.4, 114.6, 68.8, 65.3, 63.1, 53.7, 36.3, 18.0, 11.7; HRMS (ES$^+$) calculated for $C_{25}H_{41}NO_4Si$ (M+H)$^+$: 448.2805, found: 448.2902.

4-[(S)-2-Amino-3-(triisopropyl-silanoxy)-propyl]-phenol (22):

To a solution of 21 (6.05 g, 13.5 mmol, 1.0 equiv) in THF (135 mL) at room temperature, was added morpholine (11.8 mL, 135.6 mmol, 10 equiv), then tetrakis(triphenylphosphine)palladium(0) (1.56 g, 1.35 mmol, 0.1 equiv) in the dark. The solution was warmed to 47° C. The reaction was stirred at 47° C. for 10 hours, after which time the solution was cooled to room temperature and the THF was removed under reduced pressure. Purification by flash chromatography (30% EtOAc/hexane→100% EtOAc) afforded 22 (3.9 g, 90%) as a brown solid with a minor amount of Ph$_3$PO. $R_f$=0.2 (EtOAc); FTIR (film, cm$^{-1}$) 2938, 2866, 1515, 1462, 1251, 1105; $^1$H NMR (500 MHz, CDCl$_3$) δ7.01 (d, J=8.5 Hz, 2H), 6.71 (d, J=8.5 Hz, 2H), 4.5 (br s, 2H), 3.75 (dd, J=10.0, 3.5 Hz, 1H), 3.61, (dd, J=9.5, 6.5 Hz, 1H), 3.19 (br s, 1H), 2.79 (dd, J=13.3, 6.0 Hz, 1H), 2.64 (dd, J=13.8, 7.5 Hz, 1H), 1.05 (m, 21H); $^{13}$C NMR (100 MHz, CDCl$_3$) δ155.1, 130.3, 129.1, 115.8, 115.6, 66.2, 54.9, 37.9, 18.1, 11.9; HRMS (ES$^+$) calculated for $C_{18}H_{33}NO_2Si$ (M+H)$^+$: 324.2281, found: 324.2374.

4-[(S)-2-(3,5-Bis-allyloxy-4-bromo-benzylamino)-3-(triisopropyl-silanyloxy)-propyl]-phenol (23):

A solution of 6 (2.2 g, 7.4 mmol, 0.9 equiv) in MeOH (100 mL) was transferred via canula to 22 (2.6 g, 8.2 mmol, 1.0 equiv). To the mixture at 0° C. was added acetic acid (4.8 mL) followed by sodium cyanoborohydride (250 mg, 4 mmol, 0.5 equiv). The reaction was stirred at 0° C. for 30 minutes, after which time additional sodium cyanoborohydride (250 mg, 4 mmol, 0.5 equiv) was added. The reaction was then stirred at room temperature for 15 hours, after which time saturated aqueous sodium chloride (100 mL) and 10% sodium hydroxide in saturated aqueous sodium chloride (150 mL) were added. The mixture was extracted with 5% hexane in EtOAc (4×200 mL). The organics were combined, washed with brine, dried over $MgSO_4$, and concentrated. Purification by flash chromatography (20→25% EtOAc/hexane) afforded 23 (2.95 g, 66% from 6) as a white solid. $R_f$=0.2 (30% EtOAc/hexane); FTIR (film, cm$^{-1}$) 2937, 2865, 1586, 1515, 1456, 1433, 1360, 1246, 1105; $^1$H NMR (500 MHz, CDCl$_3$) δ6.98 (d, J=8.0 Hz, 2H), 6.69 (d, J=8.0 Hz, 2H), 6.45 (s, 2H), 6.06–5.99 (m, 2H), 5.46 (dd, J=17.3, 1.5 Hz, 2H), 5.27 (dd, J=11.0, 1.5 Hz, 2H), 4.49, (d, J=5.0 Hz, 4H), 3.8 (d, J=13.0 Hz, 1H), 3.75 (d, J=13.5 Hz, 1H) 3.68–3.61 (m, 2H), 2.93–2.88 (m, 1H), 2.76–2.67 (m, 2H), 1.05 (m, 21H); $^{13}$C NMR (100 MHz, CDCl$_3$) δ156.1, 154,8, 140.3, 132.7, 130.3, 130.2, 117.6, 115.6, 106.2, 100.6, 69.7, 64.6, 60.5, 51.7, 36.6, 18.1, 11.9; MS (AP$^+$) calculated for $C_{31}H_{46}BrNO_4Si$ (M+H)$^+$: 604.2380, found: 604.4.

Carbonic acid allyl ester 4-[(S)-2-[allyloxycarbonyl-(3,5-bis-allyloxy-4-bromo-benzyl)-amino]-3-(triisopropyl-silanyloxy)-propyl]-phenyl ester (24):

To a solution of 23 (2.74 g, 4.53 mmol, 1.0 equiv, azeotropically dried from toluene) in CH$_2$Cl$_2$ (80 mL) at room temperature was added 2,6-lutidine (1.85 mL, 15.9 mmol, 3.5 equiv) followed by allylchloroformate (1.44 mL, 13.6 mmol, 3.0 equiv). The reaction was stirred at room temperature for 1.5 hours during which time the solution became pink, and after which time saturated aqueous ammonium chloride was added. The mixture was extracted with CH$_2$Cl$_2$ (3×100 mL). The organics were combined, washed with brine, dried over Na$_2$SO$_4$, and concentrated. Purification by flash chromatography (25% EtOAc/hexane) afforded 24 (3.4 g, 97%) as a yellow oil. $R_f$=0.86 (50% EtOAc/hexane); FTIR (film, cm$^{-1}$) 2938, 2860, 1760, 1701, 1588, 1455, 1419, 1241, 1218, 1104; $^1$H NMR (500 MHz, DMSO, 80° C.) δ7.13 (d, J=8.5 Hz, 2H), 7.1 (d, J=9.0 Hz, 2H), 6.56 (s, 2H), 6.05–5.95 (m, 3H), 5.91–5.83 (m, 1H), 5.41 (dd, J=17.3, 1.8 Hz, 2H), 5.39 (dd, J=17.0, 1.5 Hz, 1H), 5.29 (dd, J=10.3, 1.3 Hz, 1H), 5.25 (dd, J=11.0, 1.5 Hz, 2H), 5.20 (d, J=17.0 Hz, 1H), 5.15 (d, J=10.5 Hz, 1H), 4.71 (d, J=5.5 Hz, 2H), 4.52 (d, J=4.5 Hz, 4H), 4.50 (d, J=5.5 Hz, 2H), 4.37 (d, J=16.0 Hz, 1H), 4.28, (d, J=16.0 Hz, 1H), 4.19 (m, 1H), 3.77–3.68 (m, 2H), 2.94–2.86 (m, 2H), 1.0 (m, 21H); $^{13}$C NMR (100 MHz, DMSO, 80° C.) δ155.2, 152.2, 148.9, 139.7, 136.0, 132.9, 132.7, 131.5, 129.2, 120.2, 118.1, 116.9, 116.6, 106.0, 105.8, 99.6, 69.3, 69.1, 68.1, 64.9, 63.3, 60.3, 34.0, 17.2, 11.0; HRMS (ES$^+$) calculated for $C_{39}H_{54}BrNO_8Si$ (M+H)$^+$: 772.2802, found: 772.2911.

Carbonic acid allyl ester 4-{(S)-2-[allyloxycarbonyl-(3,5-bis-allyloxy-4-bromo-benzyl)-amino]-3-hydroxy-propyl}-phenyl ester (25):

To 24 (1.15 g, 1.49 mmol, 1.0 equiv) in THF (20 mL) in a high density polyethylene vial was added hydrogen fluoride-pyridine (1 mL) once an hour for 4 hours (4 mL total), after which time saturated aqueous ammonium chloride was added and the THF was removed under reduced pressure. The remaining solution was extracted with CH$_2$Cl$_2$. The organics were combined, washed with brine, dried over Na$_2$SO$_4$, and concentrated. Purification by flash chromatography (20→60% EtOAc/hexane) afforded 25 (0.86 g, 94%) as a colorless oil. $R_f$=0.23 (50% EtOAc/hexane); $[α]^{28}_D$=−29.24° (c=1, CH$_2$Cl$_2$); FTIR (neat, cm$^{-1}$) 3447, 2932, 1761, 1695, 1588, 1435, 1421, 1242; $^1$H NMR (400 MHz, DMSO, 80° C.) δ7.18–7.12 (m, 2H), 7.10–7.04 (m, 2H), 6.63 (s, 2H), 6.07–5.94 (m, 3H), 5.90–5.78 (m, 1H), 5.42 (dd, J=15.2, 2.0 Hz, 2H), 5.39 (dd, J=14.0, 1.6 Hz, 1H), 5.30 (dd, J=10.4, 1.6 Hz, 1H), 5.25 (dd, J=10.6, 1.8 Hz, 2H) 5.18 (d, J=16.8 Hz, 1H), 5.13 (d, J=10.4 Hz), 4.73–4.71 (m, 2H), 4.55–4.54 (m, 4H), 4.72 (d, J=4.0 Hz, 2H), 4.36 (d, J=16.0 Hz, 1H), 4.24 (d, J=16.4 Hz, 1H), 4.21–4.12 (m, 1H), 3.62–3.57 (m, 1H), 3.53–3.49 (m, 1H), 2.90–2.77 (m, 2H); $^{13}$C NMR (100 MHz, DMSO, 80° C.) δ155.3, 155.1, 152.2, 148.8, 140.1, 136.3, 132.9, 132.8, 131.5, 129.3, 120.1, 116.8, 116.6, 116.3, 105.8, 105.6, 99.1, 69.2, 69.0, 68.1, 64.7, 61.3, 60.5, 48.1, 34.3; HRMS (ES$^+$) calculated for $C_{30}H_{34}BrNO_8$ (M+H)$^+$: 616.1468, found: 616.1570.

III. Solid-Phase Synthesis of Core Enone (9)

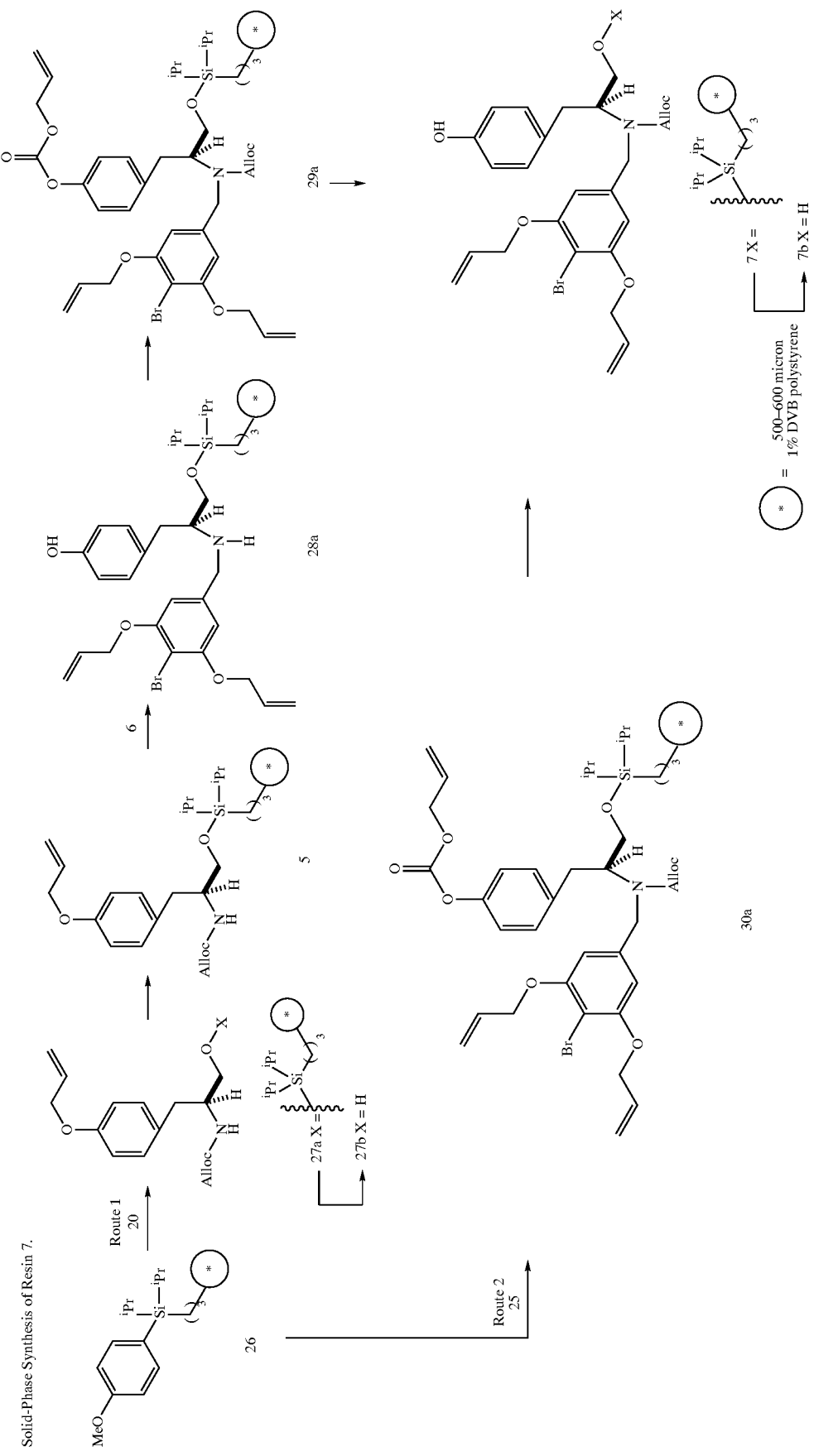
Scheme III.1
Solid-Phase Synthesis of Resin 7.

Resin (27a):

To silicon-functionalized resin 26 (3.65 g, 1.43 mequiv Si/g, 5.22 mmol Si, 1.0 equiv. Si) in a pear-shaped flask (100 mL) was added $CH_2Cl_2$ (35 mL) at room temperature. After 10 minutes, the solvent was removed via canula and the resin was washed with $CH_2Cl_2$ (15 mL, 2×10 minutes, via canula). $CH_2Cl_2$ (15 mL) and 2,6-lutidine (1.1 mL, 9.44 mmol, 1.8 equiv) were then added. After 5 minutes with gentle swirling by hand, trimethylsilylchloride (1.1 mL, 8.67 mmol, 1.7 equiv) was added dropwise over 5 minutes. The mixture was swirled gently by hand over 15 minutes, after which time the solvent was removed via canula and the resin was washed with $CH_2Cl_2$ (15 mL, 3×5 minutes, via canula). A 5% trifluoromethanesulfonic acid/$CH_2Cl_2$ solution (48 mL, 27.1 mmol, 5.2 equiv) was then added over 10 minutes. The resin turned bright red/orange upon acid treatment. The mixture was swirled gently by hand over 15 minutes, after which time the solvent was removed via canula and the resin was washed with $CH_2Cl_2$ (15 mL, 3×5 minutes, via canula). $CH_2Cl_2$ (15 mL) and 2,6-lutidene (4.9 mL, 42.1 mmol, 8.1 equiv) were then added. The resin decolorized upon base addition. The mixture was swirled gently by hand over 5 minutes, after which time 6 (2.3 g, 7.9 mmol, 1.5 equiv), azeotroped from toluene and dissolved in $CH_2Cl_2$ (5 mL) was added. The reaction was swirled gently by hand over 10 minutes and then sealed under argon. The solution was left standing for 20 hours, after which time the heterogeneous mixture was poured into a 100 mL peptide reaction vessel and the solution was drained. The resin was washed with $CH_2Cl_2$ (3×10 minutes), THF (2×10 minutes), $CH_2Cl_2$ (1×10 minutes) and hexanes (2×5 minutes). Excess 20 was recovered upon concentration of the washings. Air drying afforded 27a as a colorless resin.

[(S)-2-(4-Allyloxy-phenyl)-1-hydroxymethyl-ethyl]-carbamic acid allyl ester (27b):

To vacuum-dried resin 27a (51.3 mg) in a high density polyethylene vial was added 10% HF-pyridine in THF (1 mL). After 1.5 hours, methoxytrimethylsilane (2 mL) was added to quench unreacted HF. After 30 minutes, the solution was removed and the beads were washed with THF (2×3 mL). The washings and reaction solution were combined and concentrated. Purification by flash chromatography (50% EtOAc/hexane) afforded a white solid (9.2 mg, 0.62 mmol/g) with spectroscopic characteristics identical to 20. Theoretical Loading Level=1.13 mmol/g; Loading efficiency=55%.

Resin (5):

To resin 27a (150 mg, 0.62 mmol/g, 0.093 mmol, 1.0 equiv) in a 2 mL BioRad tube was added 25% morpholine/THF (1.7 mL). After 10 minutes, $Pd(PPh_3)_4$ (87 mg, 0.075 mmol, 0.8 equiv) was added in the dark. The tube was sealed under argon and tumbled for 20 hours, after which time the tube was attached to a Promega wash station. The solvent was drained and the resin was washed with $CH_2Cl_2$ (2×1 minute, 1×5 minutes), THF (3×10 minutes), 10% $CH_3CN$/THF (1×10 minutes), 0.1 M dimethyldithiocarbamic acid sodium hydrate in 25% $H_2O$/THF (2×15 min with tumbling), 25% $CH_3CN$/THF (1×10 minutes), 50% $CH_3CN$/THF (1×10 minutes), 75% $CH_3CN$/THF (1×10 minutes), 90% $CH_3CN$/THF (1×10 minutes), and $CH_3CN$ (1×10 minutes). Air drying afforded 5 white beads.

Resin (28a):[vi]

To resin 5 (138.5 mg, 0.67 mmol/g, 0.093 mmol, 1.0 equiv) and 6 (411 mg, 1.38 mmol, 14.8 equiv, recrystallized from hexanes) in a 10 mL pear-shaped flask was added $CH_2Cl_2$ (1.5 mL). After complete dissolution of 6, $CH(OCH_3)_3$ (1.5 mL) was added. The reaction was sealed under argon at room temperature. After 20 hours, the solvent was drained via canula and the resin was washed (under argon) with 25% $CH(OCH_3)_3$ in $CH_2Cl_2$ (1'10 min), $CH_2Cl_2$ (4×10 min), and 25% $CH(OCH_3)_3$ in $CH_2Cl_2$ (1×10 min). $NaBH_3CN$ (87 mg, 1.38 mmol, 14.8 equiv) dissolved in 10% acetic acid in $CH(OCH_3)_3$ (20 μl in 2 mL) was then added with gentle swirling at room temperature. After 20 hours, the solvent was removed and excess 6 was recovered. The resin was washed with $CH_2Cl_2$ (2×1 minute, 1×5 minutes), THF (3×10 minutes), 10% $CH_3CN$/THF (1×10 minutes), 25% $CH_3CN$/THF (1×10 minutes), 50% $CH_3CN$/THF (1×10 minutes), 75% $CH_3CN$/THF (1×10 minutes), 90% $CH_3CN$/THF (1×10 minutes), and $CH_3CN$ (1×10 minutes). Air drying afforded 28a as white beads.

Resin (29a):

To resin 28a (89.4 mg, 0.56 mmol/g, 0.05 mmol, 1.0 equiv) in a 10 ml pear-shaped flask was added $CH_2Cl_2$ (1 mL), $iPr_2NEt$ (467 μL, 2.68 mmol, 53.6 equiv), benzoyl chloride (190 μL, 1.79 mmol, 35.8 equiv) at room temperature. After 20 hours, the solvent was drained and the resin was washed with $CH_2Cl_2$ (2×1 minute, 1×5 minutes), THF (3×10 minutes), 10% $CH_3CN$/THF (1×10 minutes), 25% $CH_3CN$/THF (1×10 minutes), 50% $CH_3CN$/THF (1×10 minutes), 75% $CH_3CN$/THF (1×10 minutes), 90% $CH_3CN$/THF (1×10 minutes), and $CH_3CN$ (1×10 minutes). Air drying afforded 29a as white beads.

Resin (7, route 1):

To 29a in a 10 mL BioRad tube under argon was added 10% piperidine in THF (10 mL) via at room temperature. The reaction vessel was sealed and tumbled on an orbital stirrer. After 20 hours, the solvent was drained by gravity and washed with THF (3×15 minutes), $CH_2Cl_2$ (1×15 minutes), 75% $CH_2Cl_2$/hexane (1×15 minutes), 50% $CH_2Cl_2$/hexane (1×15 minutes), and 25% $CH_2Cl_2$/hexane (1×15 minutes). Air drying afforded 17a as a white beads.

Figure 45A:
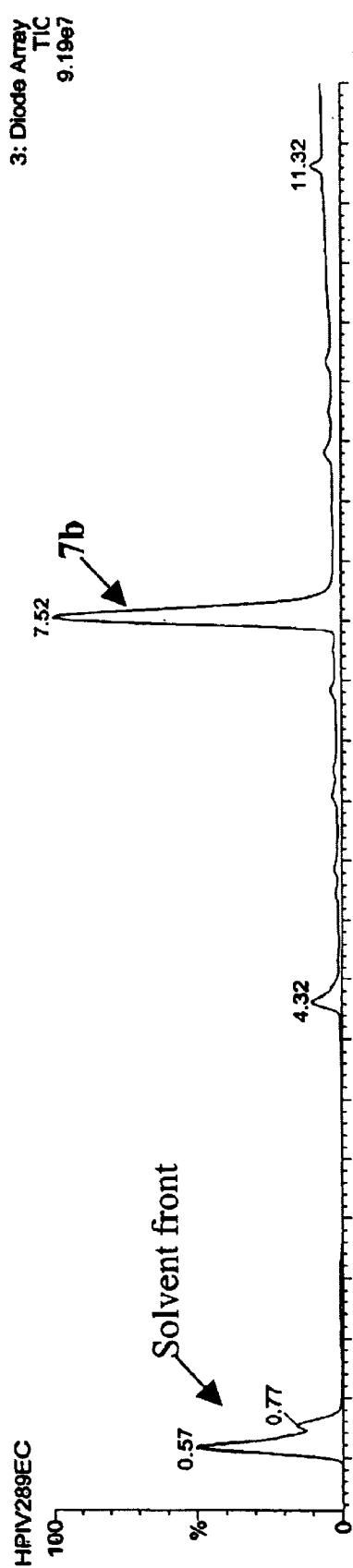
FIG. 45 depicts HPLC chromatograms for unpurified compound 7b, when compound 7b is obtained (A) by route 1 or (B) by route 2.

(3,5-Bis-allyloxy-4-bromo-benzyl)-[(S)-1-hydroxymethyl-2-(4-hydroxy-phenyl)-ethyl]-carbamic acid allyl ester (7b, route 1):

To vacuum-dried resin 7 (65.5 mg) in a high density polyethylene vial was added 10% HF-pyridine in THF (1 mL). After 1.5 hours, methoxytrimethylsilane (2 mL) was added to quench unreacted HF. After 30 minutes, the solution was removed and the beads were washed with THF (2×3 mL). The washings and reaction solution were combined and concentrated. Purification by flash chromatography (50% EtOAc/hexane) afforded a clear oil (14.6 mg, 0.42 mmol/g). Theoretical Loading Level[1] (from 27b)=0.54 mmol/g; Yield from 27b=78% (5 steps). $R_f$=0.28 (50% EtOAc/hexane); FTIR (film, $cm^{-1}$) 3342, 2925, 1670, 1588, 1515, 1432, 1419, 1225; $^1H$ NMR (400 MHz, DMSO, 80° C.) δ8.88 (s, 1H), 6.90–6.89 (m, 2H), 6.66–6.62 (m, 4H), 6.07–5.96 (m, 2H), 5.83 (br s, 1H), 5.45–5.40 (m, 2H), 5.26–5.23 (m, 2H), 5.20–5.11 (m, 2H), 4.54 (br s, 4H), 4.47 (br s, 2H), 4.34 (dd, J=16.0, 3.6 Hz, 1H), 4.20 (dd, J=16.2, 3.2 Hz, 1H), 4.11 (m, 1H), 3.55 (br s, 1H), 3.49–3.45 (m, 1H), 2.74–2.63 (m, 2H); $^{13}C$ NMR (100 MHz, $CDCl_3$) δ155.3, 155.1, 140.3, 133.1, 132.9, 129.2, 128.5, 116.8, 116.3, 114.7, 105.6, 99.0, 69.0, 64.7, 61.3, 60.8, 48.1, 34.2; $MS(ES^+)$ calculated for $C_{26}H_{30}BrNO_6$: 531.1257, found: 531.7. For HPLC chromatogram of unpurified 7b, see FIG. 45A.

Resin (30a):

To silicon-functionalized resin 26 (5.87 g, 1.45 mequiv Si/g, 8.51 mmol Si, 1.0 equiv Si) in a pear-shaped flask (200 mL) under positive argon pressure was added $CH_2Cl_2$ (70 mL) at room temperature. After 10 minutes, the solvent was removed via canula and the resin was washed with $CH_2C_2$ (30 mL, 2×10 minutes, via canula). $CH_2Cl_2$ (30 mL) and 2,6-lutidine (1.8 mL, 15.45 mmol, 1.8 equiv) were then added. After 5 minutes with gentle swirling by hand, trimethylsilylchloride (1.75 mL, 13.79 mmol, 1.6 equiv) was added dropwise over 5 minutes. The mixture was swirled gently by hand over 15 minutes, after which time the solvent was removed via canula and the resin was washed with $CH_2Cl_2$ (30 mL, 3×5 minutes, via canula). A 5% trifluoromethanesulfonic acid/$CH_2Cl_2$ solution (90 mL, 50.86 mmol, 6.0 equiv) was then added over 10 minutes. The resin turned bright red/orange upon acid treatment. The mixture was swirled gently by hand over 15 minutes, after which time the solvent was removed via canula and the resin was washed with $CH_2Cl_2$ (30 mL, 3×5 minutes, via canula). $CH_2Cl_2$ (30 mL) and 2,6-lutidene (7.9 mL, 67.82 mmol, 8.0 equiv) were then added. The resin decolorized upon base addition. The mixture was swirled gently by hand over 5 minutes, after which time 25 (6.3 g, 10.22 mmol, 1.2 equiv), azeotroped from toluene and dissolved in $CH_2Cl_2$ (30 mL) was added. The reaction was swirled gently by hand over 10 minutes and then sealed under argon. The solution was left standing for 20 hours, after which time the heterogeneous mixture was poured into a 100 mL peptide reaction vessel and the solution was drained. The resin was washed with $CH_2Cl_2$ (3×10 minutes), THF (2×10 minutes), $CH_2Cl_2$ (1×10 minutes) hexanes (2×5 minutes). Excess 25 was recovered upon concentration of the reaction solvent and washings. Air drying afforded 30a as a colorless resin.

Resin (7, route 2):

To 30a in a 100 mL peptide reaction vessel under positive argon pressure was added 10% piperidine in THF (100 mL) via canula at room temperature. The reaction vessel was sealed and tumbled on an orbital stirrer. After 20 hours, the solvent was drained by gravity and washed with THF (3×15 minutes), $CH_2Cl_2$ (1×15 minutes), 75% $CH_2Cl_2$/hexane (1×15 minutes), 50% $CH_2Cl_2$/hexane (1×15 minutes), and 25% $CH_2Cl_2$/hexane (1×15 minutes drying afforded 7 as a colorless resin.

Figure 45B:
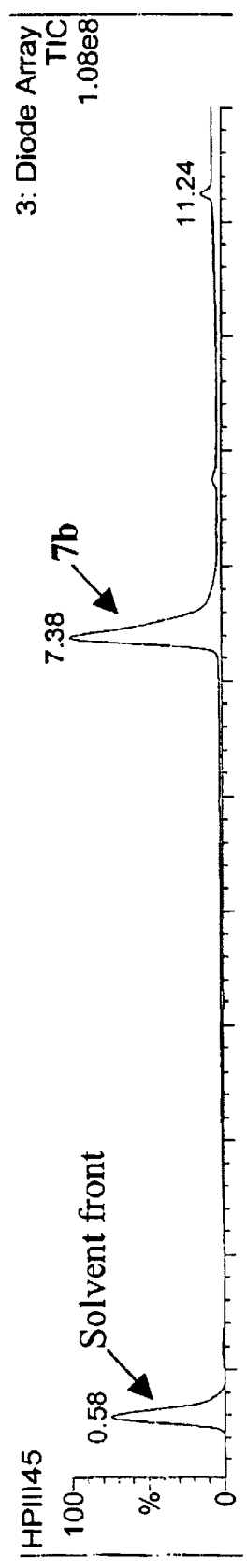

(3,5-Bis-allyloxy-4-bromo-benzyl)-[(S)-1-hydroxymethyl-2-(4-hydroxy-phenyl)-ethyl]-carbamic acid allyl ester (7b, route 2):

To vacuum-dried resin 7 (46.92 mg, 205 beads, 4369 beads/g and 47.02 mg, 211 beads, 4487 beads/g) in two separate high density polyethylene vials was added 10% HF-pyridine in THF (1 mL). The vials were sealed and gently agitated for 1.5 hours after which time the methoxytrimethylsilane (2 mL) was added to quench unreacted HF. After 30 minutes, the solution was removed and the beads were washed with THF (2×3 mL). The washings and reaction solution were combined and concentrated. Purification by flash chromatography (50% EtOAc/hexane) of each afforded a white solid (15.1 mg, 138 nmol/bead and 17.2 mg, 153 nmol/bead, respectively, average loading level=146 nmol/bead, 0.65 mmol/g) with spectroscopic characteristics identical to 7b, route 1. Theoretical Loading Level=0.90 mmol/g; Loading efficiency=72%. For HPLC chromatogram of unpurified 7b,see FIG. 45B.

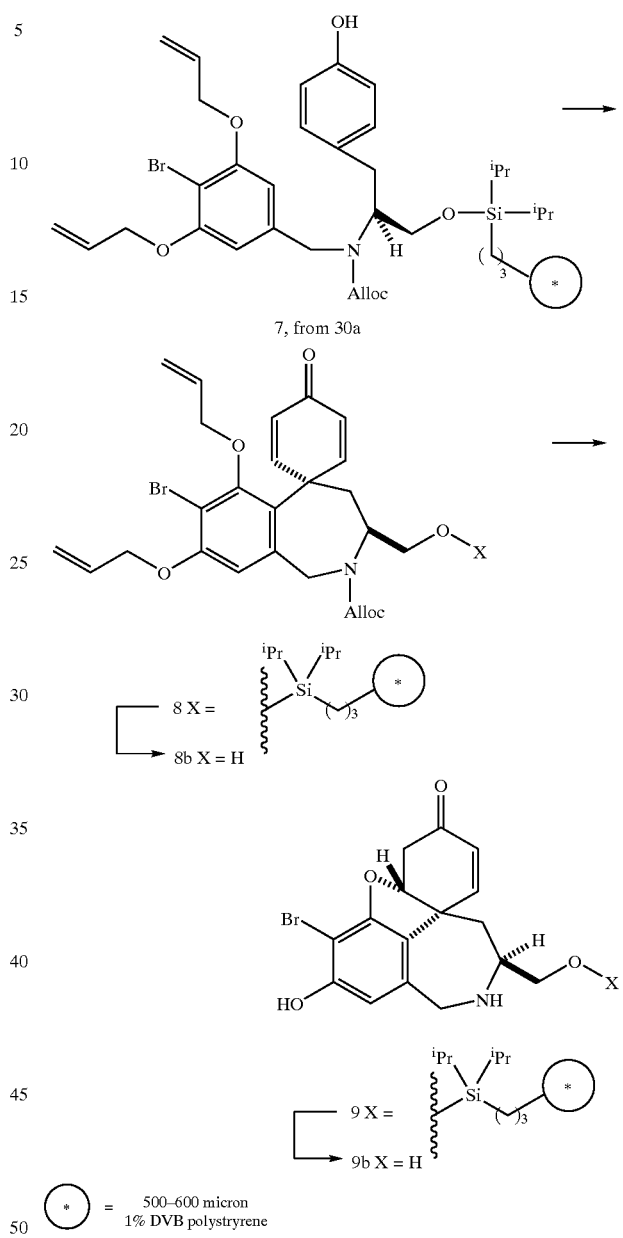

Scheme III.2

Solid-Phase Synthesis of 9.

Resin (8, from route 2):

To resin 7 (from route 2, 6 g, 0.65 mmol/g, 3.88 mmol, 1.0 equiv) in a 100 mL peptide reaction vessel under argon was added 33% $CH_2Cl_2$/hexafluoroisopropanol (93 mL). After gentle swirling by hand over 15 minutes, $PhI(OAc)_2$ (19 g, 59.0 mmol, 15.2 equiv) was added and the mixture was immediately agitated by hand followed by gently tumbling. The resin color changed from clear to green to brown. The resin was tumbled for 4 hours at room temperature, after which time the solution was drained and the resin was washed with THF (2×10 minutes), 10% $CH_3CN$/THF (1×10 minutes), 25% $CH_3CN$/THF (1×10 minutes), 50% $CH_3CN$/THF (1×10 minutes), 75% $CH_3CN$/THF (1×10 minutes), 90% $CH_3CN$/THF (1×10 minutes), and $CH_3CN$ (1×10 minutes). Air drying afforded 8 as a brown resin.

Figure 46:
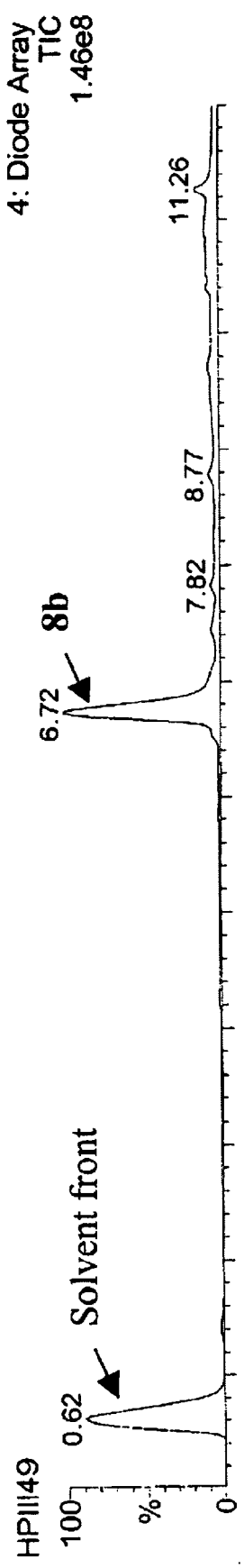
FIG. 46 depicts HPLC chromatograms for unpurified compound 8b.

6,8-Diallyloxy-7-bromo-(S)-3-hydroxymethyl-4'-oxo-5'-spiro-1'cyclohexa-2'5'-diene-1,3,4,5-tetrahydro-benzo[c]azepine-2-carboxylic acid allyl ester (8b):

To vacuum-dried resin 8 (41.53 mg, 183 beads, 4406 beads/g and 42.78 mg, 188 beads, 4395 beads/g) in two separate high density polyethylene vials was added 10% HF-pyridine in THF (1 mL). The vials were sealed and gently agitated for 1.5 hours after which time the methoxytrimethylsilane (2 mL) was added to quench unreacted HF. After 30 minutes, the solution was removed and the beads were washed with THF (2×3 mL). The washings and reaction were combined and concentrated. Purification by flash chromatography with Florisil (67% EtOAc/hexane) afforded a yellow solid (8.5 mg, 88 nmol/bead and 9.6 mg, 96 nmol/bead, respectively, average loading level=92 nmol/bead, 0.40 mmol/g). Theoretical Loading Level (from 7, route 2)=0.65 mmol/g, Yield=62%. Some cleavage of product was observed under the acidic conditions of the reaction (refer to FIG. 46 for purity). In a smaller scale reaction (183.4 mg 7), a yield of 84% was obtained upon cleavage from the resin. $R_f$=0.38 (100% EtOAc/hexane); FTIR (film, cm$^{-1}$) 3411, 2926, 1686, 1657, 1583, 1450, 1412, 1340, 1236; $^1$H NMR (400 MHz, CDCl$_3$) At room temperature, 2 rotamers are present in a ratio of 1:1.25 (see FIG. 46 and Section V.1.2) δ7.06–6.99 (m), 6.93–6.91 (m), 6.59 (s), 6.51 (s), 6.34–6.30 (m), 6.26 (d, J=10.0 Hz), 6.08–5.78 (m), 5.48 (d, J=17.2 Hz), 5.33–5.06 (m), 4.79–4.57 (m), 4.49–4.45 (m), 4.39–4.35 (m), 4.27–4.23 (m), 4.12–4.03 (m), 3.73–3.60 (m), 2.76–2.62 (m), 2.4 (br s), 1.75–1.71 (m); $^{13}$C NMR (100 MHz, CDCl$_3$) δ185.6, 158.0, 157.5, 157.1, 156.9, 156.0, 155.3, 155.2, 152.1, 151.9, 139.4, 139.3, 132.5, 132.4, 132.2, 132.1, 132.0, 131.9, 129.0, 125.2, 125.0, 124.5, 124.2, 118.7, 118.6, 118.4, 118.1, 117.0, 110.2, 110.1, 107.8, 107.7, 74.5, 69.8, 69.7, 66.5, 66.2, 64.6, 64.5, 55.4, 55.3, 47.3, 47.1, 47.0, 41.8, 41.3, 29.7; MS (ES$^+$) calculated for C$_{26}$H$_{28}$BrNO$_6$ (M+H$^+$): 530.1100, found: 530.

Figure 47:
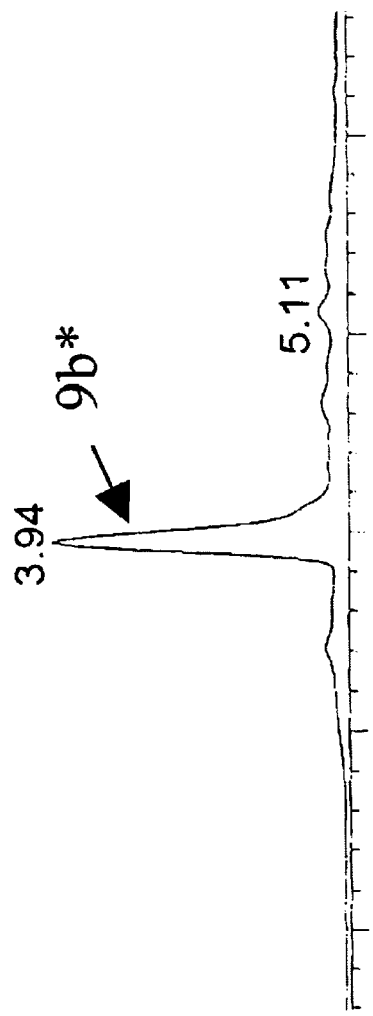
FIG. 47 depicts HPLC chromatograms for unpurified compound 9b.

Resin (9):

To resin 8 (687 mg, 0.40 mmol/g, 0.28 mmol, 1.0 equiv) in a 10 mL BioRad tube was added 25% morpholine/THF (10 mL). The resin changed color from brown to orange/yellow. After 15 minutes at room temperature, Pd(PPh$_3$)$_4$ (333 mg, 0.29 mmol, 1.0 equiv) was added in the dark. The tube was sealed under argon and tumbled for 1.5 hours, after which time the tube was attached to a Promega wash station. The solvent was drained and the resin was washed with CH$_2$Cl$_2$ (2×1 minute, 1×5 minutes), THF (3×10 minutes), 10% CH$_3$CN/THF (1×10 minutes), 25% CH$_3$CN/THF (1×10 minutes), 50% CH$_3$CN/THF (1×10 minutes), 75% CH$_3$CN/THF (1×10 minutes), 90% CH$_3$CN/THF (1×10 minutes), and CH$_3$CN (1×10 minutes). Air drying afforded 9. For HPLC chromatogram of unpurified 9b, see FIG. 47.

FIG III.5 $^1$H NMR Spectrum of Spriodienone (8b)

IV. Library Synthesis

IV.1 Introduction

A stepwise approach was taken to the synthesis of a one-bead-one compound galanthamine-like library (Scheme IV.1).

Scheme IV.1

Library Synthetic Sequence

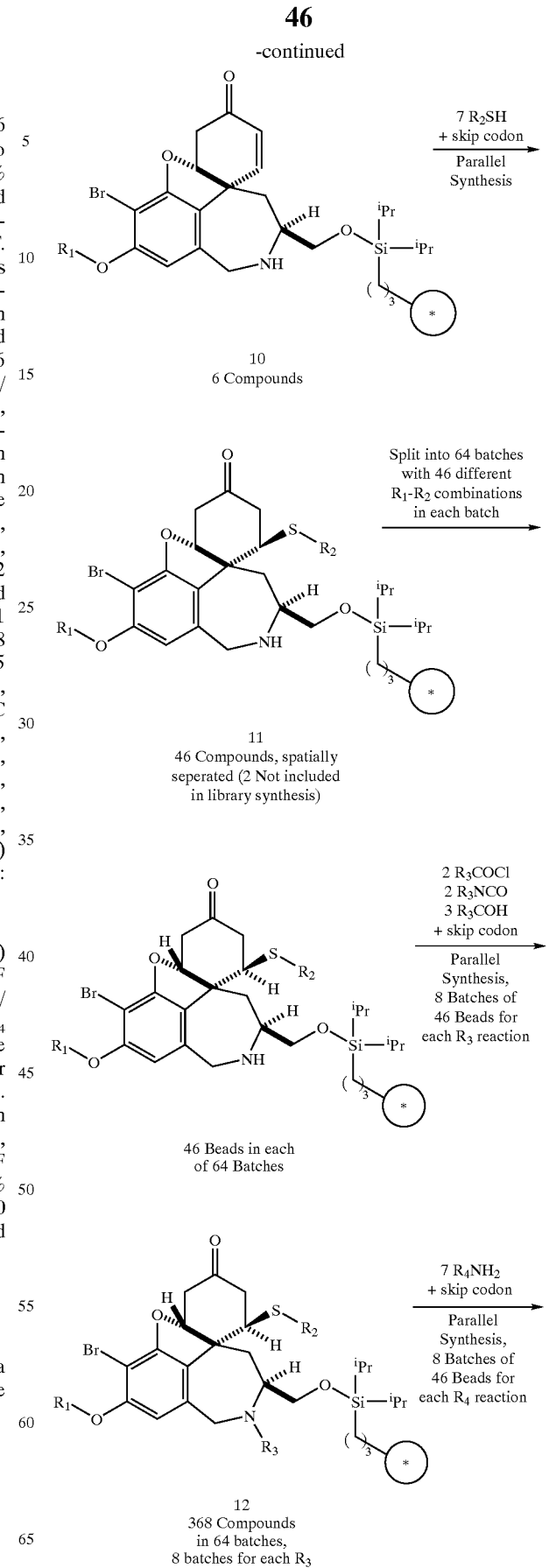

-continued

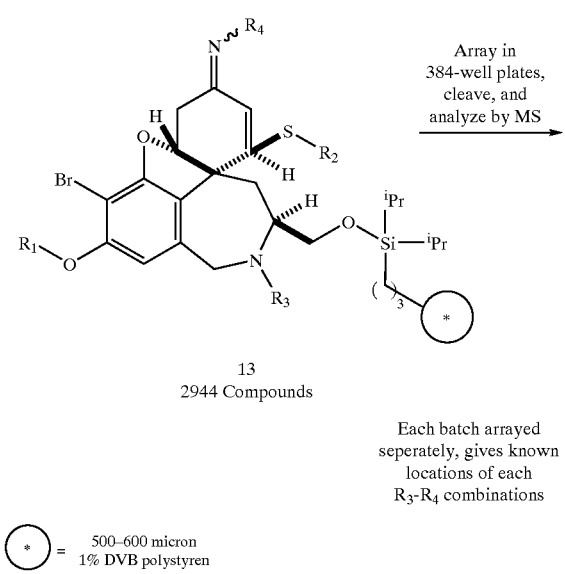

13
2944 Compounds

Each batch arrayed seperately, gives known locations of each $R_3$-$R_4$ combinations ◯* = 500–600 micron 1% DVB polystyren Building blocks were tested for their ability to couple in high yield and purity with a single common substrate. The building blocks are listed in Table IV.1 and their structures are given in FIG. IV.1.

TABLE IV.1

Building Blocks & Identification

| R1- | PHENOL FUNCTIONALIZATION | R3- | NITROGEN- FUNCTIONALIZATION |
|---|---|---|---|
| 1 | 3-Nitrobenzyl alcohol | 1 | Benzoyl chloride |
| 2 | Cyclopropylmethanol | 2 | Benzyl isocyanate |
| 3 | 3-Phenoxy-1-propanol | 3 | Ethyl isocyanate |
| 4 | 3-Cyclopentyl-1-propanol | 4 | Thiophene-2-carbonyl chloride |
| 5 | 5-Hexen-1-ol | 5 | 3-(Methylthio)propional-dehyde |
| 6 | Skip Codon | 6 | Undecanal |
|  |  | 7 | Cyclopropanecarboxal-dehyde |
|  |  | 8 | Skip Codon |

| R2- | ENONE FUNCTIONALIZATION | R4- | KETONE FUNCTIONALIZATION |
|---|---|---|---|
| 1 | Furfuryl mercaptan | 1 | p-Toluenesulfonhydrazide |
| 2 | 3-(Trifluoromethyl)benzyl mercaptan | 2 | Dansyl hydrazine |
| 3 | 3-Methyl-1-butanethiol | 3 | Methoxyamine hydrochloride |
| 4 | 4-Methoxy-alpha-toluenethiol | 4 | o-Benzylhydroxylamine hydrochloride |
| 5 | Benzyl mercaptan | 5 | Carboxymethoxylamine hemihydrochloride |
| 6 | 2-(tert Butyldimethylsily-loxy)ethylmercaptan[viii] | 6 | p-Methoxybenzenesulfonyl-hydrazide |
| 7 | Cyclopentanethiol | 7 | 4-Nitrophenylhydrazine |
| 8 | Skip Codon | 8 | Skip Codon |

Phenol Functionalization:

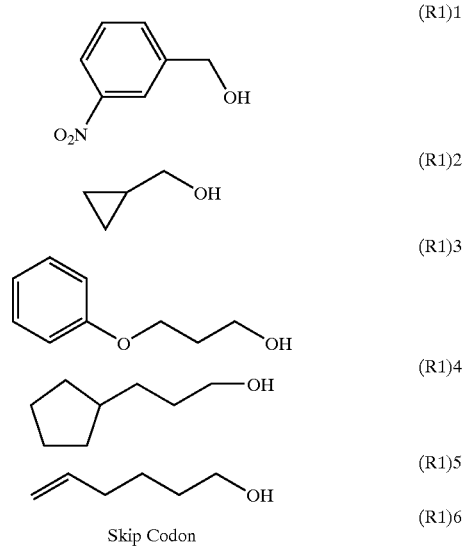

(R1)1
(R1)2
(R1)3
(R1)4
(R1)5
(R1)6 Skip Codon

Enone Functionalization

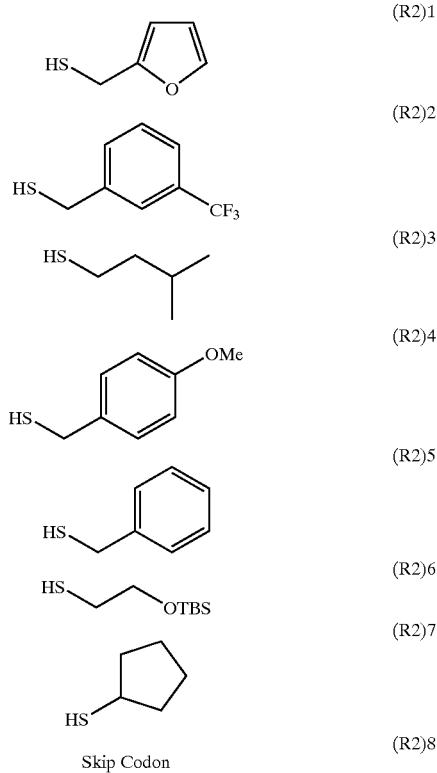

(R2)1
(R2)2
(R2)3
(R2)4
(R2)5
(R2)6
(R2)7
(R2)8 Skip Codon

Nitrogen Functionalization

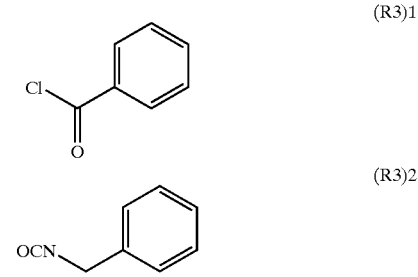

(R3)1

(R3)2

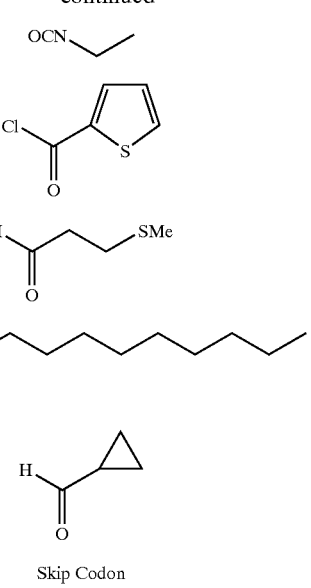

Ketone Functionalization

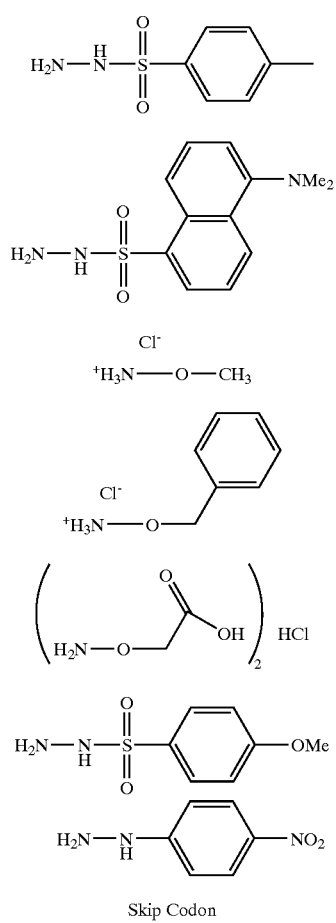

In order to identify any undesirable building block interactions during library synthesis, all (R1)(R2) combinations were synthesized in parallel (Scheme IV.1). The purity of all (R1)(R2) combinations was assessed by LCMS analysis (see Section V.3.1, FIG. 22). LCMS analysis indicated that two combinations (R1)(R2) ((R1)(R2)1 and (R1)1(R2)2) resulted in unsuccessful couplings (data not provided) and were thereof not included in the library synthesis. Three compounds from this stage of the library synthesis were characterized by NMR ((34b), (37b), (38b), Section V.4). A single bead from each of the remaining 46 spatially separated R1–R2 combinations was pooled together to form a new batch. This was repeated to generate 64 new batches that each contained all 46 (R1)(R2) combinations. All (R3) (R4) combinations were synthesized in parallel. Each of those batches was sequentially exposed to a different (R3) (R4) combination.

IV.2 Synthetic Procedures

Resin (10) (R1)2:

To 9 (687 mg, 0.428 mmol/g, 0.29 mmol, 1.0 equiv) and $PPh_3$ (946 mg, 3.6 mmol, 12.2 equiv) dissolved THF (8 mL) in a round-bottom flask (25 mL) at room temperature was added cyclopropylmethanol (292 µL, 3.6 mmol, 12.2 equiv). The mixture was gently swirled by hand and cooled to 0° C. at which time diisopropylazodicarboxylate (568 µL, 2.9 mmol, 10 equiv) was added in the dark dropwise over 5 minutes with gentle swirling by hand. The reaction was allowed to stand at 0° C. for 1 hour in the dark, at which time the mixture was poured into a BioRad tube (20 mL). The tube was attached to a Promega wash station, the solvent was drained, and the resin was washed with $CH_2Cl_2$ (2×1 minute, 1×5 minutes), THF (2×5 minutes), 10% $CH_3CN$/THF (1×5 minutes), 25% $CH_3CN$/THF (1×5 minutes), 50% $CH_3CN$/THF (1×5 minutes), 75% $CH_3CN$/THF (1×5 minutes), 90% $CH_3CN$/THF (1×5 minutes), and $CH_3CN$ (1×5 minutes). Air drying afforded Resin (10) (R1)2.

This procedure was repeated twice for full conversion. Conversion was determined by reacting two beads with benzoyl chloride (10 eq.), 2,6-lutidine (10 eq.) in DCM overnight at room temperature, detachment of the compound from the solid-support, and analysis by LCMS.

Resin (11).(R1)2($R_2$)5:

To Resin (10) (R1)2 (80.9 mg, 0.418 mmol/g, 0.034 mmol, 1.0 equiv) in a round-bottom flask (25 mL) swollen in THF (1.2 mL) at room temperature was added benzylmercaptan (398 µL, 3.4 mmol, 100 equiv) and 2,6-lutidine (396 µL, 3.4 mmol, 100 equiv). Following gentle swirling by hand over 1 minute, the mixture was cooled to 0° C. The reaction was left at 0° C. for 1 hour, after which time nBuLi (40 µL, 2.5 M in hexane, 0.1 mmol, 2.9 equiv) was added dropwise with gentle swirling by hand. The reaction was left at 0° C. for 2 hours, after which time it was fitted with a condenser and warmed to 40° C. After 18 hours at 40° C., the reaction was cooled to room temperature and 5% dry acetic acid in THF (500 µL) was added. The mixture was immediately poured into a BioRad tube (20 mL), fitted to a Promega wash station, and drained. The resin was washed with THF (1×30 seconds), 10% $H_2O$/THF (2×30 seconds), THF (2×10 minutes), 10% $CH_3CN$/THF (1×10 minutes), 25% $CH_3CN$/THF (1×5 minutes), 50% $CH_3CN$/THF (1×5 minutes), 75% $CH_3CN$/THF (1×5 minutes), 90% $CH_3CN$/THF (1×5 minutes), and $CH_3CN$ (1×5 minutes). Air drying afforded Resin (11) (R1)2($R_2$)5.

Resin (12) (R1)1-6(R2)1-8(R3)1:

A single bead from each of the 46 R1–R2 combinations (see above) was placed in a pear-shaped flask (10 mL). To the 46 beads (~92 nmol/bead, 0.0042 mmol, 1.0 equiv) was added $CH_3CN$ (2 mL). After 15 minutes, the $CH_3CN$ was removed via canula and replaced with 50% $CH_3CN$/$CH_2Cl_2$ (2 mL). After 15 minutes, the solvent was removed via canula and replaced with a stock solution (350 µL) of benzoyl chloride (16.8 µL, 0.051 mmol, 12 equiv) and 2,6-lutidine (16.9 µL, 0.051 mmol, 12 equiv) in $CH_2Cl_2$ (1 mL). The reaction was allowed to stand at room temperature for 18 hours. For those batches subsequently undergoing imine formation with one of the R4 building blocks, the solvent was removed via the canula and the resin was washed under positive argon pressure with a dry solution of 25% MeOH/CH$_2$Cl$_2$ (3×10 minutes) and reacted immediately (before drying) with the appropriate R4 building block. For those batches designated for R4-8 (skip codon), the resin was subsequently washed via canula with THF (1×5 minutes), 10% H$_2$O/THF (1×5 minutes), 10% CH$_3$CN/THF (1×5 minutes), 25% CH$_3$CN/THF (1×5 minutes), 50% CH$_3$CN/THF (1×5 minutes), 75% CH$_3$CN/THF (1×5 minutes), 90% CH$_3$CN/THF (1×5 minutes), and CH$_3$CN. The resin was arrayed directly into 384-well plates from the final wash solvent (see Section IV.3).

Resin (12) (R1)1-6(R2)1-8(R3)2:

A single bead from each of the 46 R1–R2 combinations (see above) was placed in a pear-shaped flask (10 mL). To the 46 beads (~92 nmol/bead, 0.0042 mmol, 1.0 equiv) was added CH$_3$CN (2 mL). After 15 minutes, the CH$_3$CN was removed via canula and replaced with 50% CH$_3$CN/CH$_2$Cl$_2$ (2 mL). After 15 minutes, the solvent was removed via canula and replaced with a stock solution (400 µL) of benzyl isocyanate (54.9 µL, 0.051 mmol, 12 equiv) in CH$_2$Cl$_2$ (3.5 mL). The reaction was allowed to stand at room temperature for 18 hours. For those batches subsequently undergoing imine formation with one of the R4 building blocks, the solvent was removed via canula and the resin was washed under positive argon pressure with a dry solution of 25% MeOH/CH$_2$Cl$_2$ (3×10 minutes) and reacted immediately (before drying) with the appropriate R4 building block. For those batches designated for R4-8 (skip codon), the resin was subsequently washed via canula with THF (1×5 minutes), 10% H$_2$O/THF (1×5 minutes), 10% CH$_3$CN/THF (1×5 minutes), 25% CH$_3$CN/THF (1×5 minutes), 50% CH$_3$CN/THF (1×5 minutes), 75% CH$_3$CN/THF (1×5 minutes), 90% CH$_3$CN/THF (1×5 minutes), and CH$_3$CN. The resin was arrayed directly into 384-well plates from the final wash solvent (see Section IV.3).

Resin (12) (R1)1-6(R2)1-8(R3)7:

A single bead from each of the 46 R1–R2 combinations (see above) was placed in a pear-shaped flask (10 mL). To the 46 beads (~92 nmol/bead, 0.0042 mmol, 1.0 equiv) was added a stock solution (200 µL) of cyclopropanecarboxaldehyde (59.4 µL, 0.064 mmol, 15.1 equiv) and acetic acid (15.1 µL, 0.021 mmol, 5.0 equiv) in 25% MeOH/THF (2.5 mL). The mixture was left standing at room temperature for 2 hours, after which time a stock solution (50 µL) of sodium cyanoborohydride (200 mg, 0.064 mmol, 15.1 equiv) in MeOH (2.5 mL) was added slowly., The reaction was allowed to stand at room temperature for 18 hours. For those batches subsequently undergoing imine formation with one of the R4 building blocks, the solvent was removed via canula and the resin was washed under positive argon pressure with a dry solution of 10% MeOH/THF (2×15 minutes) and reacted immediately (before drying) with the appropriate R4 building block. For those batches designated for R4-8 (skip codon), the resin was subsequently washed via canula with THF (1×5 minutes), 10% CH$_3$CN/THF (1×5 minutes), 25% CH$_3$CN/THF (1×5 minutes), 50% CH$_3$CN/THF (1×5 minutes), 75% CH$_3$CN/THF (1×5 minutes), 90% CH$_3$CN/THF (1×5 minutes), and CH$_3$CN. The resin was arrayed directly into 384-well plates from the final wash solvent (see Section IV.3).

Resin (13) (R1)1-6(R2)1-8(R3)1-8(R4)1:

To the resin (46 beads, ~92 nmol/bead, 0.0042 mmol, 1.0 equiv) and p-toluensulfonylhydrazide (59 mg, 0.32 mmol, 75 equiv) in a pear-shaped flask (10 mL) was added AcOH:MeOH:CH$_2$Cl$_2$ (1:3.8:10.4, 3.00 µL) in the dark. The mixture was kept at room temperature in the dark for 20 hours, after which time the solvent was removed via canula and the resin was washed with MeOH:DMSO:THF (1:1:2, 3×5 minutes) [Note: additional DMSO was added to dissolve any undissolved reagent], 2.5% 2,6-lutidine in 25% CH$_3$CN/THF (1×5 minutes), MeOH:DMSO:THF (1:1:2, 2×10 minutes), 25% CH$_3$CN/THF (1×5 minutes), 10% CH$_3$CN/THF (1×5 minutes), THF (1×5 minutes), 10% CH$_3$CN (1×5 minutes), 25% CH$_3$CN/THF (1×5 minutes), 50% CH$_3$CN/THF (1×5 minutes), 75% CH$_3$CN/THF, 90% CH$_3$CN/THF (1×5 minutes), and left in CH$_3$CN. The resin was arrayed directly into 384-well plates from the final wash solvent (see Section IV.3).

IV.3 Arraying and Cleavage From Resin

The resin, in CH$_3$CN, was arrayed into 384-well plates (Genetix, X5005). The bottom 0.5 inches of a 1–200 µL plastic pipette tip was removed and the remaining tip was affixed to a p100 Gilson pipetteman. Each bead was taken up into the tip in a minimal amount of CH$_3$CN (~40 µL) and dispensed into a well. This was repeated for all the beads in each batch. Bead fragments were also dispensed in a separate well. The resin was dispensed into 17 384-well plates, labelled Plate 1 and Plate 3 through Plate 18. The CH$_3$CN was allowed to evaporate over 3 hours at atmospheric pressure and room temperature. To each well was then dispensed 10% HF-pyridine in THF (30 µL). The plates were allowed to stand at room temperature, covered with another empty 384-well plate. After 1.5 hours at room temperature, methoxytrimethylsilane (20 µL) was dispensed into each well. After 30 minutes at room temperature, the solution was allowed to evaporate for 2 hours at room temperature and atmospheric pressure. Any remaining solvent was removed from the residue+bead in each well by placing the plate in a vacuum oven at room temperature for 12 hours.

IV.4 Stock Solutions Preparation and Screening

After concentrating in vacuo over 12 hours, the residue was dissolved in 6.7 µl of DMSO. The plates were then used directly for biological screening.[ix] The plates were stored between screens with an aluminum foil top at −40° C.

IV.5 LC and MS Sample Preparation

Unless otherwise stated LC and MS samples were prepared by removing an aliquot (0.5 µl) of DMSO stock from the relevant well of the completed library and diluting this material into analytical grade acetonitrile (16 µl).

V. Library Analysis

V.1 Introduction

V.1.1 Use of MS and LC analysis for Library Characterization

Figure 48A:
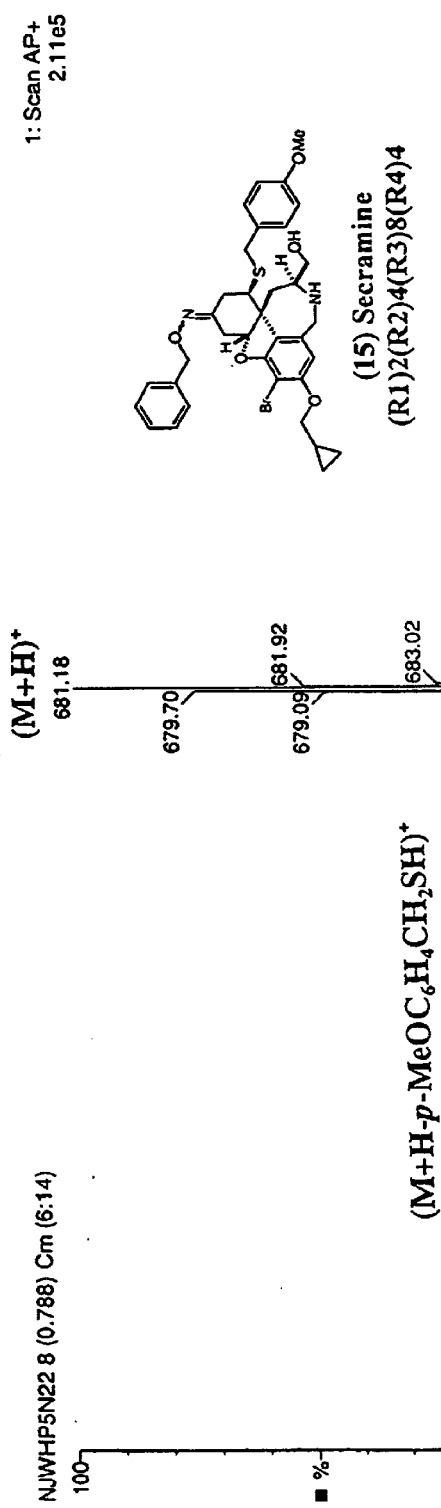
FIG. 48 depicts an exemplary use of MS and LC analysis for library characterization. Specifically, positive and negative ion mass spectra observed for plate 5 well N22 are depicted.
Figure 48B:
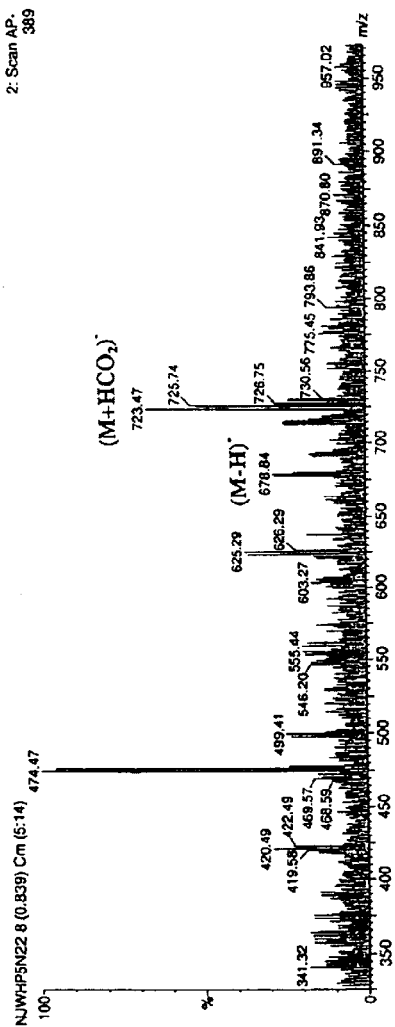

A portion (5 µl) of the analytical sample for each well (Section V.5) was introduced into the MS by automated direct infusion (Section I). Using this method it was possible to analyze 24 samples per hour, with a total analysis time of 125 hours for the library. As an example, FIG. 48 shows the negative and positive ion mass spectra obtained from the material present in plate 5 well N22. Structural assignments were carried out by manual inspection of the MS data for each well and comparison with tables of theoretical molecular weights for all (R1)1-6(R2)1-8(R3)1-8(R4)1-8 combinations. The chemical structure assigned to each compound is presented in the format (R1)1-6(R2)1-8(R3)1-8(R4)1-8 unless otherwise stated (see FIG. 48 for an example of its use). The building block numerical assignments are listed in Table IV.1.

Figure 49:
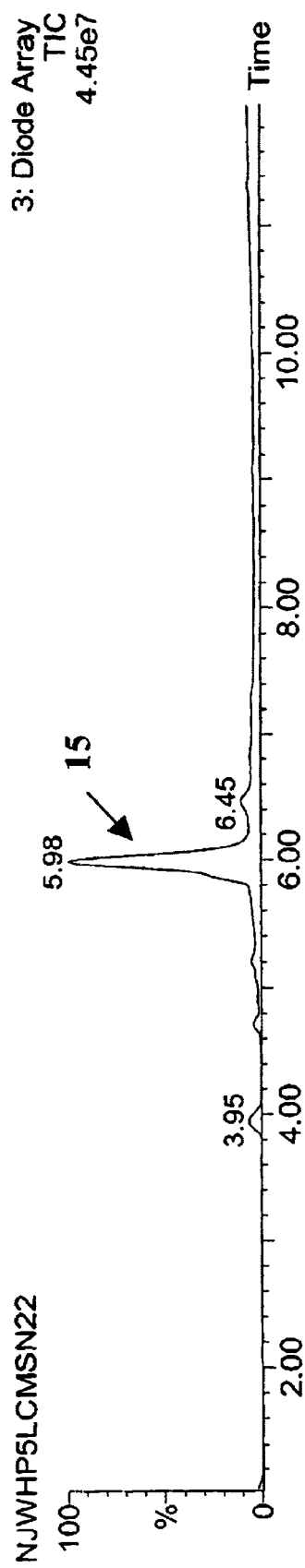
FIG. 49 depicts the LC (Diode Array) portion of LCMS of secramine (15). Solvent front omitted for clarity.

The compound in plate 5 well N22 is assigned structure (15) and is referred to as secramine (see text of paper). The LCMS data for the compound present in plate 5 well N22 confirms the assignment and purity level of (15) (FIG. 49). Fragmentations such as the observed 679/681 to 525/527 (positive ion TIC, FIG. 48) also aided structure assignment. This particular fragmentation corresponds to loss of 4-methoxy-alpha-toluenethiol from the parent molecular ion, confirming the R2 building block assignment.

Difficulties in structural assignment arising from overlapping theoretical molecular weights were minimized by:

1) keeping final batches of resin spatially separated (in any well of the library both R3 and R4 are already known)
2) imposing an additional constraint on R1 and R2 building blocks. They were selected such that a minimal molecular weight overlap existed for each of the 46 (out of 48) (R1)(R2) combinations.

For (R1)(R3) combinations in which (R1)=6 and (R3)= 1,2,3 or 4, the phenol functionality in structure (31a) is converted during R3 incorporation in the solid phase to the phenolic ester (32a) ((R3)2,3) or phenolic carbamate (33a) ((R3)1,4) (Scheme V.1.1). These functional groups typically survived incorporation of the R4 building block and HF.pyridine cleavage conditions to give (32b) and (33b) respectively. On MS analysis of these compounds, the $(M+H)^+$ ion was observed as the major ion in the positive TIC with a major fragmentation corresponding to loss of one R3 group. On LCMS analysis of these compounds a minor component assigned as the free phenol-containing derivative was occasionally observed. The possibility that the phenolic ester or carbamate groups are hydrolyzed under the biological assay conditions is an issue that is being addressed during the resynthesis of preliminary hits containing R1=6.

database designed to link chemical structure with biological screening data.

Three stages of LCMS analysis were carried out in order to determine the purity level of the library at key stages (for analytical protocols see Section I). This analysis demonstrated that typically the expected products were obtained at a high level of purity, as judged by this analytical technique. As an example, the diode array trace corresponding to the compound assigned as secramine (15) is shown in FIG. 49.

For LC data (diode array trace) in support of the successful synthesis of:

1) all (R1)(R2) combinations ((R3)8(R4)8) see Section V.3.1
2) 287 of the possible 322 (R1)(R2)(R3) combinations see Section V.3.2 (excluding (R3)8(R4)8) combinations)
3) Randomly selected (R1)(R2)(R3)(R4) combinations from each library plate (see Section V.3.3). LCMS analysis of the majority of these samples indicates the presence of two major compounds as judged by this analytical technique. Inspection of the mass spectrum of examples in which the two compounds are well resolved indicated that they have identical molecular weights. These structures are currently assigned as the E- and Z-isomers about the C=N bond (hydrazone, oxime) that may be formed during R4 incorporation. In cases where a peak corresponding to one major compound is observed, it was not determined whether predominantly one isomer was formed or whether the two isomers were not separated under the LC conditions.

Due to the presence of DMSO in the samples a strong signal in the diode array spectrum with a retention time of 0.5–1.0 minutes was typically observed. For clarity of

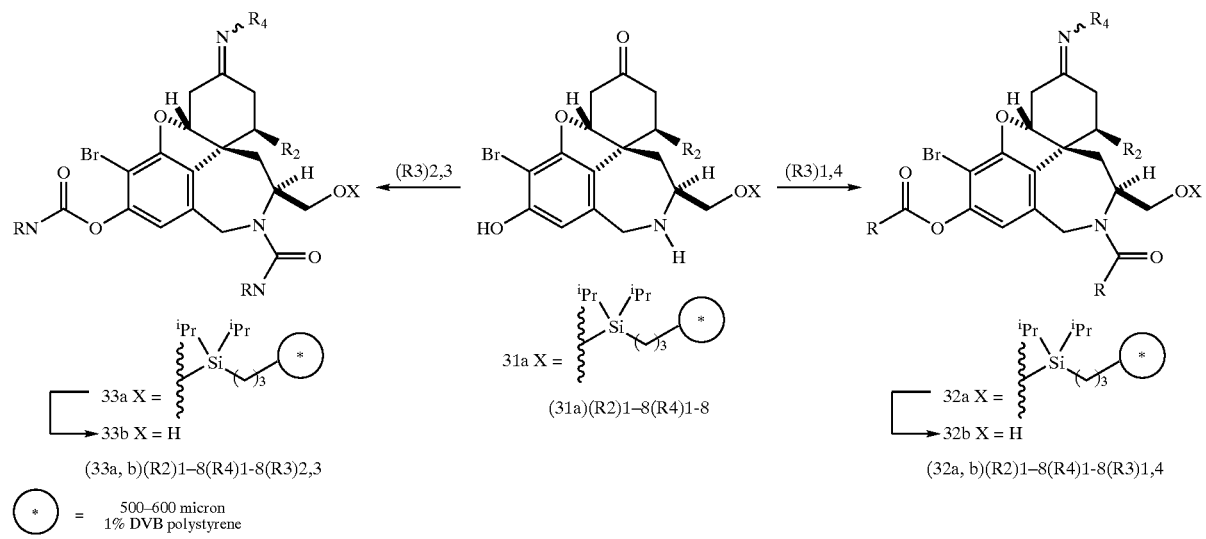

Scheme V.1.1

R3 Incorporation Leads to Phenolic Ester or Carbamate Formation for (R1)6 examples A complete structural assignment of the library, broken down by plate, quadrant and (R1)(R2)(R3)(R4) combination is given in FIGS. 7–22 (Section V.2). Of the expected 2944 compounds, 2527 have been identified (86%). See, also, Pelish et al. *J. Am. Chem. Soc.* 2001, 123, 6740–6741, and Supplemental Information at http://pubs.acs.org, the entire contents of which are hereby incorporated by reference. This information will be incorporated into a structure searchable presentation the diode array traces have been cropped to remove this peak. The presence of a UV active impurity that does not ionize in either the positive or negative APCI mode was observed in several wells (retention time 3.5–4.0 minutes). The source of this impurity is currently unknown.

V.1.2 NMR Characterization of Representative Compounds

Figure 42:
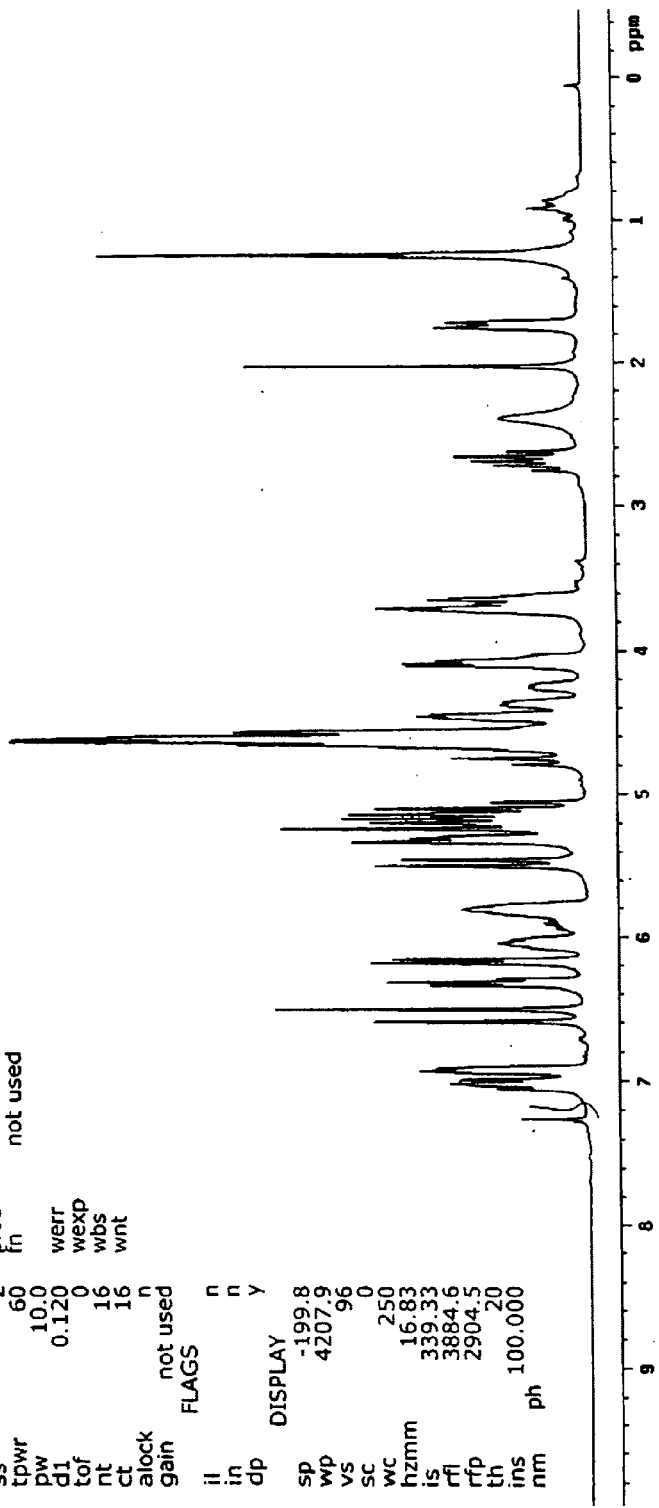
FIG. 42 depicts a $^1$H NMR spectrum of Spirodienone (8b).

In addition to the use of MS and LC analysis, the synthesis of 6 final compounds has been carried out on the solid phase on an increased scale (Section VI.4.1 for experimental details and full characterization; Section VI.4.2 for accompanying $^1$H NMR spectra). Interpretation of $^1$H NMR spectra has been complicated in cases where R4=1–7 by the presence of two compounds which are currently being assigned as E- and Z-isomers about the C=N bond (hydrazone, oxime). In addition, the presence of rotameric forms that are slow to interconvert on the NMR timescale frequently resulted in broad, unassignable spectra at room temperature (CDCl$_3$ or d$_6$-DMSO), particularly in cases where R3=1,2,3 or 4. In several cases, recording $^1$H NMR spectra for these compounds at elevated temperatures in d$_6$-DMSO, resulted in much sharper signals. The $^1$H NMR spectra of spirodienone (8b) (FIG. 42) did not simplify in this manner when recorded at temperatures up to 80° C. in d$_6$-DMSO.

V.1.3 Stereochemical Assignments

Only one diastereomer is observed for the formation of Resin 20a. The stereochemistry at C1 was established by GOESY and NOESY experiments with 29b (FIG. V.1.4, Section V.4.2).

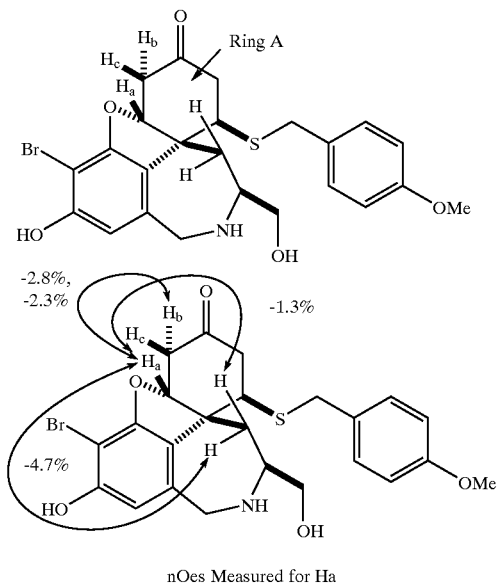

nOes Measured for Ha

FIG. V.1.3 nOe measurements and observations for 34b, H$_a$

Figure 43A:
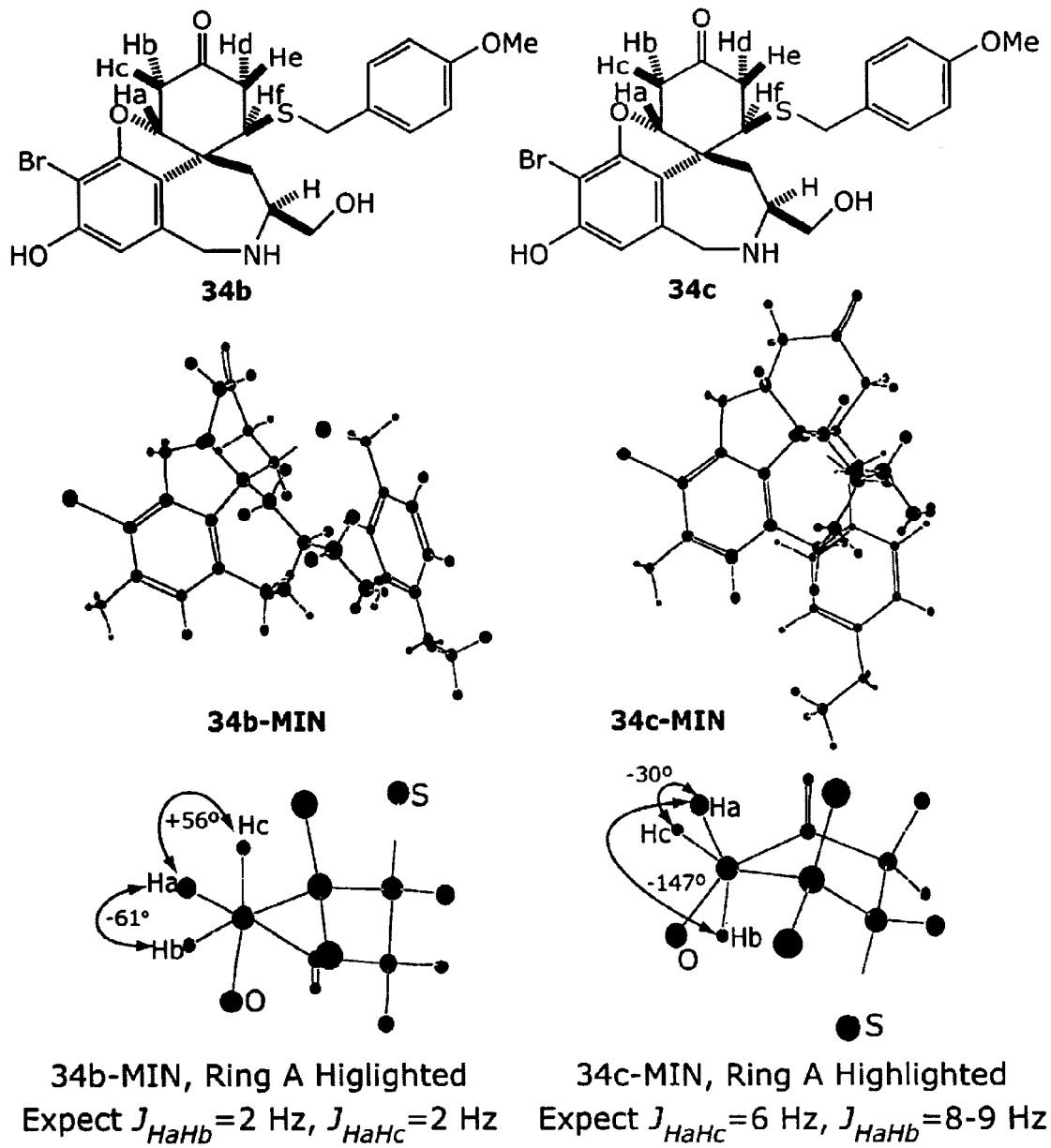
FIG. 43 depicts (A) MacroModel Energy Minimization of 34b and 34c in Chloroform; and (B) NMR Spectra of Ha, 29b in CDCl$_3$, 500 MHz.
Figure 43B:
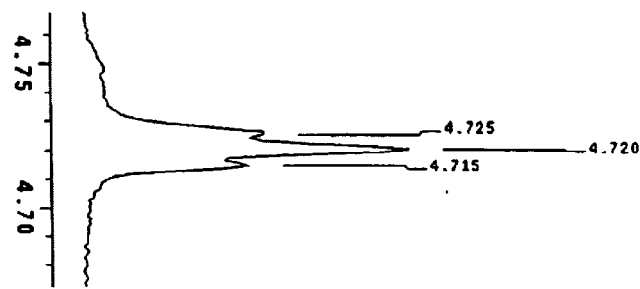

Only one diastereomer was observed for conversion of 10 to 11. FIG. V.4.2.9 and FIG. V.4.2.11 present examples of the comparison of $^1$H NMR spectra obtained with unpurified material cleaved from the resin and the material obtained by flash column chromatography. The presence of a single H$_a$ proton provides evidence of the diastereoselectivity. Molecular modeling was correlated to NMR data to assign the stereochemistry at C2 based on representative structure 34b (FIG. V.1.3). Energy-minimized conformations of 34b and 34c, 34b-MIN and 34c-MIN, respectively, were calculated using the AMBER force field on 1000 structures generated by a Monte Carlo multiconformer search in chloroform using MacroModel (Version 6.0) FIG. 43A). The dihedral angles for H$_a$–H$_b$ and H$_a$–H$_c$ differ significantly between 34b-MIN and 34c-MIN. The NMR-obtained coupling constant (FIG. 43B) for the key Ha proton in CDCl$_3$ (dd, J=2.5, 2.5 Hz) agrees with the theoretical coupling constant based on the Karplus correlation[1] for 34b-MIN (dd, J 2, 2 Hz), and not 34c-MIN (dd, J 6, 8–9 Hz).

V.2 MS Analysis for Library Structure Assignment

For structural assignments of compounds in Plate 1 see FIGS. 23, 24 and 26

FIG. 7 Structural Assignment of Compounds in Plate 3
FIG. 8 Structural Assignment of Compounds in Plate 4
FIG. 9 Structural Assignment of Compounds in Plate 5
FIG. 10 Structural Assignment of Compounds in Plate 6
FIG. 11 Structural Assignment of Compounds in Plate 7
FIG. 12 Structural Assignment of Compounds in Plate 8
FIG. 13 Structural Assignment of Compounds in Plates 9 and 10
FIG. 14 Structural Assignment of Compounds in Plate 11
See also FIGS. 23 and 24 for Structural Assignment of Compounds in Plate 11
FIG. 15 Structural Assignment of Compounds in Plate 12
FIG. 16 Structural Assignment of Compounds in Plate 13
FIG. 17 Structural Assignment of Compounds in Plate 14
FIG. 18 Structural Assignment of Compounds in Plate 15
See also FIG. 25 for Structural Assignment of Compounds in Plate 15
FIG. 19 Structural Assignment of Compounds in Plate 16
FIG. 20 Structural Assignment of Compounds in Plate 17
FIG. 21 Structural Assignment of Compounds in Plate 18
Z=a compound corresponding to this (R1)(R2)(R3)(R4) combination was not be identified.

V.3 LC analysis for Purity Assessment

V.3.1 All (R1)(R2) combinations (46)

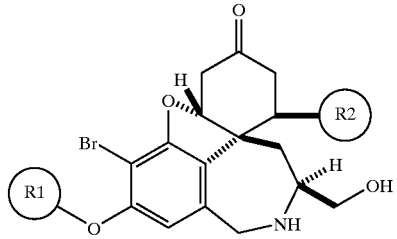

FIG. 22 Structural Assignment of all 46 R1–R2 combinations for (R3)8(R4)8

Diode Array Traces for R2 combinations with (R1)1(R3) 8(R4)8, (R1)2(R3)8(R4)8, (R1)3(R3)8(R4)8, (R1)4(R3)8 (R4)8, (R1)5(R3)8(R4)8, and (R1)6(R3)8(R4)8 were obtained using LC analysis protocol B (Section I). All other spectra were obtained using LC analysis protocol A (Section I). See also, Pelish et al., J. Am. Chem. Soc. 2001, 123, 6740–6741, and supplemental information (http://pubs.acs.org), the entire contents of which are hereby incorporated by reference.

V.3.2 (R1)(R2)(R3) Combinations 287 compounds of the theoretical maximum of 322 compounds were identified.

FIG. 23 Structural Assignment of (R1)(R2) combinations for (R3)1(R4)8 and (R3)2(R4)8
FIG. 24 Structural Assignment of (R1)(R2) combinations for (R3)3(R4)8 and (R3)4(R4)8
FIG. 25 Structural Assignment of (R1)(R2) combinations for (R3)5(R4)8 and (R3)6(R4)8
FIG. 26 Structural Assignment of (R1)(R2) combinations for (R3)7(R4)8

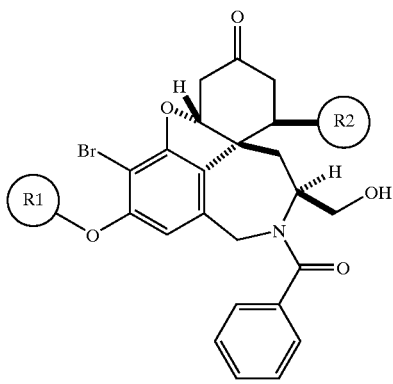

Diode Array Traces for R2 combinations with (R1)1(R3) 1(R4)8, (R1)2(R3)1(R4)8, (R1)3(R3)1(R4)8, (R1)4(R3)1(R4)8, (R1)5(R3)1(R4)8, (R1)6(R3)1(R4)8 were obtained as described above and herein. See also, Pelish et al., *J. Am. Chem. Soc.* 2001, 123, 6740–6741, and supplemental information (http://pubs.acs.org), the entire contents of which are hereby incorporated by reference.

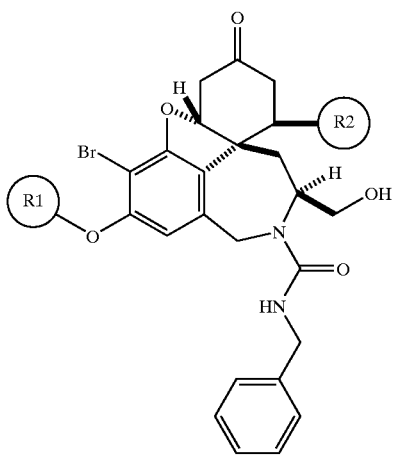

Diode Array Traces for R2 combinations with (R1)1(R3) 2(R4)8, (R1)2(R3)2(R4)8, (R1)3(R3)2(R4)8, (R1)4(R3)2(R4)8, (R1)5(R3)2(R4)8, (R1)6(R3)2(R4)8 were obtained as described above and herein. See also, Pelish et al., *J. Am. Chem. Soc.* 2001, 123, 6740–6741, and supplemental information (http://pubs.acs.org), the entire contents of which are hereby incorporated by reference.

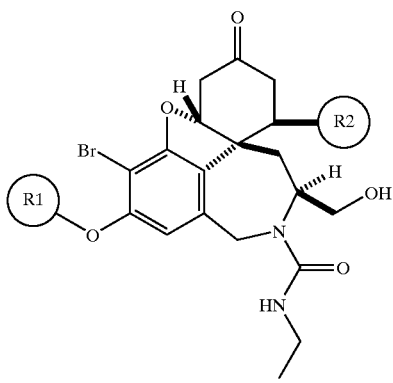

Diode Array Traces for R2 combinations with (R1)1(R3) 3(R4)8, (R1)2(R3)3(R4)8, (R1)3(R3)3(R4)8, (R1)4(R3)3 (R4)8, (R1)5(R3)3(R4)8, (R1)6(R3)3(R4)8 were obtained as described above and herein. See also, Pelish et al., *J. Am. Chem. Soc.* 2001, 123, 6740–6741, and supplemental information (http://pubs.acs.org), the entire contents of which are hereby incorporated by reference.

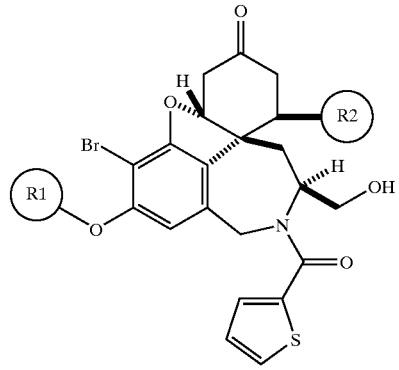

Diode Array Traces for R2 combinations with (R1)1(R3) 4(R4)8, (R1)2(R3)4(R4)8, (R1)3(R3)4(R4)8, (R1)4(R3)4 (R4)8, (R1)5(R3)4(R4)8, (R1)6(R3)4(R4)8 were obtained as described above and herein. See also, Pelish et al., *J. Am. Chem. Soc.* 2001, 123, 6740–6741, and supplemental information (http://pubs.acs.org), the entire contents of which are hereby incorporated by reference.

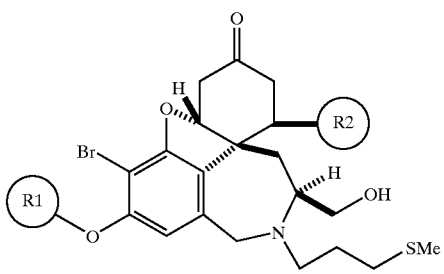

Diode Array Traces for R2 combinations with (R1)1(R3) 5(R4)8, (R1)2(R3)5(R4)8, (R1)3(R3)5(R4)8, (R1)4(R3)5 (R4)8, (R1)5(R3)5(R4)8, (R1)6(R3)5(R4)8 were obtained as described above and herein. See also, Pelish et al., *J. Am. Chem. Soc.* 2001, 123, 6740–6741, and supplemental information (http://pubs.acs.org), the entire contents of which are hereby incorporated by reference.

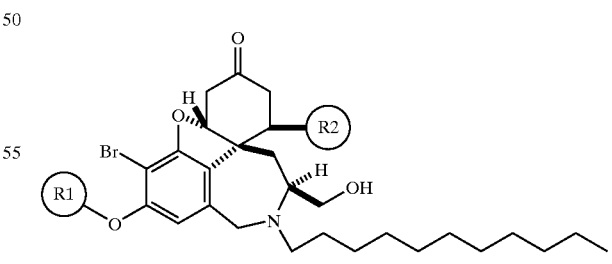

Diode Array Traces for R2 combinations with (R1)1(R3) 6(R4)8, (R1)2(R3)6(R4)8, (R1)3(R3)6(R4)8, (R1)4(R3)6 (R4)8, (R1)5(R3)6(R4)8, (R1)6(R3)6(R4)8 were described above and herein. See also, Pelish et al., *J. Am. Chem. Soc.* 2001, 123, 6740–6741, and supplemental information (http://pubs.acs.org), the entire contents of which are hereby incorporated by reference.

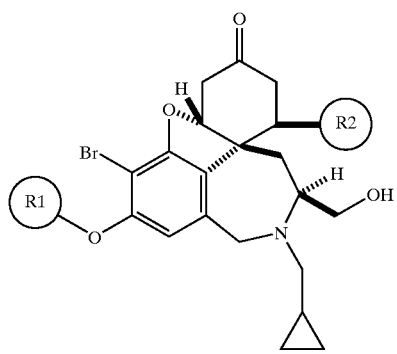

Diode Array Traces for R2 combinations with (R1)1(R3)7(R4)8, (R1)2(R3)7(R4)8, (R1)3(R3)7(R4)8, (R1)4(R3)7(R4)8, (R1)5(R3)7(R4)8, (R1)6(R3)7(R4)8 were obtained as described above and herein. See also, Pelish et al., *J. Am. Chem. Soc.* 2001, 123, 6740–6741, and supplemental information (http://pubs.acs.org), the entire contents of it which are hereby incorporated by reference.

* these spectra were obtained using LC analysis protocol B (Section I). All other spectra were obtained using LC analysis protocol A (Section I).

V.3.3 Representative Final Compounds From Library Plates 3–18

Plate 3

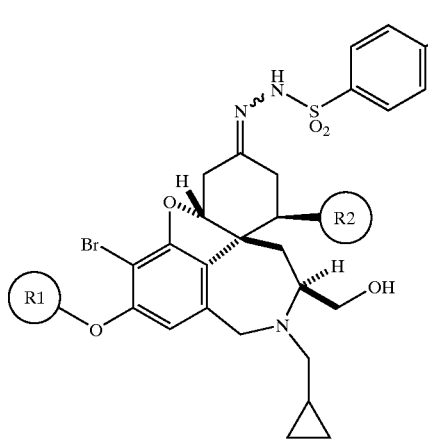
(R3)7(R4)1

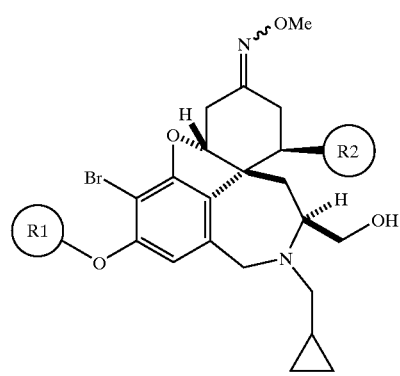
(R3)7(R4)3

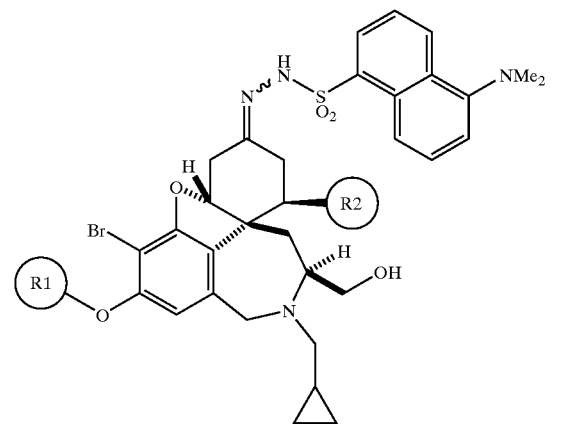
(R3)79R4)2

Plate 4

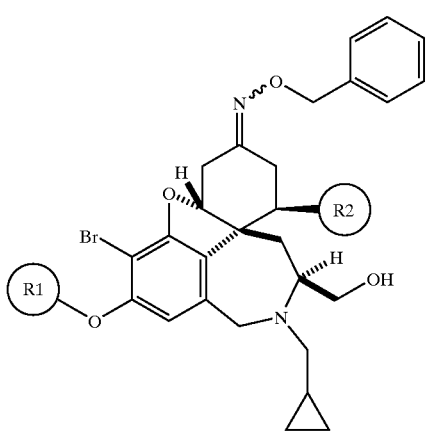
(R3)7(R4)4

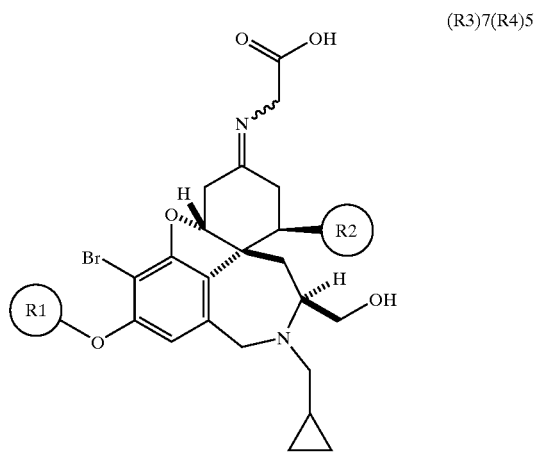
(R3)7(R4)5

61
-continued
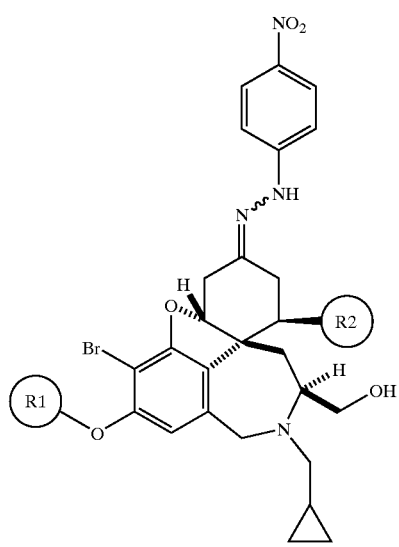
(R3)7(R4)7
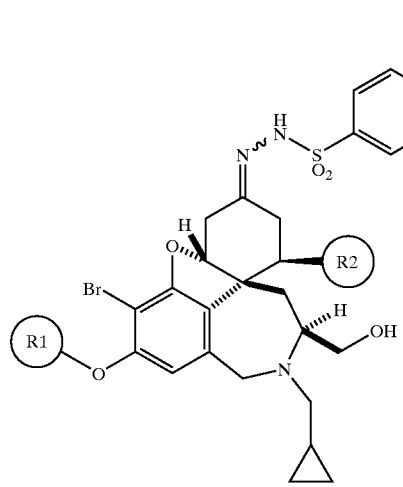
(R3)7(R4)6
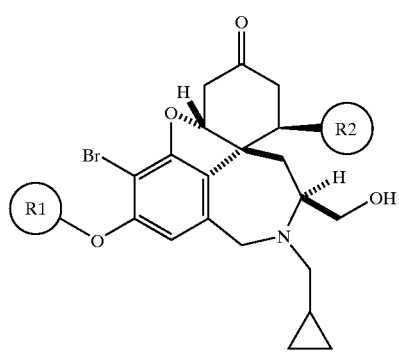
(R3)7(R4)8
(see Figure VI.3.2.37–42)
62
-continued
Plate 5
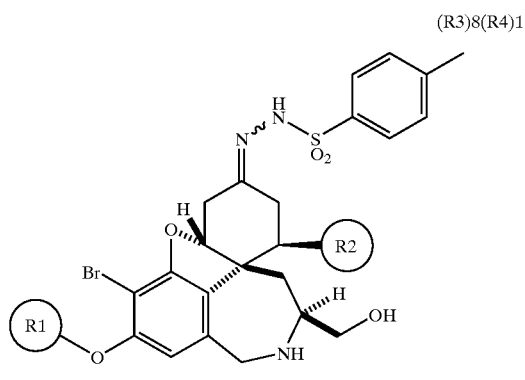
(R3)8(R4)1
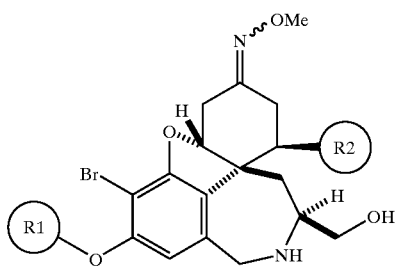
(R3)8(R4)3
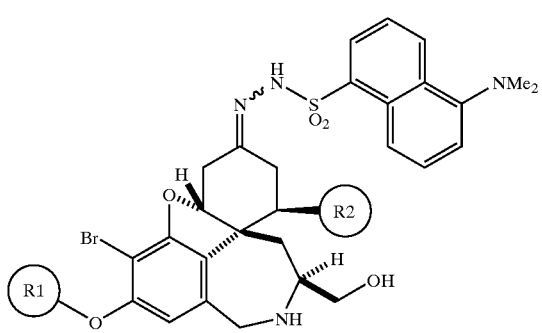
(R3)8(R4)2
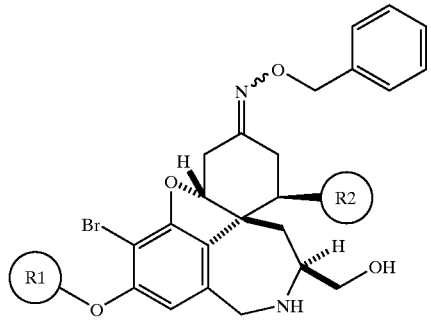
(R3)8(R4)4

-continued
Plate 6
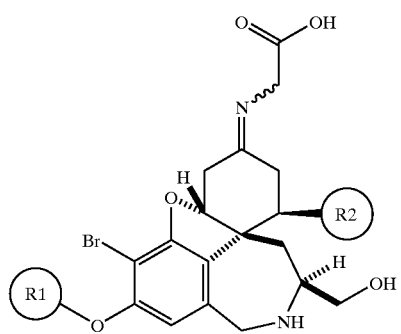
(R3)8(R4)5
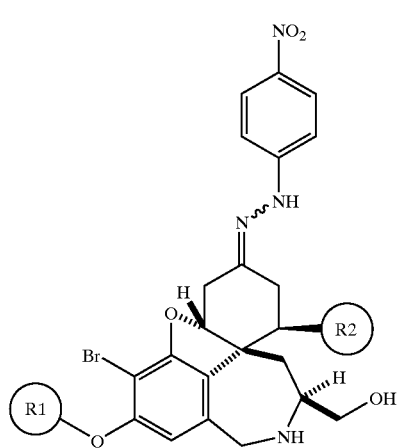
(R3)8(R4)7
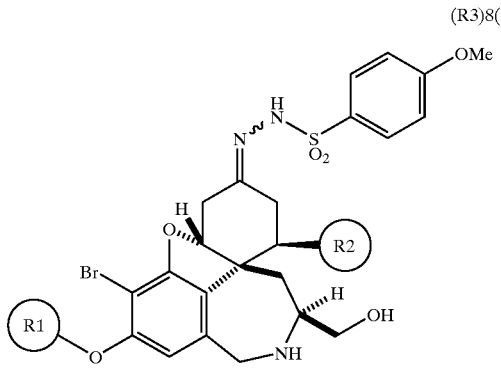
(R3)8(R4)6
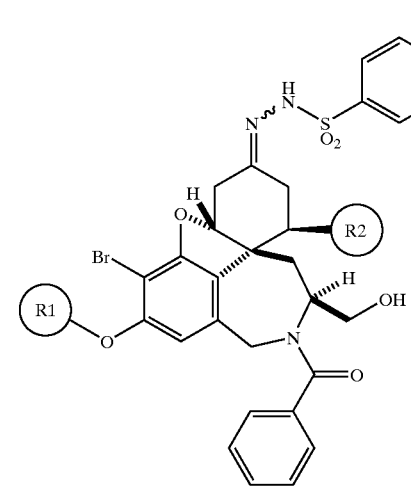
(R3)1(R4)1
-continued
Plate 7
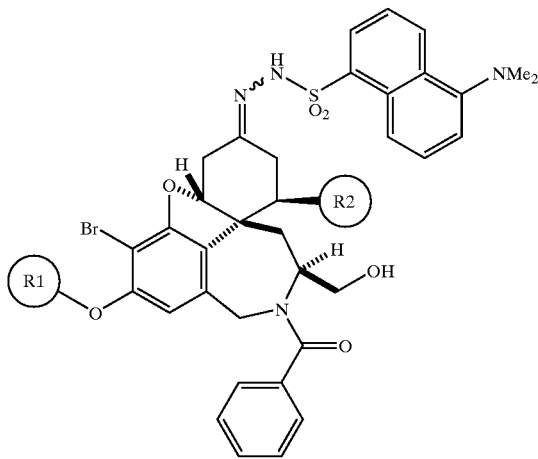
(R3)1(R4)2
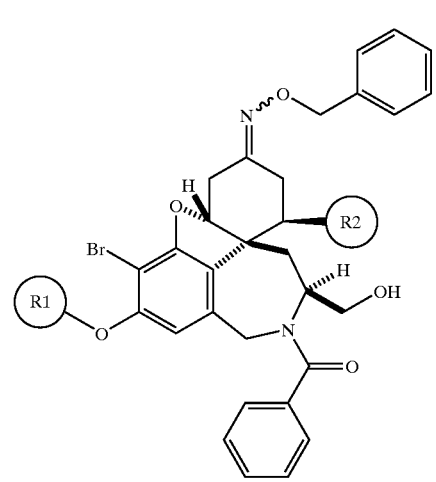
(R3)1(R4)4
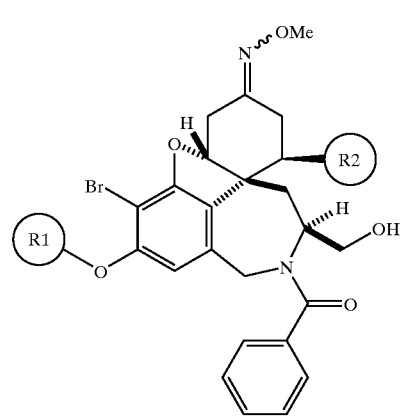
(R3)1(R4)3

65
-continued
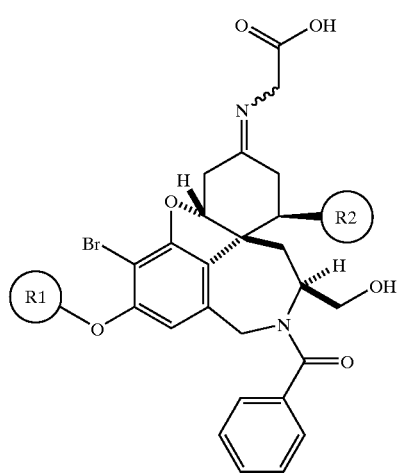
(R3)1(R4)5
Plate 8
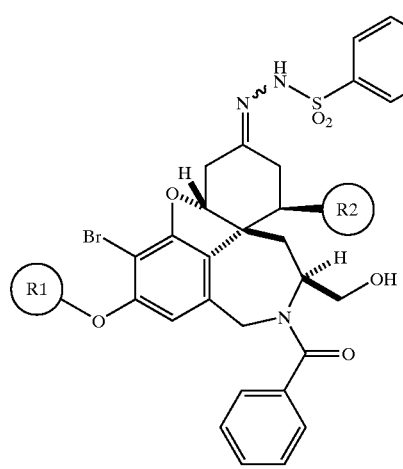
(R3)1(R4)6
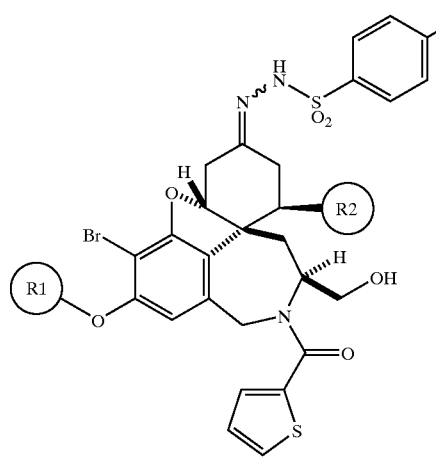
(R3)4(R4)1
66
-continued
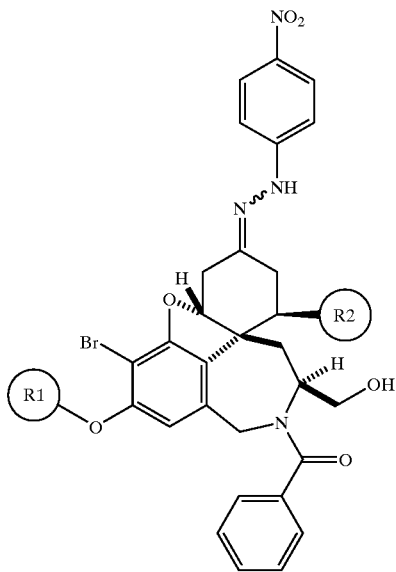
(R3)1(R4)7
(R3)4(R4)2
Plates 9 and 10
(R3)4(R4)3

67
-continued
(R3)4(R4)5
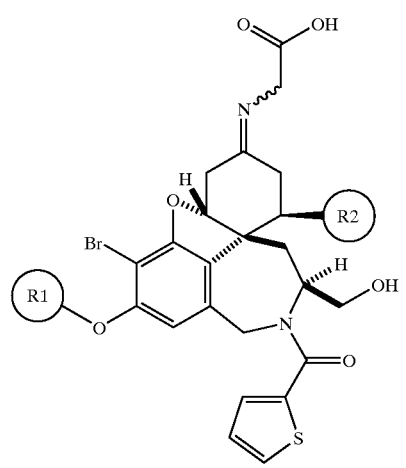
(R3)4(R4)4
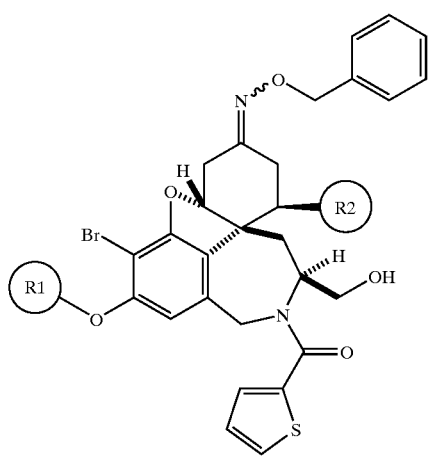
(R3)4(R4)6
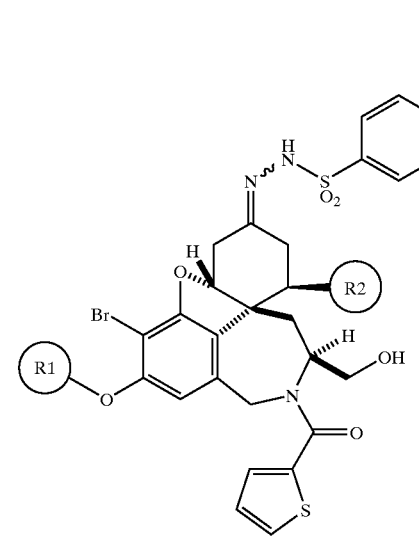
68
-continued
(R3)4(R4)7
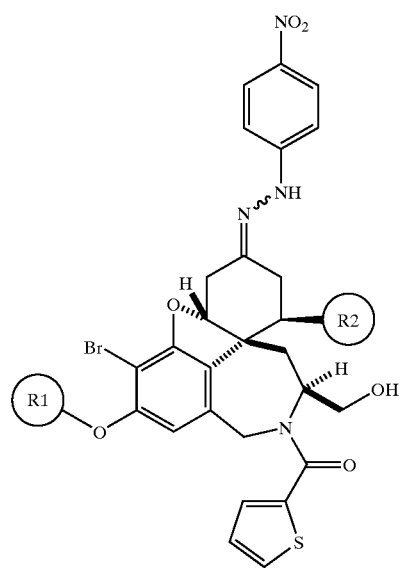
Plate 11
(R3)2(R4)1
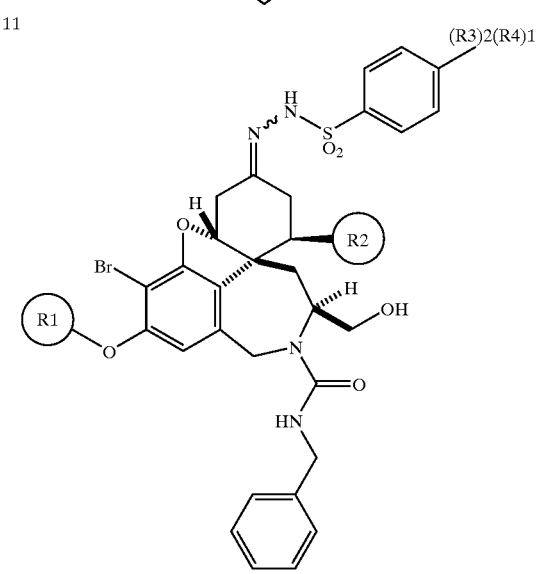
(R3)2(R4)2

Plate 12
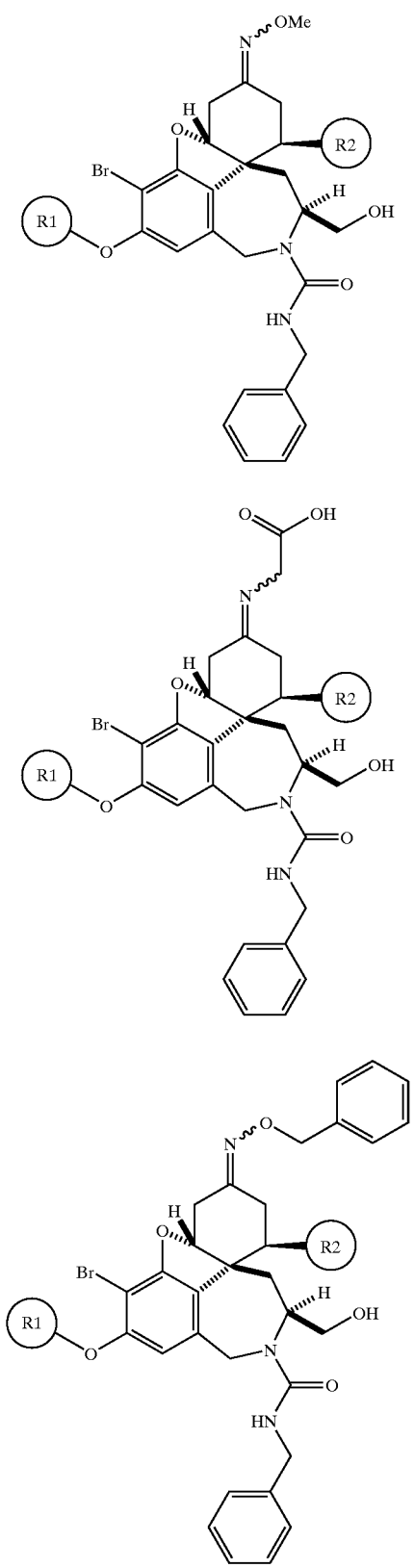
Plate 13
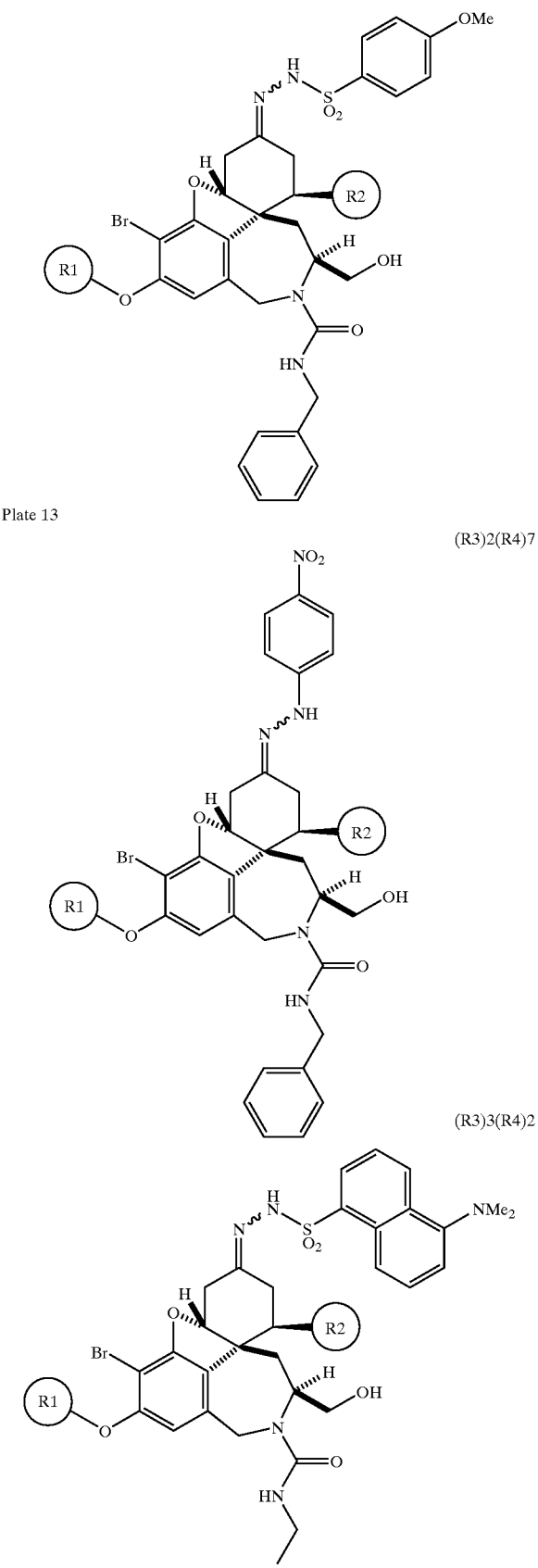

-continued
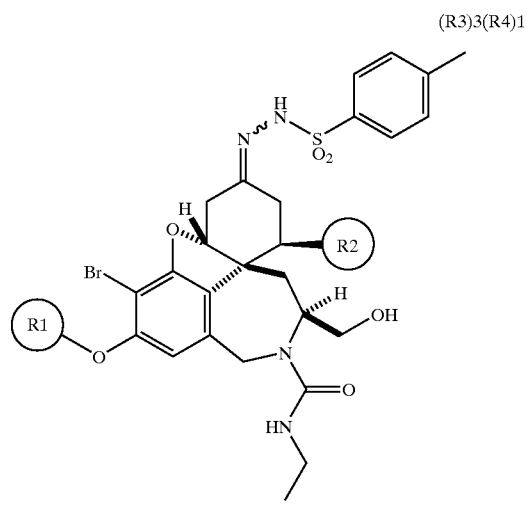
(R3)3(R4)1
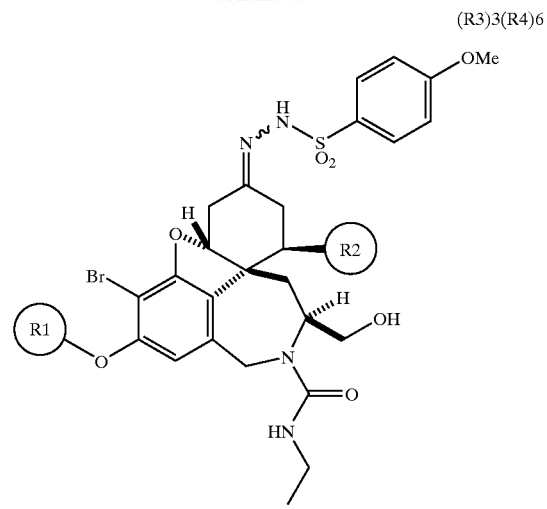
(R3)3(R4)6
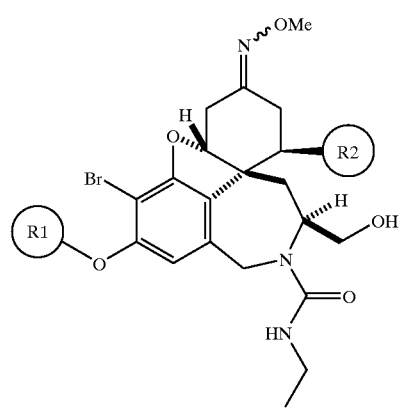
(R3)3(R4)3
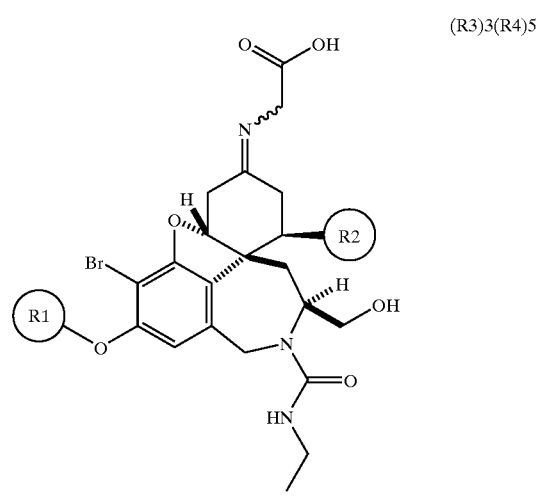
(R3)3(R4)5
Plate 14
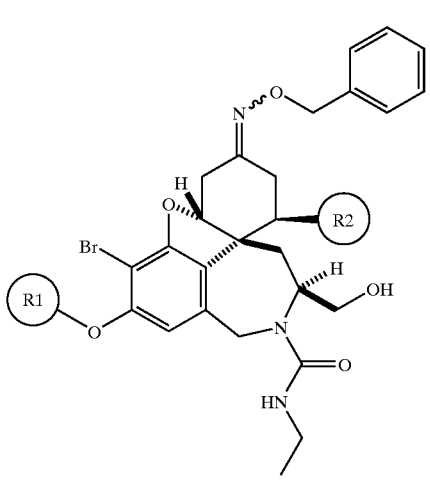
(R3)3(R4)4
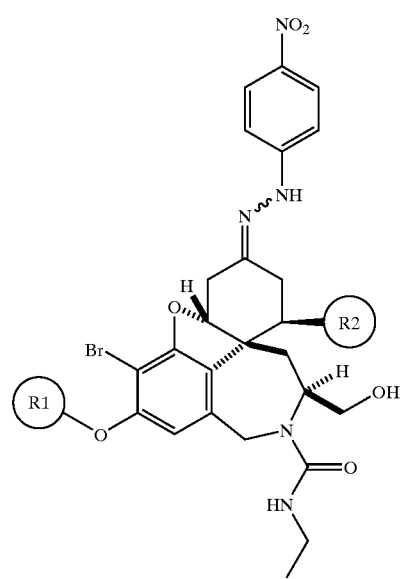
(R3)3(R4)7

-continued
Plate 15
(R3)5(R4)1
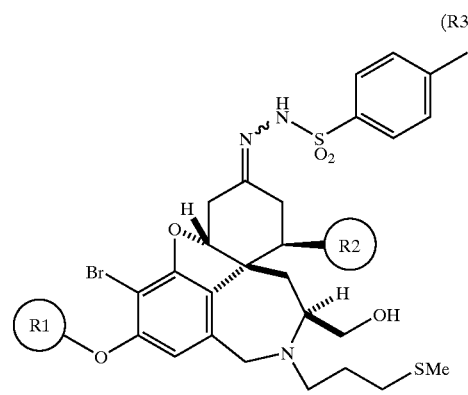
(R3)5(R4)2
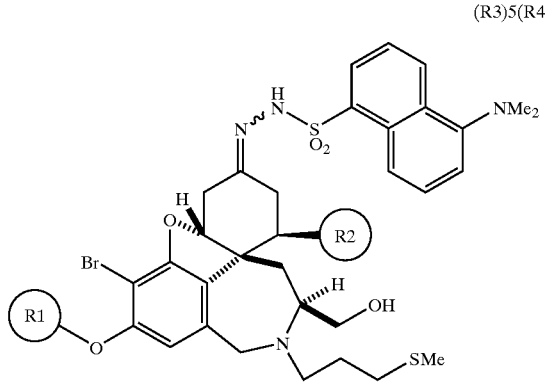
Plate 16
(R3)5(R4)3
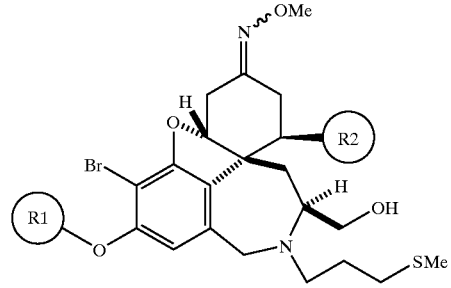
(R3)5(R4)5
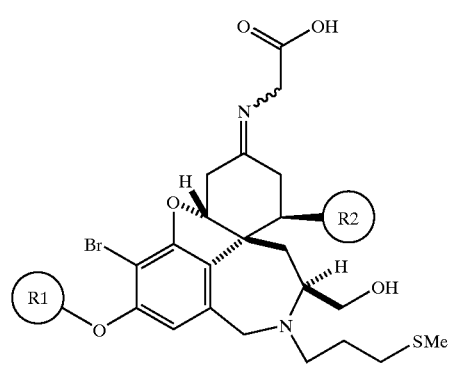
(R3)5(R4)4
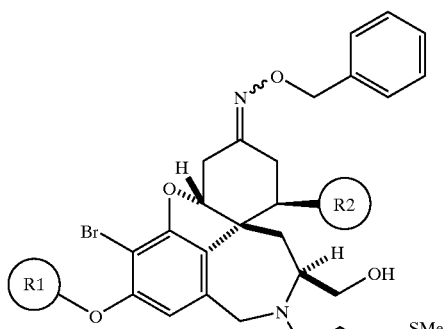
(R3)5(R4)6
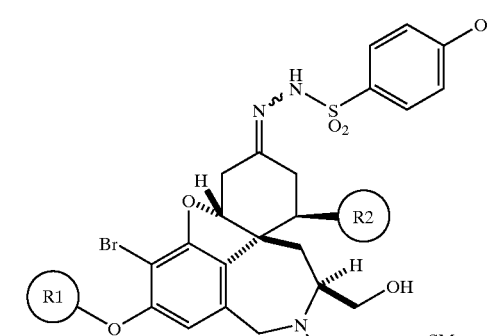
Plate 17
(R3)5(R4)7
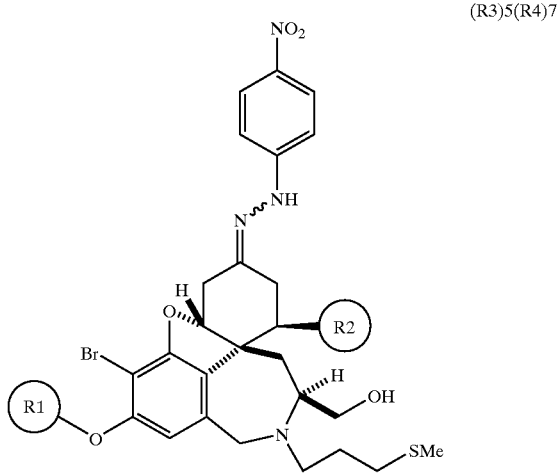
(R3)6(R4)2
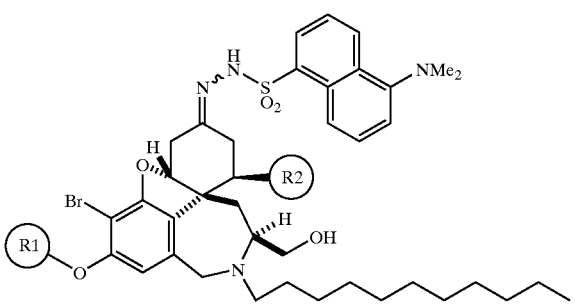

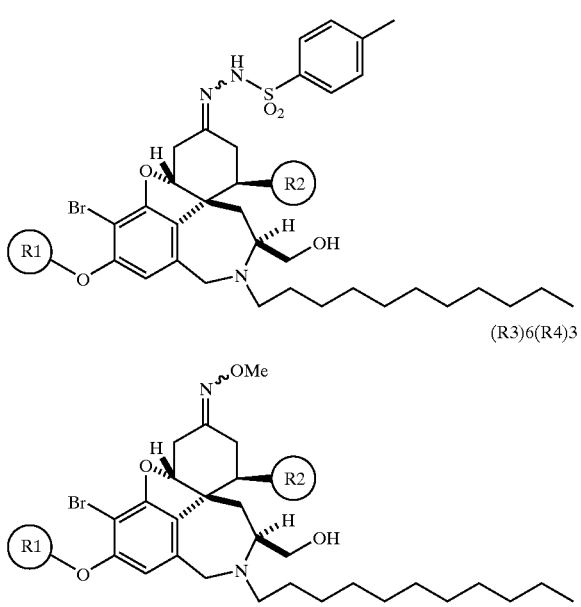

Plate 18

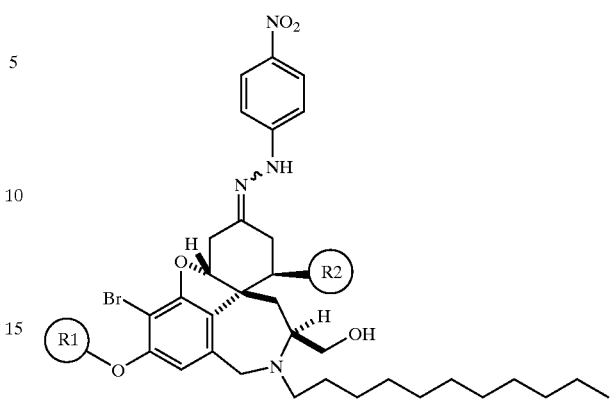

Scheme V.4.1

V.4 Representative Compound Synthesis and Analytical Data

* = 500–600 micron 1% DVB polystyren

15:
Resin 15a (40 mg) was cleaved as described for 7b. Purification by flash chromatography with Florisil (100% EtOAc→5% MeOH/EtOAc) afforded a yellow film (7.4 mg, loading level=0.27 mmol/g, theoretical loading level=0.38 mmol/g, Yield (from 8b)=71%. $R_f$=0.18 (5% MeOH/$CH_2Cl_2$); FTIR (film, $cm^{-1}$) 3368, 2938, 2873, 2306, 1607, 1510, 1429, 1364, 1250, 1176; $^1$H NMR (500 MHz, $CDCl_3$) Two isomers are present in a ratio of 1:5. δ7.42–7.34 (m), 7.31–7.28 (m), 7.19 (d, J=8.5 Hz), 6.87–6.84 (m), 6.13 (s), 6.10 (s), 5.20 (d, J=12.5 Hz), 5.16 (d, J=5 Hz), 5.15 (d, J=12.5 Hz), 5.13 (d, J=5 Hz), 4.61 (dd, J=3.0, 3.0 Hz), 4.56 (dd, J=3.0, 3.0 Hz), 3.85–3.76 (m), 3.73–3.55 (m), 3.52 (d, J=13.5 Hz), 3.30 (d, J=15.5 Hz), 3.13–3.05 (m), 3.00–2.99 (m), 2.96 (dd, J=3.7, 2.0 Hz), 2.93 (m), 2.74 (m), 2.56 (dd, J=15.7, 4.0 Hz), 2.34 (d, J=15.5 Hz), 2.08–2.05 (m), 2.01 (d, J=14.0 Hz), 1.32–1.18 (m), 1.01 (d, J=6.5 Hz), 0.96 (d, J=6.5 Hz), 0.94 (d, J=3.0 Hz), 0.65–0.61 (m), 0.40–0.35 (m); $^{13}$C NMR (100 MHz, CDCl$_3$) δ159.0, 157.5, 156.3, 154.6, 140.3, 138.3, 130.5, 130.3, 128.5, 128.4, 127.8, 127.7, 127.6, 124.3, 114.2, 114.1, 106.0, 92.3, 87.6, 75.7, 75.6, 74.2, 65.6, 59.3, 55.5, 52.6, 51.5, 43.3, 41.2, 33.9, 29.4, 27.1, 10.3, 3.3; HRMS (ES$^+$) calculated for C$_{35}$H$_{39}$BrN$_2$O$_5$S (M+H)$^+$: 679.1763, found: 679.1816.

Scheme V.4.2

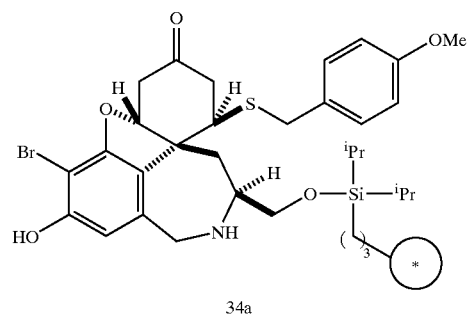

34a

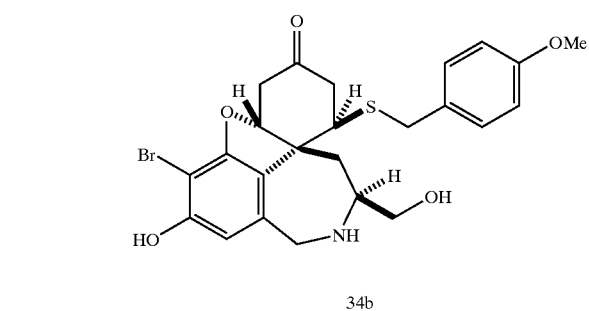

34b ( * ) = 500–600 micron 1% DVB polystyrene

34b:
Resin 34a (20 mg) was cleaved as described for 7b. Purification by flash chromatography with Florisil (100% EtOAc; 100% CH$_2$Cl$_2$; 10% MeOH/CH$_2$Cl$_2$) afforded a yellow film (2.3 mg, loading level=0.22 mmol/g, theoretical loading level=0.40 mmol/g, Yield (from 8b)=55%. R$_f$=0.14 (10% MeOH/CH$_2$Cl$_2$); FTIR (film, cm$^{-1}$) 3407, 2931, 1724, 1701, 1607, 1513, 1426, 1247; $^1$H NMR (500 MHz, (CD$_3$)$_2$C(O)) δ7.34 (d, J=8.0 Hz, 2H), 6.94 (d, J=8.5 Hz, 2H), 6.34 (s, 1H), 4.80–4.79 (dd, J=3.0, 3.0 Hz, 1H), 3.87 (d, J=13.7 Hz, 1H), 3.82 (s, 3H), 3.76 (d, J=13.5 Hz, 1H), 3.67 (d, J=15.0 Hz, 1H), 3.52, (dd, J=10.2, 4.5 Hz, 1H), 3.38, (d, J=15.0 Hz, 1H), 3.27–3.252 (m, 1H), 3.22 (dd, J=10.5, 9.0 Hz, 1H), 3.05 (dd, J=18.5, 3.0 Hz, 1H), 2.97 (m, 1H), 2.82 (dd, J=18.0, 3.0 Hz, 1H), 2.70 (dd, J=17.0, 3.50 Hz, 1H), 2.28 (dd, J=17.5, 3.0 Hz, 1H), 2.16 (d, J=14.0 Hz, 1H), 1.50–1.40 (m, 1H); $^{13}$C NMR (100 MHz, (CD$_3$)$_2$C(O)) δ160.0, 158.1, 155.5, 142.2, 131.3, 129.6, 123.6, 114.8, 109.3, 90.1, 89.4, 66.4, 59.6, 55.6, 52.6, 51.9, 44.2, 41.6, 41.2, 41.1, 35.1; HRMS (ES$^+$) calculated for C$_{24}$H$_{26}$NO$_5$S (M+H)$^+$: 520.0715, found: 520.0812.

Scheme V.4.3

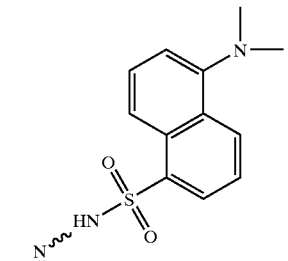

35a

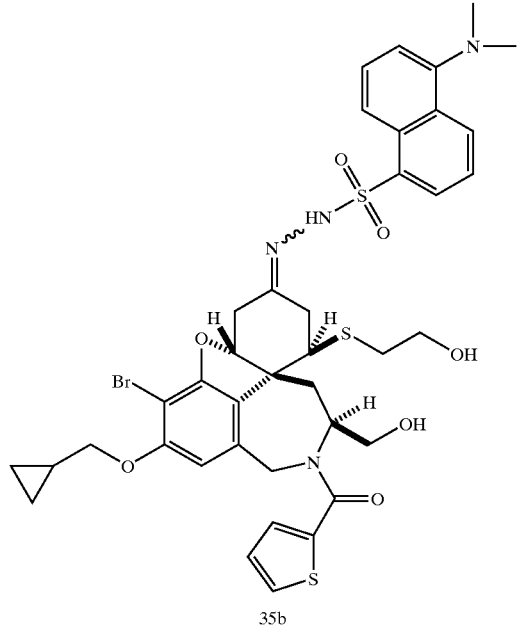

35b ( * ) = 500–600 micron 1% DVB polystyren

35b:
Resin 35a (47.5 mg) was cleaved as described for 7b. Purification by flash chromatography with Florisil (50% EtOAc/hexanes→100% EtOAc) afforded a yellow solid (12 mg, loading level=0.30 mmol/g, theoretical loading level= 0.35 mmol/g, Yield (from 8b)=86%. R$_f$=0.16 (100% EtOAc); FTIR (film, cm$^{-1}$) 3433, 2925, 2866, 2230, 1604, 1455, 1422, 1331, 1250; $^1$H NMR (400 MHz, 75° C. DMSO) Rotamers and isomers (ratio of 1:1.8) are present. δ8.51–8.45 (m), 8.41 (d, J=8.4 Hz), 8.10 (d, J=7.2 Hz), 7.70 (d, J=5.2 Hz), 7.67 (d, J=5.2 Hz), 7.64–7.53 (m), 7.24 (d, J=7.6 Hz), 7.11–7.06 (m), 4.74 (br s), 4.70 (br s), 3.18 (br s), 3.69–3.65 (m), 3.17 (dd, J=19.0, 3.2 Hz), 3.04 (s), 2.85–2.74 (m), 2.29 (br s), 2.26–2.14 (m), 2.08 (s), 1.26–1.17 (m), 0.86–0.82 (m), 0.56–0.54 (m), 0.32 (br s); HRMS (ES⁺) calculated for $C_{39}H_{43}BrN_4O_7S_3$ (M+H)⁺: 855.1477, found: 855.1515.

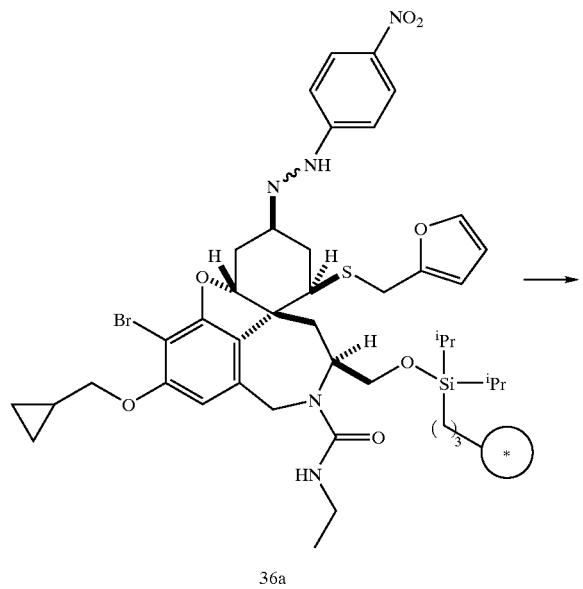

36a

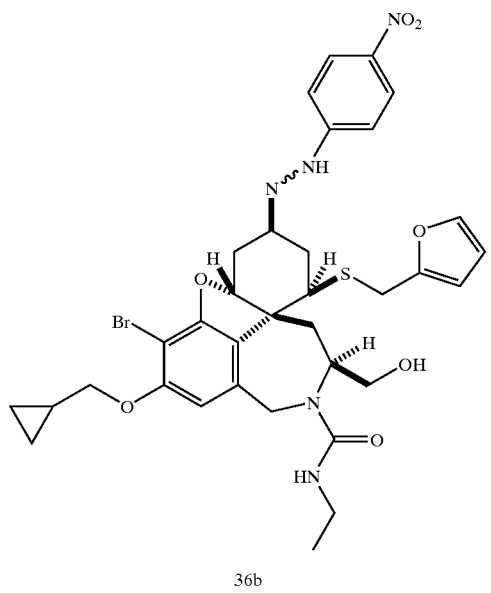

36b ( * ) = 500–600 micron 1% DVB polystyrene

36b:

Resin 36a (44.1 mg) was cleaved as described for 7b. Purification by flash chromatography with Florisil (25% EtOAc/hexanes→100% EtOAc) afforded a yellow solid (8.6 mg, loading level=0.26 mmol/g, theoretical loading level= 0.37 mmol/g, Yield (from 8b)=70%. Two isomers about the C=N are present. $R_f$=0.22 (100% EtOAc); FTIR (film, cm⁻¹) 3296, 2932, 2866, 1594, 1494, 1322, 1261; ¹H NMR (400 MHz, 65° C. DMSO) Two isomers are present in a ratio of 1:2.2 δ9.93 (s), 9.67 (s), 8.10–8.06 (m), 7.55 (s), 7.52 (s), 7.18 (d, J=8.8 Hz), 7.12 (d, J=8.8 Hz), 6.66 (s), 6.65 (s), 6.39–6.36 (m), 6.31, (d, J=2.8 Hz), 4.82 (s), 4.78 (s), 4.56–4.50 (m), 3.95–3.84 (m), 3.8 (s), 3.78–3.70 (m), 3.62–3.59 (m), 3.37 (dd, J=18.8, 2.4 Hz), 3.23 (m), 3.04–2.90 (m), 2.65 (d, J=20.0 Hz), 2.36 (d, J=16.0 Hz), 2.20 (d, J=14.0 Hz), 2.14–2.09 (m), 1.98–1.92 (m), 1.25–1.16 (m), 0.93–0.90 (m), 0.86–0.81 (m), 0.60–0.55 (m), 0.37–0.33 (m); ¹³C NMR (100 MHz, 70° C. DMSO) δ155.1, 150.4, 142.2, 138.1, 125.3, 111.2, 110.2, 73.2, 63.8, 50.7, 34.4, 27.6, 14.7, 9.6, 2.5; HRMS (ES⁺) calculated for $C_{34}H_{38}BrN_5O_7S$ (M+H)⁺: 740.1675, found: 740.1726.

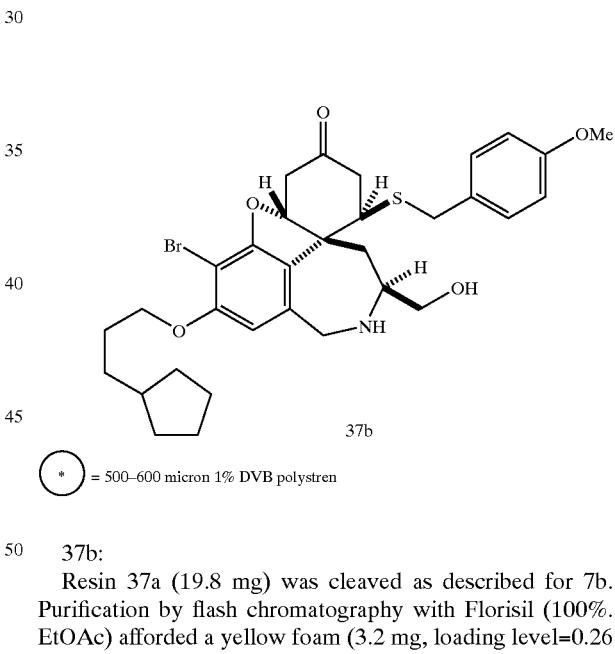

37a

37b ( * ) = 500–600 micron 1% DVB polystren

37b:

Resin 37a (19.8 mg) was cleaved as described for 7b. Purification by flash chromatography with Florisil (100% EtOAc) afforded a yellow foam (3.2 mg, loading level=0.26 mmol/g, theoretical loading level=0.38 mmol/g, Yield (from 8b)=68%. $R_f$=0.29 (100% EtOAc); ¹H NMR (500 MHz, CDCl₃) δ7.20 (d, J=8.5 Hz, 2H), 6.89 (d, J=8.5 Hz, 2H), 6.2 (s, 1 H), 4.70 (br s, 1H), 3.98–3.90 (m, 2H), 3.82 (s, 3H), 3.81–3.75 (m, 3H), 3.63 (dd, J=10.3 Hz, 4.5 Hz, 1H), 3.57 (d, J=13.5 Hz, 1H), 3.22 (d, J=16.0 Hz, 1H), 3.17 (d, J=10.0 Hz, 1H), 3.01 (m, 1H), 3.00 (m, 2H), 2.96–2.92 (m, 1H), 2.12 (d, J=2.12 Hz, 1H), 1.85–1.45 (m, 20H), 1.39–1.24 (m, 3H), 1.11 (m, 3H); ¹³C NMR (100 MHz, CDCl₃) δ205.6, 159.1, 156.5, 130.3, 127.9, 114.2, 105.7, 94.3, 88.2, 83.7, 79.2, 69.9, 58.9, 58.9, 55.5, 50.8, 42.5, 40.5, 40.2, 39.8, 34.5, 32.7, 32.4, 28.3, 25.2; MS (APCI⁺) calculated for $C_{32}H_{40}BrNO_5S$ (M+H)⁺: 630.1811, found: 630.

Scheme V.4.6

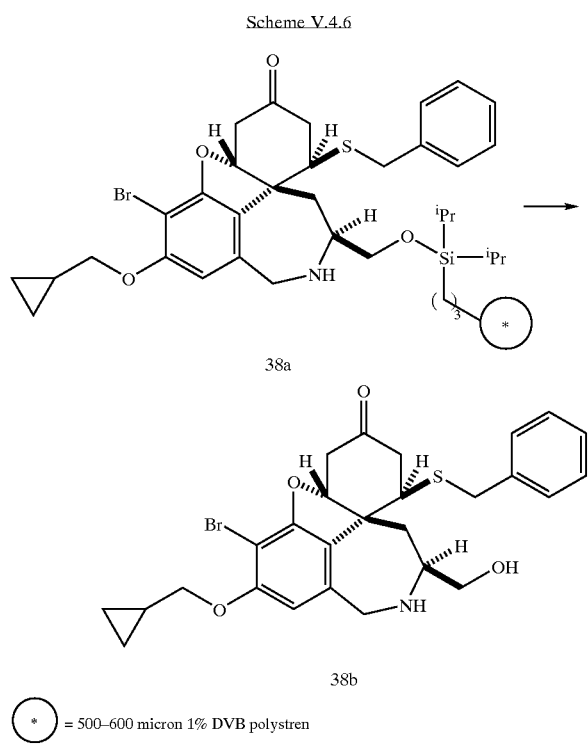

* = 500–600 micron 1% DVB polystren

38b:
Resin 38a (19.1 mg) was cleaved as described for 7b. Purification by flash chromatography with Florisil (100% EtOAc) afforded a yellow oil (3.2 mg, loading level=0.31 mmol/g, theoretical loading level=0.39 mmol/g, Yield (from 8b)=79%. $R_f$=0.23 (100% EtOAc); $^1$H NMR (400 MHz, CDCl$_3$) δ7.37–7.27 (m, 5H), 6.14 (s, 1H), 4.70 (dd, J=3.2 3.2 Hz, 1H), 3.86–3.77 (m, 4H), 3.66 (d, J=15.6 Hz, 1H), 3.61 (d, J=14.0 Hz, 1H), 3.60 (d, J=4.4 Hz), 3.58 (d, J=4.4 Hz, 1H), 2.64 (dd, J=16.0, 3.6 Hz, 1H), 2.38 (dd, J=16.0, 2.8 Hz, 1H), 2.11 (d, J=14.0 Hz, 1H), 1.32–1.24 (m, 3H), 0.66→0.61 (m, 2H), 0.38–0.34 (m, 2H); MS (APCI$^+$) calculated for $C_{27}H_{30}BrNO_4S$ (M+H)$^+$: 544.1079, found: 544.
V.4.3 NMR Spectra for Structure, Purity Assessment, and Diastereoselectivity Crude and Purified Compound NMR Spectra are provided for 3 representative compounds—15 (secramine), 37b, and 38b to establish purity of crude material. Specifically, the following spectra were obtained according to procedures generally described herein: $^1$H NMR spectrum of secramine (15); comparison of $^1$H NMR spectra of crude and purified secramine (15); $^1$H NMR spectrum of 34b; NOESY NMR spectrum of 34b; GOESY NMR spectrum of 34b; GOESY NMR spectrum of 34b; $^1$H NMR spectrum and HPLC of 35b; $^1$H NMR spectrum of 36b; comparison of $^1$H NMR spectra of crude and purified 37b to establish diastereoselectivity of conjugate addition; COSY NMR spectrum of 37b, and comparison of $^1$H NMR spectra of crude and purified 38b to establish diastereoselectivity of conjugate addition;

Comparison of the crude NMR to the purified compound NMR for 37b, and 38b (see proton H$_a$) demonstrated that only one diastereomer is present.

FIG. 90 $^1$H NMR spectrum of secramine (15)
FIG. 91 Comparison of $^1$H NMR spectra of crude and purified secramine (15)
FIG. 92 $^1$H NMR spectrum of 34b
FIG. 93 NOESY NMR spectrum of 34b
FIG. 94 GOESY NMR spectrum of 34b
FIG. 95 GOESY NMR spectrum of 34b
FIG. 96 $^1$H NMR spectrum and HPLC of 35b
FIG. 97 $^1$H NMR spectrum of 36b
FIG. 98 Comparison of $^1$H NMR spectra of crude and purified 37b to establish diastereoselectivity of conjugate addition
FIG. 99 COSY NMR spectrum of 37b
FIG. 100 Comparison of $^1$H NMR spectra of crude and purified 38b to establish diastereoselectivity of conjugate addition Example 2

Synthesis of Compounds Using Big Bead Technology

Currently we are using diversity-oriented split-pool synthesis to prepare structurally complex and diverse small molecules as vehicles to induce specific and novel biological phenotypes.[xii] Once a small molecule has demonstrated biological activity and the protein target identified, researchers can infer a role for that target within a biological system.[xiii] This is analogous and complimentary to methods used in classical genetics where random mutations are first generated and then screened in search of a specific cellular or physiological phenotype. This unbiased approach of using small molecules to dissect cellular circuitry is known as forward chemical genetics (FCG).[xiv]

In a reverse chemical genetics (RCG) assay, which is more similar to the drug discovery process, small molecules are screened for their ability to bind a pre-selected protein target.[xv] In our laboratory, small molecule printing (SMP) has provided the means for miniaturization of this process.[xvi] After identification of small molecules with suitable binding properties, experiments are performed that take advantage of their ability to modulate function rapidly and conditionally. Of course, the optimal approach to using small molecule diversity-oriented synthesis as an engine for general biological discovery is a totally integrated approach using both forward and reverse chemical genetics; this systematic approach has been given the more general name of chemical genetics.

We believe the one compound-one encoded bead strategy[xvii] is the optimal process to generate the requisite small molecules and, consequently, large databases of novel and important protein ligands. To reduce this strategy to practice and maximize its success, we surmise that it will be necessary to deliver, minimally, 50 nmol of small molecule from a single synthesis bead.[xviii] This quantity of reagent will allow for over one hundred FCG assays and several thousand RCG assays from a single synthesis bead with enough reagent remaining for confirmation of observed biological activity.[xix,xx]

No solution is currently known to the problem of delivering such large quantities of small molecules on a per bead basis (typically, most large bead/linker combinations yield ≦5 nmol/bead).[xxi] We now report our work towards developing a novel, large (>500 micron) polystyrene bead/ alkylsilyl tethered linker combination as a general solution to the problem of delivering ≧50 nmol of each product derived from a split-pool synthesis.[xxii] This is also an integrated solution that addresses the needs of both forward and reverse chemical genetics; the released small molecules can be both pin-transferred into FCG assays and undergo SMP (recapture of the liberated —OH group) for RCG assays. The key developments leading to this novel bead/linker combination are an improved method for functionalizing 'naked' large polystyrene beads, a new silicon linker for solid-phase diversity-oriented synthesis, and a modification/optimization of the solid-phase in situ Suzuki coupling conditions reported by Ellman and coworkers to synthesize diisopropylalkyl silicon functionalized resin 1 (FIG. 1).[xxiii] In addition to the specific examples that have been provided herein, it will be appreciated that the improved methods for for functionalizing 'naked' large polystyrene beads, the new silicon linker for solid-phase diversity-oriented synthesis, and the modification/optimization of the solid-phase in situ Suzuki coupling conditions reported by Ellman and coworkers to synthesize diisopropylalkyl silicon functionalized resin 1 can also be applied more generally to other related systems.

Initial Analysis.

Our initial analysis of the linker problem was primarily concerned with the end result of a diversity-oriented split-pool library synthesis; it required a quantitative linker cleavage process that is amenable to large-scale, (many beads treated simultaneously in a spatially arrayed format), does no damage to the final product(s), and leaves no impurities that are difficult to remove. Guided by similar principles used in target-oriented organic synthesis, we chose a silicon-based linker for the above as well as the following reasons[xxiv]:

The attachment of starting materials is readily accomplished in high yield. Activation of silicon as a silyl chloride or silyl triflate for silyl ether synthesis is straightforward and general. For diversity-oriented synthesis, ease and efficiency of substrate loading to solid support is critical, particularly with the intended goal of delivering ≧50 nmol of small molecule/bead.

Silicon is compatible with the widest array of modern synthetic chemistries. Because no commercially available bead/linker systems satisfied our needs, we were not encumbered with the use of known approaches that include heteroatom bond formation (typically C—O and C—N' bonds) as the method of grafting the linker onto the solid support backbone.[xxv] After removing the heteroatom(s), the linker can now be considered a bulky trialkylsilyl protecting group amenable to most modern synthetic chemistries.[xxvi] In this particular example, a strong parallel, can be drawn between the chemical stability of solid support linker 1 (FIG. 1) and the known methyldiisopropylsilyl ether protecting group.[xxvii]

With a diisopropylalkyl-substituted silyl ether (or other alkyl-substituted silyl ether) chosen as a flexible method of linking small molecules to the solid support, commercially available unfunctionalized 500–560 micron polystyrene macrobeads were selected principally because this was the only solid support known in which each bead in a population of beads has the physical capacity to deliver ≧50 nmol of each small molecule.[xxviii]

Results & Discussion

Synthesis of Bead/Linker System.

Although a body of literature concerning silicon-derived solid phase linkers exists,[xxix] to the best of our knowledge, there was no precedent for the use of large polystyrene beads (>500 micron) grafted with a 'heteroatom-free', aliphatic linker. Inspired by the work of Woolard et al,[xxiii] we chose to adapt the Suzuki coupling reaction for C—C bond formation as a route to the desired linker system. In order to carry this experiment forward, it was necessary to synthesize the Suzuki coupling partners de novo, the bromine-functionalized 1–2% dvinylbenzene (DVB) cross-linked polystyrene resin (500–560 micron) 2 and the silicon-containing alkyl borane 7.

(a) Bromination of polystyrene.

Based on the method of Frechet,[xxx] we subjected unfunctionalized 1–2% DVB cross-linked polystyrene, both 400–450 micron and 500–560 micron beads, to thallium acetate-catalyzed electrophilic aromatic bromination conditions in $CCl_4$.[xxxi] Unfortunately, experimental results using this protocol were inconsistent, yielding highly colored resins with lower than expected levels of bromine incorporation.[xxxii] These products were also brittle, which is unacceptable for library synthesis.[xxxiii] Increasing the amount of thallium catalyst (from 9 mol % to 18 mol % relative to bromine) and switching to $CH_2Cl_2$ as the reaction solvent solved these problems. Although the exact reason is unclear for this remarkable change in reactivity, one possible explanation might be increased penetration of the thallium reagent into large polystyrene beads when dissolved in $CH_2Cl_2$. Under these optimized conditions, the exact level of bromine incorporation was readily modulated by the amount of thallium catalyst and bromine used, always resulting in ≧95% yield of bromine addition with per bead levels much greater than our 50 nmol threshold limit (Table 1). Also significant is the uniform appearance of the functionalized beads, off-white with little physical damage to their spherical geometry.[xxxiv] More recently, a commercial supplier has made available large (410–500 and 500–600 micron) 1% DVB cross-linked p-bromostyrene/styrene copolymerized resins at the 1.0 and 2.0 mequiv. of Br/g loading levels which have also been used in all of the subsequent experiments (vide infra).[xxxv,xxxvi]

(b) Synthesis of Silicon-functionalized Alkyl Borane.

With access to bromine-functionalized resin as one half of the Suzuki coupling partners, the synthesis of allyl silane 6 was readily accomplished in three steps from commercially available starting materials (Scheme 1). Diisopropylchlorosilane (3) was added to a THF solution of (4-methoxyphenyl)lithium at −78° C. and allowed to come to 23° C. overnight. Aqueous work up and filtration through silica gel produced silane 4 in 94% yield. Treatment of 4 with trichloroisocyanuric acid in $CH_2C_2$ followed by filtration under inert atmosphere provided a quantitative yield of silyl chloride 5. Allylmagnesiumbromide was then added to 5, delivering allyl silane 6 in 92% overall yield after vacuum distillation.[xxxvii] The Suzuki coupling substrate, alkyl borane 7, was realized by treating a THF solution of trialkylallyl silane 6 with a nearly equimolar amount of solid 9-BBN.[xxxviii] This reagent is used without further purification or isolation.

(c) Solid-Phase Suzuki Coupling Optimization.

Several reaction conditions were screened to produce the most efficient and reproducible Suzuki coupling on the 500–560 micron polystyrene beads (Table 2). Two catalysts, $Pd(PPh_3)_4$ and $Pd(dppf)_2Cl_2$, were tested in the presence of several commonly used bases. Entry 3 describes the optimal reaction conditions. Interestingly, these conditions were identical to those originally reported by Suzuki (using NaOH as base and $Pd(PPh_3)_4$ as catalyst); none of the standard perturbations offered any improvement.[xxxix,xl] A representative procedure is as follows (Table 3, entry 6): To a 0.17 M THF solution of alkylborane 7 (1 equiv) was added 500–600 micron 1% DVB cross-linked brominated polystyrene (0.6 equiv of resin functionalized at 2.0 mequiv of Br/g) which was allowed to fully swell in the THF/borane solution (45 min). The flask was then fitted with a condenser and Pd(PPh$_3$)$_4$ (2.5 mol %) and NaOH (2 equiv. of 2 M soln.) were added. The reaction mixture was then gently refluxed for 24 h, at which time additional palladium (2.5 mol %) was added. The reaction was then continued at reflux for a total reaction time of 40 h. Subsequent experiments proved the necessity of the additional palladium catalyst.[xli] The extent of silicon incorporation was confirmed by elemental analysis, typically delivering nearly quantitative yield under the optimized conditions.[xxxii,xlii] Post-Suzuki coupling, the 500–600 micron beads (entry 7) possess ~200 nmol of Si linker/bead, well above the threshold lower limit of 50 nmol/bead.

Linker Activation, Substrate Loading, and Compound Release (a) Silicon Activation.

Because diversity-oriented synthesis strives to deliver not only structurally complex but also structurally diverse molecules in a single library, the ability to load several structurally different substrates possessing functional groups of nearly identical reactivity onto the resin under a common set of reaction conditions to a similar loading level is crucial to success.[xv] We chose to activate the linker as trialkylsilyl triflate 8 (see Table 3) as a way to minimize the variability in loading levels between different substrates.[xliii,xliv] The specific protocol was adopted directly from the work of Smith[xlv] and Porco[xlvi]; treatment of trialkylarylsilane functionalized resin 1 with excess trifluoromethanesulfonic acid for 30 min. produced 8. Washing twice with CH$_2$Cl$_2$ removed excess acid. Complete formation of 8 was readily confirmed by MAS $^{29}$Si NMR (single peak at <44.0 ppm> relative to tetramethylsilane internal standard at 0 ppm in C$_6$D$_6$). Because of the reactive nature of this species, it is recommended that the silyl triflate be used immediately after being formed.

(b) Substrate Loading.

To load the alcohols shown in Table 3, the following general protocol was developed: 8 equiv. of 2,6-lutidine (relative to silyl triflate) were added to washed resin 8 followed 15 min. later by 2 equiv of the substrate alcohol dissolved in benzene.[xlvii] This mixture is then gently agitated for 10 h, followed by thorough washing.[xlviii] Vacuum drying of the resin overnight delivered substrate functionalized resin 9. Significantly, even sterically demanding alcohols were loaded in good yield as witnessed by entries 3 and 4.

(c) Small Molecule Cleavage.

The central feature of this silicon linker is the ease at which it undergoes Si—O bond cleavage under the influence of a 5% solution of HF/pyridine in THF.[xlix] Although this reagent is corrosive and toxic, it is a relatively mild reagent for silyl ether fluorodolysis and is dispensable by an automated liquid handler making it particularly useful for large numbers of 384-well microplates in which synthesis beads will be spatially arrayed in a one bead-one well format.[1] We have found that 2.5 h was sufficient time for cleavage. Once complete, excess HF was quenched with methoxytrimethylsilane resulting only in volatile by-products that were readily removed under vacuum and do no harm to the released small molecules.[li] The purity of compounds cleaved by this method was very high (Table 3).[lii]

Conclusion

In summary, we have disclosed a route for the synthesis of an alkyl tethered diisopropylarylsilane linker on large polystyrene beads. These beads are suitable for diversity-oriented split-pool synthesis and are capable of delivering ≧50 nmol of small molecule per bead. Because this bead/linker system represents one of our central enabling technologies for the practice of chemical genetics, it was important to develop a system that can be synthesized in large scale (>100 g), stored indefinitely, and used in a 'right-off-the-shelf' fashion. To date, our results have been very encouraging as we move forward in our efforts to bring the full power of modern organic synthesis to bear on the process of dissecting cellular circuitry.

Experimental Section

General Methods.

Starting materials and reagents were purchased from commercial suppliers and used without further purification except the following: methylene chloride (CH$_2$Cl$_2$), tetrahydrofuran (THF), and diethyl ether (Et$_2$O) were passed through two activated alumina columns to remove impurities prior to use (as described in *Organometallics* 1996, 15, 1518–1520). 2,6-Lutidine was distilled from CaH$_2$ under Ar atmosphere. Unfunctionalized polystyrene (400–450 and 500–560 micron 1% DVB cross-linked) was purchased from Rapp Polymere GmbH and used without further purification. Brominated polystyrene (500–600 micron 1% DVB cross-linked PS-Br, 2.0 mequiv./g and 1.0 mequiv./g) was purchased from Polymer Labs (1462-9999)[1] and used without further purification.

([1]) This product is available from Polymer Labs. For pricing and availability information, they can be contacted at Polymer Laboratories Inc, Amherst Fields Research Park, 160 Old Farm Road, Amherst Mass. 01002, USA. Tel: 413/253 9554 or 800/767 3963, Fax: 413/253 2476

Polystyrene bromination procedure (polystyrene→2)$^2$.

([2]) For an initial reference on this procedure, see: Farrall, M. J.; Fréchet, J. M. J. *J. Org. Chem.* 1976, 41, 3877–3882. Early work in the Schreiber lab on this procedure began with Kris Depew.

The 500–560 μm polystyrene beads were weighed out into a 2 liter flask containing a stir bar and subsequently sealed under inert atmosphere and purged using a balloon. The 80 g of beads were then swollen in CH$_2$Cl$_2$ (1.2 L, ~1 g of resin/15 mL of solvent) for 1 h. To this solution was added 9.4 g of thallic acetate (24.6 mmol).$^3$ This was allowed to stir gently for 1 h.$^4$ The solution turned orange with a small amount of white precipitate on the bottom of the flask. To this mixture was added 7.0 mL bromine (21.6 g/135 mmol) via syringe over a 15 minute period.$^5$ After each portion of Br$_2$ was added, the solution would turn orange for a few seconds and then lose color. Only near the end of the addition did the color remain for longer than a few minutes. The mixture was then stirred at room temperature for 1 h at which time most of the color (but not all) had dissipated.$^6$ The reaction was quenched by slow addition of 10 mL of MeOH; it was then allowed to stir for 10 min. The whole slurry was then filtered directly into a waste flask to remove solvent and dissolved catalyst. The beads on filter are then washed liberally with CH$_2$Cl$_2$. The beads were re-suspended in a second liter of CH$_2$Cl$_2$ and gently agitated for 20 minutes. This was repeated a second time. The wash procedure was completed as follows: after the two CH$_2$Cl$_2$ washes, the beads were washed with THF (1 L×20 min), THF/IPA (3:1; 1 L×20 min), THF/H2O (3:1; 1 L×20 min.× 2), DMF (1 L×20 min), THF/IPA (3:1; 1 L×20 min), THF (1 L×20 min), CH$_2$Cl$_2$ (1 L×20 min). After finishing the wash protocol, the beads were air-dried for 3 h and then placed under vacuum to remove trace solvent and water. This experiment resulted in resin that possessed 1.43 mequiv. of Br/g of functionalized resin as determined by elemental analysis.

($^3$) Thallic acetate is very toxic therefore double gloving as a precaution is worthwhile. Also, only thallic acetate from a freshly opened bottle from Aldrich Chemical Co. should be used in the reaction—other sources as well as older batches from Aldrich have been used with limited success.
($^4$) Precaution must be taken when stirring swollen beads, they are very fragile and vigorous stirring will do damage to the resin.
($^5$) To 'custom' load brominated resin, assume that the efficiency of bromine incorporation is 95% and use the desired mmol of Br$_2$/g polystyrene along with the appropriate ratio of thallic acetate relative to bromine.
($^6$) This procedure differs from the earlier method by not requiring heat or the use of carbon tetrachloride as solvent however, it does require the use of more thallic acetate.

Diisopropyl(4-methoxyphenyl)silane (4).

A solution of p-bromoanisole (28.6 mL, 228 mmol, 1 equiv.) in THF (550 mL) was chilled to −78° C. ($CO_2$(s), acetone). n-BuLi (91.2 mL, 228 mmol, 2.5M in hexanes, 1 equiv.) was added via cannula over a 5 min period. After 5 min a white precipitate begins to form. The mixture was stirred for 30 min at −78° C., after which chlorodiisopropylsilane (34.6 g, 228 mmol, 1 equiv.) was slowly added via syringe. After 1 h the ice bath was removed and the solution was allowed to come to 23° C. with stirring overnight. The reaction was quenched with $NH_4Cl_{(sat'd)}$ (50 mL) and extracted with ether (3×500 mL). The combined organic extracts were washed with brine, dried ($MgSO_4$), filtered and concentrated in vacuo to yield a light yellow oil. Filtration through $SiO_2$ (gradient: 3–5% EtOAc/hexanes) yielded 47.7 g (94%) of a colorless oil. This material could also be purified by distillation bp=76–85° C. @ 275 mTorr (40 g, 63%). TLC $R_f$=0.61 (9:1 Hexanes/EtOAc). IR (film) 2393, 1853, 1710, 1691, 1658, 1584, 1482, 1346 $cm^{-1}$. $^1H$ NMR (500 MHz, $CDCl_3$) δ7.48 (d, 2H, J=8.10, C3-H, C7-H), 6.95 (d, 2H, J=8.10, C4-H, C6-H), 3.97 (s, 1H, Si—H), 3.85 (s, 3H, C1-H), 1.39 (q, 2H, J=3.0, C8-H, C11-H), 1.10 (d, 6H, J=6.5, C9-H, C10-H), 1.03 (d, 6H, J=7.5, C12-H, C13-H). $^{13}C$ NMR (125 MHz, $CDCl_3$) δ137.13, 113.73, 113.62, 55.18, 18.95, 18.72, 11.08. Anal. Calcd for $C_{13}H_{22}OSi$: C, 70.21; H, 9.97; Si, 12.63. Found: C, 70.43; H, 9.83; Si, 12.39.

Chloro(4-methoxyphenyl)diisopropylsilane (5).

Diisopropyl(4-methoxyphenyl)silane (47.7 g, 214 mmol, 1.0 equiv.), was taken up in $CH_2Cl_2$ (700 mL). The solution was cooled to 0° C. and trichloroisocyanuric acid (16.6 g, 71.3 mmol, 0.33 equiv.) was carefully added in three equal portions, making sure that each portion has at least 7 min to react before the next is added (caution: adding trichloroisocyanuric acid too rapidly results in a rapid evolution of gas). The mixture was stirred at 0° C. for 40 min followed by warming to 23° C. with stirring. The solids were filtered under an inert atmosphere and the filtrate concentrated in vacuo to yield 54.8 g (98%) of a cloudy oil. The chlorosilane, which is unstable, was used immediately and without purification in the next step.

Allyl(4-methoxyphenyl)diisopropylsilane (6).

To the crude chloro(4-methoxyphenyl)diisopropylsilane (54.8 g, 214 mmol, 1.0 equiv.) was added THF (335 mL) via cannula under positive argon pressure. The solution was chilled to 0° C. and treated with allylmagnesiumchloride (128 mL, 256 mmol, 2.0 M in THF, 1.2 equiv.). After 3 h at 0° C., the solution was allowed to warm to 23° C. with stirring overnight. The mixture was treated with $NH_4Cl_{sat'd}$ (50 mL) and the aqueous layer extracted with ether (3×500 mL). The combined organic extracts were washed with brine, dried ($MgSO_4$), filtered, concentrated in vacuo. The crude material was purified by silica gel chromatography (3–5% EtOAc/hexanes) to yield 52.86 g (94%) of a slightly cloudy, viscous oil. This reagent distills at 130° C. at 500 mtorr as a colorless oil. TLC $R_f$=0.40 (9:1 Hexanes/EtOAc). IR (film) 2942, 2865, 1630, 1595, 1504, 1463, 1277 $cm^{-1}$. $^1H$ NMR (500 MHz, $CDCl_3$) δ7.32 (d, 2H, J=6.84, C3-H, C7-H), 6.18 (d, 2H, J=6.84, C4-H, C6-H), 5.82 (q, 1H, J=8.5, 8.5, C15-H), 4.88 (d, 1H, J=17.05, C16-Hb), 4.76 (d, 1H, J=9.77, C16-Ha), 1.82 (d, 2H, J=7.32, C14-H), 1.17 (q, 2H, J=7.3, C8-H, C11-H), 0.94 (d, 6H, J=7.3, C9-H, C10-H), 0.90 (d, 6H, J=7.3, C12-H, C13-H). $^{13}C$ NMR (125 MHz, $CDCl_3$) δ160.51, 136.48, 135.70, 125.78, 113.78, 113.62, 55.09, 19.34, 18.22, 18.17, 17.68, 11.30. Anal. Calcd for $C_{16}H_{26}OSi$: C, 73.22; H, 9.98; Si, 10.70.

Representative Suzuki Coupling Procedure (2→1).

This procedure is included because commercially available palladium(0) did not perform as well as freshly made material. To a standard Schlenk apparatus was added palladium dichloride (275 mg, 1.55 mmol, 1.0 equiv.) and triphenylphosphine (2.04 g, 7.77 mmol, 5.0 equiv.) followed by DMSO (20.0 mL). The mixture was heated at 155° C. until total dissolution of solid material occurred. The mixture was then cooled for two minutes. Hydrazine hydrate (303 μL, 6.22 mmol, 4.0 equiv.) was added by syringe over a one minute period and the solution was immediately cooled in a cold water bath to initiate crystallization. When the first few crystals formed the flask was removed from the ice bath and covered in foil. Once formed the crystals are washed sequentially with ethanol (4×3 mL) and diethyl ether (2×1 mL). The yellow solid was protected from light and dried in vacuo overnight yielding 1.76 g of bright yellow crystals (98% yield)[7].

[7] Coulson, D. R. *Inorg. Synth.* 1972, 13, 121–124.

Alkyl borane 7 (6→7).

Solid 9-BBN dimer (6.29 g, 53.0 mmol, 0.95 equiv.) was weighed out in a glove box and sealed under an argon atmosphere. Freshly distilled THF (365 mL) and allyl(4-methoxyphenyl)diisopropylsilane (6, 14.64 g, 55.8 mmol, 1.0 equiv.) were added via syringe and the mixture was allowed to stir for 3 h at 23° C. The overall concentration of the allyl(4-methoxyphenyl)diisopropylsilane in THF is 0.16 M which is the appropriate concentration for the subsequent Suzuki coupling. The yield of this reaction is assumed to be nearly quantitative.

Suzuki Coupling to produce silicon functionalized 1.

To alkyl-borane containing THF solution (53.0 mmol in 365 mL of THF, 1.74 equiv.) was added the brominated polystyrene 2 (15.25 g, 2 mequiv./g, 30.5 mmol of Br, 1.0 equiv.). Care was taken to maintain an argon blanket over the solution. Reagent 2 was allowed to swell for 45 min followed by addition of tetrakis(triphenylphosphine)palladium(0) (880 mg, 0.76 mmol, 0.025 equiv.) and $NaOH_{aq}$ (61 mmol, 30.5 mL of a 2M NaOH solution, 2.0 equiv.). The reaction was then heated to mild reflux with gentle stirring for 24 h. An additional amount of Pd(0) (880 mg, 0.76 mmol, 0.025 equiv.) was added after the first 24 h and the reaction continued to reflux for another 16 h. Generally, the biphasic reaction mixture turns slightly green from its initial yellow color. Upon completion, the mixture was filtered and the beads washed repeatedly (see procedure below). Large beads (500–600 micron, in this instance) require time to take up the washing solvent. It is unnecessary to agitate the beads during the washing, but it is important to allow resin enough time to take up the solvent. Wash procedure: THF (2×200 mL×45 min), 3:1 THF/1 M aq. NaCN (1×200 mL×1 h or until all dark color is gone), 3:1 THF/$H_2O$ (2×200 mL×45 min), 3:1 THF/IPA (2×200 ml×45 min), THF (2×200 mL×45 min), DCM (2×200 mL×45 min). The beads were air-dried overnight, then placed on a lyophilizer for 24 h, producing an almost colorless resin (white). $^1H$ NMR (500 MHz, $CD_2Cl_2$, nanoprobe) δ7.34 (C3-H, C7-H), 6.82 (C4-H, C6-H), 5.27 ($CH_2Cl_2$), 3.69 (C1-H), 1.76 (C14-H), 1.48 ($H_2O$), 1.22(C15-H, C16-H), 1.16 (C8-H, C11-H), 0.97 (C9-H, C10-H), 0.91 (C12-H, C13-H).[8] Anal. Found: C, 83.54; H, 8.28; Si, 4.35; Br<0.02; Cl, 0.247. 2.0 mmol p-bromopolystyrene beads, quantitatively loaded with all carbon silicon linker, contain 41 mg of Si/g resin or 4.1% Si. Assuming quantitative loading, the mass of 1 g resin increases to 1.37 g, so linker loading is calculated to be ~1.45 mequiv./mol. Thus resin loading is estimated from two elemental analyses parameters, %Si and %Br. The %Br<0.02 by weight indicates qualitative disappearance of bromine (note that halogens can be confused by elemental analysis, therefore it is necessary to perform separate Br and Cl analysis), while percent silicon indicates the loading level. Percent silicon typically ranges from 3.79 to 4.05. The procedure used to calculate percent silicon can overestimate the actual amount of silicon by 0.2–0.3% as these numbers are calculated by weighing ash resultant from sample digestion with acid and residue combustion, which leaves some elements unresolved from silicon. 4.35% Si is equivalent to 43.5 mg Si per. gram resin or 1.54 mequiv. Si/g. Actual loading used in subsequent calculations is 1.45 mequiv./g, the theoretical maximum. There are 9,350 beads/gram of 500–600 micron copolymerized p-bromopolystyrene beads with 2.0 mmol Br/g loading level. We assume quantitative conversion, justified by disappearance of bromine and appearance of appropriate amount of silicon. The number of polystyrene beads in one gram of resin is then scaled with 37% mass increase, or about 6,800 beads/g.

([8]) Linewidths, tether length, etc. effect on NMR spectra, see: P. A. Keifer, J.Org.Chem., 1996, 61, 1558–1559.

General experimental for conversion of tetralkylsilane 1 to silyl triflate functionalized resin 8.

Silicon functionalized resin 1 (1.43 mequiv. Si/g) that had been dried under hi-vac for 12 h was weighed (200 mg, 0.286 mmol, 1 equiv.) into a 10 mL polypropylene PD-10 column fitted with a teflon™ stopcock and swollen in $CH_2Cl_2$ (2.0 mL, 10 mL of solvent/g of resin) under $N_2$ atmosphere for 30 min. The solvent was then drained under positive $N_2$ pressure and 3.8 mL of a 4% tifluoromethanesulfonic acid/$CH_2Cl_2$ solution (6 equiv. of TfOH relative to Si) was added by syringe. The resin turned bright red/orange upon acid treatment and was then gently agitated for 30 min. while still under $N_2$ atmosphere. Once activation was completed, two $CH_2Cl_2$ washes removed excess acid.

Loading of trans-2-phenyl-1-cyclohexanol onto resin 8.

Treatment of 8 with 2,6-lutidine (0.27 mL, 8 equiv. relative to Si) for 15 min. followed by addition of 0.5 mL of an azeotropically dried 1.0 M solution of trans-2-phenyl-1-cyclohexanol (2 equiv) resulted in a colorless resin. The beads are then gently agitated for an additional 10 h under $N_2$ atmosphere. The beads were drained, exposed to atmosphere, and subjected to the following wash protocol: $CH_2Cl_2$ (2×3 mL×45 min.), THF (2×3 mL×30 min.), THF/IPA (3:1, 2×3 mL×30 min.), THF/$H_2O$ (3:1, 2×3 mL×30 min.); THF/IPA (3:1, 2×3 mL×30 min.), DMF (2×3 mL×30 min.), THF (2×3 mL×30 min.). The resin was air-dried for 3 h and then placed under hi-vac for 24 h to remove trace solvent and $H_2O$. The mass of the loaded and dried resin was 207.0 mg, indicating an apparent loading efficiency of 74% based on weight gain. Single bead cleavage experiments resulted in an average per bead loading of 137 nmol/bead (69% efficiency, data included in table). See the supporting information for details. This procedure is applicable for loading all alcohols listed in Table 3.

MAS-$^1$H NMR of trans-2-phenyl-1-cyclohexanol (500 MHz, $CD_2Cl_2$, nanoprobe) δ7.30–7.20 (5 H), 3.72–3.64 (broad s, 1 H), 2.45–2.40 (broad, 1 H), 2.13–2.10 (broad, 1H), 1.89–1.85 (broad, 1H), 1.79–1.75 (broad, 1H), 1.60–1.32 (complex, 6H).

Cleavage of 8 from resin.

Vacuum-dried resin 8 was weighed (100.0 mg) out into a solvent-resistant scintillation vial and allowed to swell in 1.0 mL of THF for 30 min. The THF solution was removed and replaced with a fresh 0.95 mL of THF and 0.05 mL of HF/pyridine solution (7:3 ratio of HF/pyr, available from Aldrich Chemical Co.). The vial was sealed and agitated for 3 h at which time 0.1 mL of methoxytrimethylsilane was added to quench unreacted HF. (Note: quench is mildly exothermic therefore use caution). The beads are further agitated for 30 min to ensure complete quenching. The solution was removed and the beads washed twice with additional 1.0 mL portions of fresh THF. All solvents were combined and concentrated in vacuo, delivering 16.3 mg of trans-2-phenyl-1-cyclohexanol as a white solid. Based on the assumption that 100% of the material loaded onto the resin is cleaved and recovered, this amount of material represents 71% of the theoretical maximum or approximately 143 nmol/bead.

Supporting Information Available.

Experimental details regarding equipment, disposables and representative single bead cleavage experiments and analyses are available (7 pages) free of charge via the Internet at http://pubs.acs.org.

TABLE 1

Bromination of Polystyrene

| Entry | Resin Size (microns) | Br Loading (theoretical)[a] | nmol/bead | % yield |
|---|---|---|---|---|
| (1) | 500–560 | 0.97 mequiv/g (1.00) | 92 | 97 |
| (2) | 500–560 | 1.31 mequiv/g (1.36) | 127 | 96 |
| (3)[b] | 500–560 | 1.43 mequiv/g (1.49) | 147 | 96 |
| (4)[c] | 500–560 | 1.74 mequiv/g (1.84) | 176 | 95 |
| (5) | 400–450 | 1.86 mequiv/g (1.93) | 95 | 96 |

[a]Determined by elemental analysis (ref. xxxii).
[b]Performed on >80 g scale.
[c]This loading is identical on a per bead basis to commercially available 500–600 micron beads (after factoring in size distribution) at 2 mequiv of Br/g (ref xxxvi).

TABLE 2

Solid phase Suzuki Coupling Optimization.[a]

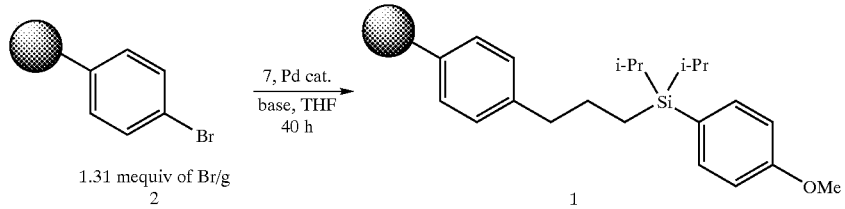

| Entry | Base | Pd(PPh$_3$)$_4$ yield, (Si linker/bead) | Pd(dppf)$_2$ yield, (Si linker/bead) |
|---|---|---|---|
| (1) | Na$_2$CO$_3$ | 88%, (112 nmol) | 77%, (98 nmol) |
| (2) | K$_2$CO$_3$ | 91%, (116 nmol) | 46%, (58 nmol) |
| (3) | NaOH | 98%, (124 nmol) | 80%, (102 nmol) |
| (4) | NaOMe | 83%, (105 nmol) | 76%, (97 nmol) |
| (5) | K$_3$PO$_4$ | 98%, (124 nmol) | 51%, (65 nmol) |
| (6)[b] | NaOH | 98%, (204 nmol) | — |

[a]Entries 1–5 were run on 500–560 micron PS beads with 127 nmol of Br/bead initial loading.
[b]Entry 6 represents the commercially available 500–600 micron beads initially loaded at 208 mequiv of Br/g as determined by elemental analysis.

TABLE 3

Small Molecule Loadings.

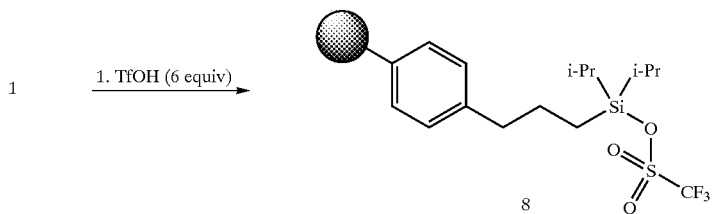

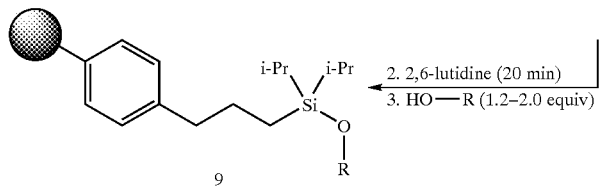

| Entry | Substrate (equiv used) | Recovered (per bead)[a] |
|---|---|---|
| (1)[b] | HO~~~NHFMOC (1.5) | 90% (114 nmol) |
| (2)[c] | (structure shown) (1.2) | 73% (146 nmol) |
| (3) | (steroid structure) (2.0) | 76% (152 nmol) |

TABLE 3-continued

Small Molecule Loadings.

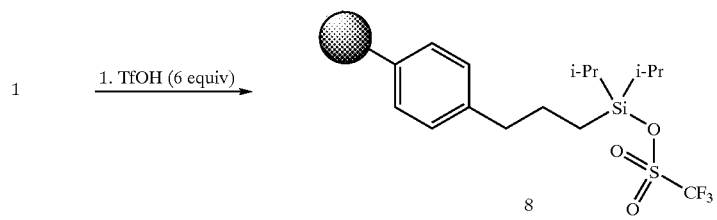

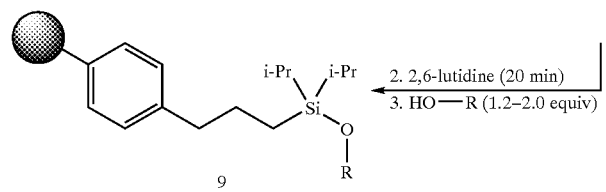

| Entry | Substrate (equiv used) | Recovered (per bead)[a] |
|---|---|---|

R = [structure shown]

| (4)[d] | trans-2-phenyl-1-cyclohexanol (2.0) | 69% (137 nmol) |
| (5)[d] | 4-bromo-3,5-dimethylphenol (2.0) | 79% (158 nmol) |

[a]Material recovered is an indirect determination of the efficiency of substrate loading. All material recovered was >95% pure as determined by HPLC analysis using a photodiode array detector.
[b]Entry 1 was run on 500–560 micron beads and loading was determined by standard Fmoc cleavage analysis.
[c]Loading was run on ~6 g of resin in a single experiment.
[d]These loadings were confirmed by HPLC analysis and recovered material.

Scheme 1

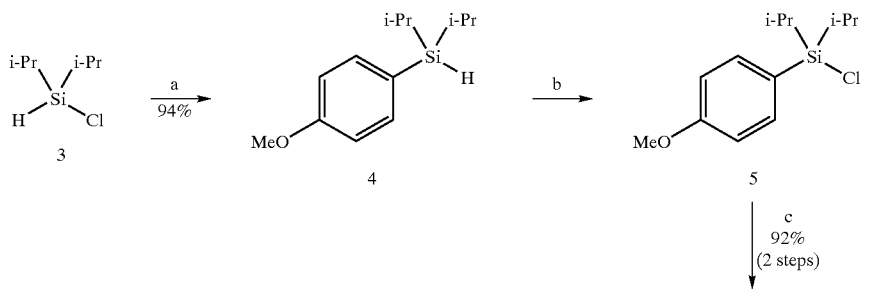

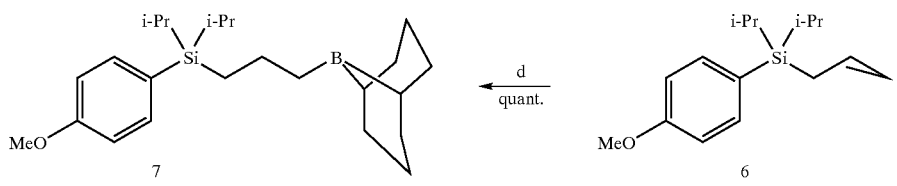

(a) 4-lithioanisole, THF, -78° C.; (b) trichlorosiocyanuric acid, CH$_2$Cl$_2$, 0° C.; (c) allymagnesiumchloride, THF, 0° C.; (d) 9-BBN, THF, rt, 3h.

| Supporting Information | |
|---|---|
| 1. General Methods | S1 |
| 2. Representative Substrate Loading Procedure. | S3 |
| 3. General Cleavage Process. | S4 |
| 4. Data for Single Bead Cleavage Experiments | S6 |

I. General Methods

Starting materials and reagents were purchased from commercial suppliers and used without further purification except the following: methylene chloride ($CH_2Cl_2$), tetrahydrofuran (THF), and diethyl ether ($Et_2O$) were passed through two activated alumina columns to remove impurities prior to use (as described in *Organometallics* 1996, 15, 1518–1520). 2,6-Lutidine was distilled from $CaH_2$ under Ar atmosphere. Unfunctionalized polystyrene (400–450 and 500–560 micron 1% DVB cross-linked) was purchased from Rapp Polymere GmbH and used without further purification. Brominated polystyrene (500–600 micron 1% DVB cross-linked PS-Br, 2.0 mequiv./g and 1.0 mequiv./g) was purchased from Polymer Labs (1462-9999)[9] and used without further purification.

[9] This product is available from Polymer Labs. For pricing and availability information, they can be contacted at Polymer Laboratories Inc, Amherst Fields Research Park, 160 Old Farm Road, Amherst, Mass. 01002, USA. Tel: 413/253 9554 or 800/767 3963, Fax: 413/253 2476

Oxygen- or moisture-sensitive solution-phase reactions were carried out under $N_2$ or Ar atmosphere in oven-dried (140° C., ≧4 h) glassware. Small-scale solid phase reactions (1–50 mg resin) were performed in 2.0 mL fritted polypropylene Bio-Spin® chromatography columns (Bio-Rad Laboratories, Hercules, Calif.; 732-6008). Medium-scale solid phase reactions (50–250 mg) were performed in 10.0 mL polypropylene PD-10 columns (Pharmacia Biotech, Piscataway, N.J.; 17-0435-01). Agitation of solid phase reactions was accomplished using a 360° rotator from Barnstead/Thermolyne (model no. 415110). Large-scale solid phase reactions (>500 mg) were carried out in oven-dried (140° C., ≧4 h), fritted peptide synthesis vessels available from ChemGlass (Vineland, N.J.) equipped with inlets for vacuum and inert atmosphere. Small scale linker cleavage reactions (1 bead→50 mg of resin) were carried out in 1.5 mL eppendorf tubes ( ). Larger scale cleavage reactions are performed in Wheaton scintillation vials available from Fisher Scientific (cat no. 03-341-25A).

Air- and/or moisture-sensitive liquids were transferred by syringe or cannula and were introduced into the reaction vessel through rubber septa or through a stopcock under $N_2$ or Ar positive pressure. Air- and/or moisture-sensitive solids were transferred in a glove box or atmosbag. Unless otherwise stated, reactions were stirred with a teflon™ covered stir bar and carried out at RT. Concentration refers to the removal of solvent using a Büchi rotary evaporator followed by use of a vacuum pump at approximately 1 torr. Column chromatography was performed using Merck 60 Å (230–400 mesh ASTM) silica gel. Thin layer chromatography (TLC) analyses were performed using Merck 60 $F_{254}$ 0.25 μm silica gel plates. Vacuum removal of solvents for linker cleavage reactions was accomplished using a Genevac HT-4 Atlas Evaporator.

Proton nuclear magnetic resonance spectra ($^1H$ NMR) were measured on a Varian Unity Inova 500 spectrometer (500 MHz). Carbon nuclear magnetic resonance ($^{13}C$ NMR) spectra were recorded on a Varian Unity Inova 500 spectrometer (125 MHz). Magic Angle Spinning NMR (MAS NMR) were recorded on a Varian Unity Inova 500 spectrometer using a NanoProbe. All $^1H$ and $^{13}C$ NMR chemical shifts are reported in ppm downfield from tetramethylsilane (0.00 ppm) or residual solvents ($CDCl_3$, 7.26 ppm/77.7 ppm). Infrared spectra (IR) were measured on a Bruker Vector 22 ATR-based Infrared Spectrometer, $\nu_{max}$ in $cm^{-1}$.

Elemental analyses (Anal) were performed by Robertson Microlit Laboratories Inc., Madison, N.J. 07940 and were reported in percent atomic abundance. Tandem high pressure liquid chromatography/mass spectral (LCMS) analyses were performed on a Micromass Platform II mass spectrometer in atmospheric pressure chemical ionization (APCI) mode after separation performed on a Waters Alliance 2690 separations module. The actual separation was performed on a Waters Symmetry® $C_{18}$ 3.5 μm, 2.1×50 mm column with a flow rate of 0.4 mL/min and a 12 min gradient of 15–100% $CH_3CN$ in $H_2O$, constant 0.1% formic acid buffer using a Waters 996 photodiode array detector.

II. Representative Substrate Loading Procedure

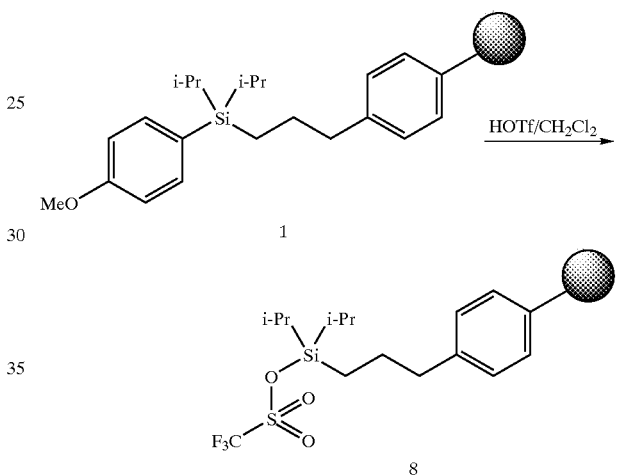

Conversion of tetralkylsilane to silyl triflate functionalized resin 8.

Silicon functionalized resin 1 (1.43 mequiv. Si/g) that had been dried under hi-vac for 12 h was weighed (200 mg, 0.286 mmol, 1 equiv.) into a 10 mL polypropylene PD-10 column fitted with a teflon™ stopcock and swollen in $CH_2Cl_2$ (2.0 mL, 10 mL of solvent/g of resin) under $N_2$ atmosphere for 30 min. The solvent was then drained under positive $N_2$ pressure and 3.8 mL of a 4% tifluoromethanesulfonic acid/$CH_2Cl_2$ solution (6 equiv. of TfOH relative to Si) was added by syringe. The resin turned bright red/orange upon acid treatment and was then gently agitated for 30 min. while still under $N_2$ atmosphere. Once activation was completed, two $CH_2Cl_2$ washes removed excess acid.

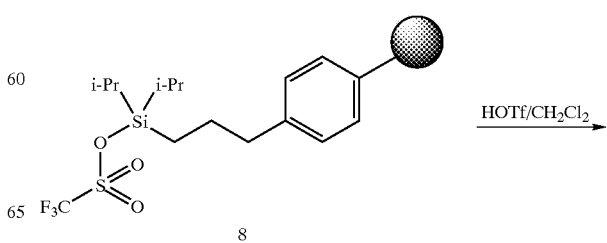

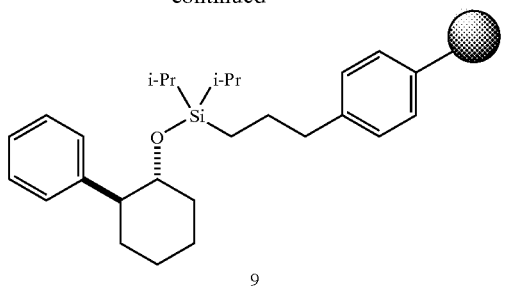

9

Loading of trans-2-phenyl-1-cyclohexanol onto resin 8.

Treatment of 8 with 2,6-lutidine (0.27 mL, 8 equiv. relative to Si) for 15 min. followed by addition of 0.5 mL of an azeotropically dried 1.0 M solution of trans-2-phenyl-1-cyclohexanol (2 equiv) resulted in a colorless resin 9. The beads are then gently agitated for an additional 10 h under $N_2$ atmosphere. The beads were drained, exposed to atmosphere, and subjected to the following wash protocol: $CH_2Cl_2$ (2×3 mL×45 min.), THF (2×3 mL×30 min.), THF/IPA (3:1, 2×3 mL×30 min.), THF/$H_2O$ (3:1, 2×3 mL×30 min.); THF/IPA (3:1, 2×3mL×30 min.), DMF (2×3 mL×30 min.), THF (2×3 mL×30 min.). The resin was air-dried for 3 h and then placed under hi-vac for 24 h to remove trace solvent and $H_2O$. The mass of the loaded and dried resin was 207.0 mg, indicating an apparent loading efficiency of 74% based on weight gain.

MAS-$^1$H NMR, 5 beads, (500 MHz, $CD_2Cl_2$, nanoprobe) δ7.34 (C3-H, C7-H), 6.82 (C4-H, C6-H), 5.27 ($CH_2Cl_2$), 3.69 (C1-H), 1.76 (C14-H), 1.48 ($H_2O$), 1.22(C15-H, C16-H), 1.16 (C8-H, C11-H), 0.97 (C9-H, C10-H), 0.91 (C12-H, C13-H)

III. General Cleavage Process

Bulk cleavage of resin for determination of loading by compound recovery.

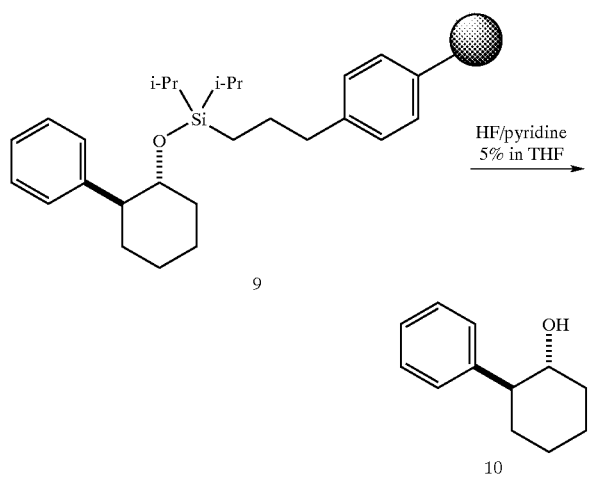

Vacuum-dried resin 9 was weighed (100.0 mg) out into a solvent-resistant scintillation vial and allowed to swell in 1.0 mL of THF for 30 min. The THF solution was removed and replaced with a fresh 0.95 mL of THF and 0.05 mL of HF/pyridine solution (7:3 ratio of HF/pyr, available from Aldrich Chemical Co.). The vial was sealed and agitated for 3 h at which time 0.1 mL of methoxytrimethylsilane was added to quench unreacted HF. (Note: quench is mildly exothermic therefore use caution). The beads are further agitated for 30 min to ensure complete quenching. The solution was removed and the beads washed twice with additional 1.0 mL portions of fresh THF. All solvents were combined and concentrated in vacuo, delivering 16.3 mg of trans-2-phenyl-1-cyclohexanol as a white solid. Based on the assumption that 100% of the material loaded onto the resin is cleaved and recovered, this amount of material represents 71% of the theoretical maximum or approximately 143 nmol/bead.

General determination of average per bead loading by HPLC analysis for entries 4 and 5, Table 3.

Figure 50:
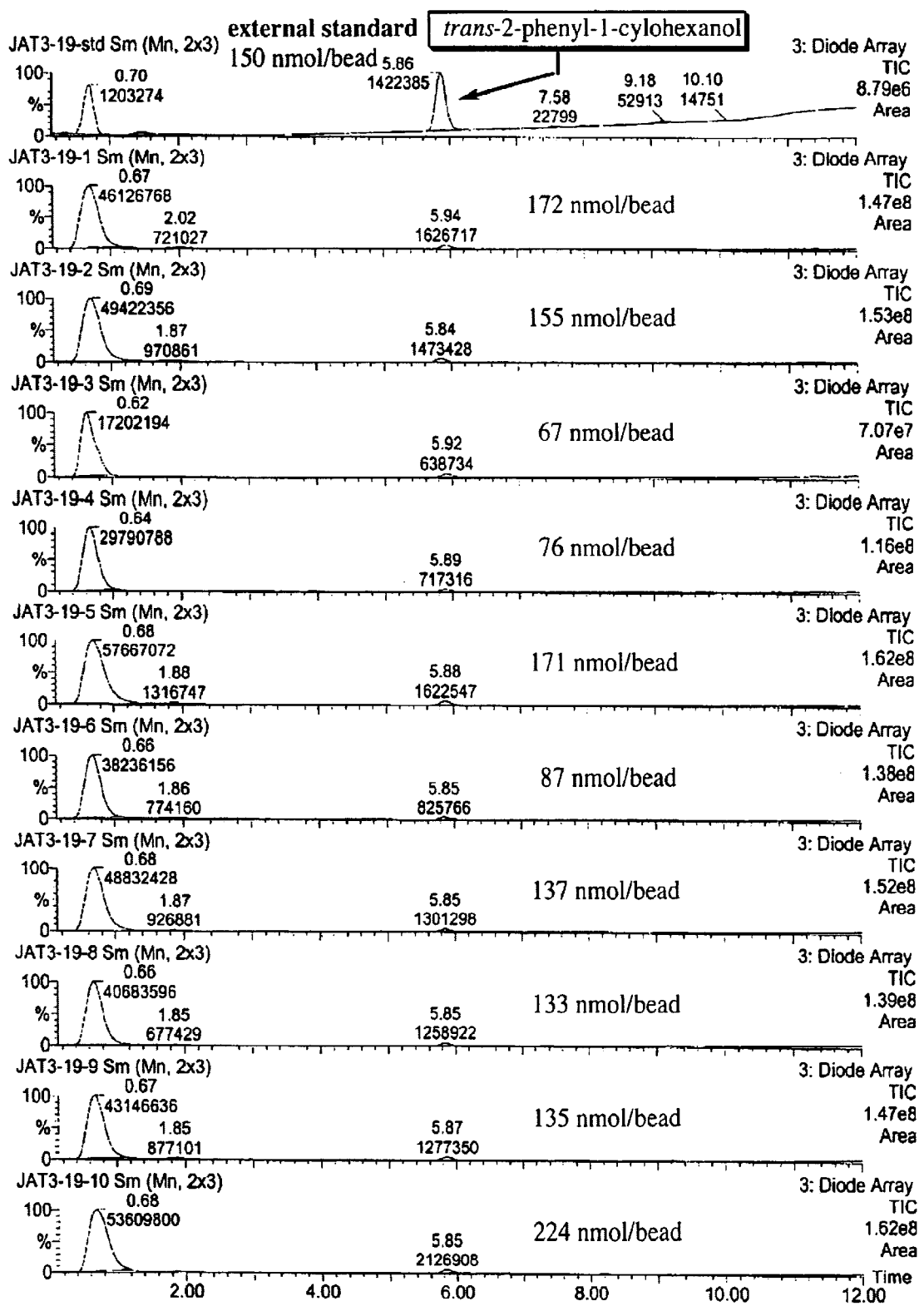
FIG. 50 depicts ten LC traces from the cleavage of 10 separate beads containing trans-2-phenyl-1-cyclohexanol. The large peak at 0.70 min. arises from residual pyridine and the solvent front of the injected solution. The average bead loading from this experiment is approximately 137 mol/bead.
Figure 51:
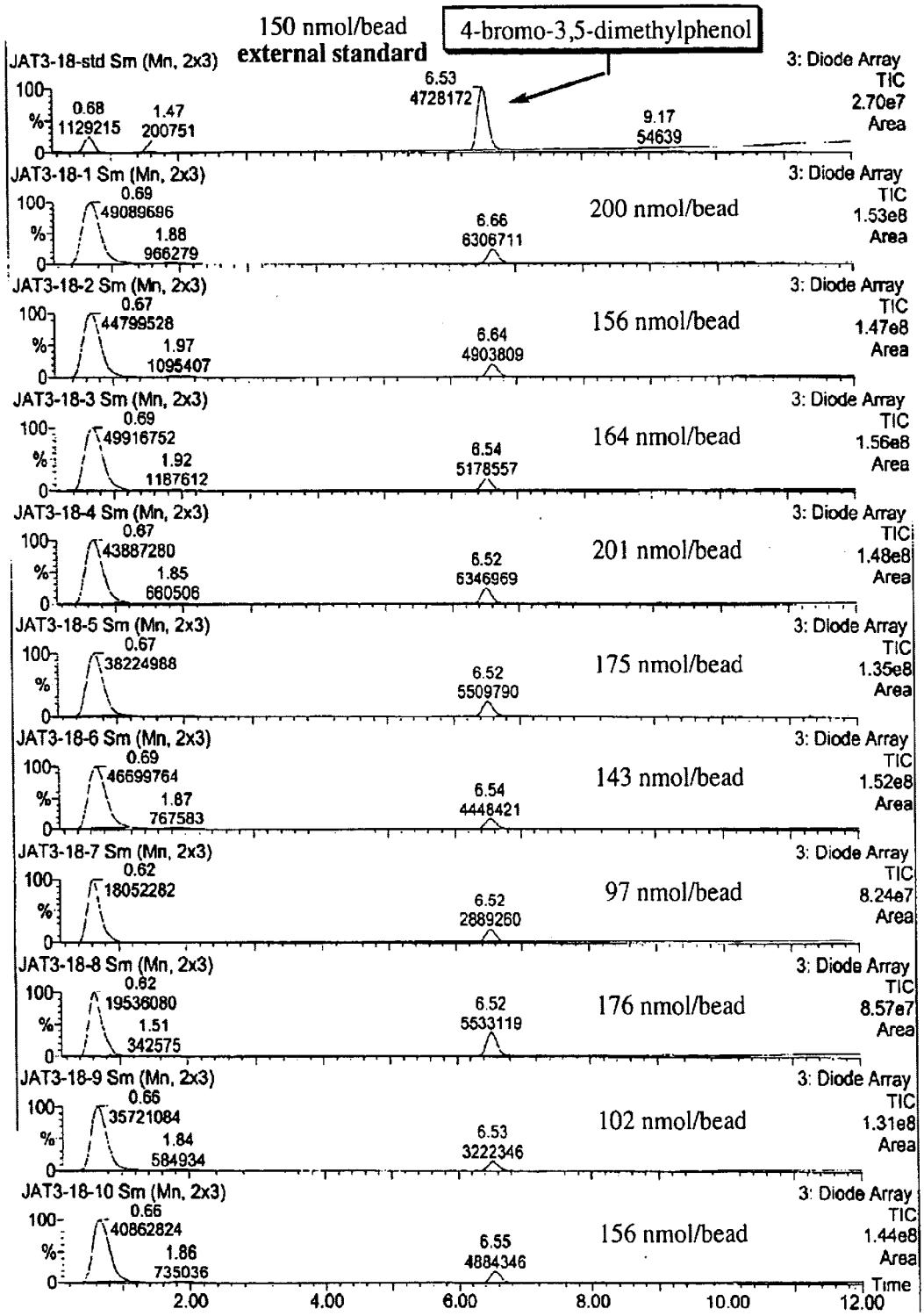
FIG. 51 depicts ten LC traces from the cleavage of 10 separate beads containing 4-bromo-3,5-dimethylphenol. The large peak at 0.70 min. arises from residual pyridine and the solvent front of the injected solution. The average bead loading from this experiment is approximately 158 mol/bead.

Ten separate beads from the above loading experiment (loading of trans-2-phenyl-1-cyclohexanol, vide supra) were placed into 10 unique 500 μL Eppendorf tubes and swelled in 47.5 μL of THF for 30 min. To each of these tubes was added 2.5 μL of a HF/pyridine solution. Each of the tubes were sealed and agitated for 2.5 h followed by addition of 10 μL of TMSOMe. The tubes were resealed and agitated for an additional 30 min. to ensure complete quenching of HF. The remaining solvent was removed from the Eppendorf tubes using an HT-4 Atlas Evaporator from Genevac (~30 min) and the remaining residue was taken up in 100 μL of THF to separate the cleaved molecules from the bead. The beads were washed with a second 50 μL of THF for 30 min. and was pooled with the original wash solution. All THF was removed under reduced pressure, the residue taken up in 100 μL of $CH_3CN$ and used in a 5 μL injection onto the LCMS system (details described in the General Methods section) for LC analysis relative to an external standard. This same experiment was performed on resin loaded with 4-bromo-3,5-dimethylphenol (Table 3, entry 5). Data for both experiments (LC/traces) is included in FIGS. 50 and 51.

Example 3

Biological Testing

Cell and Protein Based Screens

Figure 27:
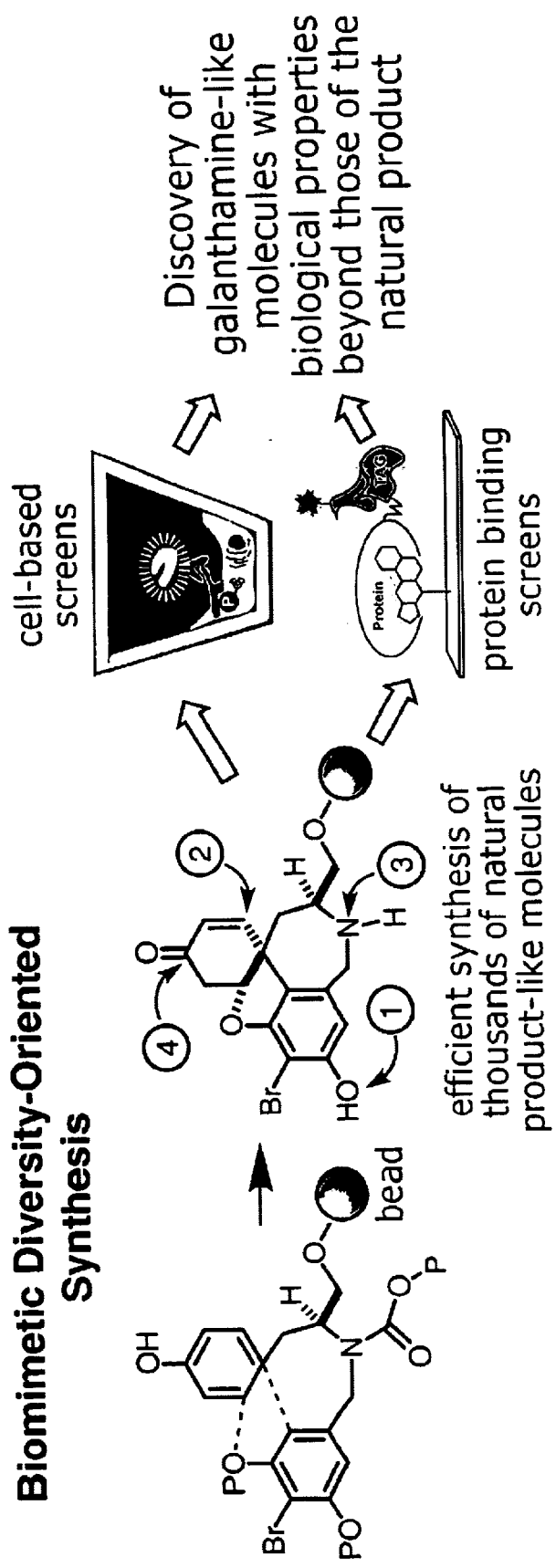
FIG. 27 depicts biomimetic diversity-oriented synthesis.

It will be appreciated that the small molecule compounds of the present invention may be screened in any of a variety of biological assays, for example, cell-based assays may be employed (see FIG. 27). Such cell-based assays generally involve contacting a cell with a compound and detecting any of a number of events, such as binding of the compound to the cell, initiation of a biochemical pathway or physiological change in the cell, changes in cell morphology, initiation or blockage of the cell cycle etc.

Figure 28:
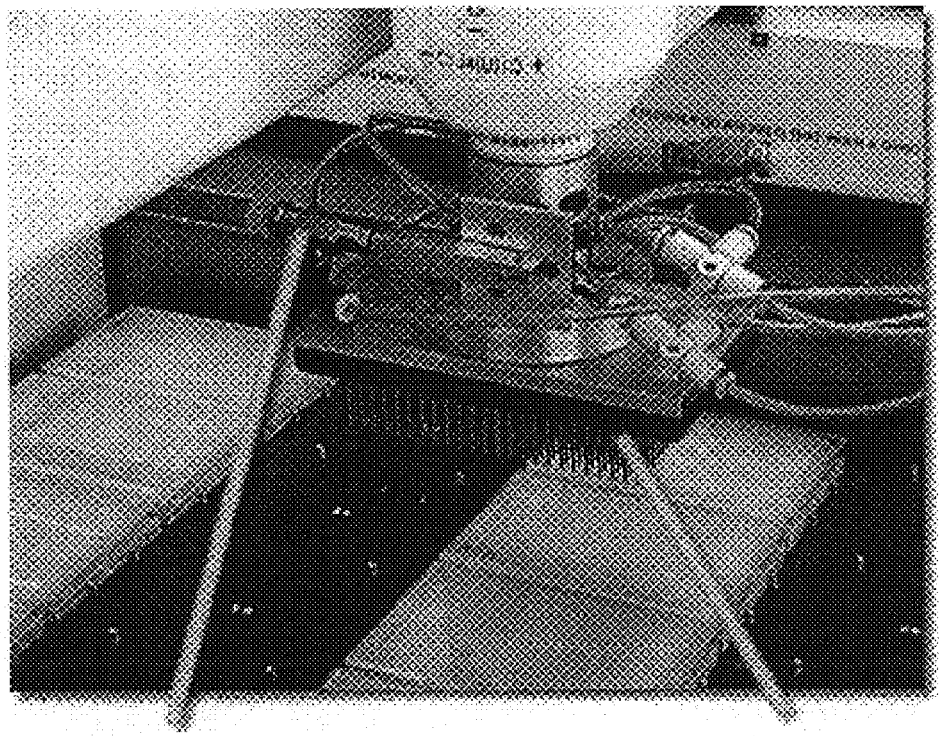
FIG. 28 depicts a robotic 384 pin arrayer.

As but one example, once synthesized, the compounds may be arrayed in 384-well plates, as shown in FIG. 28, by a robotic 384 pin arrayer and assayed for their ability to bind to a particular cell type present in the well. Detection can be carried out, for example, by detecting a tag that is attached to the small molecule. Alternatively, the small molecule may be detected by using a second molecule that has a tag, the second molecule specifically binding the small molecule, e.g., a tagged antibody specific to the small molecule.

Alternatively or additionally, inventive compounds may be studied in such assays. In such assays, the compounds are bound to a solid support and then contacted with a protein of interest. The presence or absence of binding between the compound and the protein is then detected. In certain cases, the protein itself is tagged with a molecule that can be detected, e.g., with a fluorescent molecule. Alternatively, the protein is detected by utilizing any immunoassay, such as the ELISA.

Figure 29:
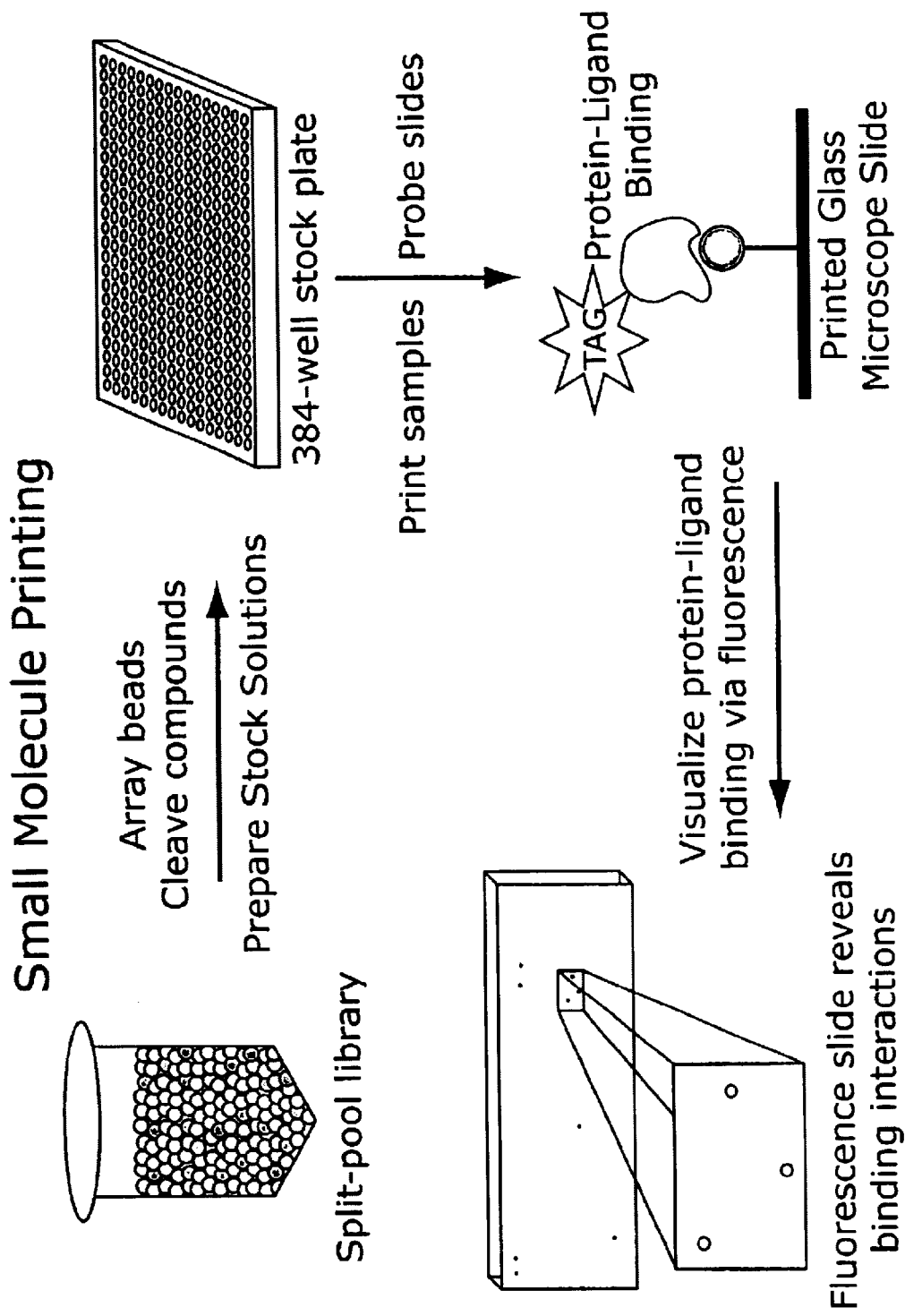
FIG. 29 depicts small molecule printing.
Figure 30:
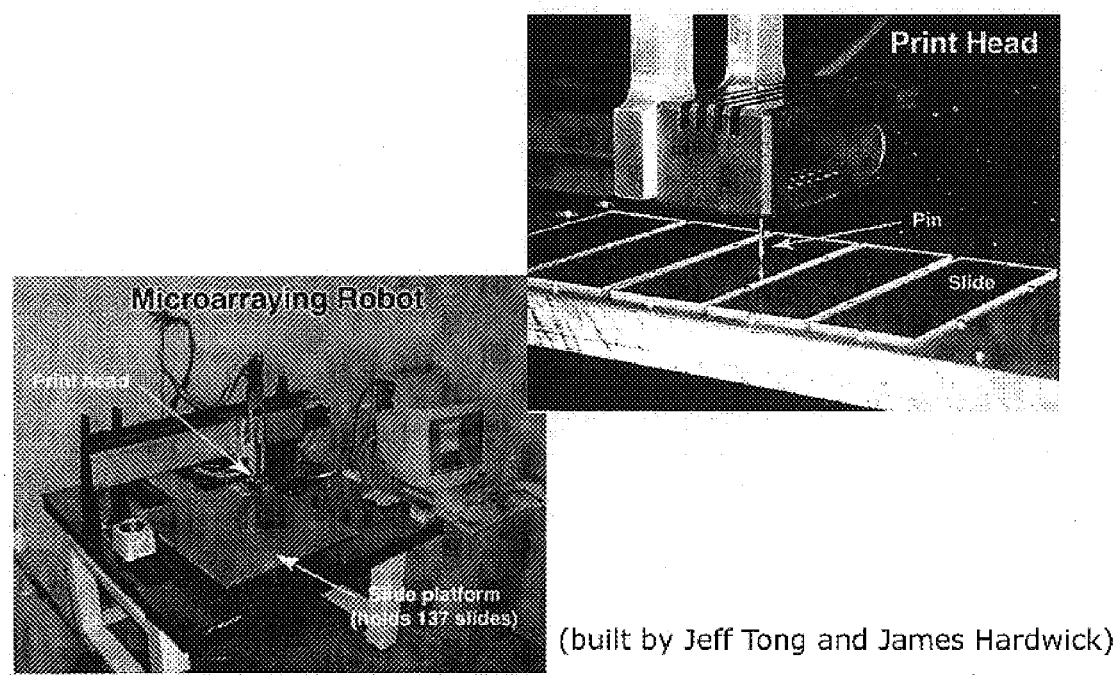
FIG. 30 depicts small molecule microarraying robot.

For example, a process known as small molecule printing (see, for example, U.S. Ser. No. 09/567,910, filed May 10, 2000, the entire contents of which are hereby incorporated by reference, may be utilized to screen proteins that interact with the library compounds. First, a split pool library is arrayed onto beads. The compounds are then cleaved from the beads and prepared in a standard stock solution, such as DMSO. The compounds are then arrayed onto a 384-well stock plate. Next, the compounds are printed onto glass slides, e.g., a glass microscope slides, and the slides are probed with a tagged ligand, e.g., a tagged protein of interest. Binding between a compound and the ligand is then detected by any available means appropriate to the tag being utilized, e.g., via fluorescence. (See FIGS. 29 and 30).

Although any of the general assay methods described above may identify galanthamine-like molecules having biological properties beyond those of the natural product, certain assays are of special interest, including but not limited to those as described below.

Protein Trafficking

Figure 31:
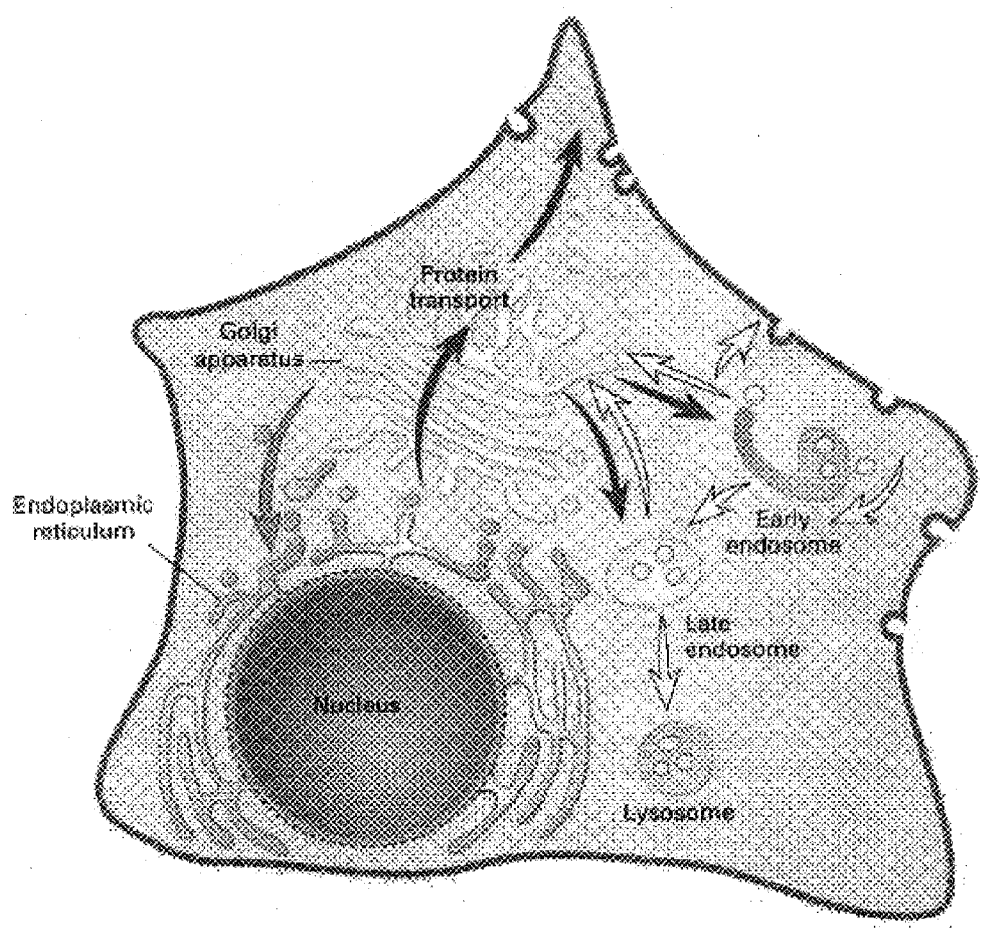
FIG. 31 depicts the secretory pathway.

Protein trafficking (or vesicle transport) is the general process in eukaryotic cells by which proteins synthesized in the endoplasmic reticulum (ER) are transported via the golgi network to the various compartments in the cell where they will carry out their function (see FIG. 31). Some proteins are transported through the golgi apparatus all the way to the cell surface where they are secreted (exocytosis). Such proteins include membrane bound receptors or other membrane proteins, neurotransmitters, hormones, and digestive enzymes. The transport process uses a series of transport vesicles that shuttle a protein from one membrane-bound compartment (donor compartment) to another (acceptor compartment) until the protein reaches its proper destination (Rothmanet al. (1996) *Science* 272:227–34).

The process of vesicle transport begins with the budding of a vesicle out of the donor compartment. The vesicle containing the protein to be transported is surrounded by a protective coat made up of protein subunits recruited from the cytosol. The initial budding and coating processes are controlled by cytosolic GTP-binding proteins (GTPB). When GTP binds and activates the GTPB, the GTP-GTPB complex binds to the donor compartment and initiates the vesicle assembly process. The coated vesicle containing the GTP-GTPB complex detaches from the donor compartment and is transported through the cytosol. During the transport process, the GTP is hydrolyzed to GDP, and the inactivated GTPB dissociates from the transport vesicle and is recycled. At this point, the protective coat of the vesicle becomes unstable and dissociates from the enclosed vesicle. The uncoated vesicle is recognized by its acceptor compartment through exposed surface identifiers (v-SNAREs) which bind with corresponding molecules on the acceptor compartment membrane (t-SNAREs). The transport process ends when the vesicle fuses with the target membrane.

Figure 32:
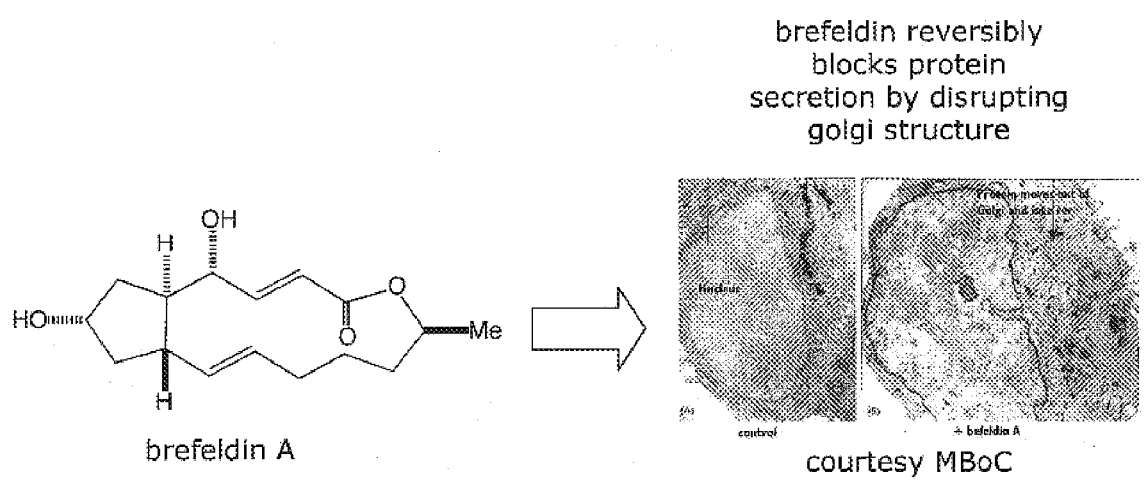
FIG. 32 depicts the effect of brefeldin A.

Many of the proteins involved in synaptic vesicle transport have been identified and the biochemical interactions between them have been characterized. Interestingly, many of these proteins are homologous to yeast proteins involved in yeast secretory pathways. In addition, many agents that disrupt the golgi apparatus and interfere with trafficking have been identified, e.g., monensin, bafilomycin, ilimaquinone, retinoic acid, okadaic acid, and nocodazole. Another agent, brefeldin A, is a natural compound that blocks protein secretion by disrupting the structure of the golgi apparatus, as shown in FIG. 32. The present invention expands the limited pool of molecules presently available that block protein trafficking by identifying additional compounds with this activity.

It will be appreciated that cell-based phenotypic assays are commonly used to identify a block in protein trafficking from the endoplasmic reticulum to the golgi apparatus, or a block in exocytosis. Such phenotypic assays generally involve visualizing the transport of an intracellular protein within the cell. For example, a fluorescence immunoassay may be used to assess the location of a protein known to be shuttled from the endoplasmic reticulum to the golgi apparatus or to be exocytosed. Alternatively, cells may be transfected with an expression vector expressing a protein that is known to be trafficked that is a fusion protein with a fluorescent protein, such as green fluorescent protein. The location of the protein within a cell may be assessed by fixing the cell and visualizing the cell using fluorescence microscopy. Such assays are amenable to high-throughout screening via multiplexing, as described below.

Indeed, the present invention identifies certain compounds as potent inhibitors of the movement of a specific cellular protein from the endoplasmic reticulum to the golgi apparatus or as a potent inhibitor of the movement of a specific cellular protein from the golgi apparatus to the plasma membrane. In one exemplary embodiment, the present invention identifies an inventive compound, secramine, as detailed herein, as a potent inhibitor of the movement of a specific cellular protein from the golgi apparatus to the plasma membrane. However, galanthamine, the parent molecule of the inventive library, has no observable effect on the secretory pathway. This demonstrates that compounds resembling natural products are capable of dramatically effecting a biological process where the natural product itself shows no activity. Thus, the present invention provides compounds that effect protein trafficking and secretion, which may be useful probe reagents for exploring these cellular pathways.

Figure 33:
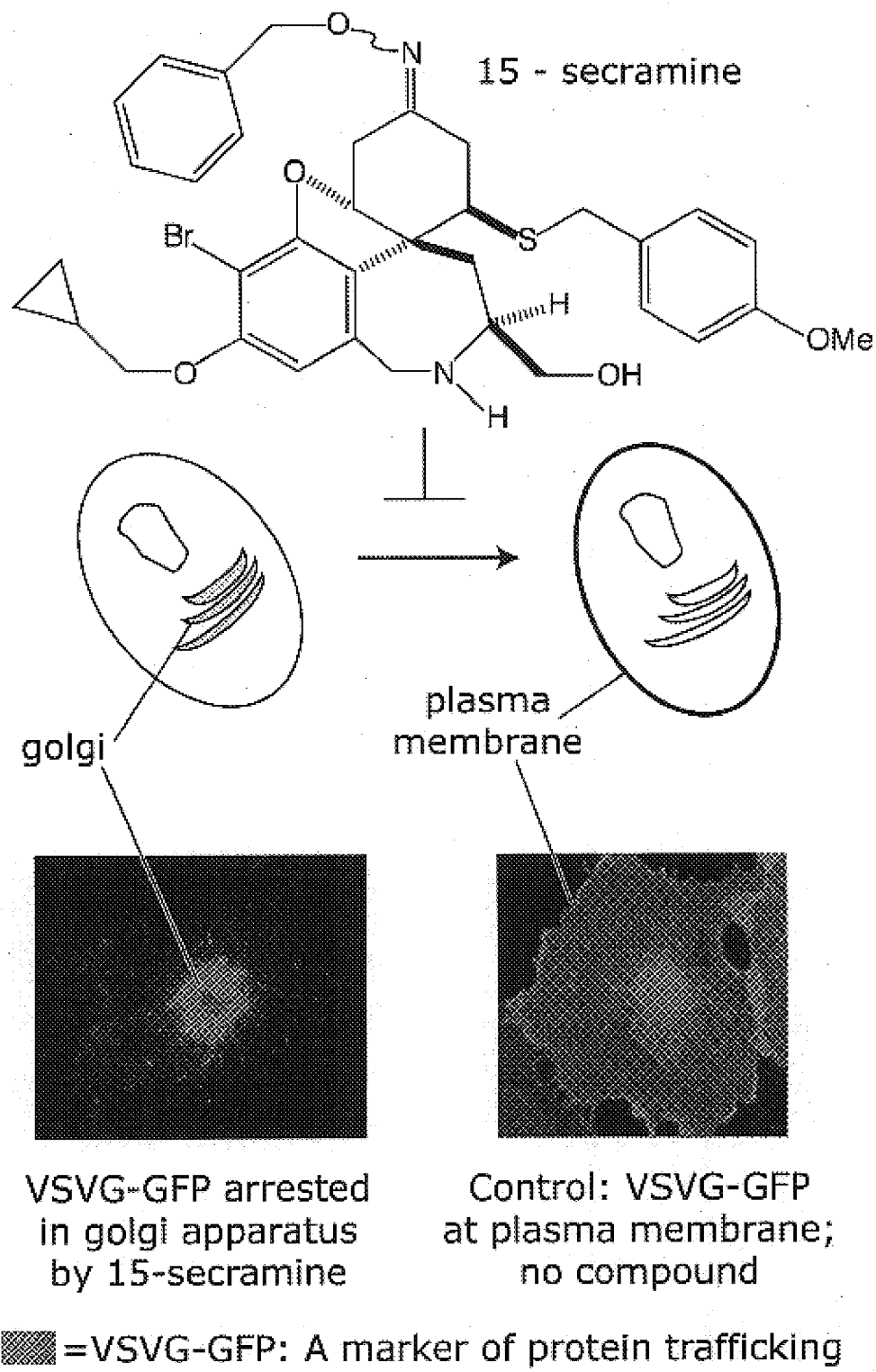
FIG. 33 depicts the effect of secramine on protein trafficking.

The present example illustrates an effective assay for identifying compounds that effect protein trafficking. The library of compounds described herein was screened using a cell-based phenotypic assay. The fluorescent fusion protein viral glycoprotein ts045 (VSVG-GFP) was used to monitor the ability of individual library members to block protein trafficking, as described in Presley et al. *Nature* 1997, 389, 81–85 and Scales et al. Cell 1997 19;90(6):1137–48, each of which are incorporated herein by reference (FIG. 33).

Briefly, VSVG from the ts045 mutant strain of vesicular stomatitis virus has been widely used to study membrane transport because of its reversible misfolding and retention in the endoplasmic reticulum at 40° C. and its ability to move out of the endoplasmic reticulum at 32° C. (Kreis et al. *Cell* 46, 929–927,1986; Beckers et al. *Cell* 501, 523–534, 1987; Bergmann et al. *Methods Cell Biol.* 32, 85–110, 1989). Green fluorescent protein is attached to the cytoplasmic tail of VSVG. To examine how VSVG-GFP is transported from the endoplasmic reticulum to the golgi and then to the plasma membrane in the presence and absence of compound, cells in the presence and absence of compound are placed on the stage, of a fluorescent microscope warmed to 32° C. and fluorescent images were colleced at distince intervals, e.g., evey 3.6 seconds. Inhibition of the phenotye at 32° C. is determined by dramatic slow down of VSVG-GFP moving from one compartment to another.

Figure 34:
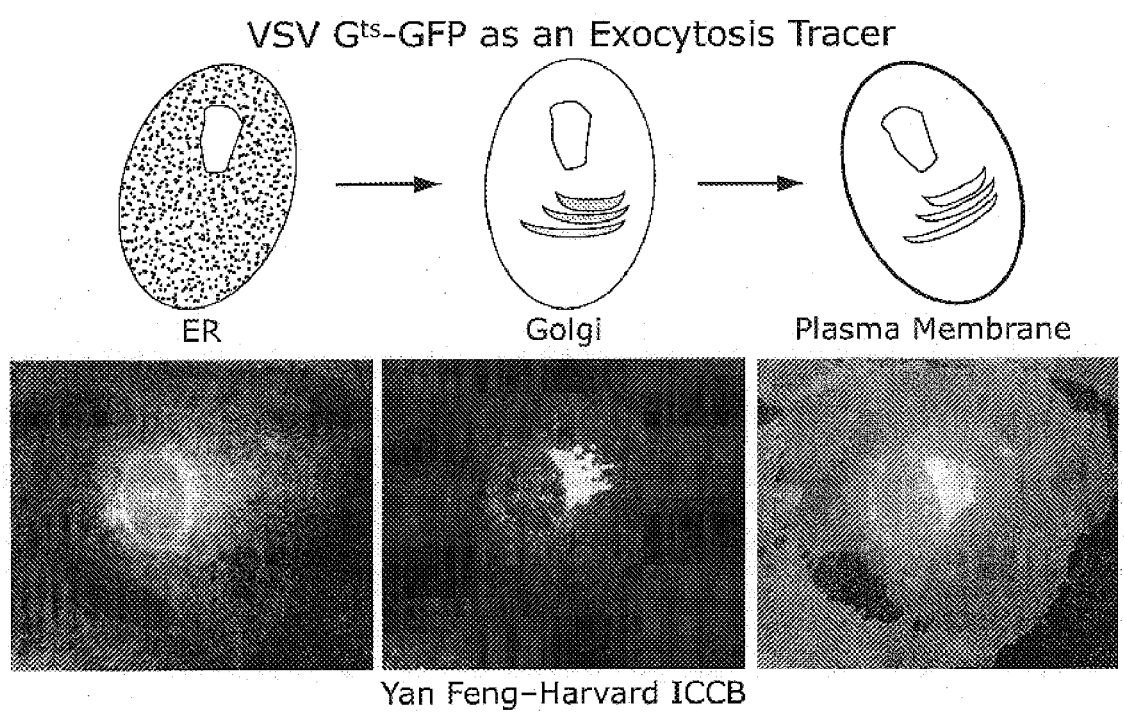
FIG. 34 depicts VSV Gts-GFP as an Exocytosis Tracer.

Specifically, VSV-GFP was expressed in BSC1 cells at 40° C. Compounds were added to cells for 1 hour at 40° C. and then the cells were shifted to 32° C. for 2.5 hours before fixing and insepction using the fluorescent microscope. In the absence of compound, at this time point, the VSVG-GFP protein has alredy moved from the endoplasmic reticulum through the golgi to the plasma membrane. As shown in FIG. 34, the VSVG$^{ts}$-GFP fusion protein is an effective exocytosis tracer, its localization being successively detected in the endoplasmic reticulum, the golgi apparatus, and the plasma membrane at 30° C. as protein trafficking proceeds. Compounds were screened on cells expressing the VSVG$^{ts}$-GFP fusion protein. Disruption of VSVG$^{ts}$-GFP fusion protein trafficking verified compounds capable of blocking the secretory pathway.

Figure 35:
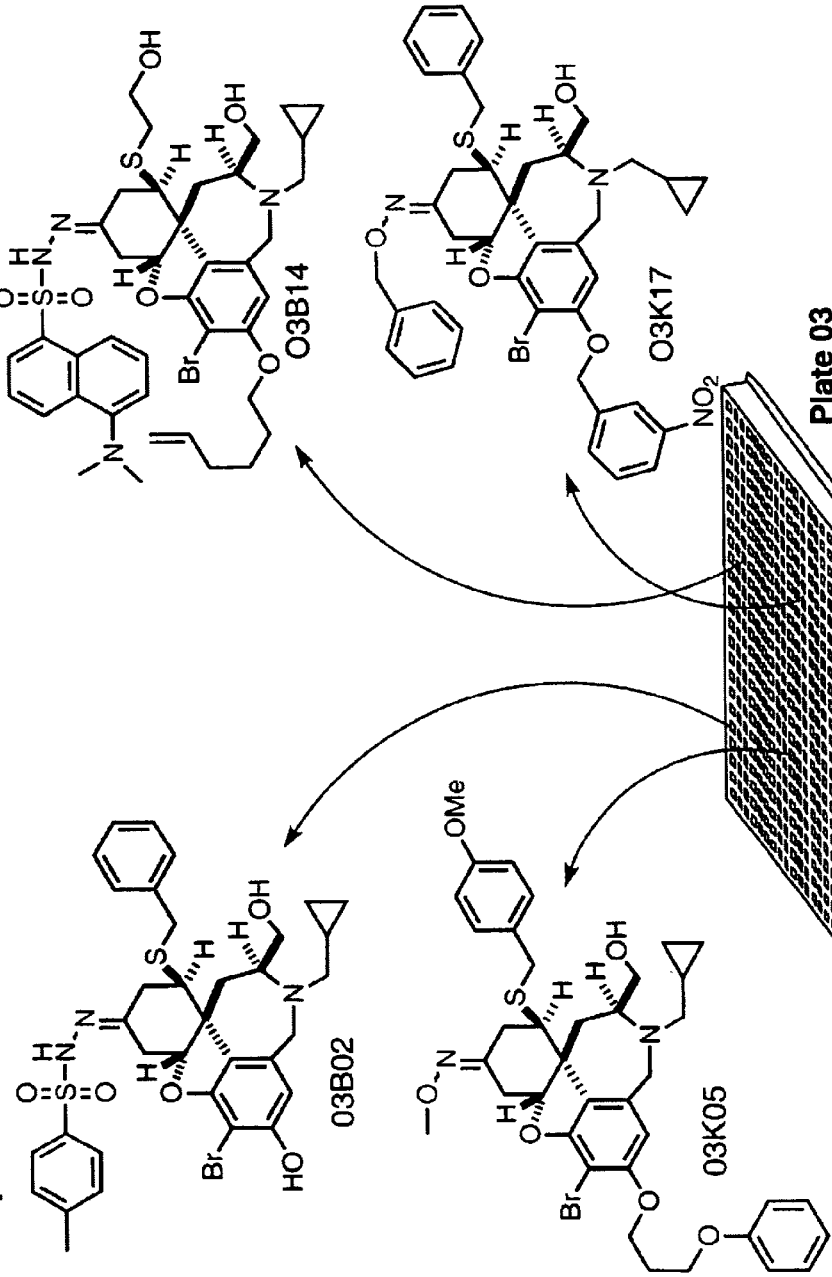
FIG. 35 depicts arrayed inventive compounds.

The compounds, as shown in FIG. 4 were arrayed in 384-well plates containing cells as solutions in DMSO (FIG. 35). This was accomplished using a robotic 384 pin arrayer, as shown in FIG. 28 and as described above. Cells were then visualized by fluorescence microscopy on a plate reader.

The compounds, as shown in FIG. 4 were arrayed in 384-well plates containing cells as solutions in DMSO (FIG. 109). This was accomplished using a robotic 384 pin arrayer, as shown in FIG. 102 and as described above. Cells were then visualized by fluorescence microscopy on a plate reader.

The results of the inhibitor screens at 7.5 μM compound initially identified several compounds that inhibit export from the endoplasmic reticulum and several compounds that block transport from the golgi apparatus. Resynthesis and titration of the compound activity follows the same protocol as described above. For example, inventive compounds identified that inhibit movement from the endoplasmic reticulum to the golgi apparatus include: (note: compounds are described referring to a numbering system detailing the "R" groups, as detailed in Example 1. For example, compound 1234 refers to a compound that, for the R1 building block, has building block number 1; for the R2 building block, has building block number 2; for the R3 building block, has building block number 3; for the R4 building block, has building block number 4, as detailed in the chart in Example 1.

Compounds identified that inhibit transport from the endoplasmic reticulum to the golgi apparatus include:

6173, 5673, 1578, 6578, 1878, 4574, 6473, 4873, 6773, and 6573.

Compounds identified that inhibit transport from the golgi apparatus to the plasma membrane include: 2874, 6176, 5676, 3777, 4886, 5188, 4686, 2888, 2288, 1888, 4488, 5677, 6381, 2181, 3843, 5628, 5682, 2581, 4181, 2781, 5481, 4381, 2481, 2381, 4882, 6481, 5581, 3381, 5781, 2582, 5381, 2884, 6584, 2684, 5658, 5684, 4684, 2583, 4283, 1883, 4684, 6884,1684, 3784, 1883, 2284, 2586, 5586, 2286, 4486, 3786, 2385, 2786, 4786, 2687, 6787, 2187, 4287, 3187, 3287, 6813, 6662, 3 1 11 8, 2 4 11 8, 5 5 11 8, 5678, 1 4 11 8, 4878, 5848, 3618, 6618, 1771, 5371, 3371, 5672, 4672, 4172, 4872, 5871, 6271, 2871, 6271, 2371, 6372, 5372, 3671, 4771, 4871, 4371, 4671, 1372, 6771, 6171, 1671, 3672, 2772, 3871, 2271, 4571, 3472, 3173, 3873, 2173, 2874, 1873, 6174, 3274, and 5273.

Figure 36:
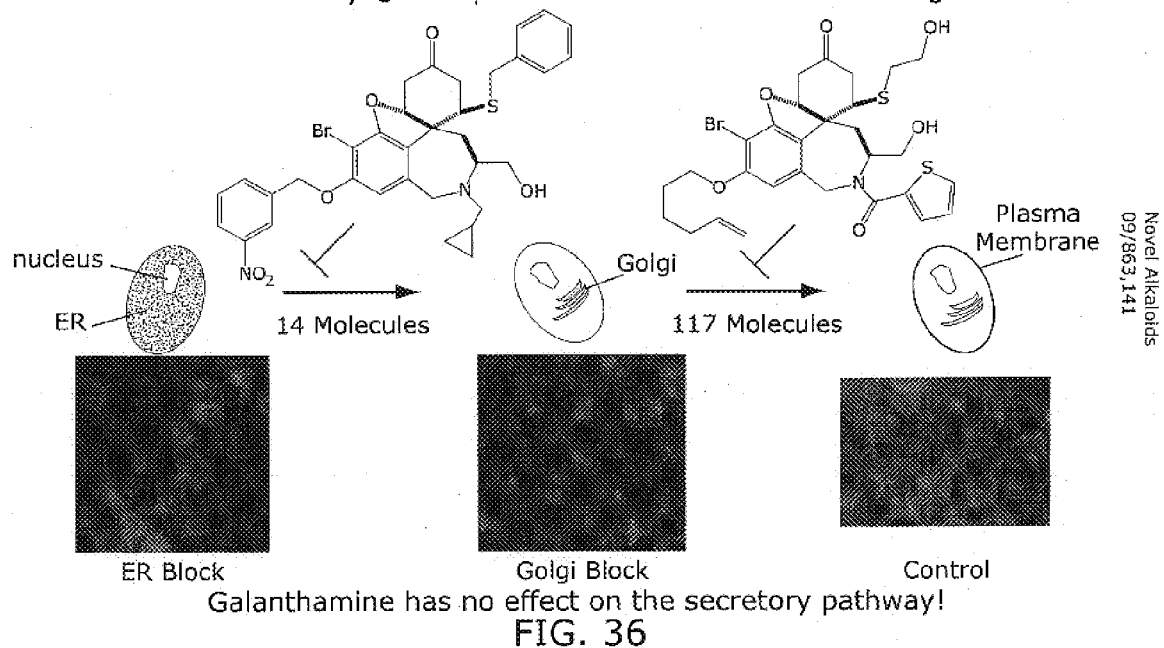
FIG. 36 depicts a screen of the inventive library.
Figure 37:
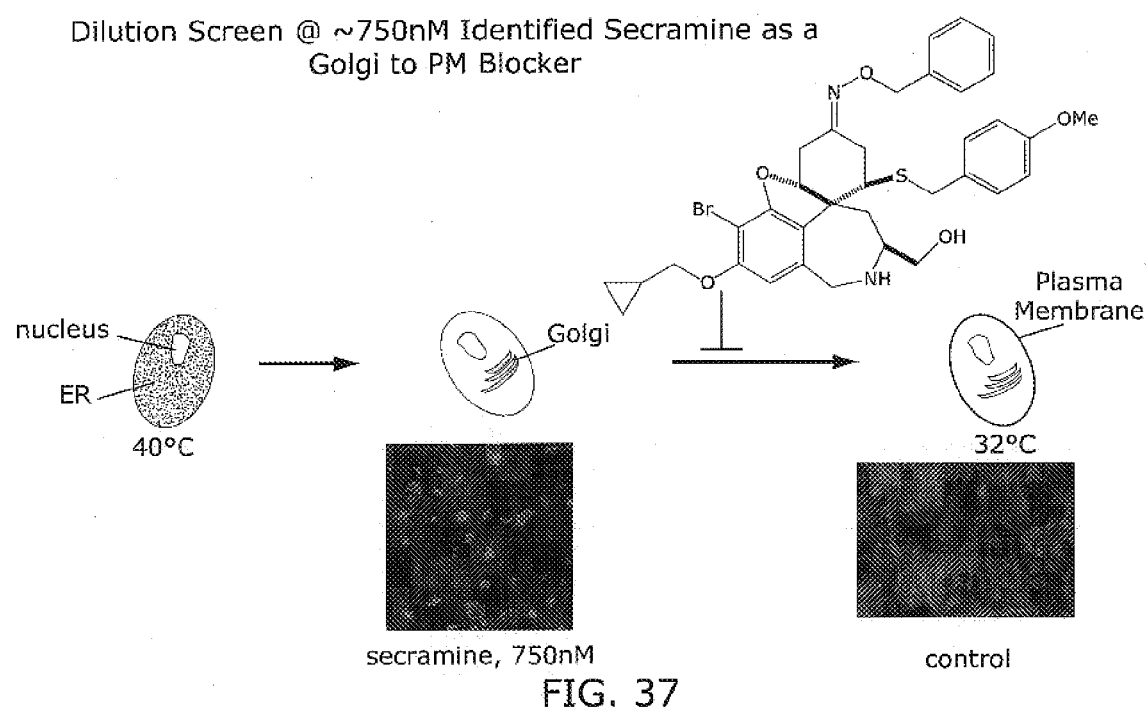
FIG. 37 depicts a dilution screen identifying secramine as a Golgi to PM Blocker.
Figure 38:
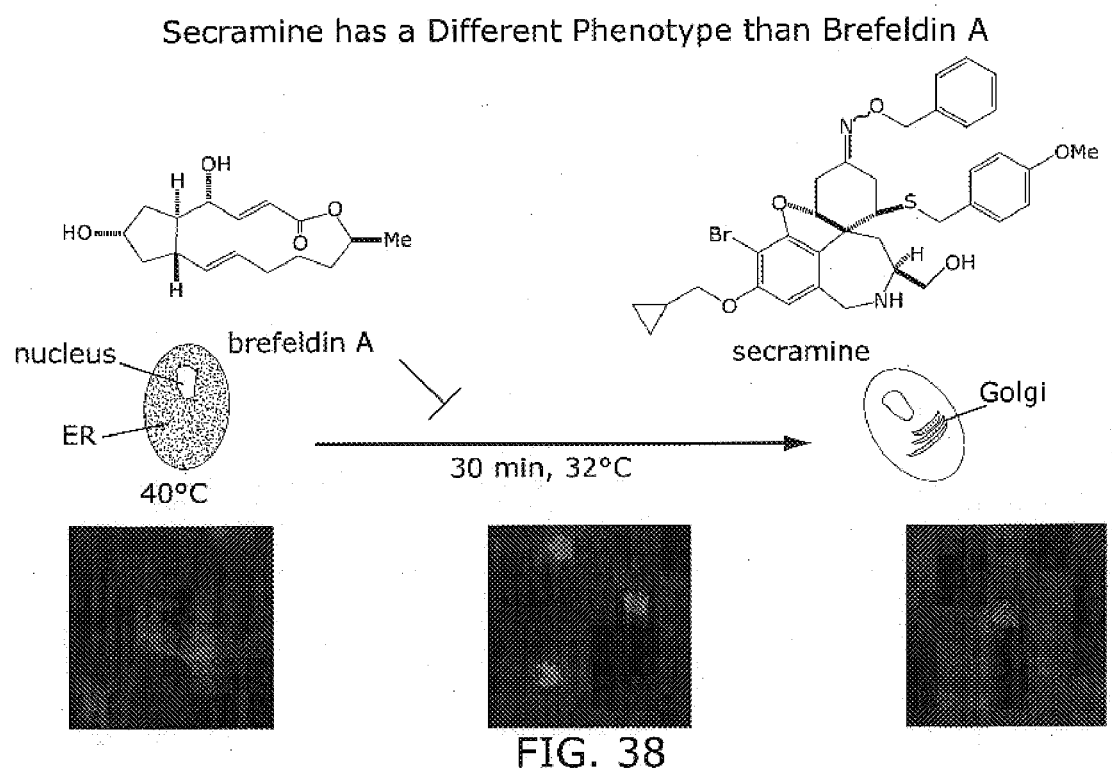
FIG. 38 depicts the effects of secramine compared with brefeldin A.
Figure 39A:
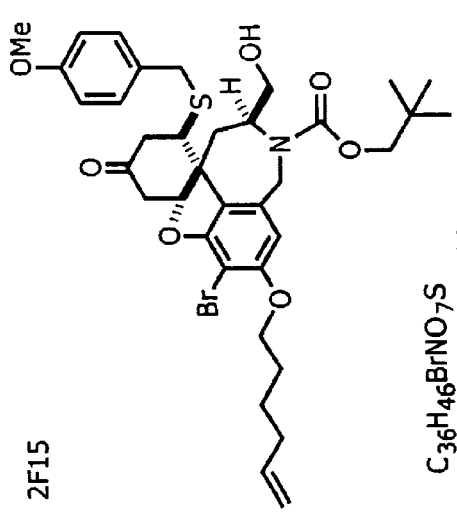
FIGS. 39–41 depict inventive compounds identified in antiprotozoal assay.
Figure 39A:
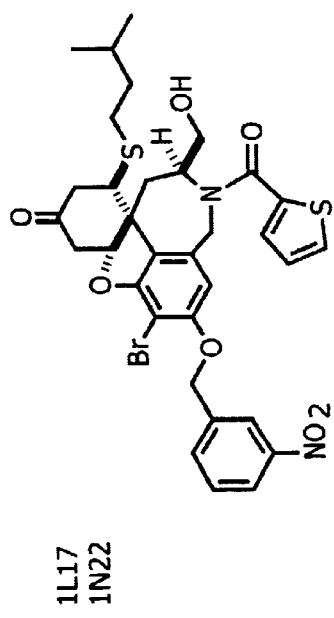
Figure 39B:
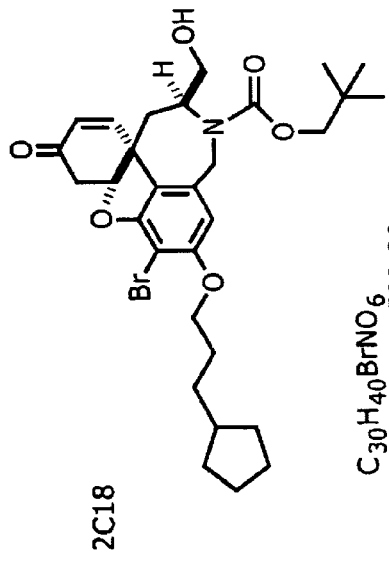
Figure 39B:
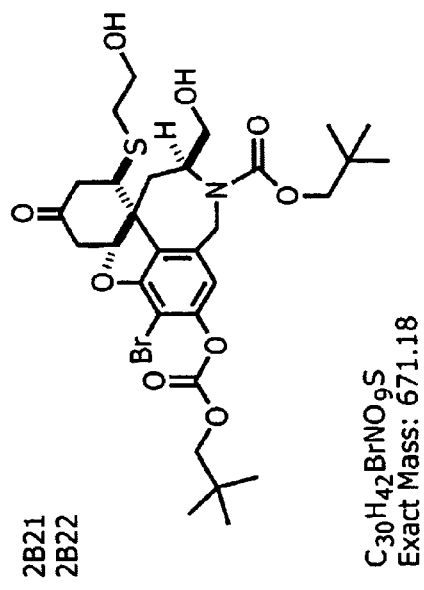
Figure 39B:
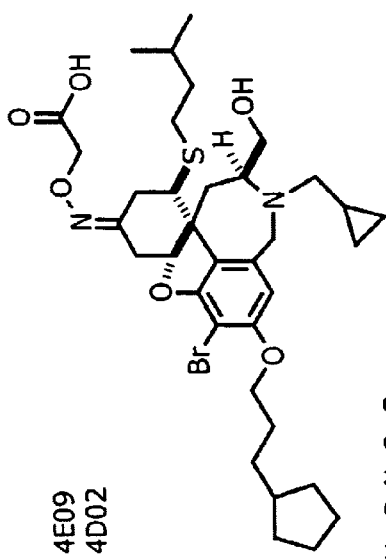
Figure 40A:
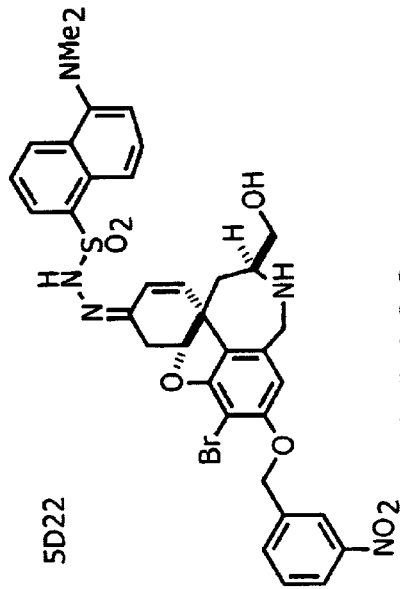
Figure 40A:
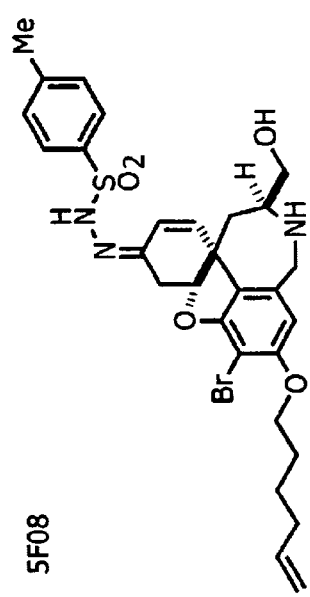
Figure 40A:
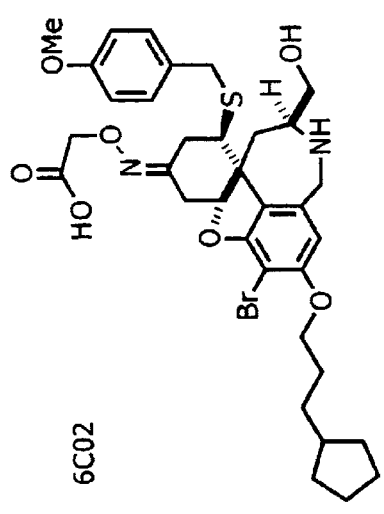
Figure 40B:
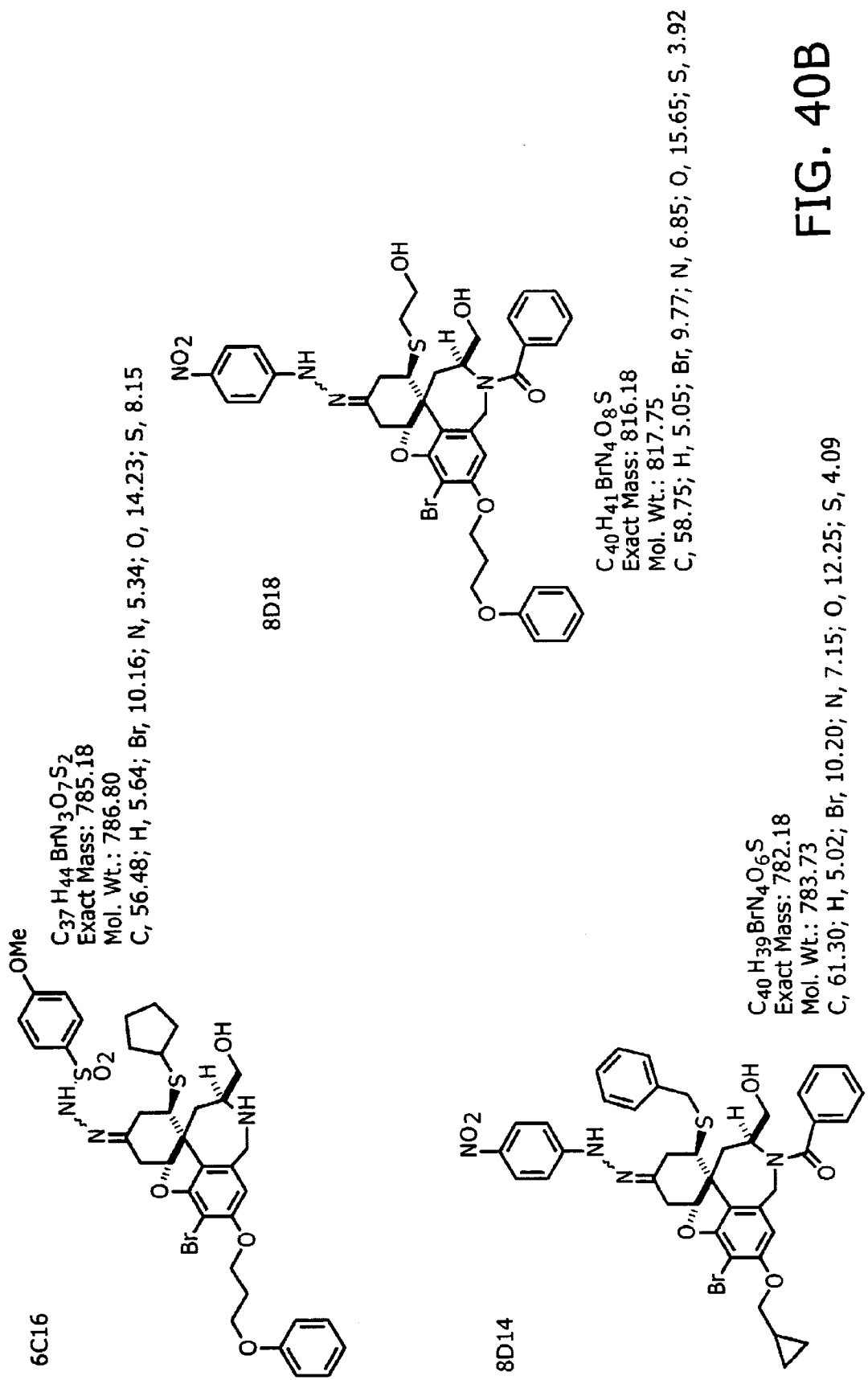
Figure 41A:
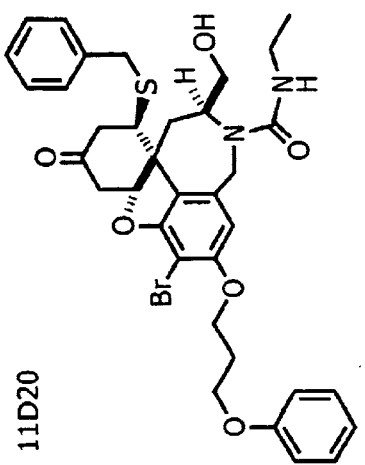
Figure 41A:
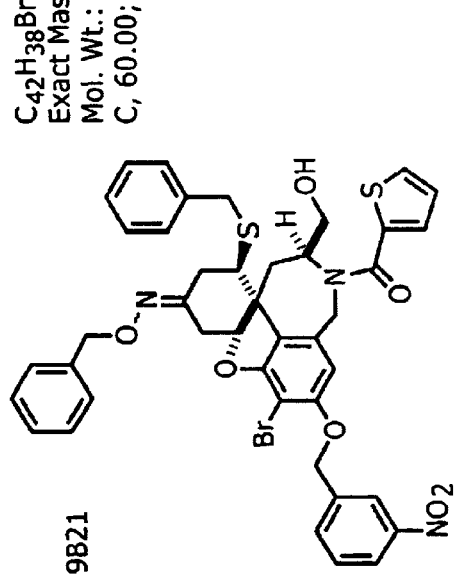
Figure 41A:
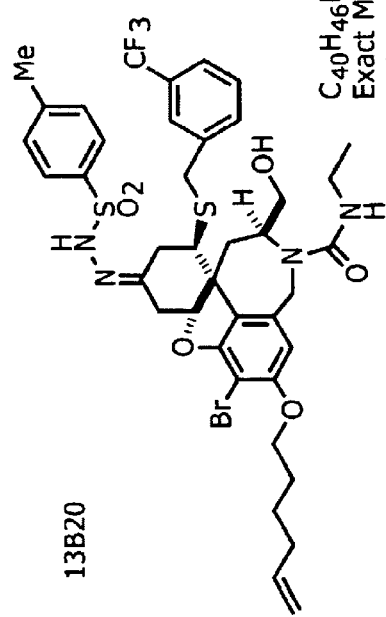
Figure 41B:
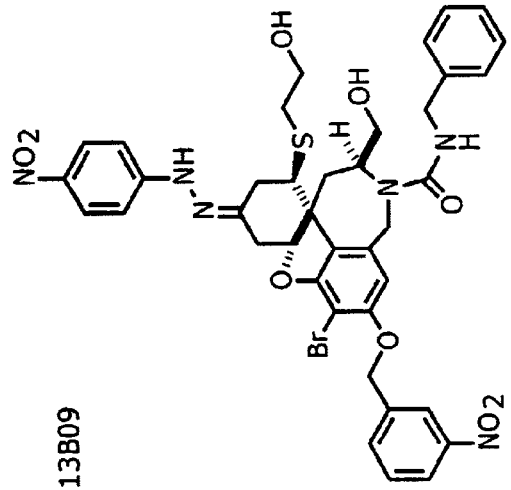
Figure 41B:
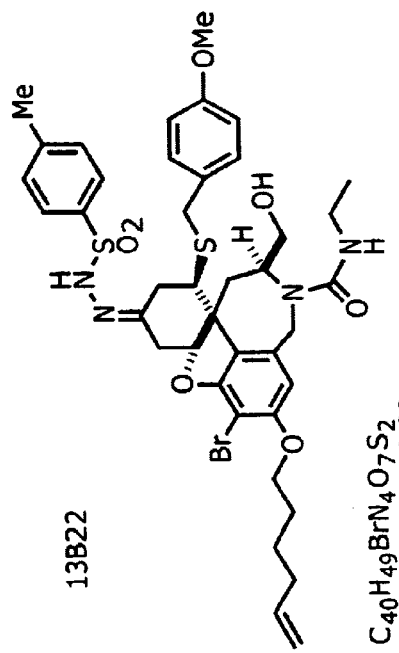
Figure 41B:
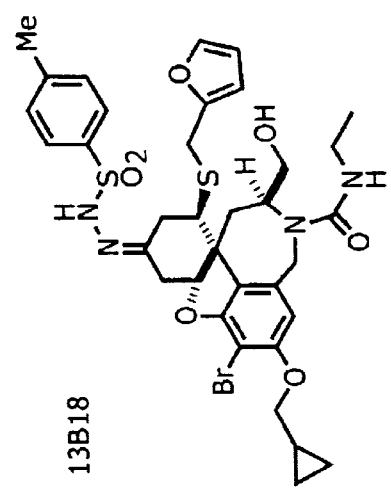

Additional assays were carried out at a diluted concentration of 750 nM compound, which identified one compound (15) secramine, 2484, as a potent inhibitor of VSVG-GFP movement from the golgi apparatus to the plasma membrane. VSVG-GFP accumulated in the golgi instead of reaching the plasma membrane. In analogy to the yeast sec mutants, Novick et al., Cell 1980, 21, 205–215, and as a result of its secondary amine and the phenotype it induces, we have named this compound secramine. Cell based experiments with secramine confirmed its ability to block protein trafficking from the golgi apparatus to the plasma membrane at 2 μM. In contrast, when galanthamine was applied to this same assay it had no effect on the secretory pathway. The discovery of active molecules from this screen demonstrates that compounds resembling natural products are capable of dramatically effecting a biological process where the natural product itself shows no activity (See, FIGS. 36, 37 and 38).

Wound Healing

The present invention further relates to compounds that promote the repair of damaged tissues in animals, particularly in humans, and, more particularly, to the modulation of the healing of wounds in such tissue.

An endless variety of pathological and non-pathological causes results in injury and tissue wounds. A variety of cells have been determined to cooperate in response to injury to repair the damaged tissue and heal the wound. Cells resident in the local tissue participate in the process of wound healing, as do circulating blood cells specifically recruited into the wound itself and the area nearby. Dramatic changes in cellular function are required by both the resident and recruited cells in order to initiate, coordinate, and sustain the complex process of wound healing. Damaged cells and disrupted tissue matrix must be removed, and new cells must be born, grow, and mature to replace those cells that were lost. Finally, the tissue matrix must be resynthesized and remodeled. Even the microvasculature may need to be rebuilt to supply the new tissue with blood flow.

Wound healing is a complex process involving interactions among a variety of different cell types. Among recruited cells, macrophages are considered essential for normal wound healing. Macrophages are a rich source of peptide cytokines, which, as a group, are thought to be integral to the tissue repair responses to local injury. It is well known that individual cytokines can act on more than one cell type and can have more than one effect. Cytokines, especially interferon-alpha (INF-alpha), INF-alpha, and INF-alpha 2b, may also reduce scar formation. These cytokines decrease the proliferation rate of fibroblasts and reduce the rate of collagen and fibronectin synthesis by reducing the production of mRNA. New cytokines continue to be described, and new functions are being attributed to them, as well as to previously described cytokines.

The normal wound repair process consists of three phases—inflammation, proliferation, and remodeling that occur in a predictable series of cellular and biochemical events. Furthermore, wounds are classified according to various criteria: etiology, lasting, morphological characteristics, communications with solid or hollow organs, the degree of contamination, etc. In the last few years many authors use the Color Code Concept, which classifies wounds as red, yellow and black wounds. Compounds of the present invention may be screened for their effect on any of these phases or criteria.

Stimulation of local wound healing generally includes use of such compounds as antiseptic solutions that disinfect the area and topical antibiotic treatments. In addition, growth factors (e.g., epidermal growth factor (EGF), transforming growth factor-beta (TGF-beta), insulin-like growth factor (IGF), platelet-derived growth factor (PDGF), fibroblast growth factor (FGF), interleukins (ILs), and colony-stimulating factor (CSF)) play a role in many wound healing processes, including cell division, migration, differentiation, protein expression, and enzyme production. Moreover, growth factors have a potential ability to heal wounds by stimulating angiogenesis and cellular proliferation, affecting the production and degradation of the extracellular matrix, and by being chemotactic for inflammatory cells and fibroblasts. Acute wounds contain many growth factors that play a crucial role in the initial phases of wound healing.

Applications of some drugs (antioxidants—asiaticoside, vitamin E and ascorbic acid; calcium D-pantothenate, exogenous fibronectin; antileprosy drugs—oil of hydnocarpus; alcoholic extract of yeast) accelerate wound healing. Thymic peptide thymosin beta 4 (T beta 4R) topically applicated, increases collagen deposition and angiogenesis and stimulates keratinocyte migration. Thymosin alpha 1 (T alpha 1R), peptide isolated from the thymus, is a potent chemoattractant which accelerates angiogenesis and wound healing. Furthermore, expression of nitric oxide synthase (NOS) and heat shock proteins (HSP) have an important role in wound healing, as well as the trace elements zinc, copper, manganese.

According to the present invention, compounds that either have the activities of any of the above wound healing agents or modify (enhance or reduce) the activities of the above wound healing agents may be easily identified. Those skilled in the art will appreciate that the availability of the wide variety of wound healing agents indicates that assays for identifying such agents are well known in the art. A typical assay for identifying compounds having would healing activity involves 1) creating a wound, 2) applying a compound to the wound, and 3) after an appropriate amount of time, visualizing the wound to determine the extent of closure, as compared to the extent of closure in the absence of compound. It will be appreciated that wound healing assays may be conducted on cells in vivo or in vitro, and such are provided herein.

The present example illustrates an assay for identifying compounds that are candidate wound healing agents. 5500 BS-C-1 epithelial cells are plated in 384 well clear bottom plates (30 µl total volume). The cells are incubated overnight or until cells form a confluent monolayer. The monolayers are mechanically wounded using a 96 floating pin array, and this procedure is repeated 4 times for one 384 well plate. Immediately after wounding 40 nl of compound is pin transferred into plates. The plate is then incubated for 7 hrs to allow cells to migrate in to heal the wound. The cells are then fixed using 4% paraformaldehyde and stained with rhodamine phalloidin to image actin and hoechst to image the nuclei. The plate is imaged with a 4× objective using the automated microscope from Image1. Each image is visually inspected and the extent of wound healing categorized. Certain inventive compounds have been identified as having interesting phenotypes and specifically have been found to affect the would healing, or cell migration; that is the compounds affect migration into the wound, affect cell density, affect migration/adhesion of the cells such that they pile upon each other, affect morphology along the front of migration, or affect morphology along the front of migration. Inventive compounds exhibiting one or more of these include (referring to Example 1 detailing specific building blocks by the numbers listed below for R1, R2, R3 and $R^4$ building blocks respectively) include: 3474, 6284, 4786, 2486, 5257, 6613, 4463, 1587, 4687, 6761, 6261, 1337, 6237, 2536, 5236, 2137, 5661, 6811, 5611, 1762, 5312, 5612, 6813, 2838, 5514, 2283, 3584, 4583, 6784, 5584, 1883, 5583, 3484, 6384, 3688, 6878, 1478, 6578, 2 8 11 8, 5778, 1678, 3672, 3284, 4586, 6458, 1658, 2498, 6198, 5898, 2298, 3598, 4671, 5872, 2688, 3887, 3173, 5674, 2674, 2875, 6176, 5875, 6375, 2275, 5776, 6275, 5876, 5381, 3188, 2588, 5388, 1482, 5481, 4882, 3582, 4682, 5581, and 5781.

Identification of Antimicrobials

Antimicrobial agents, such as antibiotics, have been effective tools in the treatment of infectious diseases during the last half century: From the time that antibiotic therapy was first developed to the late 1980s, there was almost complete control over bacterial infections in developed countries. The emergence of resistant bacteria, especially during the late 1980s and early 1990s, is changing this situation. The increase in antibiotic resistant strains has been particularly common in major hospitals and care centers. The consequences of the increase in resistant strains include higher morbidity and mortality, longer patient hospitalization, and an increase in treatment costs. (B. Murray, *New Engl. J. Med.* 330: 1229–1230 (1994)).

Many different bacterial populations that are resistant to many antibiotics have been identified over the past twenty-five years. These populations include opportunistic and virulent pathogens that were previously susceptible to antibiotic treatment. Resistant opportunistic pathogens are particularly problematic for debilitated or immunocompromised patients. The development of tolerance and resistance in virulent pathogens poses a significant threat to the ability to treat disease in all patients, compromised as well as noncompromised.

One major factor that has contributed to the increase in the number of resistance strains is the over-use and/or inappropriate administration of antimicrobials in the treatment arena. Newly acquired resistance is generally due to the relatively rapid mutation rate in bacteria. Another contributing factor is the ability of many microorganisms to exchange genetic material that confers resistance, e.g., exchanging of resistance plasmids (R plasmids) or resistance transposons.

For example, following years of use to treat various infections and diseases, penicillin resistance has become increasingly widespread in the microbial populations that were previously susceptible to the action of these drugs. Some microorganisms produce β-lactamase, an enzyme that destroys the antimicrobial itself, while some microorganisms have undergone genetic changes that result in alterations to the cell receptors known as the penicillin-binding proteins, such that pennicillin no longer effictively binds to the receptors. As but another example, other organisms have evolved in a manner that prevents the lysis of cells to which the drug has bound. The drug therefore inhibits the growth of the cell, but does not kill the cell. This appears to contribute to the relapse of disease following premature discontinuation of treatment, as some of the cell remain viable and may begin growing once the antimicrobial is removed from their environment.

The first report of penicillin resistance occurred in Austrailia in 1967. Since this initial report, additional penicillin resistant strains have been reported worldwide. In addition, strains having resistance to numerous other antibiotics have also been reported, including chloramphenicol, erythromycin, tetracycline, clindamycin, rifampin, and sulfamethoxazole-trimethoprim.

Infections by naturally resistant opportunistic or virulent pathogens are difficult to treat with current antibiotics. There is an urgent medical need for new antibiotic molecules which can override the mechanisms of resistance and maintain the level of public health we enjoy today.

The compounds of the present invention may be screened for antimicrobial activity. Those skilled in the art will appreciate that any compound that inhibits the division of a microbial cell, e.g., yeast, fungi, bacteria, and the like, may be identified, and such assays are well known in the art. Bacterial cells divide by first initiating DNA replication. At the end of the bacterial cell cycle, the chromosomes segregate and the cells divide by forming a septum that cuts the cells in two, a process known as septation. Many of the proteins that regulate bacterial replication and septation have yet to be identified.

a. Vibrio Cholera Inhibitors

Certain of the inventive compounds have been identified as having an antibacterial effect (either bacteriocidal or bacteriostatic) using the following assay: An overnight culture of Vibrio cholerae strain M329 is diluted 1:10000 in fresh growth medium. The freshly diluted culture is dispensed in 25 microliter volumes to each well of an appropriate number of 384-well microtiter plates. The compounds and library of compounds as described herein were transferred to corresponding wells in the cell-containing 384 well microtiter plates. The microtiter plates were then incubated for 12–18 hours at 30° C. before being imaged with a CCD camera or a luminescence plate reader. The microtiter plates that contain positive hits (dark non luminescent wells) were then welled on and assayed for viable bacteria.

Certain of the inventive compounds that exhibit bacteriocidal activity include 2873, 6273, 3173, 5686, 1878, 1678, and 6578. Inventive compounds that exhibit bacteriostatic activity include: 2573, 2773, 6784, 2778, 4735, 4715, 2373, 6174, 3755, 3287, 5286, 6677, 2675, 6777, 2373, 6174, 5388, 5776, 6382, 2684, 6384, 6284, 5858, 6165, 6865, 6465, 6585, 6473, 6674, 6771, 4678, and 2173.

b. *Toxoplams gondii* Inhibitors

It will be appreciated that certain of the inventive compounds have demonstrated anti-protozoal activity, more particularly anti-toxoplasma activity, and these compounds are depicted in FIGS. 113–115.

Protozoa are unicellular eukaryotic microorganisms that lack cell walls and are usually motile and colorless. They are distinguished from algae by their lack of chlorophyll, from fungi by their motility and absence of a cell wall, and from slime molds by their lack of fruiting body formation.

Protozoa are generally classified into four major groups based on their life cycles or mechanisms of motility: the flagellates, the cilliates, the amoeba, and the sporozoa (or apicomplexa). The flagellates are protozoa that employ from one to eight or so flagella for movement. The ciliates employ cilia, which are shorter than flagella and present in large numbers. Protozoa which move by extending pseudopodia are called amoeba. The fourth major group, the sporozoa or apicomplexa, are non-motile, intracellular parasites (except during their sexual stage) that penetrate host cells by a mechanism involving their characteristic apical complex. Some protozoa do not fit into any of these four groups, such as the non-motile, intracellular microsporidia, which penetrate host cells by an injection mechanism.

Clinically important representatives of the flagellate group include *Giardia lamblia, Trichomonas vaginalis,* Leishmania spp., and Trypanosoma spp. *G. lamblia* is a waterborne intestinal parasite which occurs worldwide, causing diarrhea, and other intestinal symptoms. The most commonly used drugs used to treat giardiasis are metronidazole and other members of the 5-nitroimidazoles. Unfortunately, Metronidazole is mutagenic in the Ames test (Vogd et al., *Mutation Research*, vol. 26, 483–490 (1974)) and has various toxic side effects. In addition, the development of resistance to these drugs in Giardia and other protozoan parasites such as *Entamoeba histolytica* and *Trichomonas vaginalis* also limits their effectiveness. Leishmaniasis, a life-threatening disease caused by Leishmania spp., is a major health problem worldwide with an estimated 10–15 million people infected and 400,000 new cases each year. There is currently no satisfactory treatment for leishmaniasis. The treatment of choice is pentavalent antimony in the form of sodium stibogluconate or meglumine antimonate. Both drugs are administered intravenously, have severe adverse side effects, require hospitalization during treatment, and are not always effective (M. Ouelette and B. Papadopoulou, *Parasitology Today*, vol. 9, pp. 150–153 (1993)). Trypanosoma spp. cause life-threatening diseases in humans, including African sleeping sickness and Chagas disease, as well as a number of important diseases in domestic animals. Leishmania and Trypanosoma are closely-related genera, representing the major pathogens in the kinetoplastid group of protozoa.

The ciliates are generally non pathogenic, except for *Balantidium coli* which is an intestinal parasite of domestic animals, in particular, swine. Occasionally, *B. coli* infects humans, producing a severe dysentery.

The amoeba group includes the intestinal parasite *Entamoeba histolytica* which causes amoebic dysentery and extraintestinal abscesses of organs such as the liver and lung. The most commonly used drug for treating *E. histolytica* infection is metronidazole. Other free-living amoeba which occasionally cause infections in humans include Acanthamoeba and Naegleria spp.; these infections are typically difficult to treat.

The sporozoa are a large group of protozoa, all of which are obligate parasites. Representative sporozoas are the malaria parasite Plasmodium spp., the human pathogen Cryptosporidium spp., *Toxoplasma gondii*, and several parasites veterinary importance including Sarcocystis spp., Theileria spp., and Eimeria spp. (causing coccidiosis in fowl and domestic animals). Cryptosporidium parvum is a common cause of intestinal infection leading to self-limited diarrhea, but in the immunocompromized individual *C. parvum* infection is chronic and life-threatening. There is currently no effective treatment for cryptosporidiosis.

*Toxoplasma gondii* is the causative agent in toxoplasmosis, an important disease in immunocompromised patients as well as congenitally-infected fetuses. *Toxoplama gondii* is also pathogenic to animals, particularly sheep, in which it causes abortion, stillbirth, and fetal mummification. The pathology of toxoplasmosis in its human and animal hosts is a direct result of repeated cycles of host cell invasion, parasite replication, and host cell lysis. In addition, *Toxoplasma gondii* causes encephalitis, a dangerous life-threatening disease. Toxoplasmic encephalitis is currently treated with a combination of pyrimethamine and sulfadiazine, the side effects of which are frequently so severe as to require discontinuation of the treatment.

Microsporidia are obligate, intracellular pathogens which cause intestinal and systemic infections in immunocompromized patients, as well as economically important infections in fish and invertebrates. Microsporidiosis in patients suffering from acquired immune deficiency syndrome (AIDS) is primarily associated with Encephalitozoon species (including *E. intestinalis, E. cuniculi,* and *E. hellem*) and *Enterocytozoon bieneusi*. Microsporidiosis is a frequent cause of chronic diarrhea in AIDS patients and may also be found outside of the intestine in the eye, biliary tract, nasal sinuses, urinary tract and respiratory tract.

It will be appreciated that there is an urgent need for new chemotherapeutic agents to combat protozoal parasites that are sufficiently effective, do not have harmful side effects, and are not difficult or expensive to administer. Preferably, the anti-protozoal compounds are active against a broad spectrum of protozoa, while remaining non-toxic to human and other mammalian cells. Current approaches for identifying compounds that are anti-protozoal agents often rely on classical genetic systems, e.g., the identification of temperature sensitive mutants, inducible promoters and the like. For example, high-throughput screening assays such as those described in U.S. Patent Application No. 60/292,805, "Identification of antiprotozoal agents", filed May 22, 2001, herewith, may be used.

As will be appreciated by those skilled in the art, the anti-protozoal agents identified may be used in pharmaceutical compositions that may be used for the eradication or inactivation of harmful protozoal parasites. This includes compounds that inhibit the invasion of a cell by protozoal parasites, such as flagellates (*Giardia lamblia, Trichomonas vaginalis*, Leishmania spp., and Trypanosoma spp. *G. lamblia*), cilliates (e.g., *Balantidium coli*), amoebas (e.g., *Entamoeba histolytica*, Acanthamoeba spp., and Naegleria spp.), and sporozoas (or apicomplexa) (e.g., Plasmodium spp., Cryptosporidium spp., *Toxoplasma gondii*, Sarcocystis spp., Theileria spp., and Eimeria spp), microsporidia (Encephalitozoon species (including *E. intestinalis, E. cuniculi*, and *E. hellem*) and *Enterocytozoon bieneus*), and the like. The pharmaceutical compositions may thus be utilized as preventative and/or disinfectant agents.

Additionally, it will be appreciated that pharmaceutically acceptable derivatives of the anti-protozoal compounds identified using the assays described herein. Furthermore, the methods of treating animals (e.g., equines, bovines, felines, canines, swine, ovines, birds, insects, and humans) using these anti-protozoal compounds and pharmaceutical compositions thereof, or either of these in combination with one or more additional therapeutic agents as provided, as described in detail herein.

High-throughput assay systems for the identification of anti-protozoal agents are illustrated herein using a protozoa of the apicomplexa family of protozoa, *Toxoplasma gondii*. As demonstrated by the present example, the ability or inability of the parasite to invade a cell may be determined by detecting the number of parasites on the exterior vs. the interior of a host cell.

The process of host cell invasion by *Toxoplasma gondii* initiates with the of attachment of the parasite to the host cell membrane. Once attached, the protozoa secretes a cocktail of proteins that initiate degradation of the cell wall. After the cell is permeated, invagination of the host cell begins and is complete when the parasite is entirely engulfed by the host cell. The process of vacuole formation is then initiated within the cell. The process of invasion is then complete and the parasite begins the process of replication inside the cell before it exits the cell and begins the invasion process again in other host cells. The assay described herein may identify compounds capable of inhibiting protozoal infection that can effect any stage of the Toxoplasma life cycle.

Identification of Anti-Protozoal Agents Using Labeled Protozoa

The following protocol is carried out in all wells of a 384 well plate. The media covering a confluent monolayer of host cells is removed and replaced with a previously prepared solution of a test compound in media. The host cells are BSC-1 cells, a monkey kidney cell line (however, any host cell may be used since *Toxoplasma gondii* can invade essentially any nucleated cell). A solution of *T. gondii* tachyzoites expressing the yellow fluorescent protein is then added and the host cells and labeled parasites are preincubated with the compound at a temperature at which invasion does not occur (20–22° C.). It will be appreciated that a variety of fluorescent proteins (e.g., green, red, and yellow) are available in the art (see, e.g., Harpur et al. *Nat. Biotechnol.* 19(2):167–169 (2001); Mizuno et la. *Biochemistry* 40(8): 2502–2510 (2001);Huang et al. *Traffic* 2(5):345–357 (2001)). After 15 minutes the assay plate is temperature shifted to 37° C., a temperature at which host cell invasion by the parasites occurs in the absence of compound. After 1 hour, excess parasites are removed by repeat rounds of washing. External parasites are immunostained using dye-conjugated anti-SAG1 antibody. The dye is an Alexa dye (red) (Molecular Probes). The cells are then fixed by treating the cells for 30 minutes with formaldehyde/gluteraldehyde solution in Hanks buffer. Those skilled in the art will appreciate that antibodies may be attached to a wide variety of labels available in the art, see for example, U.S. Pat. No. 6,027,890, incorporated herein by reference.

Automated image acquisition and analysis techniques are used to determine the number of invaded parasites. Digital fluorescence images are collected on a fully automated fluorescence microscope having an automated XY stage and a Z-motor that is required for computer controlled auto focusing, and the number of invading vs. external parasites quantitated automatically from the stored images (Metamorph software by Universal Imaging). Positive results from the automated analysis are confirmed, e.g., by manual re-examination of individual wells under the microscope.

In order to quantitate invasion, the number of parasites inside the cell, which are yellow only, are counted. Alternatively, the total number of external parasites (which are both red and yellow) are subtracted from the total number of parasites, both internal and external (which are labeled yellow and red). Compounds that lower the invasion level by 80% or raise it (by 2 fold) compared to control values (cells plus parasites in the absence of test compound) are considered as preliminary hits in this assay to be followed up with secondary screening.

Identification of Anti-protozoal Compounds Using Antibody Detection

The following protocol is carried out in all wells of a 384 well plate and visualized as described above using fluroescence microscopy. The media covering a confluent monolayer of BSC-1 host cells was removed and replaced with a previously prepared solution of a test compound under examination in media. A solution of wild-type *T. gondii* tachyzoites (that are not labeled) is then added and the host cells and parasites are preincubated with the compound at a temperature at which invasion does not occur (20–22° C.). After 15 minutes the assay plate was temperature shifted to 37° C., a temperature at which host cell invasion by the parasites occurs in the absence of compound. After 1 hour, excess parasites were removed by repeat rounds of washing. External parasites were immunostained using dye-conjugated anti SAG1 antibody. The dye is an Alexa dye (red) (Molecular Probes) The cells were then fixed by treating the cells for 30 minutes with formaldehyde/gluteraldehyde solution in Hanks buffer, which permeabilizes the cells. All parasites (internal and external) are then stained with a second SAG1 antibody that is labeled with a green fluorescent label.

Automated image acquisition and analysis techniques were used to determine the number of invaded parasites. In order to quantitate invasion, the number of parasites inside the cell, which are green only, are counted. Alternatively, the total number of external parasites (which are both red and green) are subtracted from the total number of parasites (both internal and external, which are labeled green and red). As noted above, compounds that lower the invasion level by 80% or raise it (by 2 fold) compared to control values (cells plus parasites in the absence of test compound) are considered as preliminary hits in this assay. The SAG1 antibody may be used twice because there is enough SAG1 on the surface of these parasites that you do not saturate all of the sites with the first antibody.

References referring back to Example 2:

[i] Still, W. C.; Kahn, M.; Mitra, A. *J. Org. Chem.* 1978, 43, 2923.
[ii] Pangborn, A. B.; Giardello, M. A.; Grubbs, R. H.; Rosen, R. K.; and Timmers, F. J. *Organometalllics* 1996, 15, 1518.
[iii] Tallarico, J. A.; Depew, K. M.; Pelish, H. E.; Westwood, N. J.; Lindsley, C. W.; Shair, M. D.; Schreiber, S. L.; Foley, M. A. *J. Comb. Chem.* in press.
[iv] Kurth, M. J.; O'Brien, M. J.; Hakon, H.; and Yanuck, M. *J. Org. Chem.* 1985, 50, 2626.
[v] Using a procedure described by Hamada, Y.; Shibata, M; Sugiura, T.; Kato, S.; and Shioiri, T. *J. Org. Chem.* 1987, 52, 1252.
[vi] Morey, A. D. *Tet. Lett.* 2000, 41, 7405.
[vii] Bennett, William D.; Christensen, J. W.; Hamaker, L. K.; Peterson, M. L.; Rhodes, M. R.; Saneii, H. H. *Advanced Chemtech Handbook of Combinatorial and Solid Phase Organic Chemistry*, Louisville, 1998.
[viii] Yoshida, A.; Hayashi, T.; Takeda, N.; Oida, S.; Ohki, E.; *Chem.Pharm.Bull.* 1981, 29(7), 1854.
[ix] Mayer T. U.; Kapoor T. M.; Haggarty S. J.; King R. W.; Schreiber S. L.; Mitchison T. J. *Science* 1999, 286, 971.
[x] http://sweb.med.harvard.edu/~iccb/
[xi] Karplus, M. *J. Chem. Phys.* 1959, 30, 11.
[xii] Schreiber, S. L. *Bioorg. Med. Chem.* 1998, 6, 1127–1152. (b) Mitchison, T. J. *Chem. Biol.* 1994, 1, 3–6. (c) http://iccb.med.harvard.edu. (d) http://www-schreiber.chem.harvard.edu.
[xiii] Mayer, T. U.; Kapoor, T. M.; Haggarty, S. J.; King, R. W.; Schreiber, S. L.; Mitchison T. J., *Science* 1999, 286, 971–974.
[xiv] (a) Peterson, R. T.; Link, B. A.; Dowling, J. E.; Schreiber, S. L. *Proc. Natl. Acad. Sci. U.S.A.* 2000, in press. (b) Tan, D. S.; Foley, M. A.; Stockwell, B. R. Shair, M. D.; Schreiber, S. L. *J. Am. Chem. Soc.* 1999, 121, 9073–9087.
[xv] Schreiber, S. L. *Science* 2000, 287, 1964–1969.
[xvi] (a) MacBeath, G.; Koehler, A. N.; Schreiber, S. L. *J. Am. Chem. Soc.* 1999, 121, 7967–7968. (b) Hergenrother, P. J.; Depew, K. M.; Schreiber, S. L. *J. Am. Chem. Soc.* 2000, 122, 7849–7850.
[xvii] Currently we use a modification of the binary encoding method first described by Still to elucidate the chemical history of each synthesis bead. Ohlmeyer, M. H.; Swanson, R. N.; Dillard, L. W.; Reader, J. C.; Asouline, G.; Kobayashi, R.; Still, W. C. *Proc. Natl. Acad. Sci.* 1993, 90, 10922–10926. Modifications of this technique will be disclosed in the near future.
[xviii] The 50 nmol of small molecule will give rise to a 5 mM stock solution in 10 μL of DMSO. Our current infrastructure readily supports the automated handling of these volumes of reagents and solvents for library arraying requirements and biological assays.
[xix] Using robotic pin-transfer methods, our largest pin transfer array consumes approximately 100 nL of stock DMSO solution upon each use. For the process of compound printing (see ref. xvi), approximately one nanoliter of stock solution is removed from each well in a typical source plate.
[xx] This amount of material also allows for the use of traditional methods of analysis (MAS-NMR, HPLC, LC-MS, etc.) to assist in determining the identity of each small molecule in the event that the binary encoding/decoding protocol fails. See ref xvii.
[xxi] For an example of a high capacity bead using heteroatom grafted dendrimers, see: Fromont, C.; Bradley, M. *J. Chem. Soc., Chem. Commun.* 2000, 283–284.
[xxii] (a) Furka, A.; Sebestyen, F.; Asgdom, M.; Dibo, G. *Int. J. Pept. Protein Res.* 1991, 37, 487–493. (b) Lam, K. S.; Salmon, S. E.; Hersh, E. M.; Hruby, V. J.; Kazmierski, W. M.; Knapp, R. J. *Nature* 1991, 354, 82–84.
[xxiii] Woolard, F. X.; Paetsch, J.; Ellman, J. A. *J. Org. Chem.* 1997, 62, 6102–6103.
[xxiv] For review of the relative stabilities and cleavage conditions of silylethers, see: Nelson, T. D.; Crouch, R. D. *Synthesis* 1996, 1031–1069.
[xxv] We felt it was important to exclude heteroatoms from the tether (graft unit) to remove the possibility of unexpected reactivity/interference that could erode confidence in each split-pool synthetic step. For a recent review of linker chemistry, see: Guillier, F.; Orain, D.; Bradley, M. *Chem. Rev.* 2000, 100, 2091–2157: See also: James, I. W. *Tetrahedron* 1999, 55, 4855–4946.
[xxvi] Greene, T.; Wuts, P. G. M. *Protecting Groups in Organic Synthesis;* 3$^{rd}$ ed.; Wiley: New York, 1999.
[xxvii] Kunz, H.; Waldman, H. *Comprehensive Organic Synthesis;* Trost, B. M.; Fleming, I., Eds.; Pergammon: Oxford, 1991; Vol. 6, p. 631.
[xxviii] This product is available from RAPP Polymere GmbH. Unfunctionalized 1–2% DVB cross-linked polystyrene 500–560 micron beads number 11,500 beads/g; unfunctionalized 400–450 micron beads number 23,000 beads/g.
[xxix] (a) Stover, H. D. H.; Lu, P. Z.; Frechet, J. M. *J. Polymer Bulletin* 1991, 25, 575–582. (b) Boehlm, T. L.; Showalter, H. D. H. *J. Org. Chem.* 1996, 61, 6498–6499. (c) Stranix, B. R.; Liu, H. Q.; Darling, G. D. *J. Org. Chem.* 1997, 62, 6183–6186. (d) Hu, Y.; Porco, J. A.; Labadie, J. W.; Gooding, O. W. *J. Org. Chem.* 1998, 63, 4518–4521. (e) Plunkett, M. J.; Ellman, J. A. *J. Org. Chem.* 1997, 62, 2885–2893. (f) Briehn, C. A.; Kirshbaum, T.; Bäuerle, P. *J. Org. Chem.* 2000, 65, 352–359.
[xxx] Farrall, M. J.; Frechet, J. M. J. *J. Org. Chem.* 1976, 41, 3877–3882.
[xxxi] McKillop, A.; Bromley, D.; Taylor, E. C. *Tetrahedron Lett.* 1969, 10, 1623–1626.
[xxxii] Bromine and silicon loading levels were determined by elemental analyses of the resin beads. All analyses were performed by Robertson Microlit Labs, Madison, N.J., 07940.
[xxxiii] Good mechanical stability of the large polystyrene beads is critical. During the course of a library synthesis, the repeated handling, chemical reactions, swelling/solvation, and drying steps associated with multiple synthetic transformations tends to degrade the overall physical integrity of the resin.
[xxxiv] This information comes from visual inspection of the resin using a dissecting microscope.
[xxxv] Polymer Laboratories Inc., Amherst, Mass. 01002, USA, has provided these products.
[xxxvi] The calculated per bead loading of the 1.0 mequiv. of Br/g (10,240 beads/g) and 2.0 mequiv. of Br/g (9,400 beads/g) 500–600 micron PS beads are 98 nmol and 212 nmol respectively.
[xxxvii] This sequence of reactions has been successfully done on a 300 g scale.
[xxxviii] Brown, H. C. *Organic Synthesis via Boranes;* Wiley: New York, 1975.
[xxxix] Miyaura, N.; Suzuki, A. *Chem. Rev.* 1995, 95, 2457–2483.
[xl] For previous examples of solid phase Suzuki coupling procedures, see: Larhed, M.; Lindeberg, G.; Hallberg A. *Tetrahedron Lett.* 1996, 37, 8219–8222. (b) Piettre, S. R.; Baltzer, S. *Tetrahedron Lett.* 1997, 38, 1197–1200. (c)

Vanier, C.; Wagner, A.; Mioskowski, C. *Tetrahedron Lett.* 1999, 40, 4335–4338.

($^{xli}$) Time course and catalyst loading levels were examined; data not shown.

($^{xlii}$) This chemistry has been performed on >100 g of resin in a single experiment.

($^{xliii}$) Corey, E. J.; Cho, H.; Rücker, C.; Hua, D. H. *Tetrahedron Lett.* 1981, 22, 3455–3458.

($^{xliv}$) This silicon linker has also been activated and loaded as the diisopropylalkylsilyl chloride through treatment with a $CH_2Cl_2$ solution of dry HCl.

($^{xlv}$) Smith, E. M. *Tetrahedron Lett.* 1999, 40, 3285–3288.

($^{xlvi}$) Porco, J. A.; Hu, Y. *Tetrahedron Lett.* 1999, 40, 3289–3292.

($^{xlvii}$) Typically the substrate alcohol is dissolved in benzene and trace water is removed azeotropically using a rotary evaporator. Methylene chloride can also be used for dissolution of the substrate when solubility in benzene is problematic.

($^{xlviii}$) The volume of a solvent used in each-washing step is approximately 10 mL/g of resin. See ref. 1 for details about developing wash protocols.

($^{xlix}$) This reagent is approximately a 7:3 mixture of HF and pyridine. This reagent can be further buffered with additional pyridine in the cleavage cocktail.

($^{l}$) Blackwell, H. E. et al, unpublished results.

($^{li}$) Hu, Y.; Porco, J. A. *Tetrahedron Lett.* 1998, 39, 2711–2714.

($^{lii}$) For examples of specific chemistries performed on this bead/linker combination, see: (a) Lee, D.; Sello, J.; Schreiber, S. L. *Organic Letters* 2000, 2, 709–712. (b) Spring, D. R.; Krishnan, S.; Schreiber S. L. *J. Am. Chem. Soc.* 2000, 122, 5656–5657. (c) Blackwell, H. E.; Clemons, P. A.; Schreiber, S. L. Presented at the 220th National Meeting of the American Chemical Society, Washington, D.C., August 2000.

What is claimed is:

1. A compound having the structure (I):

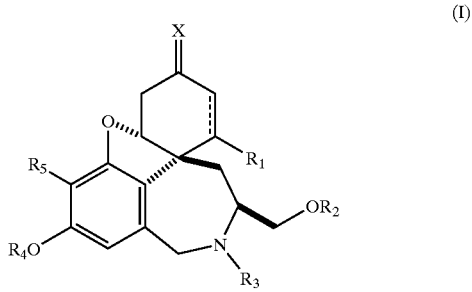

(I)

wherein $R_1$ is hydrogen or halogen, or is an aliphatic, heteroaliphatic, aryl, heteroaryl, alkylaryl, alkylheteroaryl moiety or is $SR_A$, $N(R_A)_2$, or $OR_A$, wherein $R_A$ is hydrogen or is an aliphatic, heteroaliphatic, aryl, heteroaryl, alkylaryl, or alkylheteroaryl moiety;

$R_2$ is hydrogen or is an aliphatic, heteroaliphatic, aryl, heteroaryl, alkylaryl, or alkylheteroaryl moiety $R_2$ is a solid support optionally attached through a linker moiety;

$R_3$ is hydrogen or is an aliphatic, heteroaliphatic, aryl, heteroaryl, alkylaryl, alkylheteroaryl moiety or wherein $R_3$ is —CN; —O(CN)$R_x$; —C(O)$R_x$; —CO$_2$($R_x$); —CON($R_x$)$_2$; —OC(O)$R_x$; —OCO$_2R_x$; —OCON($R_x$)$_2$; —N($R_x$)$_2$; —S(O)$_2R_x$; wherein each occurrence of $R_x$ is independently hydrogen, aliphatic, heteroaliphatic, aryl, heteroaryl, alkylaryl, or alkylheteroaryl;

$R_4$ is hydrogen or is an aliphatic, heteroaliphatic, aryl, heteroaryl, alkylaryl, alkylheteroaryl moiety;

$R_5$ is hydrogen, halogen, —NO$_2$, —CN, —C(O)$R_x$, —CO$_2$($R_x$), —CON($R_x$)$_2$, —OC(O)$R_x$, —OCO$_2R_x$, —OCON($R_x$)$_2$, —N($R_x$)$_2$, —S(O)$_2R_x$, wherein each occurrence of $R_x$ independently includes aliphatic, heteroaliphatic, aryl, heteroaryl, alkylaryl, or alkylheteroaryl; or $R_5$ is an aliphatic heteroaliphatic, aryl, heteroaryl, alkylaryl, alkylheteroaryl moiety, or is $SR_A$, $N(R_A)_2$, or $OR_A$, wherein $R_A$ is an aliphatic, heteroaliphatic, aryl, heteroaryl, alkylaryl, or alkylheteroaryl moiety;

X is O, S or NR$_6$, wherein R$_6$ is OR$_7$, NHR$_7$, or NH(S(=O)$_2$)R$_7$, wherein R$_7$ is aliphatic, heteroaliphatic, aryl, heteroaryl, alkylaryl, or alkylheteroaryl; and wherein each of the foregoing aliphatic, heteroaliphatic, alkylaryl, or alkylheteroaryl moieties may be cyclic or acyclic, and linear or branched; and each of the foregoing aliphatic, heteroaliphatic, aryl, heteroaryl alkylaryl, or alkylheteroaryl moieties may be unsubstituted or substituted with one or more substituents independently selected from the group consisting of aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)$R_x$; —CO$_2$($R_y$); —CON($R_y$)$_2$; —OC(O)$R_y$; —OCO$_2R_y$; —OCON($R_y$)$_2$; and —S(O)$_2R_y$; wherein each occurrence of $R_y$ independently includes aliphatic, heteroaliphatic, aryl, heteroaryl alkylaryl, or alkylheteroaryl; and wherein the dotted line indicates the absence of a bond or indicates a bond, whereby a single bond or double bond is present, respectively.

2. The compound of claim 1, wherein X is NR$_6$, R$_1$ is SR$_A$, and the compound has the structure (II):

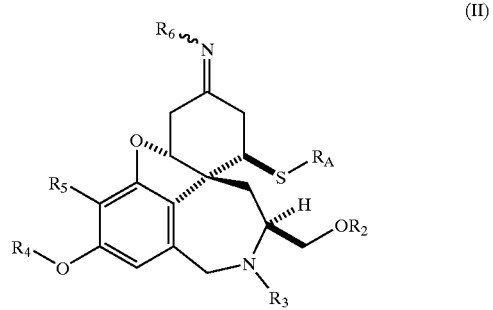

(II)

wherein $R_A$ is hydrogen or is an aliphatic, heteroaliphatic, aryl, heteroaryl, alkylaryl, or alkylheteroaryl moiety; and $R_6$ is OR$_7$, NHR$_7$, or NH(S(=O)$_2$)R$_7$, wherein R$_7$ is aliphatic, heteroaliphatic, aryl, heteroaryl, alkylaryl, or alkylheteroaryl;

wherein each of the foregoing aliphatic, heteroaliphatic, alkylaryl, or alkylheteroaryl moieties may be cyclic or acyclic, and linear or branched; and each of the foregoing aliphatic, heteroaliphatic, aryl, heteroaryl, alkylaryl, or alkylheteroaryl moieties may be unsubstituted or substituted with one or more substituents independently selected from the group consisting of aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_y$); —CON(R$_y$)$_2$; —OC(O)R$_y$; —OCO$_2$R$_y$; —OCON(R$_y$)$_2$; —N(R$_y$)$_2$; and —S(O)$_2$R$_y$; wherein each occurrence of R$_y$ independently includes aliphatic, heteroaliphatic, aryl, heteroaryl, alkylaryl, or alkylheteroaryl.

3. The compound of claim 1, wherein R$_1$ is SR$_A$; wherein R$_A$ is hydrogen or is an alkyl, heteroalkyl, aryl, heteroaryl, alkylaryl, or alkylheteroaryl moiety, and wherein each of the foregoing alkyl and heteroalkyl moieties may be cyclic or acyclic, or branched or unbranched, and wherein each of the foregoing alkyl, heteroalkyl, aryl, heteroaryl, alkylaryl or alkylheteroaryl moieties may be unsubstituted or substituted with one or more substituents independently selected from the group consisting of aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_y$); —CON(R$_y$)$_2$; —OC(O)R$_y$; —OCO$_2$R$_y$; —OCON(R$_y$)$_2$; —N(R$_y$)$_2$; and —S(O)$_2$R$_y$, wherein each occurrence of R$_y$ independently includes aliphatic, heteroaliphatic, aryl, heteroaryl, alkylaryl, or alkylheteroaryl.

4. The compound of claim 1, wherein R$_1$ is one of the following structures:

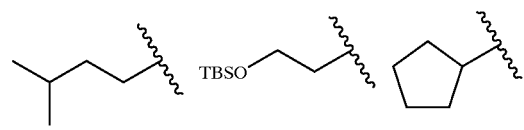

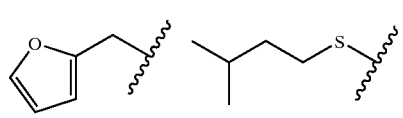

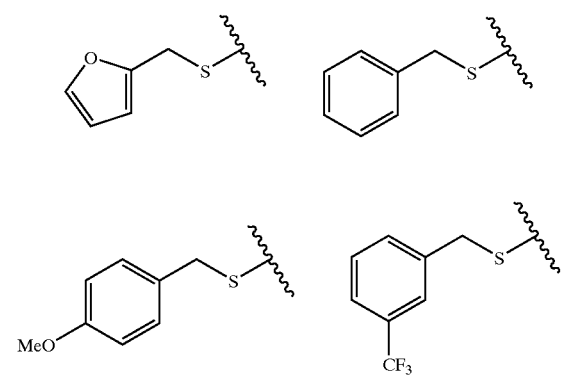

or R$_1$ is a skip codon, and the compound has the structure:

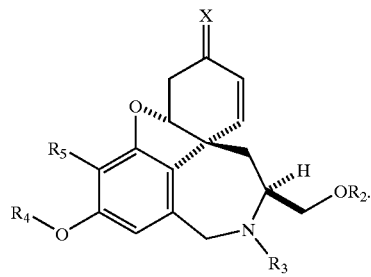

5. The compound of claim 2, wherein R$_A$ is hydrogen or is an alkyl, heteroalkyl, aryl, heteroaryl, alkylaryl, or alkylheteroaryl moiety, and wherein each of the foregoing alkyl and heteroalkyl moieties may be cyclic or acyclic, or branched or unbranched, and wherein each of the foregoing alkyl, heteroalkyl, aryl, heteroaryl, alkylaryl or alkylheteroaryl moieties may be unsubstituted or substituted with one or more substituents independently selected from the group consisting of aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_y$); —CON(R$_y$)$_2$; —OC(O)R$_y$; —OCO$_2$R$_y$; —OCON(R$_y$)$_2$; —N(R$_y$)$_2$; and —S(O)$_2$R$_y$; wherein each occurrence of R$_y$ independently includes aliphatic, heteroaliphatic, aryl, heteroaryl, alkylaryl, or alkylheteroaryl.

6. The compound of claim 5, wherein R$_A$ is one of the following structures:

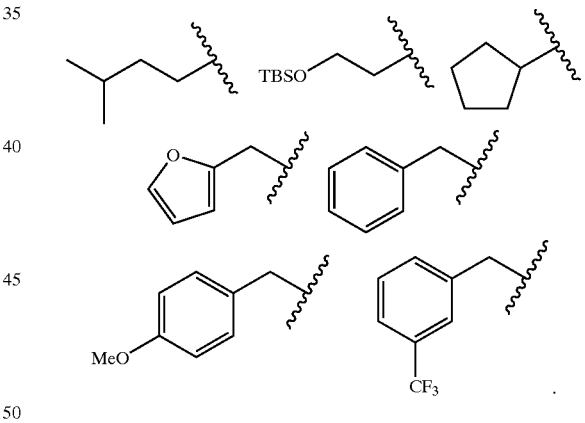

7. The compound of claim 1 or 2, wherein R$_2$ is a solid support optionally attached through a linker moiety.

8. The compound of claim 7, wherein the linker moiety has the structure:

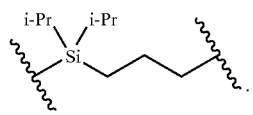

9. The compound of claim 1 or 2, wherein R$_2$ is hydrogen.

10. The compound of claim 1 or 2, wherein R$_3$ is hydrogen, an alkyl, heteroalkyl, aryl, heteroaryl, alkylaryl, alkylheteroaryl moiety, —C(O)R$_x$ or —CON(R$_x$)$_2$; wherein each occurrence of R$_x$ is independently hydrogen, alkyl, heteroalkyl, aryl, heteroaryl, alkylaryl, or alkylheteroaryl, wherein each of the foregoing alkyl and heteroalkyl moieties may be cyclic or acyclic, or branched or unbranched, and wherein each of the foregoing alkyl, heteroalkyl, aryl, heteroaryl, alkylaryl or alkylheteroaryl moieties may be unsubstituted or substituted with one or more substituents independently selected from the group consisting of aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH, —CH$_2$NH$_2$; —CH$_2$SO$_2$CH$_3$; —C(O)R$_x$; —CO$_2$(R$_y$); —CON(R$_y$)$_2$; —OC(O)R$_y$; —OCO$_2$R$_y$; —OCON(R$_y$)$_2$; —N(R$_y$)$_2$; and —S(O)$_2$R$_y$; wherein each occurrence of R$_y$ independently includes aliphatic, heteroaliphatic, aryl, heteroaryl, alkylaryl, or alkylheteroaryl.

11. The compound of claim 10, wherein R$_3$ is hydrogen or one of the following structures:

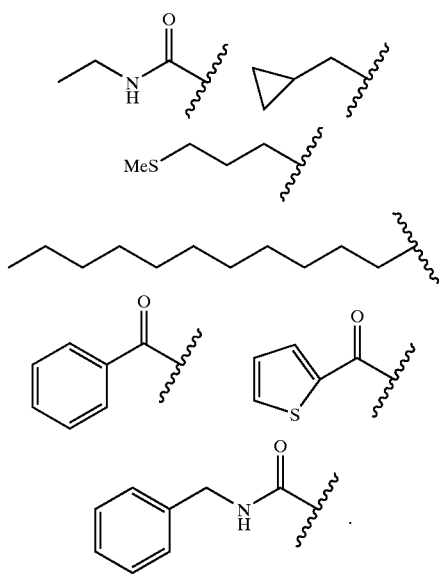

12. The compound of claim 1 or 2, wherein R$_4$ is hydrogen or is an alkyl, heteroalkyl, aryl, heteroaryl, alkylaryl, alkylheteroaryl moiety, wherein each of the foregoing alkyl and heteroalkyl moieties may be cyclic or acyclic, or branched or unbranched, and wherein each of the foregoing alkyl, heteroalkyl, aryl, heteroaryl, alkylaryl or alkylheteroaryl moieties may be unsubstituted or substituted with one or more substituents independently selected from the group consisting of aliphatic; heteroaliphatic; aryl; heteroaryl; alkylaryl; alkylheteroaryl; alkoxy; aryloxy; heteroalkoxy; heteroaryloxy, alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; CH$_2$SO$_2$CH$_3$; —C(O)R$_x$; —CO$_2$(R$_y$); —CON (R$_y$)$_2$; —OC(O)R$_y$; —OCO$_2$R$_y$; —OCON(R$_y$)$_2$; —N(R$_y$)$_2$; and —S(O)$_2$R$_y$; wherein each occurrence of R$_y$ independently includes aliphatic, heteroaliphatic, aryl, heteroaryl, alkylaryl, or alkylheteroaryl.

13. The compound of claim 12, wherein R$_4$ is hydrogen or one of the following structures:

-continued

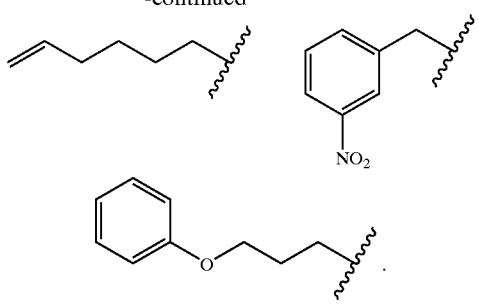

14. The compound of claim 1 or 2, wherein R$_5$ is halogen.

15. The compound of claim 14, wherein R$_5$ is Br.

16. The compound of claim 1, wherein X is NR$_6$; wherein R$_6$ is OR$_7$, NHR$_7$, or NH(S(=O)$_2$)R$_7$, wherein R$_7$ is alkyl, heteroalkyl, aryl, heteroaryl, alkylaryl, or alkylheteroaryl, wherein any of the foregoing alkyl, heteroalkyl, alkylaryl, or alkylheteroaryl substituents may be branched or unbranched, cyclic or acyclic, and wherein any of the foregoing alkyl heteroalkyl, alkylaryl, alkylheteroaryl, aryl or heteroaryl substituents may be unsubstituted or substituted with one or more substituents independently selected from the group consisting of aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_y$); —CON(R$_y$)$_2$; —OC(O)R$_y$; —OCO$_2$R$_y$; —OCON(R$_y$)$_2$; —N(R$_y$)$_2$; and —S(O)$_2$R$_y$; wherein each occurrence of R$_y$ independently includes aliphatic, heteroaliphatic, aryl, heteroaryl, alkylaryl, or alkylheteroaryl.

17. The compound of claim 16, wherein R$_6$ is —OMe, —OBn, or one of the following structures:

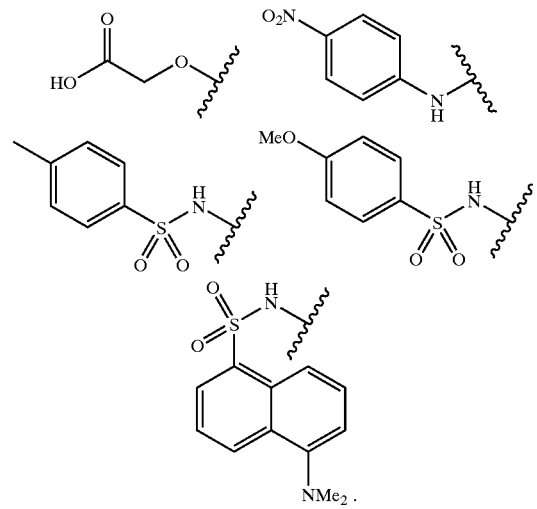

18. The compound of claim 2, wherein R$_6$ is OR$_7$, NHR$_7$, or NH(S(=O)$_2$)R$_7$, wherein R$_7$ is alkyl, heteroalkyl, aryl, heteroaryl, alkylaryl, or alkylheteroaryl, wherein any of the foregoing alkyl, heteroalkyl, alkylaryl, or alkylheteroaryl substituents may be branched or unbranched, cyclic or acyclic, and wherein any of the foregoing alkyl, heteroalkyl, alkylaryl, alkylheteroaryl, aryl or heteroaryl substituents may be unsubstituted or substituted with one or more substituents independently selected from the group consisting of aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_y$); —CON(R$_y$)$_2$; —OC(O)R$_y$; —OCO$_2$R$_y$; —OCON(R$_y$)$_2$; —N(R$_y$)$_2$; and —S(O)$_2$R$_y$, wherein each occurrence of R$_y$ independently includes aliphatic, heteroaliphatic, aryl, heteroaryl, alkylaryl, or alkylheteroaryl.

19. The compound of claim 18, wherein R$_6$ is —OMe, —OBn, or one of the following structures:

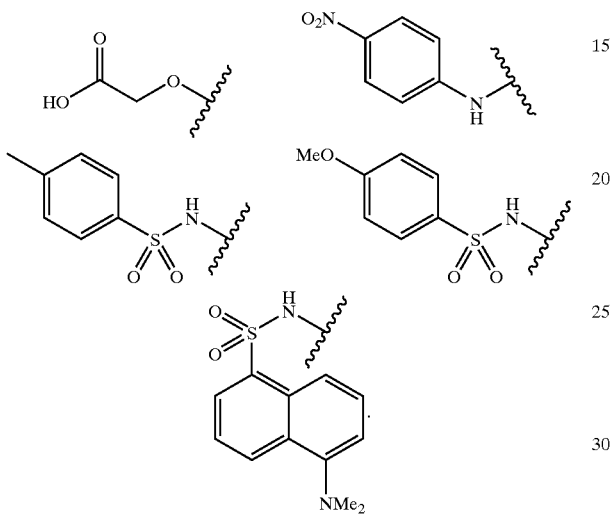

20. The compound of claim 1 wherein X is O.

21. The compound of claim 1 having the structure:

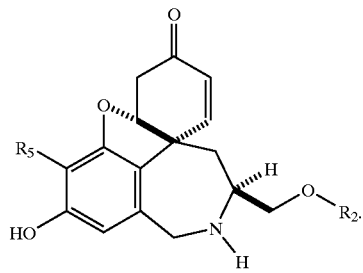

22. The compound of claim 1 having the structure:

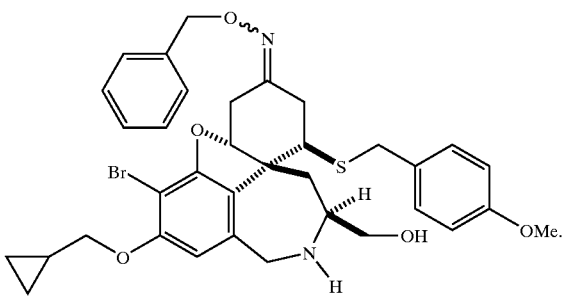

* * * * *

UNITED STATES PATENT AND TRADEMARK OFFICE
CERTIFICATE OF CORRECTION

PATENT NO. : 6,797,819 B1
DATED : September 28, 2004
INVENTOR(S) : Shair et al.

It is certified that error appears in the above-identified patent and that said Letters Patent is hereby corrected as shown below:

Title page,
Item [75], Inventors, replace "Matthew Shair, Boston, MA (US); Nicholas Westwood, St. Andrews Fife (GB); Henry Efrem Pelish, Boston MA (US)" with -- Matthew Shair, Lexington, MA (US); Nicholas Westwood, Dundee (GB); Henry Efrem Pelish, Boston, MA (US); Thomas Kirchhausen, Brighton, MA (US); Yan Feng, Andover, MA (US) --.
Item [75], *Attorney, Agent, or Firm,* replace "Brenda Herschbach Jarrell; Nèdege M. Lagneau; Choate, Hall & Stewart" with -- Brenda Herschbach Jarrell; Nadège M. Lagneau; Choate, Hall & Stewart --.

Signed and Sealed this

Fourteenth Day of February, 2006

JON W. DUDAS
*Director of the United States Patent and Trademark Office*